US011421033B2

(12) United States Patent
Wang et al.

(10) Patent No.: US 11,421,033 B2
(45) Date of Patent: Aug. 23, 2022

(54) INSULIN IMMUNOGLOBULIN FUSION PROTEINS

(71) Applicant: THE SCRIPPS RESEARCH INSTITUTE, La Jolla, CA (US)

(72) Inventors: Feng Wang, Beijing (CN); Matthew S. Tremblay, San Diego, CA (US); Travis Young, La Jolla, CA (US); Nicole Alvarez, San Marcos, CA (US); Yan Liu, San Diego, CA (US); Juanjuan Du, San Diego, CA (US); Peter G. Schultz, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 85 days.

(21) Appl. No.: 16/663,239

(22) Filed: Oct. 24, 2019

(65) Prior Publication Data

US 2020/0115458 A1 Apr. 16, 2020

Related U.S. Application Data

(63) Continuation of application No. 15/756,296, filed as application No. PCT/US2016/050213 on Sep. 2, 2016, now Pat. No. 10,501,546.

(60) Provisional application No. 62/214,605, filed on Sep. 4, 2015.

(51) Int. Cl.

| | |
|---|---|
| ***C07K 16/46*** | (2006.01) |
| ***C07K 16/28*** | (2006.01) |
| ***C07K 14/62*** | (2006.01) |
| ***A61P 3/10*** | (2006.01) |

(52) U.S. Cl.

CPC ............ *C07K 16/2851* (2013.01); *A61P 3/10* (2018.01); *C07K 14/62* (2013.01); *C07K 16/2854* (2013.01); *C07K 2317/24* (2013.01); *C07K 2319/00* (2013.01)

(58) Field of Classification Search

CPC ............................ C07K 16/2851; C07K 14/62

See application file for complete search history.

(56) References Cited

U.S. PATENT DOCUMENTS

| | | | |
|---|---|---|---|
| 3,773,919 | A | 11/1973 | Boswell et al. |
| 6,372,716 | B1 | 4/2002 | Bush et al. |
| 6,566,329 | B1 | 5/2003 | Meyn et al. |
| 6,685,940 | B2 | 2/2004 | Andya et al. |
| 8,192,957 | B2 | 6/2012 | Weiss |
| 8,501,440 | B2 | 8/2013 | Weiss |
| 9,034,372 | B2 | 5/2015 | Lau et al. |
| 10,501,546 | B2 | 12/2019 | Wang et al. |
| 2006/0258852 | A1 | 11/2006 | Lugovskoy et al. |
| 2006/0292140 | A1 | 12/2006 | Ponath et al. |
| 2007/0136826 | A1 | 6/2007 | Dunn et al. |
| 2010/0273988 | A1 | 10/2010 | Kimura |
| 2011/0195896 | A1 | 8/2011 | Weiss et al. |
| 2013/0028918 | A1 | 1/2013 | Song et al. |
| 2013/0029918 | A1 | 1/2013 | Chen |
| 2013/0078216 | A1 | 3/2013 | Dunlevy et al. |
| 2013/0129723 | A1 | 5/2013 | Blankenship et al. |
| 2013/0142742 | A1 | 6/2013 | Thiebault et al. |
| 2013/0156786 | A1 | 6/2013 | Corvey et al. |
| 2013/0253172 | A1 | 9/2013 | Gurney et al. |
| 2015/0299324 | A1 | 10/2015 | Hofer et al. |
| 2016/0015821 | A1 | 1/2016 | Hubbell et al. |
| 2016/0060354 | A1 | 3/2016 | Avila et al. |

FOREIGN PATENT DOCUMENTS

| | | | |
|---|---|---|---|
| CN | 103298488 | A | 9/2013 |
| EP | 0133988 | A2 | 3/1985 |
| EP | 2166021 | A1 | 3/2010 |
| JP | 2013516967 | A | 5/2013 |
| WO | WO-9315722 | A1 | 8/1993 |
| WO | WO-9420069 | A1 | 9/1994 |
| WO | WO-0246227 | A2 | 6/2002 |
| WO | WO-2005051422 | A1 | 6/2005 |
| WO | WO-2005066348 | A2 | 7/2005 |
| WO | WO-2008047914 | A1 | 4/2008 |
| WO | WO-2011086143 | A2 | 7/2011 |
| WO | WO-2011086143 | A3 | 12/2011 |
| WO | WO-2013133450 | A1 | 9/2013 |
| WO | WO-2013134365 | A1 | 9/2013 |
| WO | WO-2014023709 | A1 | 2/2014 |
| WO | WO-2014059213 | A1 | 4/2014 |
| WO | WO-2017041001 | A2 | 3/2017 |

OTHER PUBLICATIONS

Altschul et al. Basic local alignment search tool. J Mol Biol 215(3):403-410 (1990).
Chamow, et al. Immunoadhesins: principles and applications. Trends Biotechnol. 14(2):52-60 (1996).
Eppstein, et al. Biological activity of liposome-encapsulated murine interferon gamma is mediated by a cell membrane receptor. Proc Natl Acad Sci U S A. 82(11):3688-92 (1985).
International Application No. PCT/US2016/050213 International Preliminary Report on Patentability dated Mar. 15, 2018.
International Search Report and Written Opinion in PCT/US16/50213 dated Mar. 16, 2017.
Karlin et al. Methods for assessing the statistical significance of molecular sequence features by using general scoring schemes. PNAS USA 87: 2264-2268 (1990).
Karlin, et al. Applications and statistics for multiple high-scoring segments in molecular sequences. PNAS USA 90:5873-5877 (1993).
Langer, et al. Biocompatibility of polymeric delivery systems for macromolecules. J Biomed Mater Res. 15(2):267-277 (1981).
Langer, R. Controlled release of macromolecules. Chem. Tech. 12:98-105 (1982).

(Continued)

*Primary Examiner* — Gyan Chandra
(74) *Attorney, Agent, or Firm* — Wilson Sonsini Goodrich & Rosati

(57) ABSTRACT

Disclosed herein are immunoglobulin fusion proteins comprising an insulin therapeutic peptide and an immunoglobulin region that targets the insulin therapeutic peptide to the liver of an individual in need thereof. Further disclosed herein are compositions comprising the immunoglobulin fusion proteins and methods for using the immunoglobulin fusion proteins for the treatment or prevention of a disease or condition in a subject, for example, diabetes and diabetes related conditions.

16 Claims, 26 Drawing Sheets

Specification includes a Sequence Listing.

(56) References Cited

OTHER PUBLICATIONS

Rudikoff et al. Single amino acid substitution altering antigen-binding specificity. PNAS 79:1979-1983 (1982).
Sidman et al. Controlled release of macromolecules and pharmaceuticals from synthetic polypeptides based on glutamic acid. Biopolymers, 22(1):547-556 (1983).
U.S. Appl. No. 15/756,296 Office Action dated Apr. 4, 2019.
U.S. Appl. No. 15/756,296 Restriction Requirement dated Jan. 18, 2019.
Wang, Feng. JDRF Funded Research: Lay Abstract—Novel Liver Targeted Insulin, p. 1-2 (Feb. 26, 2015).
Yang et al. Engineering a long-acting, potent GLP-1 analog for microstructure-based transdermal delivery. PNAS 113(15):4140-4145 (2016).
Zhao, X. et al. Construction and Characterization of an Anti-Asialoglycoprotein Receptor Single-Chain Variable-Fragment-Targeted Melittin. Biotechnology and applied biochemistry, 58(6):405-411 (2011).
Zhu, et al. Construction and characterization of pta gene-deleted mutant of Clostridium tyrobutyricum for enhanced butyric acid fermentation. Biotechnol Bioeng. 90(2):154-166 (2005).
Dondelinger et al., Understanding the Significance and Implications of Antibody Numbering and Antigen-Binding Surface/Residue Definition. Front Immunol. 9:2278 (2018).
Pearson, WR. An introduction to sequence similarity ("Homology") searching. Current protocols in bioinformatics/editorial board. Chapter 3: Unit 3.1 (2013).
Cao et al., Characterization of a single-chain variable fragment (scFv) antibody directed against the human asialoglycoprotein receptor. Biotechnol Appl Biochem. 44(Pt 2):65-72 (2006).

Ins2-L2-Ab3

Ins1-L3-Ab4 Fab

Ins1-L3-Ab5 Fab

Ins7-L3-Ab4 Fab

Ins7-L3-Ab5 Fab

FIG. 47

Alignment

```
Human ASGPR        QNSQLQEELRGLRETFSNFTASTEAQVKGLSTQGGNVGRKMKSLESQLEK
Cyno Monkey ASGPR  QN▒QLQ▒ELRGLRET▒SNFTASTEAQVKGLSTQGGNVGRKMKSLESQLEK
Rat ASGPR          QNSQL▒E▒LR▒LR▒▒FSNFT▒STE▒QVK▒L▒TQG▒▒VGRKMK▒▒ESQLEK
Mouse ASGPR        QNSQL▒E▒LLALR▒▒FSNLT▒STE▒QVK▒LSTQGSSVGRKMK▒▒ESKLEK

Human ASGPR        QQKDLSEDHSSLLLHVKQFVSDLRSLSCQMAALQGNGSERTCCPVNWVEH
Cyno Monkey ASGPR  QQKDLSEDHSSLLLHVKQFVSDLRSLSCQMAALQGNGSER▒CCPVNWVEH
Rat ASGPR          ▒Q▒DL▒EDHS▒LLLHVKQLVSD▒RSLSCQMAAL▒GNGSER▒CCP▒NWVE▒
Mouse ASGPR        QQKDLTEDHSSLLLHVKQLVSD▒RSLSCQMAAF▒GNGSERTCCP▒NWVE▒

Human ASGPR        ERSCYWFSRSGKAWADADNYCRLEDAHLVVVTSWEEQKFVQHHIGPVNTW
Cyno Monkey ASGPR  ERSCYWFSRSGKAWADADNYCRLEDAHLVVVTSWEEQKFVQHHIGPVNTW
Rat ASGPR          E▒SCYWFS▒S▒K▒W▒▒AD▒YC▒LE▒AHLVVVTSWEEQ▒FVQ▒H▒GP▒NTW
Mouse ASGPR        E▒SCYWFS▒S▒R▒W▒▒AD▒YC▒LE▒AHLVVVTSRDEQNFLQRHMGP▒NTW

Human ASGPR        MGLHDQNGPWKWVDGTDYETGFKNWRPEQPDDWYGHGLGGGEDCAHFTDD
Cyno Monkey ASGPR  MGLHDQNGPWKWVDGTDYETGFKNWRPEQPDDWYGHGLGGGEDCAHFTDD
Rat ASGPR          ▒GL▒DQNGPWKWVDGTDYETGFKNWRP▒QPDDWYGHGLGGGEDCAHFT▒D
Mouse ASGPR        ▒GL▒DQNGPWKWVDGTDYETGFQNWRPEQPDNWYGHGLGGGEDCAHFT▒D

Human ASGPR        GRWNDDVCQRPYRWVCETELDKASQEPPLL
Cyno Monkey ASGPR  GRWNDDVCQRPYRWVCETEL▒KASQEPPLL
Rat ASGPR          G▒WNDDVC▒RPYRWVCETEL▒KA▒▒▒▒▒▒▒
Mouse ASGPR        GRWNDDVC▒RPYRWVCETKLDKA▒▒▒▒▒▒▒
```

INSULIN IMMUNOGLOBULIN FUSION PROTEINS

PRIORITY

This application is a continuation of U.S. patent application Ser. No. 15/756,296, filed Feb. 28, 2018, which is a U.S. National Stage Entry of International Application Number PCT/US2016/050213, filed Sep. 2, 2016, which claims the benefit of priority from U.S. Provisional Patent Application Ser. No. 62/214,605 filed Sep. 4, 2015, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 10, 2016, is named 41135-750_601_SL.txt and is 203,055 bytes in size.

BACKGROUND OF THE INVENTION

A pharmacologic limitation of current insulin therapies in type 1 diabetes (T1D) patients is that portal-systemic insulin concentration gradient, which ensures that the liver is exposed to higher concentrations of insulin than peripheral tissues, is absent in T1D patients. Subcutaneous injection of insulin results in peripheral hyperinsulinemia, which is associated with atherosclerosis, cancer, hypoglycemia, and other adverse metabolic effects. In contrast, intraportal insulin infusion or adequate hepatic insulinization in T1D patients requires lower doses of insulin and is associated with more rapid and significant lowering of plasma glucose and hemoglobin A1c levels, as well as normalization of circulating cortisol, growth hormone, glucagon, and three-carbon precursors such as lactate, pyruvate, and alanine.

SUMMARY OF THE INVENTION

Disclosed herein are insulin compositions and methods of using the same that address limitations of current insulin therapies with a liver-biased tissue distribution profile, thus focusing the glucose-lower effects of insulin on the liver. One such composition is an insulin fusion protein comprises an insulin molecule fused to an immunoglobulin having an antigen binding domain specific for an antigen of a liver cell. For example, the antigen binding domain is specific for asialoglycoprotein receptor (ASGPR), a molecule selectively expressed on hepatocytes. The anti-ASGPR portion of the fusion protein may be designed to lack or have a reduced rate of internalization to allow the insulin molecule to interact with the insulin receptor. In many cases, an insulin fusion protein has improved efficacy over the insulin molecule administered without a fused immunoglobulin region. Accordingly, the dosing requirements of the insulin fusion protein may be lower than those of current insulin therapies. Furthermore, in some cases, the insulin molecule of a fusion protein comprising an anti-ASGPR domain may be distributed to the liver by at least 2-fold over an insulin molecule of a fusion protein comprising an anti-ASGPR domain lacking binding specificity for ASGPR (control), or the insulin molecule alone.

In one aspect of the disclosure, provided herein are insulin immunoglobulin fusion proteins comprising an insulin therapeutic peptide and a first immunoglobulin region comprising one or more portions of an antigen binding domain, wherein the antigen binding domain has specificity for an antigen of a liver cell. In some embodiments, the antigen is expressed by a hepatocyte. In some embodiments, the antigen is asialoglycoprotein receptor (ASGPR). In some embodiments, the antigen binding domain binds to a one or more amino acids of an epitope of ASGPR having SEQ ID NO: 162, wherein the one or more amino acids is selected from R10, G11, F19, G35, N36, Q47, S56, L83, W134, E135, K138, V140, H142, and K173. In some embodiments, the one or more amino acids of the epitope comprise any combination of W134, E135, K138, V140, H142, and K173.

In some embodiments, the first immunoglobulin region comprises a CDR having an amino acid sequence that differs from one or more of SEQ ID NOS: 45-47 and 55 by no more than 2 amino acids. In some embodiments, the first immunoglobulin region comprises a first CDR having an amino acid sequence that differs from SEQ ID NO: 45 by no more than 2 amino acids. In some embodiments, the first immunoglobulin region comprises a second CDR having an amino acid sequence that differs from SEQ ID NO: 46 by no more than 2 amino acids. In some embodiments, the first immunoglobulin region comprises a second CDR having an amino acid sequence that differs from SEQ ID NO: 55 by no more than 2 amino acids. In some embodiments, the first immunoglobulin region comprises a third CDR having an amino acid sequence that differs from SEQ ID NO: 47 by no more than 2 amino acids. In some embodiments, the first immunoglobulin region comprises a variable region having an amino acid sequence at least about 75% identical to an amino acid sequence selected from SEQ ID NO: 39 and SEQ: 43. In some embodiments, the first immunoglobulin region comprises a variable region having an amino acid sequence at least about 85% homologous to an amino acid sequence selected from SEQ ID NO: 39 and SEQ: 43. In some embodiments, the first immunoglobulin region comprises an amino acid sequence at least about 75% identical to an amino acid sequence selected from SEQ ID NOS: 29, 34, 36-40 and 43. In some embodiments, the first immunoglobulin region comprises an amino acid sequence at least about 85% homologous to an amino acid sequence selected from SEQ ID NOS: 29, 34, 36-40 and 43. In some embodiments, the insulin immunoglobulin fusion protein further comprises a second immunoglobulin region. In some embodiments, the second immunoglobulin region comprises one or more portions of the antigen binding domain. In some embodiments, the second immunoglobulin region comprises a CDR having an amino acid sequence that differs from one or more of SEQ ID NOS: 48-50 by no more than 2 amino acids. In some embodiments, the second immunoglobulin region comprises a first CDR having an amino acid sequence that differs from SEQ ID NO: 48 by no more than 2 amino acids. In some embodiments, the second immunoglobulin region comprises a second CDR having an amino acid sequence that differs from SEQ ID NO: 49 by no more than 2 amino acids. In some embodiments, the second immunoglobulin region comprises a third CDR having an amino acid sequence that differs from SEQ ID NO: 50 by no more than 2 amino acids. In some embodiments, the second immunoglobulin region comprises a variable region having an amino acid sequence at least about 75% identical to an amino acid sequence selected from SEQ ID NOS: 41 and 44. In some embodiments, the second immunoglobulin region comprises a variable region having an amino acid sequence at least about 85% homologous to an amino acid sequence selected from SEQ ID NOS: 41 and 44. In some embodiments, the second immunoglobulin region comprises an amino acid sequence at least about 75% identical to an amino acid sequence selected from SEQ ID NOS: 30, 33, 35, 41, 42, and 44. In some embodiments, the second immunoglobulin region comprises an amino acid sequence at least about 85% homologous to an amino acid sequence selected from SEQ ID NOS: 30, 33, 35, 41, 42, and 44.

In some embodiments, the first immunoglobulin region comprises a CDR having an amino acid sequence that differs from one or more of SEQ ID NOS: 48-50 by no more than 2 amino acids. In some embodiments, the first immunoglobulin region comprises a first CDR having an amino acid sequence that differs from SEQ ID NO: 48 by no more than 2 amino acids. In some embodiments, the first immunoglobulin region comprises a second CDR having an amino acid sequence that differs from SEQ ID NO: 49 by no more than 2 amino acids. In some embodiments, the first immunoglobulin region comprises a third CDR having an amino acid sequence that differs from SEQ ID NO: 50 by no more than 2 amino acids. In some embodiments, the first immunoglobulin region comprises a variable region having an amino acid sequence at least about 75% identical to an amino acid sequence selected from SEQ ID NO: 41 and SEQ: 44. In some embodiments, the first immunoglobulin region comprises a variable region having an amino acid sequence at least about 85% homologous to an amino acid sequence selected from SEQ ID NO: 41 and SEQ: 44. In some embodiments, the first immunoglobulin region comprises an amino acid sequence at least about 75% identical to an amino acid sequence selected from SEQ ID NOS: 30, 33, 35, 41, 42, and 44. In some embodiments, the first immunoglobulin region comprises an amino acid sequence at least about 85% homologous to an amino acid sequence selected from SEQ ID NOS: 30, 33, 35, 41, 42, and 44. In some embodiments, the insulin immunoglobulin fusion protein further comprises a second immunoglobulin region. In some embodiments, the second immunoglobulin region comprises one or more portions of the antigen binding domain. In some embodiments, the second immunoglobulin region comprises a CDR having an amino acid sequence that differs from one or more of SEQ ID NOS: 45-47 and 55 by no more than 2 amino acids. In some embodiments, the second immunoglobulin region comprises a first CDR having an amino acid sequence that differs from SEQ ID NO: 45 by no more than 2 amino acids. In some embodiments, the second immunoglobulin region comprises a second CDR having an amino acid sequence that differs from SEQ ID NO: 46 by no more than 2 amino acids. In some embodiments, the second immunoglobulin region comprises a second CDR having an amino acid sequence that differs from SEQ ID NO: 55 by no more than 2 amino acids. In some embodiments, the second immunoglobulin region comprises a third CDR having an amino acid sequence that differs from SEQ ID NO: 47 by no more than 2 amino acids. In some embodiments, the second immunoglobulin region comprises a variable region having an amino acid sequence at least about 75% identical to an amino acid sequence selected from SEQ ID NO: 39 and SEQ: 43. In some embodiments, the second immunoglobulin region comprises a variable region having an amino acid sequence at least about 85% homologous to an amino acid sequence selected from SEQ ID NO: 39 and SEQ: 43. In some embodiments, the second immunoglobulin region comprises an amino acid sequence at least about 75% identical to an amino acid sequence selected from SEQ ID NOS: 29, 34, 36-40 and 43. In some embodiments, the second immunoglobulin region comprises an amino acid sequence at least about 85% homologous to an amino acid sequence selected from SEQ ID NOS: 29, 34, 36-40 and 43.

In some embodiments, the insulin therapeutic peptide is connected to the amino-terminus of the first immunoglobulin region. In some embodiments, the first immunoglobulin region comprises SEQ ID NO: 155 (QVQLX$_1$QX$_2$GAE), wherein $X_1$ and $X_2$ are independently selected from a naturally or non-naturally occurring amino acid. In some embodiments, $X_1$ is Q or V. In some embodiments, $X_2$ is P or S. In some embodiments, $X_1$ is V and $X_2$ is S. In some embodiments, the first immunoglobulin region comprises SEQ ID NO: 156 (EX$_1$VLTQSPX$_2$T), wherein $X_1$ and $X_2$ are independently selected from a naturally or non-naturally occurring amino acid. In some embodiments, $X_1$ is T or I. In some embodiments, $X_2$ is T or G. In some embodiments, $X_1$ is I and $X_2$ is G.

In some embodiments, the insulin therapeutic peptide is connected to the first immunoglobulin region by a linker peptide. In some embodiments, the linker peptide comprises between 3 and 50 amino acids, and the linker peptide comprises an amino acid sequence selected from: (a) an amino acid sequence having at least 50% glycine, serine, or glycine and serine amino acids; and (b) an amino acid sequence having at least 50% glycine, alanine, or glycine and alanine amino acids. In some embodiments, the linker peptide comprises an amino acid sequence at least 90% identical to any one of SEQ ID NOS: 141-147. In some embodiments, the linker comprises a protease cleavage site.

In some embodiments, the insulin therapeutic peptide comprises a single amino acid chain having the formula: B-C-A (SEQ ID NO: 182) or A-C-B (SEQ ID NO: 183); wherein B comprises SEQ ID NO: 157 (FVNQHLCGSX$_A$LVEALYLVCGERGFFYTX$_B$X$_C$T); A comprises SEQ ID NO 158: GIVEQCCX$_D$SICSLYQLENYCN; and C comprises a connecting peptide having between 3 and 50 amino acids; and wherein $X_A$, $X_B$, $X_C$ and $X_D$ are independently selected from a naturally or non-naturally occurring amino acid. In some embodiments, $X_A$ is D or H. In some embodiments, $X_B$ is D or P. In some embodiments, $X_C$ is P or K. In some embodiments, $X_D$ is H or T. In some embodiments, the connecting peptide comprises an amino acid sequence comprising at least 50% glycine amino acids. In some embodiments, the connecting peptide comprises SEQ ID NO: 159 (GGGX$_1$X$_2$), wherein $X_1$ and $X_2$ are independently selected from a naturally or non-naturally occurring amino acid. In some embodiments, $X_1$ is P, G or S. In some embodiments, $X_2$ is R, S, G or K. In some embodiments, C comprises a protease cleavage site. In some embodiments, the insulin therapeutic peptide comprises an amino acid sequence selected from SEQ ID NOS: 111, 113, 116, 118, 119-140. In some embodiments, the insulin therapeutic peptide comprises an amino acid sequence at least 90% identical to any one of SEQ ID NOS: 111, 113, 116, 118, 119-140.

In some embodiments, the insulin therapeutic peptide comprises a single amino acid chain having the formula B-C-A or A-C-B; wherein B comprises an amino acid sequence having no more than 2 amino acid differences from SEQ ID NO: 160 (FVNQHLCGSHLVEALYLVCGERGFFYT); A comprises an amino acid sequence having no more than 2 amino acid differences from SEQ ID NO: 161 (GIVEQCCTSICSLYQLENYC); and C comprises a connecting peptide having between 3 and 50 amino acids. In some embodiments, B comprises SEQ ID NO: 160. In some embodiments, A comprises SEQ ID NO: 161. In some embodiments, the connecting peptide comprises an amino acid sequence having at least 50% glycine amino acids. In some embodiments, the connecting peptide comprises SEQ ID NO: 159 (GGGX$_1$X$_2$), wherein $X_1$ and $X_2$ are independently selected from a naturally or non-naturally occurring amino acid. In some embodiments, $X_1$ is P, G or S. In some embodiments, $X_2$ is R, S, G or K. In some embodiments, C comprises a protease cleavage site.

In some embodiments, insulin therapeutic peptide comprises an A peptide comprising SEQ ID NO: 158 (GIVEQCCX$_D$SICSLYQLENYCN), and $X_D$ is a naturally or non-naturally occurring amino acid. In some embodiments, $X_D$ is selected from H and T. In some embodiments, one or more cysteine amino acids of the A peptide is present in a disulfide bond with a cysteine amino acid of a B peptide. In some embodiments, the B peptide comprises SEQ ID NO: 157 (FVNQHLCGSX$_A$LVEALYLVCGERGFFYTX$_B$X$_C$T); and $X_A$, $X_B$, and $X_C$ are independently selected from a naturally or non-naturally occurring amino acid. In some embodiments, $X_A$ is D or H. In some embodiments, $X_B$ is D or P. In some embodiments, $X_C$ is P or K. In some embodiments, the B peptide comprises an amino acid sequence having no more than 2 amino acid differences from SEQ ID NO: 160 (FVNQHLCGSHLVEALYLVCGERGFFYT). In some embodiments, B comprises SEQ ID NO: 160.

In some embodiments, the insulin therapeutic peptide comprises an A peptide comprising an amino acid sequence having no more than 2 amino acid differences from SEQ ID NO: 161 (GIVEQCCTSICSLYQLENYC). In some embodiments, the A peptide comprises SEQ ID NO: 161. In some embodiments, one or more cysteine amino acids of the A peptide is present in a disulfide bond with a cysteine amino acid of a B peptide. In some embodiments, the B peptide comprises SEQ ID NO: 157 (FVNQHLCGSX$_A$LVEALYLVCGERGFFYTX$_B$X$_C$T); and $X_A$, $X_B$, and $X_C$ are independently selected from a naturally or non-naturally occurring amino acid. In some embodiments, $X_A$ is D or H. In some embodiments, $X_B$ is D or P. In some embodiments, $X_C$ is P or K. In some embodiments, the B peptide comprises an amino acid sequence having no more than 2 amino acid differences from SEQ ID NO: 160 (FVNQHLCGSHLVEALYLVCGERGFFYT). In some embodiments, B comprises SEQ ID NO: 160.

In some embodiments, the insulin therapeutic peptide comprises an amino acid sequence having no more than 2 amino acid differences from any of SEQ ID NOS: 109-140. In some embodiments, the insulin therapeutic peptide comprises an amino acid sequence having at least 75% sequence identity to any of SEQ ID NOS: 109-140. In some embodiments, the insulin therapeutic peptide comprises an amino acid sequence having at least 85% sequence homology to any of SEQ ID NOS: 109-140.

In some embodiments, the insulin immunoglobulin fusion protein comprises an amino acid sequence having no more than 5 amino acid differences from any of SEQ ID NOS: 78, 79, 81-85, 87-92, 95-98. In some embodiments, the insulin immunoglobulin fusion protein comprises an amino acid sequence having at least 75% sequence identity to any of SEQ ID NOS: 78, 79, 81-85, 87-92, 95-98. In some embodiments, the insulin immunoglobulin fusion protein comprises an amino acid sequence having at least 85% sequence homology to any of SEQ ID NOS: 78, 79, 81-85, 87-92, 95-98.

Further provided herein is a method of treating a disease or condition in a subject in need thereof, the method comprising administering to the subject a therapeutically effective amount of the insulin immunoglobulin fusion protein. In some embodiments, the method further comprises administering to the subject an additional therapeutic agent. In some embodiments, the additional therapeutic agent is an insulin or insulin containing molecule lacking a moiety that targets the additional therapeutic agent to the liver and/or a hepatocyte. In some embodiments, the additional therapeutic agent comprises an insulin B peptide, insulin A peptide, insulin C peptide, or a combination thereof. In some embodiments, the additional therapeutic agent comprises an amino acid sequence differing from a sequence selected from SEQ ID NOS: 138-140, 157 and 158, by no more than 2 amino acids. In some embodiments, the additional therapeutic agent comprises an amino acid sequence selected from SEQ ID NOS: 138-140. In some embodiments, the additional therapeutic agent is administered in a composition with the insulin immunoglobulin fusion protein. In some embodiments, the additional therapeutic agent is administered in a composition separate from the insulin immunoglobulin fusion protein. In some embodiments, the insulin immunoglobulin fusion protein is administered via a subcutaneous, intravenous, intramuscular, infusion (e.g., pump), transdermal, oral or nasal route. In some embodiments, the additional therapeutic agent is administered via a subcutaneous, intravenous, intramuscular, infusion (e.g., pump), transdermal, oral or nasal route. In some embodiments, the disease or condition is diabetes. In some embodiments, the disease or condition is obesity.

Further provided herein is a genetic construct comprising a nucleic acid sequence encoding an amino acid sequence of the insulin immunoglobulin fusion protein. Further provided herein is a first expression vector comprising the first genetic construct. Further provided herein is a mammalian expression host comprising the first expression vector.

In another aspect of the disclosure, provided herein are compositions comprising a molecule of Formula XVII:

I-L-G (Formula XVII)

wherein:

I has the formula B-A, A-B, B-C-A, or A-C-B; wherein B comprises an insulin B chain; A comprises an insulin A chain; if present, C comprises a connecter connecting B and A; and B-A, A-B, or both B-A and A-B are linked by a moiety or disulfide bond;

L comprises a linker; and

G comprises an immunoglobulin, immunoglobulin fragment, peptide or other ligand that has specificity for binding to an antigen expressed or displayed by a hepatocyte.

In some embodiments, I has the formula B-A or A-B, and B-A or A-B are linked by a disulfide bond. In some embodiments, I has the formula B-A or A-B, and B-A or A-B are chemically linked by a moiety. In some embodiments, I has the formula B-C-A or A-C-B, and the connecter is a connecting peptide comprising 2 to 50 amino acids. In some embodiments, the connecting peptide comprises an amino acid sequence having at least 50% glycine amino acids. In some embodiments, the connecting peptide comprises SEQ ID NO: 159 (GGGX$_1$X$_2$), wherein $X_1$ and $X_2$ are independently selected from a naturally or non-naturally occurring amino acid. In some embodiments, $X_1$ is P, G or S. In some embodiments, $X_2$ is R, S, G or K. In some embodiments, C comprises a protease cleavage site. In some embodiments, I has the formula B-C-A or A-C-B, and the connecter is a linker that chemically conjugates B and A.

In some embodiments, the insulin B chain comprises a sequence of SEQ ID NO: 157 (FVNQHLCGSX$_A$LVEALYLVCGERGFFYTX$_B$X$_C$T); and $X_A$, $X_B$, and $X_C$ are independently selected from a naturally or non-naturally occurring amino acid. In some embodiments, $X_A$ is D or H. In some embodiments, $X_B$ is D or P. In some embodiments, $X_C$ is P or K. In some embodiments, the insulin B chain comprises an amino acid sequence having no more than 1, 2, 3 or 4 amino acid differences from SEQ ID NO: 160

(FVNQHLCGSHLVEALYLVCGERGFFYT). In some embodiments, the insulin B chain comprises SEQ ID NO: 160. In some embodiments, the insulin B chain comprises a sequence at least about 75% identical to an insulin B chain in any one of SEQ ID NOS: 109-140. In some embodiments, the insulin B chain is selected from human insulin B chain, porcine insulin B chain and bovine insulin B chain. In some embodiments, the insulin A chain comprises a sequence of SEQ ID NO: 158 (GIVEQCC$X_D$SICSLYQLENYCN), and $X_D$ is a naturally or non-naturally occurring amino acid. In some embodiments, $X_D$ is selected from H and T.

In some embodiments, the insulin A chain comprises an amino acid sequence having no more than 1, 2, 3 or 4 amino acid differences from SEQ ID NO: 161 (GIVEQCCTSICS-LYQLENYC). In some embodiments, the insulin A chain comprises SEQ ID NO: 161. In some embodiments, the insulin A chain comprises a sequence at least about 75% identical to an insulin A chain in any one of SEQ ID NOS: 109-140. In some embodiments, the insulin A chain is selected from human insulin A chain, porcine insulin A chain and bovine insulin A chain.

In some embodiments, the linker comprises a linker peptide. In some embodiments, the linker peptide comprises between 3 and 100 amino acids. In some embodiments, the linker peptide comprises an amino acid sequence selected from: (a) an amino acid sequence having at least 50% glycine, serine, or glycine and serine amino acids; and (b) an amino acid sequence having at least 50% glycine, alanine, or glycine and alanine amino acids. In some embodiments, the linker peptide comprises an amino acid sequence at least 90% identical to any one of SEQ ID NOS: 141-147. In some embodiments, the linker comprises a protease cleavage site.

In some embodiments, the antigen is ASGPR. In some embodiments, G comprises an immunoglobulin or immunoglobulin fragment. In some embodiments, the immunoglobulin or immunoglobulin fragment comprises: (a) a heavy chain variable region sequence comprising SEQ ID NO: 45; (b) a heavy chain variable region sequence comprising SEQ ID NO: 46; (c) a heavy chain variable region sequence comprising SEQ ID NO: 55; (d) a heavy chain variable region sequence comprising SEQ ID NO: 47; (e) a light chain variable region sequence comprising SEQ ID NO: 48; (f) a light chain variable region sequence comprising SEQ ID NO: 49; (g) a light chain variable region sequence comprising SEQ ID NO: 50; (h) a combination of (a), (b) and (d); (i) a combination of (a), (c) and (d); (j) a combination of (e), (f) and (g); (k) a combination of (h) and (j); or (l) a combination of (i) and (j). In some embodiments, the immunoglobulin or immunoglobulin fragment comprises a heavy chain variable region sequence comprising SEQ ID NOS: 45, 46 and 47. In some embodiments, the immunoglobulin or immunoglobulin fragment comprises a heavy chain variable region sequence comprising SEQ ID NOS: 45, 55 and 47. In some embodiments, the immunoglobulin or immunoglobulin fragment comprises a heavy chain variable region sequence that differs from SEQ ID NO: 39 or SEQ ID NO: 43 by no more than 2 amino acids. In some embodiments, the immunoglobulin or immunoglobulin fragment comprises a heavy chain variable region sequence at least about 75% identical to SEQ ID NO: 39 or SEQ ID NO: 43. In some embodiments, the immunoglobulin or immunoglobulin fragment comprises a heavy chain variable region sequence at least about 85% homologous to SEQ ID NO: 39 or SEQ ID NO: 43. In some embodiments, the immunoglobulin or immunoglobulin fragment comprises a sequence that differs from a sequence selected from SEQ ID NOS: 29, 34, 36-40 and 43 by no more than 2 amino acids. In some embodiments, the immunoglobulin or immunoglobulin fragment comprises a sequence at least about 75% identical to a sequence selected from SEQ ID NOS: 29, 34, 36-40 and 43. In some embodiments, the immunoglobulin or immunoglobulin fragment comprises a sequence at least about 85% homologous to a sequence selected from SEQ ID NOS: 29, 34, 36-40 and 43.

In some embodiments, the immunoglobulin or immunoglobulin fragment comprising a CH1 domain. In some embodiments, the CH1 domain comprises a sequence at least about 85% homologous to SEQ ID NO: 40. In some embodiments, the immunoglobulin or immunoglobulin fragment comprises a human Fc region. In some embodiments, the immunoglobulin or immunoglobulin fragment comprises a light chain variable region sequence comprising SEQ ID NOS: 48-50. In some embodiments, the immunoglobulin or immunoglobulin fragment comprises a light chain variable region sequence that differs from SEQ ID NO: 41 or SEQ ID NO: 44 by no more than 2 amino acids. In some embodiments, the immunoglobulin or immunoglobulin fragment comprises a light chain variable region sequence at least about 75% identical to SEQ ID NO: 41 or SEQ ID NO: 44. In some embodiments, the immunoglobulin or immunoglobulin fragment comprises a light chain variable region sequence at least about 85% homologous to SEQ ID NO: 41 or SEQ ID NO: 44. In some embodiments, the immunoglobulin or immunoglobulin fragment comprises a sequence that differs from a sequence selected from SEQ ID NOS: 30, 33, 35, 41, 42, and 44 by no more than 2 amino acids. In some embodiments, the immunoglobulin or immunoglobulin fragment comprises a sequence at least about 75% identical to a sequence selected from SEQ ID NOS: 30, 33, 35, 41, 42, and 44. In some embodiments, the immunoglobulin or immunoglobulin fragment comprises a sequence at least about 85% homologous to a sequence selected from SEQ ID NOS: 30, 33, 35, 41, 42, and 44. In some embodiments, the immunoglobulin or immunoglobulin fragment is humanized.

In some embodiments, G binds to one or more amino acids of an epitope of ASGPR having SEQ ID NO: 162, wherein the one or more amino acids is selected from R10, G11, F19, G35, N36, Q47, S56, L83, W134, E135, K138, V140, H142, and K173. In some embodiments, the one or more amino acids of the epitope comprises any combination of W134, E135, K138, V140, H142, and K173.

In some embodiments, G is an immunoglobulin or immunoglobulin fragment comprising a CDR having an amino acid sequence that differs from one or more of SEQ ID NOS: 45-47 and 55 by no more than 2 amino acids. In some embodiments, G is an immunoglobulin or immunoglobulin fragment comprising a variable region having an amino acid sequence at least about 75% identical to an amino acid sequence selected from SEQ ID NO: 39 and SEQ: 43. In some embodiments, G is an immunoglobulin or immunoglobulin fragment comprising a variable region having an amino acid sequence at least about 85% homologous to an amino acid sequence selected from SEQ ID NO: 39 and SEQ: 43. In some embodiments, G is an immunoglobulin or immunoglobulin fragment comprising an amino acid sequence at least about 75% identical to an amino acid sequence selected from SEQ ID NOS: 29, 34, 36-40 and 43. In some embodiments, G is an immunoglobulin or immunoglobulin fragment comprising an amino acid sequence at least about 85% homologous to an amino acid sequence selected from SEQ ID NOS: 29, 34, 36-40 and 43. In some embodiments, G is an immunoglobulin or immunoglobulin fragment comprising a CDR having an amino acid sequence that differs from one or more of SEQ ID NOS: 48-50 by no more than 2 amino acids. In some embodiments, G is an immunoglobulin or immunoglobulin fragment comprising a variable region having an amino acid sequence at least about 75% identical to an amino acid sequence selected from SEQ ID NOS: 41 and 44. In some embodiments, G is an immunoglobulin or immunoglobulin fragment comprising a variable region having an amino acid sequence at least about 85% homologous to an amino acid sequence selected from SEQ ID NOS: 41 and 44. In some embodiments, G is an immunoglobulin or immunoglobulin fragment comprising an amino acid sequence at least about 75% identical to an amino acid sequence selected from SEQ ID NOS: 30, 33, 35, 41, 42, and 44. In some embodiments, G is an immunoglobulin or immunoglobulin fragment comprising an amino acid sequence at least about 85% homologous to an amino acid sequence selected from SEQ ID NOS: 30, 33, 35, 41, 42, and 44.

Further provided herein is a method of treating a disease or condition in a subject in need thereof, the method comprising administering to the subject a therapeutically effective amount of the composition having Formula XVII. In some embodiments, the method further comprises administering to the subject an additional therapeutic agent. In some embodiments, the additional therapeutic agent is an insulin or insulin containing molecule lacking a moiety that targets the additional therapeutic agent to the liver and/or a hepatocyte. In some embodiments, the additional therapeutic agent comprises an insulin B peptide, insulin A peptide, insulin C peptide, or a combination thereof. In some embodiments, the additional therapeutic agent comprises an amino acid sequence differing from a sequence selected from SEQ ID NOS: 138-140, 157 and 158, by no more than 2 amino acids. In some embodiments, the additional therapeutic agent comprises an amino acid sequence selected from SEQ ID NOS: 138-140. In some embodiments, the additional therapeutic agent is administered with the composition having Formula XVII. In some embodiments, the additional therapeutic agent is administered in a composition separate from the composition having Formula XVII. In some embodiments, the composition having Formula XVII is administered via a subcutaneous, intravenous, intramuscular, infusion (e.g., pump), transdermal, oral or nasal route. In some embodiments, the additional therapeutic agent is administered via a subcutaneous, intravenous, intramuscular, infusion (e.g., pump), transdermal, oral or nasal route. In some embodiments, the disease or condition is diabetes. In some embodiments, the disease or condition is obesity.

In another aspect of the disclosure, provided herein are immunoglobulins for specific binding to asialoglycoprotein receptor (ASGPR), the immunoglobulin comprising: (a) a heavy chain variable region sequence comprising SEQ ID NO: 45; (b) a heavy chain variable region sequence comprising SEQ ID NO: 46; (c) a heavy chain variable region sequence comprising SEQ ID NO: 55; (d) a heavy chain variable region sequence comprising SEQ ID NO: 47; (e) a light chain variable region sequence comprising SEQ ID NO: 48; (f) a light chain variable region sequence comprising SEQ ID NO: 49; (g) a light chain variable region sequence comprising SEQ ID NO: 50; (h) a combination of (a), (b) and (d); (i) a combination of (a), (c) and (d); (j) a combination of (e), (f) and (g); (k) a combination of (h) and (j); or (l) a combination of (i) and (j). In some embodiments, the immunoglobulin comprises a heavy chain variable region sequence comprising SEQ ID NOS: 45, 46 and 47. In some embodiments, the immunoglobulin comprises a heavy chain variable region sequence comprising SEQ ID NOS: 45, 55 and 47. In some embodiments, the immunoglobulin comprises a heavy chain variable region sequence that differs from SEQ ID NO: 39 or SEQ ID NO: 43 by no more than 2 amino acids. In some embodiments, the immunoglobulin comprises a heavy chain variable region sequence at least about 75% identical to SEQ ID NO: 39 or SEQ ID NO: 43. In some embodiments, the immunoglobulin comprises a heavy chain variable region sequence at least about 85% homology to SEQ ID NO: 39 or SEQ ID NO: 43. In some embodiments, the immunoglobulin comprises a sequence that differs from a sequence selected from SEQ ID NOS: 29, 34, 36-40 and 43 by no more than 2 amino acids.

In some embodiments, the immunoglobulin comprises a sequence at least about 75% identical to a sequence selected from SEQ ID NOS: 29, 34, 36-40 and 43. In some embodiments, the immunoglobulin comprises a sequence at least about 85% homologous to a sequence selected from SEQ ID NOS: 29, 34, 36-40 and 43. In some embodiments, the immunoglobulin comprises comprising a CH1 domain. In some embodiments, the CH1 domain comprises a sequence at least about 85% homologous to SEQ ID NO: 40. In some embodiments, the immunoglobulin comprises a human Fc region. In some embodiments, the immunoglobulin comprises a light chain variable region sequence comprising any one of SEQ ID NOS: 48-50.

In some embodiments, the immunoglobulin comprises a light chain variable region sequence that differs from SEQ ID NO: 41 or SEQ ID NO: 44 by no more than 2 amino acids. In some embodiments, the immunoglobulin comprises a light chain variable region sequence at least about 75% identical to SEQ ID NO: 41 or SEQ ID NO: 44. In some embodiments, the immunoglobulin comprises a light chain variable region sequence at least about 85% homology to SEQ ID NO: 41 or SEQ ID NO: 44. In some embodiments, the immunoglobulin comprises a sequence that differs from a sequence selected from SEQ ID NOS: 30, 33, 35, 41, 42, and 44 by no more than 2 amino acids. In some embodiments, the immunoglobulin comprises a sequence at least about 75% identical to a sequence selected from SEQ ID NOS: 30, 33, 35, 41, 42, and 44. In some embodiments, the immunoglobulin comprises a sequence at least about 85% homologous to a sequence selected from SEQ ID NOS: 30, 33, 35, 41, 42, and 44. In some embodiments, the immunoglobulin is humanized.

Further provided herein is an immunoglobulin that competes with the immunoglobulin described herein for binding to ASGPR.

Further provided herein is a method of targeting a molecule to a hepatocyte in a subject in need thereof, the method comprising administering to the subject a composition comprising the molecule and the immunoglobulin. In some embodiments, the molecule is fused or linked to the immunoglobulin. In some embodiments, the molecule comprises a human insulin B chain, human insulin A chain, or a derivative or combination thereof. In some embodiments, the subject has diabetes.

In another aspect of the disclosure, provided herein are methods of treating a disease or condition associated with glucose metabolism in a subject in need thereof, the method comprising administering an effective amount of an insulin immunoglobulin fusion protein comprising an insulin therapeutic peptide and an immunoglobulin region comprising an antigen binding domain, wherein the antigen binding domain targets a hepatocyte receptor. In some embodiments, the hepatocyte receptor is ASGPR. In some embodiments, the disease or condition is diabetes. In some embodiments, the disease or condition is obesity.

In some embodiments, the method further comprises administering to the subject an additional therapeutic agent. In some embodiments, the additional therapeutic agent is an insulin or insulin containing molecule lacking a moiety that targets the additional therapeutic agent to the liver and/or a hepatocyte. In some embodiments, the additional therapeutic agent comprises an insulin B peptide, insulin A peptide, insulin C peptide, or a combination thereof. In some embodiments, the additional therapeutic agent comprises an amino acid sequence differing from a sequence selected from SEQ ID NOS: 138-140, 157 and 158, by no more than 2 amino acids. In some embodiments, the additional therapeutic agent comprises an amino acid sequence selected from SEQ ID NOS: 138-140. In some embodiments, the additional therapeutic agent is administered in a composition with the insulin immunoglobulin fusion protein. In some embodiments, the additional therapeutic agent is administered in a composition separate from the insulin immunoglobulin fusion protein. In some embodiments, the insulin immunoglobulin fusion protein is administered via a subcutaneous, intravenous, intramuscular, infusion (e.g., pump), transdermal, oral or nasal route. In some embodiments, the additional therapeutic agent is administered via a subcutaneous, intravenous, intramuscular, infusion (e.g., pump), transdermal, oral or nasal route.

In some embodiments, the insulin therapeutic peptide has the formula B-A, A-B, B-C-A, or A-C-B; wherein B comprises an insulin B chain; A comprises an insulin A chain; if present, C comprises a connecter connecting B and A; and B-A, A-B, or both B-A and A-B are linked by a moiety or disulfide bond. In some embodiments, B-A or A-B, and B-A or A-B are linked by a disulfide bond. In some embodiments, the connecter is a connecting peptide comprising 2 to 50 amino acids. In some embodiments, the connecting peptide comprises an amino acid sequence having at least 50% glycine amino acids. In some embodiments, the connecting peptide comprises SEQ ID NO: 159 (GGG$X_1X_2$), wherein $X_1$ and $X_2$ are independently selected from a naturally or non-naturally occurring amino acid. In some embodiments, $X_1$ is P, G or S. In some embodiments, $X_2$ is R, S, G or K. In some embodiments, C comprises a protease cleavage site. In some embodiments, the insulin B chain comprises a sequence of SEQ ID NO: 157 (FVNQHLCGS$X_A$LVEALYLVCGERGFFYT$X_BX_C$T); and $X_A$, $X_B$, and $X_C$ are independently selected from a naturally or non-naturally occurring amino acid. In some embodiments, $X_A$ is D or H. In some embodiments, $X_B$ is D or P. In some embodiments, $X_C$ is P or K.

In some embodiments, the insulin B chain comprises an amino acid sequence having no more than 1, 2, 3 or 4 amino acid differences from SEQ ID NO: 160 (FVNQHLCGSHLVEALYLVCGERGFFYT). In some embodiments, the insulin B chain comprises a sequence at least about 75% identical to an insulin B chain in any one of SEQ ID NOS: 109-140. In some embodiments, insulin B chain is selected from human insulin B chain, porcine insulin B chain and bovine insulin B chain. In some embodiments, the insulin A chain comprises a sequence of SEQ ID NO: 158 (GIVEQCC$X_D$SICSLYQLENYCN), and $X_D$ is a naturally or non-naturally occurring amino acid. In some embodiments, $X_D$ is selected from H and T. In some embodiments, the insulin A chain comprises an amino acid sequence having no more than 1, 2, 3 or 4 amino acid differences from SEQ ID NO: 161 (GIVEQCCTSICSLYQLENYC). In some embodiments, the insulin A chain comprises a sequence at least about 75% identical to an insulin A chain in any one of SEQ ID NOS: 109-140. In some embodiments, the insulin A chain is selected from human insulin A chain, porcine insulin A chain and bovine insulin A chain.

In some embodiments, the immunoglobulin region comprises: (a) a heavy chain variable region sequence comprising SEQ ID NO: 45; (b) a heavy chain variable region sequence comprising SEQ ID NO: 46; (c) a heavy chain variable region sequence comprising SEQ ID NO: 55; (d) a heavy chain variable region sequence comprising SEQ ID NO: 47; (e) a light chain variable region sequence comprising SEQ ID NO: 48; (f) a light chain variable region sequence comprising SEQ ID NO: 49; (g) a light chain variable region sequence comprising SEQ ID NO: 50; (h) a combination of (a), (b) and (d); (i) a combination of (a), (c) and (d); (j) a combination of (e), (f) and (g); (k) a combination of (h) and (j); or (l) a combination of (i) and (j). In some embodiments, the immunoglobulin region comprises a sequence at least about 75% identical to a sequence selected from SEQ ID NOS: 29, 30 and 33-44. In some embodiments, the immunoglobulin region comprises a sequence at least about 85% homologous to a sequence selected from SEQ ID NOS: 29, 30 and 33-44. In some embodiments, the immunoglobulin region is humanized. In some embodiments, the antigen binding domain binds to one or more amino acids of an epitope of ASGPR having SEQ ID NO: 162, wherein the one or more amino acids is selected from R10, G11, F19, G35, N36, Q47, S56, L83, W134, E135, K138, V140, H142, and K173.

In another aspect of the disclosure, provided herein are insulin immunoglobulin fusion proteins comprising an insulin therapeutic peptide and a first immunoglobulin region comprising an amino acid sequence of an antigen binding domain; wherein the insulin immunoglobulin fusion proteins are targeted to the liver. The insulin immunoglobulin fusion protein may be targeted to the liver by the binding of the antigen binding domain to an antigen expressed by a hepatocyte. In some embodiments, the antigen comprises an amino acid sequence of asialoglycoprotein receptor (ASGPR). In some embodiments, the first immunoglobulin region comprises an amino acid sequence that is about or at least about 80%, 85%, 90%, 95% or 100% identical to an amino acid sequence derived from an anti-ASGPR antibody. In some embodiments, the first immunoglobulin region comprises an amino acid sequence that is about or at least about 80%, 85%, 90%, 95% or 100% identical to an amino acid sequence of any one of SEQ ID NOS: 29, 30, 33-56, 16, or a combination thereof. In some embodiments, the insulin immunoglobulin fusion protein is configured to bind to the antigen via the amino acid sequence of the antigen binding domain. In some embodiments, the insulin immunoglobulin fusion protein binds to the antigen with an affinity that is at least about 50%, 60%, 70%, 80%, 90%, or 95% of an affinity of the antigen binding domain within a native immunoglobulin. A native immunoglobulin may include, without limitation, an antibody, or region thereof (e.g., Fab), comprising the antigen binding domain configured to bind the antigen expressed by a hepatocyte, wherein the antibody does not comprise and/or is not connected to, a non-antibody moiety (e.g., therapeutic peptide/protein, small molecule).

In some embodiments, the amino acid sequence of the antigen binding domain comprises an amino acid sequence of a variable region derived from a variable light chain, a variable heavy chain, or both a variable light chain and a variable heavy chain. In some embodiments, the insulin immunoglobulin fusion protein further comprises a second immunoglobulin region comprising a second amino acid sequence of the antigen binding domain. In some cases, the second amino acid sequence of the antigen binding domain comprises an amino acid sequence of a variable region derived from a variable light chain, a variable heavy chain, or both a variable light chain and a variable heavy chain. In some embodiments, the first immunoglobulin region is humanized. In some embodiments, the first immunoglobulin region is a mouse immunoglobulin region.

In some embodiments, an activity of the insulin therapeutic peptide in the insulin immunoglobulin fusion protein is comparable to an activity of reference insulin therapeutic peptide. A reference therapeutic peptide may include a native formulation of the insulin therapeutic peptide, wherein the native formulation comprises the insulin therapeutic peptide not linked to an immunoglobulin, or region thereof. In some embodiments, the activity of the insulin therapeutic peptide in the insulin immunoglobulin fusion protein is at least about 50%, 60%, 70%, 80%, 90%, or 95% of the activity of the reference insulin therapeutic peptide. In some embodiments, the insulin therapeutic peptide of the insulin immunoglobulin fusion protein has an $EC_{50}$ that is at least about 10%, 20%, 50%, or 100% less than an $EC_{50}$ of a reference insulin therapeutic peptide in a hepatocyte activity assay. In some cases, the reference insulin therapeutic peptide comprises an amino acid sequence that is about or at least about 80%, 85%, 90%, 95%, or 100% identical to an amino acid sequence of any one of SEQ ID NOS: 109-140, 157, 158, 160, 161, or a combination thereof. In some cases, the reference insulin therapeutic peptide comprises an amino acid sequence derived from human insulin, porcine insulin, bovine insulin, or a combination thereof. In some cases, the reference insulin therapeutic peptide comprises an amino acid sequence derived from human insulin B chain, human insulin A chain, or a combination thereof. In some embodiments, the reference insulin peptide comprises an insulin analog, or a portion thereof. Non-limiting examples of insulin analogs include glargine, glulisine, insulin detemir, and insulin degludec.

In some embodiments, the insulin therapeutic peptide, or an amino acid sequence thereof, is linked to the amino terminus or the carboxyl terminus of the first immunoglobulin region. In some cases, the insulin therapeutic peptide, or an amino acid sequence thereof, is linked to the amino terminus of the first immunoglobulin region. In some embodiments, the insulin therapeutic peptide, or an amino acid sequence thereof, is linked to the first immunoglobulin region by a linker. In some cases, the linker comprises an amino acid sequence. In some cases, the linker comprises from about 3 to about 40 amino acids. In some cases, the linker comprises one or more glycine residues; wherein the one or more glycine residues make up at least about 30%, 40% or 50% of the linker amino acid sequence. In some embodiments, the linker comprises a protease cleavage site. In some cases, the protease cleavage site is located at the amino terminus, carboxyl terminus, or within the linker peptide amino acid sequence. In some cases, the protease cleavage site is recognized by a proprotein convertase.

In some embodiments, the insulin therapeutic peptide comprises an amino acid sequence derived from insulin B chain, an amino acid sequence derived from insulin A chain, or a combination thereof. In some embodiments, the insulin B chain comprises an amino acid sequence that is about or at least about 80%, 85%, 90%, 95% or 100% identical to human insulin B chain. In some embodiments, the insulin A chain comprises an amino acid sequence that is about or at least about 80%, 85%, 90%, 95% or 100% identical to human insulin A chain. In some embodiments, the insulin therapeutic peptide comprises an amino acid sequence derived from insulin B chain and an amino acid sequence derived from insulin A chain. In some embodiments, the amino acid sequence derived from insulin B chain is connected to the amino acid sequence derived from insulin A chain. In some instances, the connection is via a connecting peptide. In some instances, the connecting peptide comprises from about 3 to about 25 amino acids. In some instances, the connecting peptide comprises one or more glycine residues, and wherein the one or more glycine residues make up at least about 30%, 40%, or 50% of the connecting peptide amino acid sequence. In some cases, the connecting peptide comprises a protease cleavage site. In some cases, the protease cleavage site of the connecting peptide is located at the amino terminus, carboxyl terminus, or within the connecting peptide amino acid sequence. In some cases, the protease cleavage site of the connecting peptide is recognized by a proprotein convertase. In some embodiments, the insulin therapeutic peptide comprises from amino to carboxyl terminus: the amino acid sequence derived from insulin B chain, the connecting peptide, and the amino acid sequence derived from insulin A chain. In some embodiments, the insulin therapeutic peptide comprises from amino to carboxyl terminus: the amino acid sequence derived from insulin A chain, the connecting peptide, and the amino acid sequence derived from insulin B chain.

In some embodiments, the insulin therapeutic peptide comprises an amino acid sequence that is about or at least about 80%, 85%, 90%, 95%, or 100% identical to an amino acid sequence of SEQ ID NOS: 109-140, 157, 158, 160, 161.

In some embodiments, the immunoglobulin fusion protein comprises a first chain comprising a first amino acid sequence of the insulin therapeutic peptide; and a second chain comprising a second amino acid sequence of the insulin therapeutic peptide linked to the first immunoglobulin region. In some embodiments, the first amino acid sequence of the insulin therapeutic peptide comprises an amino acid sequence derived from insulin B chain and the second amino acid sequence of the insulin therapeutic peptide comprises an amino acid sequence derived from insulin A chain. In some embodiments, the first amino acid sequence of the insulin therapeutic peptide comprises an amino acid sequence derived from insulin A chain and the second amino acid sequence of the insulin therapeutic peptide comprises an amino acid sequence derived from insulin B chain. In some implementations, the first amino acid sequence of the insulin therapeutic peptide is connected to the second amino acid sequence of the insulin therapeutic peptide. In some cases, the connection is via one or more disulfide bonds.

In some embodiments, the insulin therapeutic peptide comprises an amino acid sequence that is about or at least about 80%, 85%, 90%, 95%, or 100% identical to an amino acid sequence of SEQ ID NOS: 109-140, 157, 158, 160, 161.

In another aspect of the disclosure, provided herein are insulin immunoglobulin fusion proteins comprising an insulin therapeutic peptide; and a first immunoglobulin region comprising an amino acid sequence of an antigen binding domain; wherein the insulin therapeutic peptide, or an amino acid sequence of a region thereof, is connected to the amino terminus or carboxyl terminus of the first immunoglobulin region; and wherein the insulin immunoglobulin fusion protein is configured to bind to the antigen via the amino acid sequence of the antigen binding domain. In some embodiments, the insulin immunoglobulin fusion protein binds to the antigen with an affinity that is at least about 50%, 60%, 70%, 80%, 90%, or 95% of an affinity of the antigen binding domain within a native immunoglobulin. In some embodiments, an activity of the insulin therapeutic peptide in the insulin immunoglobulin fusion protein is comparable to an activity of a reference insulin therapeutic peptide. In some embodiments, the activity of the insulin therapeutic peptide in the insulin immunoglobulin fusion protein is at least about 50%, 60%, 70%, 80%, 90%, or 95% of the activity of the reference insulin therapeutic peptide. In some cases, the reference insulin therapeutic peptide comprises an amino acid sequence that is about or at least about 80%, 85%, 90%, 95%, or 100% identical to an amino acid sequence of any one of SEQ ID NOS: 109-140, 157, 158, 160, 161, or a combination thereof.

In some embodiments, the antigen binding domain is configured to bind to an antigen expressed by a hepatocyte. In some embodiments, the antigen is asialoglycoprotein receptor (ASGPR). In some embodiments, the first immunoglobulin region comprises an amino acid sequence that is about or at least about 80%, 85%, 90%, 95% or 100% identical to an amino acid sequence derived from an anti-ASGPR antibody. In some embodiments, the first immunoglobulin region comprises an amino acid sequence that is about or at least about 80%, 85%, 90%, 95% or 100% identical to an amino acid sequence of any one of SEQ ID NOS: 29, 30, 33-56, 167, or a combination thereof.

In some embodiments, the amino acid sequence of the antigen binding domain comprises an amino acid sequence of a variable region derived from a variable light chain, a variable heavy chain, or both a variable light chain and a variable heavy chain. In some embodiments, the insulin immunoglobulin fusion protein further comprises a second immunoglobulin region comprising a second amino acid sequence of the antigen binding domain. In some cases, the second amino acid sequence of the antigen binding domain comprises an amino acid sequence of a variable region derived from a variable light chain, a variable heavy chain, or both a variable light chain and a variable heavy chain.

In some embodiments, the insulin therapeutic peptide, or an amino acid sequence thereof, is linked to the amino terminus of the first immunoglobulin region. In some embodiments, the insulin therapeutic peptide, or an amino acid sequence thereof, is linked to the first immunoglobulin region by a linker. In some embodiments, the linker comprises an amino acid sequence. In some cases, the linker comprises from about 3 to about 40 amino acids. In some cases, the linker comprises one or more glycine residues; and wherein the one or more glycine residues make up at least about 30%, 40% or 50% of the linker amino acid sequence. In some cases, the linker comprises a protease cleavage site. In some cases, the protease cleavage site is located at the amino terminus, carboxyl terminus, or within the linker peptide amino acid sequence. In some cases, the protease cleavage site is recognized by a proprotein convertase.

In some embodiments, the insulin therapeutic peptide comprises an amino acid sequence derived from insulin B chain, an amino acid sequence derived from insulin A chain, or a combination thereof. In some embodiments, the insulin B chain comprises an amino acid sequence that is about or at least about 80%, 85%, 90%, 95% or 100% identical to human insulin B chain. In some embodiments, the insulin A chain comprises an amino acid sequence that is about or at least about 80%, 85%, 90%, 95% or 100% identical to human insulin A chain. In some embodiments, the insulin therapeutic peptide comprises an amino acid sequence derived from insulin B chain and an amino acid sequence derived from insulin A chain. In some embodiments, the amino acid sequence derived from insulin B chain is connected to the amino acid sequence derived from insulin A chain. In some embodiments, the connection is via a connecting peptide. In some cases, the connecting peptide comprises from about 3 to about 25 amino acids. In some cases, the connecting peptide comprises one or more glycine residues, and wherein the one or more glycine residues make up at least about 30%, 40%, or 50% of the connecting peptide amino acid sequence. In some cases, the connecting peptide comprises a protease cleavage site. In some cases, the protease cleavage site of the connecting peptide is located at the amino terminus, carboxyl terminus, or within the connecting peptide amino acid sequence. In some instances, the protease cleavage site of the connecting peptide is recognized by a proprotein convertase.

In some embodiments, the insulin therapeutic peptide comprises an amino acid sequence that is about or at least about 80%, 85%, 90%, 95%, or 100% identical to an amino acid sequence of SEQ ID NOS: 109-140, 157, 158, 160, 161.

In some embodiments, the insulin therapeutic peptide comprises from amino to carboxyl terminus: the amino acid sequence derived from insulin B chain, the connecting peptide, and the amino acid sequence derived from insulin A chain. In some embodiments, the insulin therapeutic peptide comprises from amino to carboxyl terminus: the amino acid sequence derived from insulin A chain, the connecting peptide, and the amino acid sequence derived from insulin B chain.

In some embodiments, the immunoglobulin fusion protein comprises: a first chain comprising a first amino acid sequence of the insulin therapeutic peptide; and a second chain comprising a second amino acid sequence of the insulin therapeutic peptide linked to the first immunoglobulin region. In some embodiments, the first amino acid sequence of the insulin therapeutic peptide comprises an amino acid sequence derived from insulin B chain and the second amino acid sequence of the insulin therapeutic peptide comprises an amino acid sequence derived from insulin A chain. In some embodiments, the first amino acid sequence of the insulin therapeutic peptide comprises an amino acid sequence derived from insulin A chain and the second amino acid sequence of the insulin therapeutic peptide comprises an amino acid sequence derived from insulin B chain. In some cases, the first amino acid sequence of the insulin therapeutic peptide is connected to the second amino acid sequence of the insulin therapeutic peptide. In some cases, the connection is via one or more disulfide bonds.

In some embodiments, the insulin therapeutic peptide comprises an amino acid sequence that is about or at least about 80%, 85%, 90%, 95%, or 100% identical to an amino acid sequence of SEQ ID NOS: 109-140, 157, 158, 160, 161.

In another aspect of the disclosure, provided are pharmaceutical compositions comprising any of the insulin immunoglobulin fusion proteins described herein. Further provided herein, in various embodiments, are methods of treating a disease or condition in a subject in need thereof, comprising administering to the subject a therapeutically effective amount of an insulin immunoglobulin fusion protein described herein. In some cases, the disease is diabetes. In some cases, the disease is obesity.

In another aspect of the disclosure, provided is a first genetic construct comprising a nucleic acid sequence encoding an amino acid sequence of any one of the insulin immunoglobulin fusion proteins described herein. In various embodiments, provided herein is a first expression vector comprising the first genetic construct. In various embodiments, provided herein is a mammalian expression host comprising the first expression vector. In some cases, the mammalian expression host further comprises one or more additional expression vectors. In some instances, one of the one of more additional expression vectors comprises a second genetic construct comprising a nucleic acid sequence encoding an amino acid sequence of an additional immunoglobulin domain. In some instances, one of the one or more additional expression vectors comprises a third genetic construct comprising a nucleic acid sequence encoding an amino acid sequence of a protease. In some embodiments, the first expression vector further comprises a genetic construct comprising a nucleic acid sequence encoding an amino acid sequence of an additional immunoglobulin domain. In some embodiments, the first expression vector further comprises a genetic construct comprising a nucleic acid sequence encoding an amino acid sequence of a protease.

Further provided herein, in various embodiments, is a method of producing an immunoglobulin fusion protein comprising transfecting the first expression vector transiently in a mammalian cell culture; growing the cell culture in an expression medium at a controlled temperature and percentage $CO_2$; and harvesting the secreted immunoglobulin fusion protein. In some instances, the method further comprises co-transfecting one or more additional expression vectors. In some cases, one of the one of more additional expression vectors comprises a second genetic construct comprising a nucleic acid sequence encoding an amino acid sequence of an additional immunoglobulin domain. In some cases, one of the one or more additional expression vectors comprises a third genetic construct comprising a nucleic acid sequence encoding an amino acid sequence of a protease. In some embodiments, the method further comprises purifying the harvested immunoglobulin fusion protein.

BRIEF DESCRIPTION OF THE DRAWINGS

The foregoing summary, as well as the following detailed description of the disclosure, will be better understood when read in conjunction with the appended figures. It should be understood, however, that the disclosure is not limited to the precise examples shown. It is emphasized that, according to common practice, the various features of the drawings are not to-scale. On the contrary, the dimensions of the various features are arbitrarily expanded or reduced for clarity. Included in the drawings are the following figures.

FIG. 47 shows an alignment of human (SEQ ID NO: 162), cynomolgus monkey (SEQ ID NO: 163), rat (SEQ ID NO: 164) and mouse (SEQ ID NO: 165) ASGPR.

DETAILED DESCRIPTION OF THE INVENTION

Figure 1A:
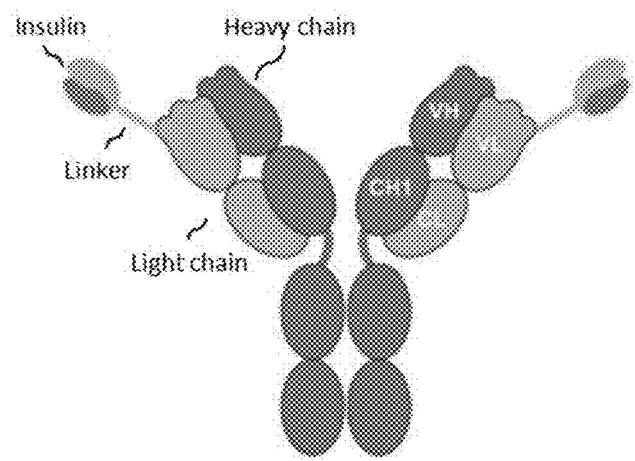
FIG. 1A depicts a schematic of an insulin immunoglobulin fusion protein comprising: an immunoglobulin heavy chain having a variable domain (VH) and constant region (CH1), and an insulin therapeutic peptide connected to the amino terminus of an immunoglobulin light chain having a variable domain (VL) and a constant region (CH1).

In one aspect of the disclosure, provided herein are insulin immunoglobulin fusion proteins comprising an insulin therapeutic peptide connected to an immunoglobulin or portion thereof. The insulin immunoglobulin fusion proteins may be useful for the treatment of various diseases and conditions associated with insulin and glucose metabolism, such as diabetes. In various embodiments, the immunoglobulin portion of the fusion protein comprises or is part of an antigen binding domain that targets the fusion protein to the liver by binding to an antigen expressed or displayed by a hepatocyte. An exemplary antigen is asialoglycoprotein receptor (ASGPR).

According to one feature of the subject matter described herein, an insulin immunoglobulin fusion protein comprises a first immunoglobulin region and an insulin therapeutic peptide; wherein the insulin therapeutic peptide, or an amino acid sequence of a region thereof, is connected to the amino terminus of the immunoglobulin region. In another feature of the subject matter described herein, an insulin immunoglobulin fusion protein comprises a first immunoglobulin region; and an insulin therapeutic peptide; wherein the insulin therapeutic peptide, or an amino acid sequence of a region thereof, is connected to the carboxyl terminus of the immunoglobulin region. The insulin therapeutic peptide, or an amino acid sequence thereof, may be connected to the immunoglobulin region with a linker. The first immunoglobulin region may comprise a single immunoglobulin domain or portion thereof, for example, a light chain domain, heavy chain domain, or a combination thereof. In some embodiments, the insulin therapeutic peptide comprises a first amino acid sequence connected to a second amino acid sequence. In some cases, the connection is through a chemical bond. In some cases, the connection is through a disulfide bond. In some cases, the connection is through a connecting peptide. In some embodiments, the immunoglobulin fusion protein further comprises one or more protease cleavage sites. In some cases, wherein the insulin immunoglobulin fusion protein comprises a linker, the linker comprises a protease cleavage site. In some cases, wherein the insulin immunoglobulin fusion protein comprises a connecting peptide, the connecting peptide comprises a protease cleavage site.

The insulin therapeutic peptides of the insulin immunoglobulin fusion proteins described herein may include an amino acid sequence from insulin B chain, insulin A chain, or a combination thereof. In some embodiments, the insulin is B chain, insulin A chain, or both chains comprise amino acid sequences derived from human insulin. In some embodiments, the insulin is B chain, insulin A chain, or both chains comprise amino acid sequences derived from non-human insulin. As a non-limiting example, porcine insulin. In some embodiments, the insulin is B chain, insulin A chain, or both chains comprise amino acid sequences derived from an insulin analog.

In some embodiments, an insulin therapeutic peptide of an insulin immunoglobulin fusion protein comprises a single chain amino acid sequence. The single chain amino acid sequence may comprise an amino acid sequence from insulin B chain, insulin A chain, or a combination thereof. In some cases, the single chain amino acid sequence of an insulin therapeutic peptide comprises an amino acid sequence from insulin B chain connected to an amino acid sequence from insulin A chain by a connecting peptide.

In some embodiments, an insulin therapeutic peptide of an insulin immunoglobulin fusion protein comprises a first chain comprising a first amino acid sequence of the therapeutic peptide and a second chain comprising a second amino acid sequence of the therapeutic peptide. In some cases, the first amino acid sequence of the insulin therapeutic protein is connected to the first immunoglobulin region. In some cases, the second amino acid sequence of the therapeutic protein is connected to the first immunoglobulin region. In some embodiments, the first chain and the second chain are connected. As a non-limiting example, the first chain and the second chain are connected by one or more disulfide bonds. The first chain amino acid sequence may comprise an amino acid sequence from insulin B chain, insulin A chain, or a combination thereof. In some cases, the first chain amino acid sequence of an insulin therapeutic peptide comprises an amino acid sequence from insulin B chain and the second chain amino acid sequence comprises an amino acid sequence from insulin A chain. In some cases, the first chain amino acid sequence of an insulin therapeutic peptide comprises an amino acid sequence from insulin A chain and the second chain amino acid sequence comprises an amino acid sequence from insulin B chain.

Exemplary embodiments of insulin immunoglobulin fusion proteins are depicted in Formulas I-XVI, wherein T is an insulin therapeutic peptide or a portion of a therapeutic peptide, L is a linker, and A is an immunoglobulin region. The therapeutic peptide, linker, connecting peptide, or any combination thereof, may comprise a protease cleavage site. The amino acids that are not connected by peptide bonds, e.g., are separate chains, are separated by a semicolon. In some embodiments, one or more of the separate chains are linked by a non-covalent bond. As a non-limiting example, one or more separate chains are linked by one or more disulfide bonds.

| Formula | Immunoglobulin fusion protein |
|---|---|
| I | $T^1$-$A^1$ |
| II | $T^1$-$A^1$; $A^2$ |
| III | $T^1$-$A^1$; $T^2$ |
| IV | $T^1$-$A^1$; $T^2$; $A^2$ |
| V | $T^1$-L-$A^1$ |
| VI | $T^1$-L-$A^1$; $A^2$ |
| VII | $T^1$-L-$A^1$; $T^2$ |
| VIII | $T^1$-L-$A^1$; $T^2$; $A^2$ |
| IX | $A^1$-$T^1$ |
| X | $A^1$-$T^1$; $A^2$ |
| XI | $A^1$-$T^1$; $T^2$ |
| XII | $A^1$-$T^1$; $T^2$; $A^2$ |
| XIII | $A^1$-L-$T^1$ |
| XIV | $A^1$-L-$T^1$; $A^2$ |
| XV | $A^1$-L-$T^1$; $T^2$ |
| XVI | $A^1$-L-$T^1$; $T^2$; $A^2$ |

The insulin therapeutic peptide, $T^n$ (n=1 or 2), represents a therapeutic peptide comprising one or more amino acid sequences derived from an insulin peptide. The insulin therapeutic peptide, $T^n$, may further comprise one or more connecting peptides. In some embodiments, $T^n$ comprises a first amino acid sequence derived from an insulin peptide, a connecting peptide, and a second amino acid sequence derived from an insulin peptide. For example, the first amino acid sequence is derived from an insulin B chain amino acid sequence and the second amino acid sequence is derived from an insulin A chain amino acid sequence, or vice versa. In some embodiments, $T^n$ comprises a first amino acid sequence derived from an insulin peptide and a connecting peptide. In some embodiments, $T^n$ comprises an amino acid derived from an insulin B chain amino acid sequence. In some embodiments, $T^n$ comprises an amino acid derived from an insulin A chain amino acid sequence. In some cases, $T^1$ comprises an amino acid sequence derived from an insulin B chain amino acid sequence and $T^2$ comprises an amino acid sequence derived from an insulin A chain amino acid sequence, wherein either $T^1$, $T^2$ or both $T^1$ and $T^2$ further comprise one or more connecting peptides. In some cases, $T^1$ comprises an amino acid sequence derived from an insulin A chain amino acid sequence and $T^2$ comprises an amino acid sequence derived from an insulin B chain amino acid sequence, wherein either $T^1$, $T^2$ or both $T^1$ and $T^2$ further comprise one or more connecting peptides. In some embodiments, the connecting peptide comprises a protease cleavage site.

The immunoglobulin region, $A^n$ (n=1 or 2), represents a first immunoglobulin region, $A^1$ and a second immunoglobulin region, $A^2$. In some embodiments, $A^1$ comprises an amino acid sequence of an immunoglobulin light chain. In some embodiments, $A^2$ comprises an amino acid sequence of an immunoglobulin light chain. In some embodiments, $A^1$ comprises an amino acid sequence of an immunoglobulin heavy chain. In some embodiments, $A^2$ comprises an amino acid sequence of an immunoglobulin heavy chain. In some embodiments, for insulin fusion proteins comprising $A^1$ and $A^2$, the two immunoglobulin regions are connected. In some cases, the two regions are connected by one or more disulfide bonds. An amino acid sequence of $A^1$ may comprise an amino acid sequence derived from an anti-ASGPR antibody. An amino acid sequence of $A^2$ may comprise an amino acid sequence derived from an anti-ASGPR antibody.

In another aspect of the disclosure, provided herein are pharmaceutical compositions comprising an immunoglobulin fusion protein disclosed herein. In some embodiments, the pharmaceutical composition further comprises a pharmaceutically acceptable excipient.

Further disclosed herein, in various aspects, are methods of treating a disease or condition in a subject in need thereof. Generally, the method comprises administering to the subject an insulin immunoglobulin fusion protein comprising an insulin therapeutic peptide. In some cases, the disease is diabetes and/or a complication thereof. In some embodiments, an insulin immunoglobulin fusion protein having the formula of I, II, III, IV, V, VI, VII, VIII, IX, X, XI, XII, XIII, XIV, XV, XVI, or any modification, portions, or additions thereof is administered to the subject.

Further disclosed herein, in various aspects, are methods of improving the delivery of an insulin therapeutic peptide. The methods may involve generation of an insulin immunoglobulin fusion protein from a genetic construct. In some embodiments, the insulin immunoglobulin fusion protein is recombinantly produced from a genetic construct encoding the insulin immunoglobulin fusion protein. In some embodiments, the construct is expressed in vitro using standard mammalian cell culture techniques. In some embodiments, one construct encoding an insulin therapeutic peptide connected to the amino or carbosyl terminus of a first immunoglobulin region is co-expressed with a second construct comprising a second immunoglobulin region, to produce a recombinant insulin immunoglobulin fusion protein. In some embodiments, a construct encoding a protease is co-expressed with an immunoglobulin fusion protein. The method may further comprise generating immunoglobulin genetic fusion constructs comprising a linker, connecting peptide, proteolytic cleavage site, or a combination thereof.

Before the present methods and compositions are described, it is to be understood that this disclosure is not limited to a particular method or composition described, and as such may vary. It is also to be understood that the terminology used herein is for the purpose of describing particular embodiments only, and is not intended to be limiting. Examples are put forth so as to provide those of ordinary skill in the art with a disclosure and description of how to make and use the immunoglobulin fusion proteins provided herein, and are not intended to limit the scope of what the inventors regard as their invention nor are they intended to represent that the provided experiments encompass all of the experiments performed. Efforts have been made to ensure accuracy with respect to numbers used but some experimental errors and deviations should be accounted for.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. Any recited combination of amino acid sequences can have the order recited, or any other order which is logically possible. As a non-limiting example, an immunoglobulin fusion protein comprising an insulin therapeutic peptide, T, and an immunoglobulin region, A, includes, for example and without limitation: T-A, A-T, T-A-T, and A-T-A.

It must be noted that as used herein and in the appended claims, the singular forms “a”, “an”, and “the” include plural referents unless the context clearly dictates otherwise. Thus, for example, reference to “a cell” includes a plurality of such cells and reference to “the peptide” includes reference to one or more peptides and equivalents thereof, e.g. polypeptides, known to those skilled in the art, and so forth.

The terms “homologous,” “homology,” or “percent homology” when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

Insulin Immunoglobulin Fusion Proteins

Various insulin immunoglobulin fusion proteins disclosed herein comprise a first immunoglobulin region and an insulin therapeutic peptide, wherein the insulin therapeutic peptide, or an amino acid sequence thereof, is connected to an amino or carboxyl terminus of the first immunoglobulin region. In various instances, the insulin immunoglobulin fusion proteins further comprise a second immunoglobulin region. The immunoglobulin region (first and/or second) may be any portion, in part or whole, of an immunoglobulin.

The immunoglobulin region may comprise an entire immunoglobulin molecule or any polypeptide comprising a fragment of an immunoglobulin including, but not limited to, heavy chain, light chain, variable domain, constant domain, complementarity determining region (CDR), framework region, fragment antigen binding (Fab) region, Fab', F(ab')2, F(ab')3, Fab', fragment crystallizable (Fc) region, single chain variable fragment (scFV), di-scFv, single domain immunoglobulin, trifunctional immunoglobulin, chemically linked F(ab')2, and any portion or combination thereof. In some embodiments, an immunoglobulin heavy chain may comprise an entire heavy chain or a portion of a heavy chain. For example, a variable domain or region thereof derived from a heavy chain may be referred to as a heavy chain or a region of a heavy chain. In some embodiments, an immunoglobulin light chain may comprise an entire light chain or a portion of a light chain. For example, a variable domain or region thereof derived from a light chain may be referred to as a light chain or a region of a light chain. The immunoglobulin region may be bispecific or trispecific. A single domain immunoglobulin includes, but is not limited to, a single monomeric variable immunoglobulin domain. The single domain immunoglobulin may be a shark variable new antigen receptor immunoglobulin fragment (VNAR). The immunoglobulin may be derived from any type known to one of skill in the art including, but not limited to, IgA, IgD, IgE, IgG, IgM, IgY, IgW. The immunoglobulin region may be a glycoprotein. The immunoglobulin region may comprise one or more functional units, including but not limited to, 1, 2, 3, 4, and 5 units. The immunoglobulin region may comprise one or more units connected by one or more disulfide bonds. The immunoglobulin region may comprise one or more units connected by a peptide linker, for example, a scFv immunoglobulin. The immunoglobulin may be a recombinant immunoglobulin including immunoglobulins with amino acid mutations, substitutions, and/or deletions. The immunoglobulin may be a recombinant immunoglobulin comprising chemical modifications. The immunoglobulin may comprise a whole or part of an immunoglobulin-drug conjugate. The immunoglobulin may comprise a small molecule. The immunoglobulin may comprise a whole or part of an immunoglobulin-drug conjugate comprising a small molecule. The immunoglobulin may be from a mammalian source. The immunoglobulin may be a chimeric immunoglobulin. The immunoglobulin region may be derived in whole or in part from an engineered immunoglobulin or recombinant immunoglobulin. The immunoglobulin may be from a humanized, human engineered or fully human immunoglobulin. The mammalian immunoglobulin may be a bovine immunoglobulin. The mammalian immunoglobulin may be a human immunoglobulin. The mammalian immunoglobulin may be a murine immunoglobulin. The mammalian immunoglobulin may be a non-human primate immunoglobulin. The immunoglobulin may be an avian immunoglobulin. The immunoglobulin may be a shark immunoglobulin.

Fusion proteins described herein may be modified by any means known in the art and can thus deviate from the embodiments described. As a non-limiting example, reference to immunoglobulin region is not limited to an antibody and includes any molecule which may bind to an antigen.

Figure 1B:
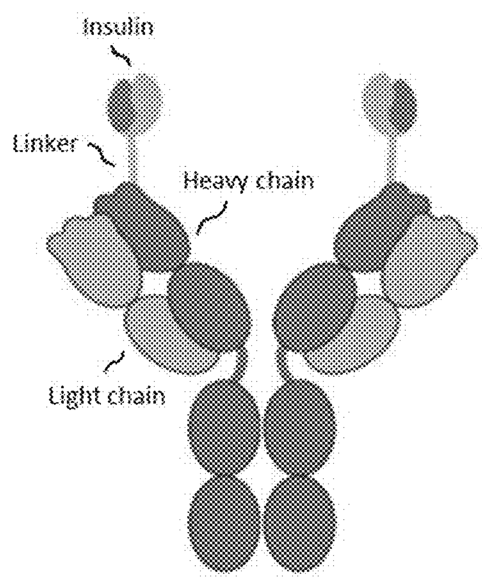
FIG. 1B depicts a schematic of an insulin immunoglobulin fusion protein comprising: an immunoglobulin light chain, and an insulin therapeutic peptide connected to the amino terminus of an immunoglobulin heavy chain.

In one aspect of the disclosure, provided are insulin immunoglobulin fusion proteins comprising an insulin therapeutic peptide and a first immunoglobulin region comprising one or more portions of an antigen binding domain, wherein the antigen binding domain has specificity for an antigen of a liver cell. An exemplary schematic showing a light chain fusion and a heavy chain fusion is shown in FIGS. 1A and 1B, respectively. The antigen targeted by the antigen binding domain may be expressed by a hepatocyte. As a non-limiting example, the antigen is asialoglycoprotein receptor (ASGPR). The antigen binding domain may bind to an epitope of an ASGPR having a sequence selected from SEQ ID NOS: 162-165. The antigen binding domain may be specific for human ASGPR over mouse ASGPR. Non-limiting examples of epitopes are shown in the sequence alignment of FIG. 47. For instance, the antigen binding domain may bind to a one or more amino acids of an epitope of human ASGPR having SEQ ID NO: 162, wherein the one or more amino acids is selected from R10, G11, F19, G35, N36, Q47, S56, L83, W134, E135, K138, V140, H142, and K173. In some cases, the one or more amino acids of the epitope comprises any combination of W134, E135, K138, V140, H142, and K173.

The immunoglobulin fusion protein may comprise an amino acid sequence that is based on or derived from any one of SEQ ID NOS: 78-98. The immunoglobulin fusion protein may comprise an amino acid sequence that is at least about 50% homologous to any one of SEQ ID NOS: 78-98. The immunoglobulin fusion protein may comprise an amino acid sequence that is at least about 60%, 65%, 70%, 75%, 80%, 85%, 90%, 95%, or 97% homologous to any one of SEQ ID NOS: 78-98. The immunoglobulin fusion protein may comprise an amino acid sequence that is at least about 70% homologous to any one of SEQ ID NOS: 78-98. The immunoglobulin fusion protein may comprise an amino acid sequence that is at least about 80% homologous to any one of SEQ ID NOS: 78-98. The immunoglobulin fusion protein may comprise an amino acid sequence that is at least about 50% identical to any one of SEQ ID NOS: 78-98. The immunoglobulin fusion protein may comprise an amino acid sequence that is at least about 60%, 65%, 70%, 75%, 80%, 85%, 90%, 95%, or 97% identical to any one of SEQ ID NOs 78-98. The immunoglobulin fusion protein may comprise an amino acid sequence that is at least about 70% identical to any one of SEQ ID NOS: 78-98. The immunoglobulin fusion protein may comprise an amino acid sequence that is at least about 80% identical to any one of SEQ ID NOS: 78-98. The immunoglobulin fusion protein may comprise an amino acid sequence that is 100% identical to any one of SEQ ID NOS: 78-98. In some embodiments, the immunoglobulin fusion protein comprises an amino acid sequence that is at least about 50%, 55%, 60%, 65%, 70%, 75%, 80%, 85%, 90%, 95%, or 97% homologous to an amino acid sequence of any one of SEQ ID NOS: 78-98. In some embodiments, the immunoglobulin fusion protein comprises an amino acid sequence that is at least about 50%, 55%, 60%, 65%, 70%, 75%, 80%, 85%, 90%, 95%, or 97% identical to an amino acid sequence of any one of SEQ ID NOS: 78-98.

The immunoglobulin fusion protein may comprise an amino acid sequence comprising 10, 20, 30, 40, 50, 60, 70, 80, 90, 100 or more amino acids based on or derived from any one of SEQ ID NOS: 78-98. The immunoglobulin fusion protein may comprise an amino acid sequence comprising 125, 150, 175, 200, 225, 250 or more amino acids based on or derived from any one of SEQ ID NOS: 78-98. The immunoglobulin fusion protein may comprise an amino acid sequence comprising 10 or more amino acids based on or derived from any one of SEQ ID NOS: 78-98. The immunoglobulin fusion protein may comprise an amino acid sequence comprising 50 or more amino acids based on or derived from any one of SEQ ID NOS: 78-98. The immunoglobulin fusion protein may comprise an amino acid sequence comprising 100 or more amino acids based on or derived from any one of SEQ ID NOS: 78-98. The immunoglobulin fusion protein may comprise an amino acid sequence comprising 200 or more amino acids based on or derived from any one of SEQ ID NOS: 78-98. The amino acids may be consecutive. Alternatively, or additionally, the amino acids are nonconsecutive. In some embodiments, the immunoglobulin fusion protein comprises amino acids derived from 1, 2, 3, 4, 5, 6, 7, 8, 9, 10 or more of SEQ ID NOS: 78-98.

The immunoglobulin fusion protein may be encoded by a nucleic acid sequence that is based on or derived from any one of SEQ ID NOS: 57-77. The immunoglobulin fusion protein may be encoded by a nucleic acid sequence that is at least about 50% homologous to any one of SEQ ID NOS: 57-77. The immunoglobulin fusion protein may be encoded by a nucleic acid sequence that is at least about 60%, 65%, 70%, 75%, 80%, 85%, 90%, 95%, or 97% homologous to any one of SEQ ID NOS: 57-77. The immunoglobulin fusion protein may be encoded by a nucleic acid sequence that is at least about 70% homologous to any one of SEQ ID NOS: 57-77. The immunoglobulin fusion protein may be encoded by a nucleic acid sequence that is at least about 80% homologous to any one of SEQ ID NOS: 57-77. The immunoglobulin fusion protein may be encoded by a nucleic acid sequence that is at least about 50% identical to any one of SEQ ID NOS: 57-77. The immunoglobulin fusion protein may be encoded by a nucleic acid sequence that is at least about 60%, 65%, 70%, 75%, 80%, 85%, 90%, 95%, or 97% identical to any one of SEQ ID NOS: 57-77. The immunoglobulin fusion protein may be encoded by a nucleic acid sequence that is at least about 70% identical to any one of SEQ ID NOS: 57-77. The immunoglobulin fusion protein may be encoded by a nucleic acid sequence that is at least about 80% identical to any one of SEQ ID NOS: 57-77. The immunoglobulin fusion protein may be encoded by a nucleic acid sequence that is 100% identical to any one of SEQ ID NOS: 57-77. In some embodiments, the immunoglobulin fusion protein is encoded by a nucleic acid sequence that is at least about 50%, 55%, 60%, 65%, 70%, 75%, 80%, 85%, 90%, 95%, or 97% homologous to an amino acid sequence of any one of SEQ ID NOS: 57-77. In some embodiments, the immunoglobulin fusion protein is encoded by a nucleic acid sequence that is at least about 50%, 55%, 60%, 65%, 70%, 75%, 80%, 85%, 90%, 95%, or 97% identical to an amino acid sequence of any one of SEQ ID NOS: 57-77.

The immunoglobulin fusion protein may be encoded by a nucleic acid sequence comprising 10, 20, 30, 40, 50, 60, 70, 80, 90, 100 or more nucleotides based on or derived from any one of SEQ ID NOS: 57-77. The immunoglobulin fusion protein may be encoded by a nucleic acid sequence comprising 125, 150, 175, 200, 225, 250, 275, 300, 325, 350, 375, 400, 425, 450, 475, 450, 500 or more nucleotides based on or derived from any one of SEQ ID NOS: 57-77. The immunoglobulin fusion protein may be encoded by a nucleic acid sequence comprising 100 or more nucleotides based on or derived from any one of SEQ ID NOS: 57-77. The immunoglobulin fusion protein may be encoded by a nucleic acid sequence comprising 500 or more nucleotides based on or derived from any one of SEQ ID NOS: 57-77. The nucleotides may be consecutive. Alternatively, or additionally, the nucleotides are nonconsecutive. In some embodiments, the immunoglobulin fusion protein is encoded by a nucleic acid sequence derived from 1, 2, 3, 4, 5, 6, 7, 8, 9, 10 or more of SEQ ID NOS: 57-77.

Further disclosed herein are nucleotide constructs comprising a nucleic acid sequence that is based on or derived from any one of SEQ ID NOS: 57-77. The nucleotide construct may be a plasmid for expression in a host cell. For example, a mammalian or bacterial expression plasmid. In some embodiments, the construct comprises a nucleic acid sequence that is at least about 50% homologous to any one of SEQ ID NOS: 57-77. In some embodiments, the construct comprises a nucleic acid sequence that is at least about 60%, 65%, 70%, 75%, 80%, 85%, 90%, 95%, or 97% homologous to any one of SEQ ID NOS: 57-77. In some embodiments, the construct comprises a nucleic acid sequence that is at least about 70% homologous to any one of SEQ ID NOS: 57-77. In some embodiments, the construct comprises a nucleic acid sequence that is at least about 80% homologous to any one of SEQ ID NOS: 57-77. In some embodiments, the construct comprises a nucleic acid sequence that is at least about 50% identical to any one of SEQ ID NOS: 57-77. In some embodiments, the construct comprises a nucleic acid sequence that is at least about 60%, 65%, 70%, 75%, 80%, 85%, 90%, 95%, or 97% identical to any one of SEQ ID NOS: 57-77. In some embodiments, the construct comprises a nucleic acid sequence that is at least about 70% identical to any one of SEQ ID NOS: 57-77. In some embodiments, the construct comprises a nucleic acid sequence that is at least about 80% identical to any one of SEQ ID NOS: 57-77. In some embodiments, the construct comprises a nucleic acid sequence that is 100% identical to any one of SEQ ID NOS: 57-77. In some embodiments, the construct comprises a nucleic acid sequence that is at least about 50%, 55%, 60%, 65%, 70%, 75%, 80%, 85%, 90%, 95%, or 97% homologous to an amino acid sequence of any one of SEQ ID NOS: 57-77. In some embodiments, the construct comprises a nucleic acid sequence that is at least about 50%, 55%, 60%, 65%, 70%, 75%, 80%, 85%, 90%, 95%, or 97% identical to an amino acid sequence of any one of SEQ ID NOS: 57-77.

Insulin Immunoglobulin Light Chain Fusions

In one feature of the disclosure, provided herein is an immunoglobulin fusion protein comprising an insulin therapeutic peptide comprising one or more regions connected to the amino or carboxyl terminus of a region of an immunoglobulin light chain, wherein the immunoglobulin fusion is referred to herein as an immunoglobulin light chain fusion. In some embodiments, the immunoglobulin fusion protein further comprises one or more regions of an immunoglobulin heavy chain. In some cases, the immunoglobulin light chain fusion is connected to the one or more regions of an immunoglobulin heavy chain by disulfide bonds or a linker. In some embodiments, the insulin therapeutic peptide comprises one or more regions of a therapeutic peptide. In some embodiments, the insulin therapeutic peptide comprises two regions of a therapeutic peptide connected by a connecting peptide. In some embodiments, the therapeutic peptide comprises a protease cleavage site. In some embodiments, the connecting peptide comprises a protease cleavage site.

In some embodiments, the immunoglobulin light chain fusion comprises an amino acid sequence comprising or derived from an amino acid sequence of an anti-ASGPR antibody. In some embodiments, the heavy chain comprises an amino acid sequence comprising or derived from an amino acid sequence of an anti-ASGPR antibody.

In one aspect of the disclosure, provided are light chain insulin immunoglobulin fusion proteins comprising an insulin therapeutic peptide and a first immunoglobulin region comprising one or more portions of an antigen binding domain, wherein the antigen binding domain has specificity for an antigen of a liver cell. The antigen targeted by the antigen binding domain may be expressed by a hepatocyte. As a non-limiting example, the antigen is asialoglycoprotein receptor (ASGPR). The first immunoglobulin region may comprise a CDR having an amino acid sequence that differs from one or more of SEQ ID NOS: 48-50 by no more than 5, 4, 3, 2 or 1 amino acids. The first immunoglobulin region may comprise a first CDR having an amino acid sequence that differs from SEQ ID NO: 48 by no more than 5, 4, 3, 2 or 1 amino acids. The first immunoglobulin region may comprise a second CDR having an amino acid sequence that differs from SEQ ID NO: 49 by no more than 5, 4, 3, 2 or 1 amino acids. The first immunoglobulin region may comprise a third CDR having an amino acid sequence that differs from SEQ ID NO: 50 by no more than 5, 4, 3, 2 or 1 amino acids. The first immunoglobulin region may comprise a variable region having an amino acid sequence at least about 75%, 80%, 85%, 90%, or 95% identical to an amino acid sequence selected from SEQ ID NO: 41 and SEQ: 44. The first immunoglobulin region may comprise a variable region having an amino acid sequence at least about 75%, 80%, 85%, 90%, or 95% homologous to an amino acid sequence selected from SEQ ID NO: 41 and SEQ: 44. The first immunoglobulin region may comprise an amino acid sequence at least about 75%, 80%, 85%, 90%, or 95% identical to an amino acid sequence selected from SEQ ID NOS: 30, 33, 35, 41, 42, and 44. The first immunoglobulin region may comprise an amino acid sequence at least about 75%, 80%, 85%, 90%, or 95% homologous to an amino acid sequence selected from SEQ ID NOS: 30, 33, 35, 41, 42, and 44. The insulin immunoglobulin fusion protein may further comprise a second immunoglobulin region. The second immunoglobulin region may comprise one or more portions of the antigen binding domain. The second immunoglobulin region may comprise a CDR having an amino acid sequence that differs from one or more of SEQ ID NOS: 45-47 and 55 by no more than 5, 4, 3, 2 or 1 amino acids. The second immunoglobulin region may comprise a first CDR having an amino acid sequence that differs from SEQ ID NO: 45 by no more than 5, 4, 3, 2 or 1 amino acids. The second immunoglobulin region may comprise a second CDR having an amino acid sequence that differs from SEQ ID NO: 46 by no more than 5, 4, 3, 2 or 1 amino acids. The second immunoglobulin region may comprise a second CDR having an amino acid sequence that differs from SEQ ID NO: 55 by no more than 5, 4, 3, 2 or 1 amino acids. The second immunoglobulin region may comprise a third CDR having an amino acid sequence that differs from SEQ ID NO: 47 by no more than 5, 4, 3, 2 or 1 amino acids. The second immunoglobulin region may comprise a variable region having an amino acid sequence at least about 75%, 80%, 85%, 90%, or 95% identical to an amino acid sequence selected from SEQ ID NO: 39 and SEQ: 43. The second immunoglobulin region may comprise a variable region having an amino acid sequence at least about 75%, 80%, 85%, 90%, or 95%, 80%, 85%, 90%, or 95% homologous to an amino acid sequence selected from SEQ ID NO: 39 and SEQ: 43. The second immunoglobulin region may comprise an amino acid sequence at least about 75%, 80%, 85%, 90%, or 95% identical to an amino acid sequence selected from SEQ ID NOS: 29, 34, 36-40 and 43. The second immunoglobulin region may comprise an amino acid sequence at least about 75%, 80%, 85%, 90%, or 95%, 80%, 85%, 90%, or 95% homologous to an amino acid sequence selected from SEQ ID NOS: 29, 34, 36-40 and 43.

The immunoglobulin light chain fusion may comprise an amino acid sequence that is based on or derived from any one of SEQ ID NOS: 79-92, 94-98. The immunoglobulin light chain fusion may comprise an amino acid sequence that is at least about 50% homologous to any one of SEQ ID NOS: 79-92, 94-98. The immunoglobulin light chain fusion may comprise an amino acid sequence that is at least about 60%, 65%, 70%, 75%, 80%, 85%, 90%, 95%, or 97% homologous to any one of SEQ ID NOS: 79-92, 94-98. The immunoglobulin light chain fusion may comprise an amino acid sequence that is at least about 70% homologous to any one of SEQ ID NOS: 79-92, 94-98. The immunoglobulin light chain fusion may comprise an amino acid sequence that is at least about 80% homologous to any one of SEQ ID NOS: 79-92, 94-98. The immunoglobulin light chain fusion may comprise an amino acid sequence that is at least about 50% identical to any one of SEQ ID NOS: 79-92, 94-98. The immunoglobulin light chain fusion may comprise an amino acid sequence that is at least about 60%, 65%, 70%, 75%, 80%, 85%, 90%, 95%, or 97% identical to any one of SEQ ID NOS: 79-92, 94-98. The immunoglobulin light chain fusion may comprise an amino acid sequence that is at least about 70% identical to any one of SEQ ID NOS: 79-92, 94-98. The immunoglobulin light chain fusion may comprise an amino acid sequence that is at least about 80% identical to any one of SEQ ID NOS: 79-92, 94-98. The immunoglobulin light chain fusion may comprise an amino acid sequence that is 100% identical to any one of SEQ ID NOS: 79-92, 94-98. The immunoglobulin heavy chain may comprise an amino acid sequence that is based on or derived from any one of SEQ ID NOS: 79-92, 94-98. The immunoglobulin heavy chain may comprise an amino acid sequence that is at least about 50% homologous to any one of SEQ ID NOS: 79-92, 94-98. The immunoglobulin heavy chain may comprise an amino acid sequence that is at least about 60%, 65%, 70%, 75%, 80%, 85%, 90%, 95%, or 97% homologous to any one of SEQ ID NOS: 79-92, 94-98. The immunoglobulin heavy chain may comprise an amino acid sequence that is at least about 70% homologous to any one of SEQ ID NOS: 79-92, 94-98. The immunoglobulin heavy chain may comprise an amino acid sequence that is at least about 80% homologous to any one of SEQ ID NOS: 79-92, 94-98. The immunoglobulin heavy chain may comprise an amino acid sequence that is at least about 50% identical to any one of SEQ ID NOS: 79-92, 94-98. The immunoglobulin heavy chain may comprise an amino acid sequence that is at least about 60%, 65%, 70%, 75%, 80%, 85%, 90%, 95%, or 97% identical to any one of SEQ ID NOS: 79-92, 94-98. The immunoglobulin heavy chain may comprise an amino acid sequence that is at least about 70% identical to any one of SEQ ID NOS: 79-92, 94-98. The immunoglobulin heavy chain may comprise an amino acid sequence that is at least about 80% identical to any one of SEQ ID NOS: 79-92, 94-98. The immunoglobulin heavy chain may comprise an amino acid sequence that is 100% identical to any one of SEQ ID NOS: 79-92, 94-98.

The insulin immunoglobulin light chain fusion may comprise an amino acid sequence comprising 10, 20, 30, 40, 50, 60, 70, 80, 90, 100 or more amino acids based on or derived from any one of SEQ ID NOS: 79-92, 94-98. The immunoglobulin light chain fusion may comprise an amino acid sequence comprising 125, 150, 175, 200 or more amino acids based on or derived from any one of SEQ ID NOS: 79-92, 94-98. The immunoglobulin light chain fusion may comprise an amino acid sequence comprising 10 or more amino acids based on or derived from any one of SEQ ID NOS: 79-92, 94-98. The immunoglobulin light chain fusion may comprise an amino acid sequence comprising 50 or more amino acids based on or derived from any one of SEQ ID NOS: 79-92, 94-98. The immunoglobulin light chain fusion may comprise an amino acid sequence comprising 100 or more amino acids based on or derived from any one of SEQ ID NOS: 79-92, 94-98. The immunoglobulin light chain fusion may comprise an amino acid sequence comprising 200 or more amino acids based on or derived from any one of SEQ ID NOS: 79-92, 94-98. The amino acids may be consecutive. Alternatively, or additionally, the amino acids are nonconsecutive. In some embodiments, the immunoglobulin light chain fusion comprises amino acids derived from 1, 2, 3, 4, 5, 6, 7, 8, 9, 10 or more of SEQ ID NOS: 79-92, 94-98.

The immunoglobulin light chain fusion may be encoded by a nucleic acid sequence that is based on or derived from any one of SEQ ID NOS: 58-71, 73-77. The immunoglobulin light chain fusion may be encoded by a nucleic acid sequence that is at least about 50% homologous to any one of SEQ ID NOS: 58-71, 73-77. The immunoglobulin light chain fusion may be encoded by a nucleic acid sequence that is at least about 60%, 65%, 70%, 75%, 80%, 85%, 90%, 95%, or 97% homologous to any one of SEQ ID NOS: 58-71, 73-77. The immunoglobulin light chain fusion may be encoded by a nucleic acid sequence that is at least about 70% homologous to any one of SEQ ID NOS: 58-71, 73-77. The immunoglobulin light chain fusion may be encoded by a nucleic acid sequence that is at least about 80% homologous to any one of SEQ ID NOS: 58-71, 73-77. The immunoglobulin light chain fusion may be encoded by a nucleic acid sequence that is at least about 50% identical to any one of SEQ ID NOS: 58-71, 73-77. The immunoglobulin light chain fusion may be encoded by a nucleic acid sequence that is at least about 60%, 65%, 70%, 75%, 80%, 85%, 90%, 95%, or 97% identical to any one of SEQ ID NOS: 58-71, 73-77. The immunoglobulin light chain fusion may be encoded by a nucleic acid sequence that is at least about 70% identical to any one of SEQ ID NOS: 58-71, 73-77. The immunoglobulin light chain fusion may be encoded by a nucleic acid sequence that is at least about 80% identical to any one of SEQ ID NOS: 58-71, 73-77. The immunoglobulin light chain fusion may be encoded by a nucleic acid sequence that is 100% identical to any one of SEQ ID NOS: 58-71, 73-77.

The immunoglobulin light chain fusion may be encoded by a nucleic acid sequence comprising 10, 20, 30, 40, 50, 60, 70, 80, 90, 100 or more nucleotides based on or derived from any one of SEQ ID NOS: 58-71, 73-77. The immunoglobulin light chain fusion may be encoded by a nucleic acid sequence comprising 125, 150, 175, 200, 225, 250, 275, 300, 325, 350, 375, 400, 425, 450, 475, 450, 500 or more nucleotides based on or derived from any one of SEQ ID NOS: 58-71, 73-77. The immunoglobulin light chain fusion may be encoded by a nucleic acid sequence comprising 100 or more nucleotides based on or derived from any one of SEQ ID NOS: 58-71, 73-77. The immunoglobulin light chain fusion may be encoded by a nucleic acid sequence comprising 500 or more nucleotides based on or derived from any one of SEQ ID NOS: 58-71, 73-77. The nucleotides may be consecutive. Alternatively, or additionally, the nucleotides are nonconsecutive. In some embodiments, the immunoglobulin light chain fusion is encoded by a nucleic acid sequence derived from 1, 2, 3, 4, 5, 6, 7, 8, 9, 10 or more of SEQ ID NOS: 58-71, 73-77.

Insulin Immunoglobulin Heavy Chain Fusions

In one feature of the disclosure, provided herein is an immunoglobulin fusion protein comprising an insulin therapeutic peptide comprising one or more regions connected to the amino or carboxyl terminus of a region of an immunoglobulin heavy chain, wherein the immunoglobulin fusion is referred to herein as an immunoglobulin heavy chain fusion. In some embodiments, the immunoglobulin fusion protein further comprises one or more regions of an immunoglobulin light chain. In some cases, the immunoglobulin heavy chain fusion is connected to the one or more regions of an immunoglobulin light chain by disulfide bonds or a linker. In some embodiments, the insulin therapeutic peptide comprises one or more regions of a therapeutic peptide. In some embodiments, the insulin therapeutic peptide comprises two regions of a therapeutic peptide connected by a connecting peptide. In some embodiments, the therapeutic peptide comprises a protease cleavage site. In some embodiments, the connecting peptide comprises a protease cleavage site.

In some embodiments, the immunoglobulin heavy chain fusion comprises an amino acid sequence comprising or derived from an amino acid sequence of an anti-ASGPR antibody. In some embodiments, the light chain comprises an amino acid sequence comprising or derived from an amino acid sequence of an anti-ASGPR antibody.

In one aspect of the disclosure, provided are heavy chain insulin immunoglobulin fusion proteins comprising an insulin therapeutic peptide and a first immunoglobulin region comprising one or more portions of an antigen binding domain, wherein the antigen binding domain has specificity for an antigen of a liver cell. The antigen targeted by the antigen binding domain may be expressed by a hepatocyte. As a non-limiting example, the antigen is asialoglycoprotein receptor (ASGPR). The first immunoglobulin region may comprise a CDR having an amino acid sequence that differs from one or more of SEQ ID NOS: 45-47 and 55 by no more than 5, 4, 3, 2 or 1 amino acids. The first immunoglobulin region may comprise a first CDR having an amino acid sequence that differs from SEQ ID NO: 45 by no more than 5, 4, 3, 2 or 1 amino acids. The first immunoglobulin region may comprise a second CDR having an amino acid sequence that differs from SEQ ID NO: 46 by no more than 5, 4, 3, 2 or 1 amino acids. The first immunoglobulin region may comprise a second CDR having an amino acid sequence that differs from SEQ ID NO: 55 by no more than 5, 4, 3, 2 or 1 amino acids. The first immunoglobulin region may comprise a third CDR having an amino acid sequence that differs from SEQ ID NO: 47 by no more than 5, 4, 3, 2 or 1 amino acids. The first immunoglobulin region may comprise a variable region having an amino acid sequence at least about 75%, 80%, 85%, 90%, or 95% identical to an amino acid sequence selected from SEQ ID NO: 39 and SEQ: 43. The first immunoglobulin region may comprise a variable region having an amino acid sequence at least about 75%, 80%, 85%, 90%, or 95% homologous to an amino acid sequence selected from SEQ ID NO: 39 and SEQ: 43. The first immunoglobulin region may comprise an amino acid sequence at least about 75%, 80%, 85%, 90%, or 95% identical to an amino acid sequence selected from SEQ ID NOS: 29, 34, 36-40 and 43. The first immunoglobulin region may comprise an amino acid sequence at least about 75%, 80%, 85%, 90%, or 95% homologous to an amino acid sequence selected from SEQ ID NOS: 29, 34, 36-40 and 43. The insulin immunoglobulin fusion protein may further comprise a second immunoglobulin region. The second immunoglobulin region may comprise one or more portions of the antigen binding domain. The second immunoglobulin region may comprise a CDR having an amino acid sequence that differs from one or more of SEQ ID NOS: 48-50 by no more than 5, 4, 3, 2 or 1 amino acids. The second immunoglobulin region may comprise a first CDR having an amino acid sequence that differs from SEQ ID NO: 48 by no more than 5, 4, 3, 2 or 1 amino acids. The second immunoglobulin region may comprise a second CDR having an amino acid sequence that differs from SEQ ID NO: 49 by no more than 5, 4, 3, 2 or 1 amino acids. The second immunoglobulin region may comprise a third CDR having an amino acid sequence that differs from SEQ ID NO: 50 by no more than 5, 4, 3, 2 or 1 amino acids. The second immunoglobulin region may comprise a variable region having an amino acid sequence at least about 75%, 80%, 85%, 90%, or 95% identical to an amino acid sequence selected from SEQ ID NOS: 41 and 44. The second immunoglobulin region may comprise a variable region having an amino acid sequence at least about 75%, 80%, 85%, 90%, or 95% homologous to an amino acid sequence selected from SEQ ID NOS: 41 and 44. The second immunoglobulin region may comprise an amino acid sequence at least about 75%, 80%, 85%, 90%, or 95% identical to an amino acid sequence selected from SEQ ID NOS: 30, 33, 35, 41, 42, and 44. The second immunoglobulin region may comprise an amino acid sequence at least about 75%, 80%, 85%, 90%, or 95% homologous to an amino acid sequence selected from SEQ ID NOS: 30, 33, 35, 41, 42, and 44.

The immunoglobulin heavy chain fusion may comprise an amino acid sequence that is based on or derived from SEQ ID NO: 78 or 93. The immunoglobulin heavy chain fusion may comprise an amino acid sequence that is at least about 50% homologous to SEQ ID NO: 78 or 93. The immunoglobulin heavy chain fusion may comprise an amino acid sequence that is at least about 60%, 65%, 70%, 75%, 80%, 85%, 90%, 95%, or 97% homologous to SEQ ID NO: 78 or 93. The immunoglobulin heavy chain fusion may comprise an amino acid sequence that is at least about 70% homologous to SEQ ID NO: 78 or 93. The immunoglobulin heavy chain fusion may comprise an amino acid sequence that is at least about 80% homologous to SEQ ID NO: 78 or 93. The immunoglobulin heavy chain fusion may comprise an amino acid sequence that is at least about 50% identical to SEQ ID NO: 78 or 93. The immunoglobulin heavy chain fusion may comprise an amino acid sequence that is at least about 60%, 65%, 70%, 75%, 80%, 85%, 90%, 95%, or 97% identical to SEQ ID NO: 78 or 93. The immunoglobulin heavy chain fusion may comprise an amino acid sequence that is at least about 70% identical to SEQ ID NO: 78 or 93. The immunoglobulin heavy chain fusion may comprise an amino acid sequence that is at least about 80% identical to SEQ ID NO: 78 or 93. The immunoglobulin heavy chain fusion may comprise an amino acid sequence that is 100% identical to SEQ ID NO: 78 or 93. The immunoglobulin light chain may comprise an amino acid sequence that is based on or derived from SEQ ID NO: 78 or 93. The immunoglobulin light chain may comprise an amino acid sequence that is at least about 50% homologous to SEQ ID NO: 78 or 93. The immunoglobulin light chain may comprise an amino acid sequence that is at least about 60%, 65%, 70%, 75%, 80%, 85%, 90%, 95%, or 97% homologous to SEQ ID NO: 78 or 93. The immunoglobulin light chain may comprise an amino acid sequence that is at least about 70% homologous to SEQ ID NO: 78 or 93. The immunoglobulin light chain may comprise an amino acid sequence that is at least about 80% homologous to SEQ ID NO: 78 or 93. The immunoglobulin light chain may comprise an amino acid sequence that is at least about 50% identical to SEQ ID NO: 78 or 93. The immunoglobulin light chain may comprise an amino acid sequence that is at least about 60%, 65%, 70%, 75%, 80%, 85%, 90%, 95%, or 97% identical to SEQ ID NO: 78 or 93. The immunoglobulin light chain may comprise an amino acid sequence that is at least about 70% identical to SEQ ID NO: 78 or 93. The immunoglobulin light chain may comprise an amino acid sequence that is at least about 80% identical to SEQ ID NO: 78 or 93. The immunoglobulin light chain may comprise an amino acid sequence that is 100% identical to SEQ ID NO: 78 or 93.

The immunoglobulin heavy chain fusion may comprise an amino acid sequence comprising 10, 20, 30, 40, 50, 60, 70, 80, 90, 100 or more amino acids based on or derived from SEQ ID NO: 78 or 93. The immunoglobulin heavy chain fusion may comprise an amino acid sequence comprising 125, 150, 175, 200, 225, 250, 275, 300, 325, 350, 375, 400, 425, 450, 475, 450, 500 or more amino acids based on or derived from SEQ ID NO: 78 or 93. The immunoglobulin heavy chain fusion may comprise an amino acid sequence comprising 10 or more amino acids based on or derived from SEQ ID NO: 78 or 93. The immunoglobulin heavy chain fusion may comprise an amino acid sequence comprising 50 or more amino acids based on or derived from SEQ ID NO: 78 or 93. The immunoglobulin heavy chain fusion may comprise an amino acid sequence comprising 100 or more amino acids based on or derived from SEQ ID NO: 78 or 93. The immunoglobulin heavy chain fusion may comprise an amino acid sequence comprising 200 or more amino acids based on or derived from SEQ ID NO: 78 or 93. The amino acids may be consecutive. Alternatively, or additionally, the amino acids are nonconsecutive.

The immunoglobulin heavy chain fusion may be encoded by a nucleic acid sequence that is based on or derived from SEQ ID NO: 57 or 72. The immunoglobulin heavy chain fusion may be encoded by a nucleic acid sequence that is at least about 50% homologous to SEQ ID NO: 57 or 72. The immunoglobulin heavy chain fusion may be encoded by a nucleic acid sequence that is at least about 60%, 65%, 70%, 75%, 80%, 85%, 90%, 95%, or 97% homologous to SEQ ID NO: 57 or 72. The immunoglobulin heavy chain fusion may be encoded by a nucleic acid sequence that is at least about 70% homologous to SEQ ID NO: 57 or 72. The immunoglobulin heavy chain fusion may be encoded by a nucleic acid sequence that is at least about 80% homologous to SEQ ID NO: 57 or 72. The immunoglobulin heavy chain fusion may be encoded by a nucleic acid sequence that is at least about 50% identical to SEQ ID NO: 57 or 72. The immunoglobulin heavy chain fusion may be encoded by a nucleic acid sequence that is at least about 60%, 65%, 70%, 75%, 80%, 85%, 90%, 95%, or 97% identical to SEQ ID NO: 57 or 72. The immunoglobulin heavy chain fusion may be encoded by a nucleic acid sequence that is at least about 70% identical to SEQ ID NO: 57 or 72. The immunoglobulin heavy chain fusion may be encoded by a nucleic acid sequence that is at least about 80% identical to SEQ ID NO: 57 or 72. The immunoglobulin heavy chain fusion may be encoded by a nucleic acid sequence that is 100% identical to SEQ ID NO: 57 or 72.

The immunoglobulin heavy chain fusion may be encoded by a nucleic acid sequence comprising 10, 20, 30, 40, 50, 60, 70, 80, 90, 100 or more nucleotides based on or derived from SEQ ID NO: 57 or 72. The immunoglobulin heavy chain fusion may be encoded by a nucleic acid sequence comprising 125, 150, 175, 200, 225, 250, 275, 300, 325, 350, 375, 400, 425, 450, 475, 450, 500 or more nucleotides based on or derived from SEQ ID NO: 57 or 72. The immunoglobulin heavy chain fusion may be encoded by a nucleic acid sequence comprising 600, 650, 700, 750, 800, 850, 900, 950, 1000 or more nucleotides based on or derived from any SEQ ID NO: 57 or 72. The immunoglobulin heavy chain fusion may be encoded by a nucleic acid sequence comprising 100 or more nucleotides based on or derived from SEQ ID NO: 57 or 72. The immunoglobulin heavy chain fusion may be encoded by a nucleic acid sequence comprising 500 or more nucleotides based on or derived from SEQ ID NO: 57 or 72. The nucleotides may be consecutive. Alternatively, or additionally, the nucleotides are nonconsecutive.

Insulin Immunoglobulin Fusion Proteins

In one feature of the disclosure, provided herein are immunoglobulin fusion proteins comprising (a) an insulin immunoglobulin light chain fusion, and (b) a second immunoglobulin region derived from an immunoglobulin heavy chain. In some cases, the immunoglobulin light chain fusion is connected to the second immunoglobulin region by one or more disulfide bonds and/or a linker. The insulin immunoglobulin light chain fusion comprises an insulin therapeutic peptide comprising one or more regions connected to the amino or carboxyl terminus of a region of an immunoglobulin light chain. In some embodiments, the insulin therapeutic peptide comprises one or more regions of a therapeutic peptide. In some embodiments, the insulin therapeutic peptide comprises two regions of a therapeutic peptide connected by a connecting peptide. In some embodiments, the therapeutic peptide comprises a protease cleavage site. In some embodiments, the connecting peptide comprises a protease cleavage site. In some embodiments, the therapeutic peptide comprises a first chain and a second chain, wherein the first chain comprises a first amino acid sequence of an insulin therapeutic peptide and the second chain comprises a second amino acid sequence of an insulin therapeutic peptide. In some embodiments, the immunoglobulin light chain fusion comprises an amino acid sequence comprising or derived from an amino acid sequence of an anti-ASGPR antibody. In some embodiments, the heavy chain comprises an amino acid sequence comprising or derived from an amino acid sequence of an anti-ASGPR antibody.

In some embodiments, the insulin immunoglobulin fusion proteins are configured to treat a metabolic disease such as obesity and/or diabetes, and/or a complication or condition thereof.

In another feature of the disclosure, provided herein are immunoglobulin fusion proteins comprising (a) an insulin immunoglobulin heavy chain fusion, and (b) a second immunoglobulin region derived from an immunoglobulin light chain. In some cases, the immunoglobulin heavy chain fusion is connected to the second immunoglobulin region by one or more disulfide bonds and/or a linker. The insulin immunoglobulin heavy chain fusion comprises an insulin therapeutic peptide comprising one or more regions connected to the amino or carboxyl terminus of a region of an immunoglobulin heavy chain. In some embodiments, the insulin therapeutic peptide comprises one or more regions of a therapeutic peptide. In some embodiments, the insulin therapeutic peptide comprises two regions of a therapeutic peptide connected by a connecting peptide. In some embodiments, the therapeutic peptide comprises a protease cleavage site. In some embodiments, the connecting peptide comprises a protease cleavage site. In some embodiments, the therapeutic peptide comprises a first chain and a second chain, wherein the first chain comprises a first amino acid sequence of an insulin therapeutic peptide and the second chain comprises a second amino acid sequence of an insulin therapeutic peptide. In some embodiments, the immunoglobulin heavy chain fusion comprises an amino acid sequence comprising or derived from an amino acid sequence of an anti-ASGPR antibody. In some embodiments, the light chain comprises an amino acid sequence comprising or derived from an amino acid sequence of an anti-ASGPR antibody.

In another feature of the disclosure, provided herein are immunoglobulin fusion proteins comprising (a) an insulin immunoglobulin light chain fusion, and (b) an insulin immunoglobulin heavy chain fusion.

In some embodiments, the immunoglobulin fusion protein comprises an amino acid sequence based on or derived from SEQ ID NO: 78 and an amino acid sequence based on or derived from SEQ ID NO: 30. The immunoglobulin fusion protein may comprise an amino acid sequence that is at least about 60%, 70%, 75%, 80%, 90%, 95%, or 97% identical to SEQ ID NO: 78 and an amino acid sequence that is at least about 60%, 70%, 75%, 80%, 90%, 95%, or 97% identical to SEQ ID NO: 30. The immunoglobulin fusion protein may comprise an amino acid sequence that is 100% identical to SEQ ID NO: 78 and an amino acid sequence that is 100% identical to SEQ ID NO: 30. In some embodiments, the immunoglobulin fusion protein is encoded by a nucleic acid sequence based on or derived from SEQ ID NO: 57 and a nucleic acid sequence based on or derived from SEQ ID NO: 2. The immunoglobulin fusion protein may be encoded by a nucleic acid sequence that is at least about 60%, 70%, 75%, 80%, 90%, 95%, or 97% identical to SEQ ID NO: 57 and a nucleic acid sequence that is at least about 60%, 70%, 75%, 80%, 90%, 95%, or 97% identical to SEQ ID NO: 2. The immunoglobulin fusion protein may be encoded by a nucleic acid sequence that is 100% identical to SEQ ID NO: 57 and a nucleic acid sequence that is 100% identical to SEQ ID NO: 2.

In some embodiments, the immunoglobulin fusion protein comprises an amino acid sequence based on or derived from SEQ ID NO: 79 and an amino acid sequence based on or derived from SEQ ID NO: 29. The immunoglobulin fusion protein may comprise an amino acid sequence that is at least about 60%, 70%, 75%, 80%, 90%, 95%, or 97% identical to SEQ ID NO: 79 and an amino acid sequence that is at least about 60%, 70%, 75%, 80%, 90%, 95%, or 97% identical to SEQ ID NO: 29. The immunoglobulin fusion protein may comprise an amino acid sequence that is 100% identical to SEQ ID NO: 79 and an amino acid sequence that is 100% identical to SEQ ID NO: 29. In some embodiments, the immunoglobulin fusion protein is encoded by a nucleic acid sequence based on or derived from SEQ ID NO: 58 and a nucleic acid sequence based on or derived from SEQ ID NO: 1. The immunoglobulin fusion protein may be encoded by a nucleic acid sequence that is at least about 60%, 70%, 75%, 80%, 90%, 95%, or 97% identical to SEQ ID NO: 58 and a nucleic acid sequence that is at least about 60%, 70%, 75%, 80%, 90%, 95%, or 97% identical to SEQ ID NO: 1. The immunoglobulin fusion protein may be encoded by a nucleic acid sequence that is 100% identical to SEQ ID NO: 58 and a nucleic acid sequence that is 100% identical to SEQ ID NO: 1.

In some embodiments, the immunoglobulin fusion protein comprises an amino acid sequence based on or derived from SEQ ID NO: 80 and an amino acid sequence based on or derived from SEQ ID NO: 31. The immunoglobulin fusion protein may comprise an amino acid sequence that is at least about 60%, 70%, 75%, 80%, 90%, 95%, or 97% identical to SEQ ID NO: 80 and an amino acid sequence that is at least about 60%, 70%, 75%, 80%, 90%, 95%, or 97% identical to SEQ ID NO: 31. The immunoglobulin fusion protein may comprise an amino acid sequence that is 100% identical to SEQ ID NO: 80 and an amino acid sequence that is 100% identical to SEQ ID NO: 31. In some embodiments, the immunoglobulin fusion protein is encoded by a nucleic acid sequence based on or derived from SEQ ID NO: 59 and a nucleic acid sequence based on or derived from SEQ ID NO: 3. The immunoglobulin fusion protein may be encoded by a nucleic acid sequence that is at least about 60%, 70%, 75%, 80%, 90%, 95%, or 97% identical to SEQ ID NO: 59 and a nucleic acid sequence that is at least about 60%, 70%, 75%, 80%, 90%, 95%, or 97% identical to SEQ ID NO: 3. The immunoglobulin fusion protein may be encoded by a nucleic acid sequence that is 100% identical to SEQ ID NO: 59 and a nucleic acid sequence that is 100% identical to SEQ ID NO: 3.

In some embodiments, the immunoglobulin fusion protein comprises an amino acid sequence based on or derived from SEQ ID NO: 81 and an amino acid sequence based on or derived from SEQ ID NO: 167. The immunoglobulin fusion protein may comprise an amino acid sequence that is at least about 60%, 70%, 75%, 80%, 90%, 95%, or 97% identical to SEQ ID NO: 81 and an amino acid sequence that is at least about 60%, 70%, 75%, 80%, 90%, 95%, or 97% identical to SEQ ID NO: 167. The immunoglobulin fusion protein may comprise an amino acid sequence that is 100% identical to SEQ ID NO: 81 and an amino acid sequence that is 100% identical to SEQ ID NO: 167. In some embodiments, the immunoglobulin fusion protein is encoded by a nucleic acid sequence based on or derived from SEQ ID NO: 60 and a nucleic acid sequence based on or derived from SEQ ID NO: 166. The immunoglobulin fusion protein may be encoded by a nucleic acid sequence that is at least about 60%, 70%, 75%, 80%, 90%, 95%, or 97% identical to SEQ ID NO: 60 and a nucleic acid sequence that is at least about 60%, 70%, 75%, 80%, 90%, 95%, or 97% identical to SEQ ID NO: 166. The immunoglobulin fusion protein may be encoded by a nucleic acid sequence that is 100% identical to SEQ ID NO: 60 and a nucleic acid sequence that is 100% identical to SEQ ID NO: 166.

In some embodiments, the immunoglobulin fusion protein comprises an amino acid sequence based on or derived from SEQ ID NO: 82 and an amino acid sequence based on or derived from SEQ ID NO: 167. The immunoglobulin fusion protein may comprise an amino acid sequence that is at least about 60%, 70%, 75%, 80%, 90%, 95%, or 97% identical to SEQ ID NO: 82 and an amino acid sequence that is at least about 60%, 70%, 75%, 80%, 90%, 95%, or 97% identical to SEQ ID NO: 167. The immunoglobulin fusion protein may comprise an amino acid sequence that is 100% identical to SEQ ID NO: 82 and an amino acid sequence that is 100% identical to SEQ ID NO: 167. In some embodiments, the immunoglobulin fusion protein is encoded by a nucleic acid sequence based on or derived from SEQ ID NO: 61 and a nucleic acid sequence based on or derived from SEQ ID NO: 166. The immunoglobulin fusion protein may be encoded by a nucleic acid sequence that is at least about 60%, 70%, 75%, 80%, 90%, 95%, or 97% identical to SEQ ID NO: 61 and a nucleic acid sequence that is at least about 60%, 70%, 75%, 80%, 90%, 95%, or 97% identical to SEQ ID NO: 166. The immunoglobulin fusion protein may be encoded by a nucleic acid sequence that is 100% identical to SEQ ID NO: 61 and a nucleic acid sequence that is 100% identical to SEQ ID NO: 166.

In some embodiments, the immunoglobulin fusion protein comprises an amino acid sequence based on or derived from SEQ ID NO: 83 and an amino acid sequence based on or derived from SEQ ID NO: 167. The immunoglobulin fusion protein may comprise an amino acid sequence that is at least about 60%, 70%, 75%, 80%, 90%, 95%, or 97% identical to SEQ ID NO: 83 and an amino acid sequence that is at least about 60%, 70%, 75%, 80%, 90%, 95%, or 97% identical to SEQ ID NO: 167. The immunoglobulin fusion protein may comprise an amino acid sequence that is 100% identical to SEQ ID NO: 83 and an amino acid sequence that is 100% identical to SEQ ID NO: 167. In some embodiments, the immunoglobulin fusion protein is encoded by a nucleic acid sequence based on or derived from SEQ ID NO: 62 and a nucleic acid sequence based on or derived from SEQ ID NO: 166. The immunoglobulin fusion protein may be encoded by a nucleic acid sequence that is at least about 60%, 70%, 75%, 80%, 90%, 95%, or 97% identical to SEQ ID NO: 62 and a nucleic acid sequence that is at least about 60%, 70%, 75%, 80%, 90%, 95%, or 97% identical to SEQ ID NO: 166. The immunoglobulin fusion protein may be encoded by a nucleic acid sequence that is 100% identical to SEQ ID NO: 62 and a nucleic acid sequence that is 100% identical to SEQ ID NO: 166.

In some embodiments, the immunoglobulin fusion protein comprises an amino acid sequence based on or derived from SEQ ID NO: 84 and an amino acid sequence based on or derived from SEQ ID NO: 34 or 36. The immunoglobulin fusion protein may comprise an amino acid sequence that is at least about 60%, 70%, 75%, 80%, 90%, 95%, or 97% identical to SEQ ID NO: 84 and an amino acid sequence that is at least about 60%, 70%, 75%, 80%, 90%, 95%, or 97% identical to SEQ ID NO: 34 or 36. The immunoglobulin fusion protein may comprise an amino acid sequence that is 100% identical to SEQ ID NO: 84 and an amino acid sequence that is 100% identical to SEQ ID NO: 34 or 36. In some embodiments, the immunoglobulin fusion protein is encoded by a nucleic acid sequence based on or derived from SEQ ID NO: 63 and a nucleic acid sequence based on or derived from SEQ ID NO: 6 or 8. The immunoglobulin fusion protein may be encoded by a nucleic acid sequence that is at least about 60%, 70%, 75%, 80%, 90%, 95%, or 97% identical to SEQ ID NO: 63 and a nucleic acid sequence that is at least about 60%, 70%, 75%, 80%, 90%, 95%, or 97% identical to SEQ ID NO: 6 or 8. The immunoglobulin fusion protein may be encoded by a nucleic acid sequence that is 100% identical to SEQ ID NO: 63 and a nucleic acid sequence that is 100% identical to SEQ ID NO: 6 or 8.

In some embodiments, the immunoglobulin fusion protein comprises an amino acid sequence based on or derived from SEQ ID NO: 85 and an amino acid sequence based on or derived from SEQ ID NO: 34 or 36. The immunoglobulin fusion protein may comprise an amino acid sequence that is at least about 60%, 70%, 75%, 80%, 90%, 95%, or 97% identical to SEQ ID NO: 85 and an amino acid sequence that is at least about 60%, 70%, 75%, 80%, 90%, 95%, or 97% identical to SEQ ID NO: 34 or 36. The immunoglobulin fusion protein may comprise an amino acid sequence that is 100% identical to SEQ ID NO: 85 and an amino acid sequence that is 100% identical to SEQ ID NO: 34 or 36. In some embodiments, the immunoglobulin fusion protein is encoded by a nucleic acid sequence based on or derived from SEQ ID NO: 64 and a nucleic acid sequence based on or derived from SEQ ID NO: 6 or 8. The immunoglobulin fusion protein may be encoded by a nucleic acid sequence that is at least about 60%, 70%, 75%, 80%, 90%, 95%, or 97% identical to SEQ ID NO: 64 and a nucleic acid sequence that is at least about 60%, 70%, 75%, 80%, 90%, 95%, or 97% identical to SEQ ID NO: 6 or 8. The immunoglobulin fusion protein may be encoded by a nucleic acid sequence that is 100% identical to SEQ ID NO: 64 and a nucleic acid sequence that is 100% identical to SEQ ID NO: 6 or 8.

In some embodiments, the immunoglobulin fusion protein comprises an amino acid sequence based on or derived from SEQ ID NO: 86 and an amino acid sequence based on or derived from SEQ ID NO: 31. The immunoglobulin fusion protein may comprise an amino acid sequence that is at least about 60%, 70%, 75%, 80%, 90%, 95%, or 97% identical to SEQ ID NO: 86 and an amino acid sequence that is at least about 60%, 70%, 75%, 80%, 90%, 95%, or 97% identical to SEQ ID NO: 31. The immunoglobulin fusion protein may comprise an amino acid sequence that is 100% identical to SEQ ID NO: 86 and an amino acid sequence that is 100% identical to SEQ ID NO: 31. In some embodiments, the immunoglobulin fusion protein is encoded by a nucleic acid sequence based on or derived from SEQ ID NO: 65 and a nucleic acid sequence based on or derived from SEQ ID NO: 3. The immunoglobulin fusion protein may be encoded by a nucleic acid sequence that is at least about 60%, 70%, 75%, 80%, 90%, 95%, or 97% identical to SEQ ID NO: 65 and a nucleic acid sequence that is at least about 60%, 70%, 75%, 80%, 90%, 95%, or 97% identical to SEQ ID NO: 3. The immunoglobulin fusion protein may be encoded by a nucleic acid sequence that is 100% identical to SEQ ID NO: 65 and a nucleic acid sequence that is 100% identical to SEQ ID NO: 3.

In some embodiments, the immunoglobulin fusion protein comprises an amino acid sequence based on or derived from SEQ ID NO: 87 and an amino acid sequence based on or derived from SEQ ID NO: 34 or 36. The immunoglobulin fusion protein may comprise an amino acid sequence that is at least about 60%, 70%, 75%, 80%, 90%, 95%, or 97% identical to SEQ ID NO: 87 and an amino acid sequence that is at least about 60%, 70%, 75%, 80%, 90%, 95%, or 97% identical to SEQ ID NO: 34 or 36. The immunoglobulin fusion protein may comprise an amino acid sequence that is 100% identical to SEQ ID NO: 87 and an amino acid sequence that is 100% identical to SEQ ID NO: 34 or 36. In some embodiments, the immunoglobulin fusion protein is encoded by a nucleic acid sequence based on or derived from SEQ ID NO: 66 and a nucleic acid sequence based on or derived from SEQ ID NO: 6 or 8. The immunoglobulin fusion protein may be encoded by a nucleic acid sequence that is at least about 60%, 70%, 75%, 80%, 90%, 95%, or 97% identical to SEQ ID NO: 66 and a nucleic acid sequence that is at least about 60%, 70%, 75%, 80%, 90%, 95%, or 97% identical to SEQ ID NO: 6 or 8. The immunoglobulin fusion protein may be encoded by a nucleic acid sequence that is 100% identical to SEQ ID NO: 66 and a nucleic acid sequence that is 100% identical to SEQ ID NO: 6 or 8.

In some embodiments, the immunoglobulin fusion protein comprises an amino acid sequence based on or derived from SEQ ID NO: 88 and an amino acid sequence based on or derived from SEQ ID NO: 34 or 36. The immunoglobulin fusion protein may comprise an amino acid sequence that is at least about 60%, 70%, 75%, 80%, 90%, 95%, or 97% identical to SEQ ID NO: 88 and an amino acid sequence that is at least about 60%, 70%, 75%, 80%, 90%, 95%, or 97% identical to SEQ ID NO: 34 or 36. The immunoglobulin fusion protein may comprise an amino acid sequence that is 100% identical to SEQ ID NO: 88 and an amino acid sequence that is 100% identical to SEQ ID NO: 34 or 36. In some embodiments, the immunoglobulin fusion protein is encoded by a nucleic acid sequence based on or derived from SEQ ID NO: 67 and a nucleic acid sequence based on or derived from SEQ ID NO: 6 or 8. The immunoglobulin fusion protein may be encoded by a nucleic acid sequence that is at least about 60%, 70%, 75%, 80%, 90%, 95%, or 97% identical to SEQ ID NO: 67 and a nucleic acid sequence that is at least about 60%, 70%, 75%, 80%, 90%, 95%, or 97% identical to SEQ ID NO: 6 or 8. The immunoglobulin fusion protein may be encoded by a nucleic acid sequence that is 100% identical to SEQ ID NO: 67 and a nucleic acid sequence that is 100% identical to SEQ ID NO: 6 or 8.

In some embodiments, the immunoglobulin fusion protein comprises an amino acid sequence based on or derived from SEQ ID NO: 89 and an amino acid sequence based on or derived from SEQ ID NO: 34 or 36. The immunoglobulin fusion protein may comprise an amino acid sequence that is at least about 60%, 70%, 75%, 80%, 90%, 95%, or 97% identical to SEQ ID NO: 89 and an amino acid sequence that is at least about 60%, 70%, 75%, 80%, 90%, 95%, or 97% identical to SEQ ID NO: 34 or 36. The immunoglobulin fusion protein may comprise an amino acid sequence that is 100% identical to SEQ ID NO: 89 and an amino acid sequence that is 100% identical to SEQ ID NO: 34 or 36. In some embodiments, the immunoglobulin fusion protein is encoded by a nucleic acid sequence based on or derived from SEQ ID NO: 68 and a nucleic acid sequence based on or derived from SEQ ID NO: 6 or 8. The immunoglobulin fusion protein may be encoded by a nucleic acid sequence that is at least about 60%, 70%, 75%, 80%, 90%, 95%, or 97% identical to SEQ ID NO: 68 and a nucleic acid sequence that is at least about 60%, 70%, 75%, 80%, 90%, 95%, or 97% identical to SEQ ID NO: 6 or 8. The immunoglobulin fusion protein may be encoded by a nucleic acid sequence that is 100% identical to SEQ ID NO: 68 and a nucleic acid sequence that is 100% identical to SEQ ID NO: 6 or 8.

In some embodiments, the immunoglobulin fusion protein comprises an amino acid sequence based on or derived from SEQ ID NO: 90 and an amino acid sequence based on or derived from SEQ ID NO: 34 or 36. The immunoglobulin fusion protein may comprise an amino acid sequence that is at least about 60%, 70%, 75%, 80%, 90%, 95%, or 97% identical to SEQ ID NO: 90 and an amino acid sequence that is at least about 60%, 70%, 75%, 80%, 90%, 95%, or 97% identical to SEQ ID NO: 34 or 36. The immunoglobulin fusion protein may comprise an amino acid sequence that is 100% identical to SEQ ID NO: 90 and an amino acid sequence that is 100% identical to SEQ ID NO: 34 or 36. In some embodiments, the immunoglobulin fusion protein is encoded by a nucleic acid sequence based on or derived from SEQ ID NO: 69 and a nucleic acid sequence based on or derived from SEQ ID NO: 6 or 8. The immunoglobulin fusion protein may be encoded by a nucleic acid sequence that is at least about 60%, 70%, 75%, 80%, 90%, 95%, or 97% identical to SEQ ID NO: 69 and a nucleic acid sequence that is at least about 60%, 70%, 75%, 80%, 90%, 95%, or 97% identical to SEQ ID NO: 6 or 8. The immunoglobulin fusion protein may be encoded by a nucleic acid sequence that is 100% identical to SEQ ID NO: 69 and a nucleic acid sequence that is 100% identical to SEQ ID NO: 6 or 8.

In some embodiments, the immunoglobulin fusion protein comprises an amino acid sequence based on or derived from SEQ ID NO: 91 and an amino acid sequence based on or derived from SEQ ID NO: 34 or 36. The immunoglobulin fusion protein may comprise an amino acid sequence that is at least about 60%, 70%, 75%, 80%, 90%, 95%, or 97% identical to SEQ ID NO: 91 and an amino acid sequence that is at least about 60%, 70%, 75%, 80%, 90%, 95%, or 97% identical to SEQ ID NO: 34 or 36. The immunoglobulin fusion protein may comprise an amino acid sequence that is 100% identical to SEQ ID NO: 91 and an amino acid sequence that is 100% identical to SEQ ID NO: 34 or 36. In some embodiments, the immunoglobulin fusion protein is encoded by a nucleic acid sequence based on or derived from SEQ ID NO: 70 and a nucleic acid sequence based on or derived from SEQ ID NO: 6 or 8. The immunoglobulin fusion protein may be encoded by a nucleic acid sequence that is at least about 60%, 70%, 75%, 80%, 90%, 95%, or 97% identical to SEQ ID NO: 70 and a nucleic acid sequence that is at least about 60%, 70%, 75%, 80%, 90%, 95%, or 97% identical to SEQ ID NO: 6 or 8. The immunoglobulin fusion protein may be encoded by a nucleic acid sequence that is 100% identical to SEQ ID NO: 70 and a nucleic acid sequence that is 100% identical to SEQ ID NO: 6 or 8.

In some embodiments, the immunoglobulin fusion protein comprises an amino acid sequence based on or derived from SEQ ID NO: 92 and an amino acid sequence based on or derived from SEQ ID NO: 34 or 36. The immunoglobulin fusion protein may comprise an amino acid sequence that is at least about 60%, 70%, 75%, 80%, 90%, 95%, or 97% identical to SEQ ID NO: 92 and an amino acid sequence that is at least about 60%, 70%, 75%, 80%, 90%, 95%, or 97% identical to SEQ ID NO: 34 or 36. The immunoglobulin fusion protein may comprise an amino acid sequence that is 100% identical to SEQ ID NO: 92 and an amino acid sequence that is 100% identical to SEQ ID NO: 34 or 36. In some embodiments, the immunoglobulin fusion protein is encoded by a nucleic acid sequence based on or derived from SEQ ID NO: 71 and a nucleic acid sequence based on or derived from SEQ ID NO: 6 or 8. The immunoglobulin fusion protein may be encoded by a nucleic acid sequence that is at least about 60%, 70%, 75%, 80%, 90%, 95%, or 97% identical to SEQ ID NO: 71 and a nucleic acid sequence that is at least about 60%, 70%, 75%, 80%, 90%, 95%, or 97% identical to SEQ ID NO: 6 or 8. The immunoglobulin fusion protein may be encoded by a nucleic acid sequence that is 100% identical to SEQ ID NO: 71 and a nucleic acid sequence that is 100% identical to SEQ ID NO: 6 or 8.

In some embodiments, the immunoglobulin fusion protein comprises an amino acid sequence based on or derived from SEQ ID NO: 95 and an amino acid sequence based on or derived from SEQ ID NO: 34 or 36. The immunoglobulin fusion protein may comprise an amino acid sequence that is at least about 60%, 70%, 75%, 80%, 90%, 95%, or 97% identical to SEQ ID NO: 95 and an amino acid sequence that is at least about 60%, 70%, 75%, 80%, 90%, 95%, or 97% identical to SEQ ID NO: 34 or 36. The immunoglobulin fusion protein may comprise an amino acid sequence that is 100% identical to SEQ ID NO: 95 and an amino acid sequence that is 100% identical to SEQ ID NO: 34 or 36. In some embodiments, the immunoglobulin fusion protein is encoded by a nucleic acid sequence based on or derived from SEQ ID NO: 74 and a nucleic acid sequence based on or derived from SEQ ID NO: 6 or 8. The immunoglobulin fusion protein may be encoded by a nucleic acid sequence that is at least about 60%, 70%, 75%, 80%, 90%, 95%, or 97% identical to SEQ ID NO: 74 and a nucleic acid sequence that is at least about 60%, 70%, 75%, 80%, 90%, 95%, or 97% identical to SEQ ID NO: 6 or 8. The immunoglobulin fusion protein may be encoded by a nucleic acid sequence that is 100% identical to SEQ ID NO: 74 and a nucleic acid sequence that is 100% identical to SEQ ID NO: 6 or 8.

In some embodiments, the immunoglobulin fusion protein comprises an amino acid sequence based on or derived from SEQ ID NO: 96 and an amino acid sequence based on or derived from SEQ ID NO: 37 or 38. The immunoglobulin fusion protein may comprise an amino acid sequence that is at least about 60%, 70%, 75%, 80%, 90%, 95%, or 97% identical to SEQ ID NO: 96 and an amino acid sequence that is at least about 60%, 70%, 75%, 80%, 90%, 95%, or 97% identical to SEQ ID NO: 37 or 38. The immunoglobulin fusion protein may comprise an amino acid sequence that is 100% identical to SEQ ID NO: 96 and an amino acid sequence that is 100% identical to SEQ ID NO: 37 or 38. In some embodiments, the immunoglobulin fusion protein is encoded by a nucleic acid sequence based on or derived from SEQ ID NO: 75 and a nucleic acid sequence based on or derived from SEQ ID NO: 9 or 10. The immunoglobulin fusion protein may be encoded by a nucleic acid sequence that is at least about 60%, 70%, 75%, 80%, 90%, 95%, or 97% identical to SEQ ID NO: 75 and a nucleic acid sequence that is at least about 60%, 70%, 75%, 80%, 90%, 95%, or 97% identical to SEQ ID NO: 9 or 10. The immunoglobulin fusion protein may be encoded by a nucleic acid sequence that is 100% identical to SEQ ID NO: 75 and a nucleic acid sequence that is 100% identical to SEQ ID NO: 9 or 10.

In some embodiments, the immunoglobulin fusion protein comprises an amino acid sequence based on or derived from SEQ ID NO: 97 and an amino acid sequence based on or derived from SEQ ID NO: 34 or 36. The immunoglobulin fusion protein may comprise an amino acid sequence that is at least about 60%, 70%, 75%, 80%, 90%, 95%, or 97% identical to SEQ ID NO: 97 and an amino acid sequence that is at least about 60%, 70%, 75%, 80%, 90%, 95%, or 97% identical to SEQ ID NO: 34 or 36. The immunoglobulin fusion protein may comprise an amino acid sequence that is 100% identical to SEQ ID NO: 97 and an amino acid sequence that is 100% identical to SEQ ID NO: 34 or 36. In some embodiments, the immunoglobulin fusion protein is encoded by a nucleic acid sequence based on or derived from SEQ ID NO: 76 and a nucleic acid sequence based on or derived from SEQ ID NO: 6 or 8. The immunoglobulin fusion protein may be encoded by a nucleic acid sequence that is at least about 60%, 70%, 75%, 80%, 90%, 95%, or 97% identical to SEQ ID NO: 76 and a nucleic acid sequence that is at least about 60%, 70%, 75%, 80%, 90%, 95%, or 97% identical to SEQ ID NO: 6 or 8. The immunoglobulin fusion protein may be encoded by a nucleic acid sequence that is 100% identical to SEQ ID NO: 76 and a nucleic acid sequence that is 100% identical to SEQ ID NO: 6 or 8.

In some embodiments, the immunoglobulin fusion protein comprises an amino acid sequence based on or derived from SEQ ID NO: 98 and an amino acid sequence based on or derived from SEQ ID NO: 37 or 38. The immunoglobulin fusion protein may comprise an amino acid sequence that is at least about 60%, 70%, 75%, 80%, 90%, 95%, or 97% identical to SEQ ID NO: 98 and an amino acid sequence that is at least about 60%, 70%, 75%, 80%, 90%, 95%, or 97% identical to SEQ ID NO: 37 or 38. The immunoglobulin fusion protein may comprise an amino acid sequence that is 100% identical to SEQ ID NO: 98 and an amino acid sequence that is 100% identical to SEQ ID NO: 37 or 38. In some embodiments, the immunoglobulin fusion protein is encoded by a nucleic acid sequence based on or derived from SEQ ID NO: 77 and a nucleic acid sequence based on or derived from SEQ ID NO: 9 or 10. The immunoglobulin fusion protein may be encoded by a nucleic acid sequence that is at least about 60%, 70%, 75%, 80%, 90%, 95%, or 97% identical to SEQ ID NO: 77 and a nucleic acid sequence that is at least about 60%, 70%, 75%, 80%, 90%, 95%, or 97% identical to SEQ ID NO: 9 or 10. The immunoglobulin fusion protein may be encoded by a nucleic acid sequence that is 100% identical to SEQ ID NO: 77 and a nucleic acid sequence that is 100% identical to SEQ ID NO: 9 or 10.

Immunoglobulin Region

The immunoglobulin fusion proteins disclosed herein comprise one or more immunoglobulin regions. For liver-targeted fusions, the immunoglobulin region comprises one or more portions of an antigen binding domain, wherein the antigen binding domain has specificity for an antigen of a liver cell. In some cases, the antigen is expressed by a hepatocyte. In some cases, the antigen is asialoglycoprotein receptor (ASGPR). The antigen binding domain may bind to one or more amino acids of an epitope of ASGPR having SEQ ID NO: 162, wherein the one or more amino acids is selected from R10, G11, F19, G35, N36, Q47, S56, L83, W134, E135, K138, V140, H142, and K173. The one or more amino acids of the epitope may comprise any combination of W134, E135, K138, V140, H142, and K173.

The immunoglobulin region of an insulin fusion protein may comprise: (a) a heavy chain variable region sequence comprising SEQ ID NO: 45; (b) a heavy chain variable region sequence comprising SEQ ID NO: 46; (c) a heavy chain variable region sequence comprising SEQ ID NO: 55; (d) a heavy chain variable region sequence comprising SEQ ID NO: 47; (e) a light chain variable region sequence comprising SEQ ID NO: 48; (f) a light chain variable region sequence comprising SEQ ID NO: 49; (g) a light chain variable region sequence comprising SEQ ID NO: 50; (h) a combination of (a), (b) and (d); (i) a combination of (a), (c) and (d); (j) a combination of (e), (f) and (g); (k) a combination of (h) and (j); or (l) a combination of (i) and (j). Immunoglobulins specific for ASGPR which are useful in the insulin immunoglobulin fusion proteins described herein include those described in any of: US 2015/0299324, US 2013/0078216, WO 2011/086143, US 2016/0060354, and US 2016/0015821. Also envisioned for use in an insulin immunoglobulin fusion protein are anti-ASGPR immunoglobulins commercially available and immunoglobulins that compete with any anti-ASGPR described herein.

In some cases, the immunoglobulin region comprises a CDR having an amino acid sequence that differs from one or more of SEQ ID NOS: 45-47 and 55 by no more than 5, 4, 3, 2 or 1 amino acids. In some cases, the immunoglobulin region comprises a CDR having an amino acid sequence that differs from SEQ ID NO: 45 by no more than 5, 4, 3, 2 or 1 amino acids. In some cases, the immunoglobulin region comprises a CDR having an amino acid sequence that differs from SEQ ID NO: 46 by no more than 5, 4, 3, 2 or 1 amino acids. In some cases, the immunoglobulin region comprises a CDR having an amino acid sequence that differs from SEQ ID NO: 55 by no more than 5, 4, 3, 2 or 1 amino acids. In some cases, the immunoglobulin region comprises a CDR having an amino acid sequence that differs from SEQ ID NO: 47 by no more than 5, 4, 3, 2 or 1 amino acids.

In some cases, the immunoglobulin region comprises a variable region having an amino acid sequence at least about 75%, 80%, 85%, 90%, or 95% identical to an amino acid sequence selected from SEQ ID NO: 39 and SEQ: 43. In some cases, the immunoglobulin region comprises a variable region having an amino acid sequence at least about 75%, 80%, 85%, 90%, or 95% homologous to an amino acid sequence selected from SEQ ID NO: 39 and SEQ: 43. In some cases, the immunoglobulin region comprises an amino acid sequence at least about 75%, 80%, 85%, 90%, or 95% identical to an amino acid sequence selected from SEQ ID NOS: 29, 34, 36-40 and 43. In some cases, the immunoglobulin region comprises an amino acid sequence at least about 75%, 80%, 85%, 90%, or 95% homologous to an amino acid sequence selected from SEQ ID NOS: 29, 34, 36-40 and 43.

In some cases, the immunoglobulin region comprises a CDR having an amino acid sequence that differs from one or more of SEQ ID NOS: 48-50 by no more than 5, 4, 3, 2 or 1 amino acids. In some cases, the immunoglobulin region comprises a CDR having an amino acid sequence that differs from SEQ ID NO: 48 by no more than 5, 4, 3, 2 or 1 amino acids. In some cases, the immunoglobulin region comprises a CDR having an amino acid sequence that differs from SEQ ID NO: 49 by no more than 5, 4, 3, 2 or 1 amino acids. In some cases, the immunoglobulin region comprises a CDR having an amino acid sequence that differs from SEQ ID NO: 50 by no more than 5, 4, 3, 2 or 1 amino acids.

In some cases, the immunoglobulin region comprises a variable region having an amino acid sequence at least about 75%, 80%, 85%, 90%, or 95% identical to an amino acid sequence selected from SEQ ID NOS: 41 and 44. In some cases, the immunoglobulin region comprises a variable region having an amino acid sequence at least about 75%, 80%, 85%, 90%, or 95% homologous to an amino acid sequence selected from SEQ ID NOS: 41 and 44. In some cases, the immunoglobulin region comprises an amino acid sequence at least about 75%, 80%, 85%, 90%, or 95% identical to an amino acid sequence selected from SEQ ID NOS: 30, 33, 35, 41, 42, and 44. In some cases, the immunoglobulin region comprises an amino acid sequence at least about 75%, 80%, 85%, 90%, or 95% homologous to an amino acid sequence selected from SEQ ID NOS: 30, 33, 35, 41, 42, and 44.

The immunoglobulin region may comprise at least a portion of a variable domain. The immunoglobulin region may comprise one or more variable domains or portions thereof. The immunoglobulin region may comprise 2, 3, 4, 5 or more variable domains or portions thereof. The immunoglobulin region may comprise an amino acid sequence comprising 10, 20, 30, 40, 50, 60, 70, 80, 90, 100, 120, 140, 160, 180, 200 or more amino acids based on or derived from an amino acid sequence of one or more variable domains. The amino acids may be consecutive. The amino acids may be non-consecutive.

The immunoglobulin region may comprise at least a portion of a constant domain. The immunoglobulin region may comprise one or more constant domains or portions thereof. The immunoglobulin region may comprise 2, 3, 4, 5, 6, 7, 8, 9, 10 or more constant domains or portions thereof. The immunoglobulin region may comprise an amino acid sequence comprising 10, 20, 30, 40, 50, 60, 70, 80, 90, 100, 120, 140, 160, 180, 200, 225, 250, 275, 300, 350, 400, 500, 600, 700, 800, 900, 1000, 1200, 1400 or more amino acids based on or derived from an amino acid sequence of one or more constant domains. The amino acids may be consecutive. The amino acids may be non-consecutive.

The immunoglobulin region may comprise at least a portion of a complementarity-determining region (CDR). The immunoglobulin region may comprise one or more complementarity-determining regions (CDRs) or portions thereof. The immunoglobulin region may comprise 2, 3, 4, 5 or more complementarity-determining regions (CDRs) or portions thereof. The immunoglobulin region may comprise 6, 7, 8 or more complementarity-determining regions (CDRs) or portions thereof. The immunoglobulin region may comprise four or more complementarity-determining regions (CDRs) or portions thereof. The immunoglobulin region may comprise 9, 10, 11 or more complementarity-determining regions (CDRs) or portions thereof. The one or more CDRs may be CDR1, CDR2, CDR3 or a combination thereof. The one or more CDRs may be CDR1. The one or more CDRs may be CDR2. The one or more CDRs may be CDR3. The CDR may be a heavy chain CDR. The one or more CDRs may be a light chain CDR.

The immunoglobulin region may comprise an amino acid sequence comprising 1, 2, 3, 4, 5, 6, 7, 8, 9, 10 or more amino acids based on or derived from an amino acid sequence of a CDR. The immunoglobulin region may comprise an amino acid sequence comprising 3 or more amino acids based on or derived from an amino acid sequence of a CDR. The immunoglobulin region may comprise an amino acid sequence comprising 5 or more amino acids based on or derived from an amino acid sequence of a CDR. The immunoglobulin region may comprise an amino acid sequence comprising 10 or more amino acids based on or derived from an amino acid sequence of a CDR. The amino acids may be consecutive. The amino acids may be non-consecutive.

The immunoglobulin region may be based on or derived from at least a portion of an anti-T cell receptor immunoglobulin. The immunoglobulin region may be based on or derived from at least a portion of an anti-B cell receptor immunoglobulin.

The immunoglobulin region may be based on or derived from an immunoglobulin or immunoglobulin fragment that binds to at least a portion of a receptor on a cell. The immunoglobulin region may be based on or derived from an immunoglobulin or immunoglobulin fragment that binds to at least a portion of a co-receptor on a cell. The immunoglobulin region may be based on or derived from an immunoglobulin or immunoglobulin fragment that binds to at least a portion of an antigen or cell surface marker on a cell. The cell may be a hematopoietic cell. The hematopoietic cell may be a myeloid cell. The myeloid cell may be an erythrocyte, thrombocyte, neutrophil, monocyte, macrophage, eosinophil, basophil, or mast cell. The hematopoietic cell may be a lymphoid cell. The lymphoid cell may be a B-cell, T-cell, or NK-cell. The hematopoietic cell may be a leukocyte. The hematopoietic cell may be a lymphocyte.

The immunoglobulin region may be based on or derived from an immunoglobulin or immunoglobulin fragment that binds to at least a portion of a receptor on a hepatocyte cell. The receptor may be ASPGR.

The immunoglobulin region may be based on or derived from an anti-ASGPR immunoglobulin. The immunoglobulin region may comprise at least a portion of an anti-ASGPR immunoglobulin. The immunoglobulin region may comprise an amino acid sequence that is at least about 50% homologous to at least a portion of an anti-ASGPR immunoglobulin. The immunoglobulin region may comprise an amino acid sequence that is at least about 60%, 65%, 70%, 75%, 80%, 85%, 90%, 92%, 95%, or 97% or more homologous to at least a portion of an anti-ASGPR immunoglobulin. The immunoglobulin region may comprise an amino acid sequence that is at least about 70% homologous to at least a portion of an anti-ASGPR immunoglobulin. The immunoglobulin region may comprise an amino acid sequence that is at least about 80% homologous to at least a portion of an anti-ASGPR immunoglobulin.

The immunoglobulin region may comprise an amino acid sequence that comprises 10, 20, 30, 40, 50, 60, 70, 80, 90 or more amino acids of an anti-ASGPR immunoglobulin sequence. The immunoglobulin region may comprise an amino acid sequence that comprises 100, 200, 300, 400, 500, 600, 700, 800, 900 or more amino acids of an anti-ASGPR immunoglobulin sequence. The immunoglobulin region may comprise an amino acid sequence that comprises 50 or more amino acids of an anti-ASGPR immunoglobulin sequence. The immunoglobulin region may comprise an amino acid sequence that comprises 100 or more amino acids of an anti-ASGPR immunoglobulin sequence. The immunoglobulin region may comprise an amino acid sequence that comprises 200 or more amino acids of an anti-ASGPR immunoglobulin sequence.

The immunoglobulin region may be based on or derived from an immunoglobulin or immunoglobulin fragment that binds to at least a portion of a receptor on a lymphocyte, B-cell, macrophage, monocytes, neutrophils and/or NK cells. The receptor may be an Fc receptor. The Fc receptor may be an Fc-gamma receptor, Fc-alpha receptor and/or Fc-epsilon receptor. Fc-gamma receptors include, but are not limited to, FcγRI (CD64), FcγRIIA (CD32), FcγRIIB (CD32), FcγRIIIA (CD16a) and FcγRIIIB (CD16b). Fc-alpha receptors include, but are not limited to, FcαRI. Fc-epsilon receptors include, but are not limited to, FcεRI and FcεRII. The receptor may be CD89 (Fc fragment of IgA receptor or FCAR).

The immunoglobulin region may be based on or derived from an immunoglobulin or immunoglobulin fragment that binds at least a portion of a co-receptor on a T-cell. The co-receptor may be a CD3, CD4, and/or CD8. The immunoglobulin region may be based on or derived from an immunoglobulin fragment that binds to a CD3 co-receptor. The CD3 co-receptor may comprise CD3-gamma, CD3-delta and/or CD3-epsilon. CD8 may comprise CD8-alpha and/or CD8-beta chains.

In some embodiments, the immunoglobulin region is not specific for a mammalian target. In some embodiments, the immunoglobulin is an anti-viral immunoglobulin. In some embodiments, the immunoglobulin is an anti-bacterial immunoglobulin. In some embodiments, the immunoglobulin is an anti-parasitic immunoglobulin. In some embodiments, the immunoglobulin is an anti-fungal immunoglobulin. In some embodiments, the immunoglobulin region is derived from an immunoglobulin vaccine.

In some embodiments, the immunoglobulin region is based on or derived from immunoglobulins including, but not limited to, actoxumab, bezlotoxumab, CR6261, edobacomab, efungumab, exbivirumab, felvizumab, foravirumab, ibalizumab (TMB-355, TNX-355), libivirumab, motavizumab, nebacumab, pagibaximab, palivizumab, panobacumab, rafivirumab, raxibacumab, regavirumab, sevirumab (MSL-109), suvizumab, tefibazumab, tuvirumab, and urtoxazumab.

In some embodiments, the immunoglobulin region is based on or derived from immunoglobulins targeting *Clostridium difficile*, Orthomyxoviruses (Influenzavirus A, Influenzavirus B, Influenzavirus C, Isavirus, Thogotovirus), *Escherichia coli, Candida*, Rabies, Human Immunodeficiency Virus, Hepatitis, *Staphylococcus*, Respiratory Syncytial Virus, *Pseudomonas aeruginosa, Bacillus anthracis*, Cytomegalovirus, or *Staphylococcus aureus*.

The immunoglobulin region may be based on or derived from an anti-viral immunoglobulin. The anti-viral immunoglobulin may be directed against an epitope of a viral protein. The anti-bacterial immunoglobulin may target one or more viruses including, but not limited to, Adenoviruses, Herpesviruses, Poxviruses, Parvoviruses, Reoviruses, Picornaviruses, Togaviruses, Orthomyxoviruses, Rhabdoviruses, Retroviruses and Hepadnaviruses. The viral protein may be from a respiratory syncytial virus. The viral protein may be an F protein of the respiratory syncytiral virus. The epitope may be in the A antigenic site of the F protein. The anti-viral immunoglobulin may be based on or derived from palivizumab. The immunoglobulin may be based on or derived from an anti-viral vaccine. The anti-viral immunoglobulin may be based on or derived from exbivirumab, foravirumab, libivirumab, rafivirumab, regavirumab, sevirumab, tuvirumab, felvizumab, motavizumab, palivizumab, and/or suvizumab.

The immunoglobulin region may be based on or derived from an anti-viral immunoglobulin G. The immunoglobulin region may comprise at least a portion of an anti-viral immunoglobulin G. The immunoglobulin region may comprise an amino acid sequence that is at least about 50% homologous to at least a portion of an anti-viral immunoglobulin G. The immunoglobulin region may comprise an amino acid sequence that is at least about 60%, 65%, 70%, 75%, 80%, 85%, 90%, 92%, 95%, or 97% or more homologous to at least a portion of an anti-viral immunoglobulin G. The immunoglobulin region may comprise an amino acid sequence that is at least about 70% homologous to at least a portion of an anti-viral immunoglobulin G. The immunoglobulin region may comprise an amino acid sequence that is at least about 80% homologous to at least a portion of an anti-viral immunoglobulin G. In some embodiments the immunoglobulin region comprises an amino acid sequence based on or derived from an anti-viral immunoglobulin M.

The immunoglobulin region may comprise an amino acid sequence that comprises 10, 20, 30, 40, 50, 60, 70, 80, 90 or more amino acids of an anti-viral immunoglobulin G sequence. The immunoglobulin region may comprise an amino acid sequence that comprises 100, 200, 300, 400, 500, 600, 700, 800, 900 or more amino acids of an anti-viral immunoglobulin G sequence. The immunoglobulin region may comprise an amino acid sequence that comprises 50 or more amino acids of an anti-viral immunoglobulin G sequence. The immunoglobulin region may comprise an amino acid sequence that comprises 100 or more amino acids of an anti-viral immunoglobulin G sequence. The immunoglobulin region may comprise an amino acid sequence that comprises 200 or more amino acids of an anti-viral immunoglobulin G sequence.

The immunoglobulin region may be based on or derived from a palivizumab immunoglobulin. The immunoglobulin region may comprise at least a portion of a palivizumab immunoglobulin. The immunoglobulin region may comprise an amino acid sequence that is at least about 50% homologous to at least a portion of a palivizumab immunoglobulin. The immunoglobulin region may comprise an amino acid sequence that is at least about 60%, 65%, 70%, 75%, 80%, 85%, 90%, 92%, 95%, or 97% or more homologous to at least a portion of a palivizumab immunoglobulin. The immunoglobulin region may comprise an amino acid sequence that is at least about 70% homologous to at least a portion of a palivizumab immunoglobulin. The immunoglobulin region may comprise an amino acid sequence that is at least about 80% homologous to at least a portion of a palivizumab immunoglobulin.

The immunoglobulin region may comprise an amino acid sequence that comprises 10, 20, 30, 40, 50, 60, 70, 80, 90 or more amino acids of a palivizumab immunoglobulin sequence. The immunoglobulin region may comprise an amino acid sequence that comprises 100, 200, 300, 400, 500, 600, 700, 800, 900 or more amino acids of a palivizumab immunoglobulin sequence. The immunoglobulin region may comprise an amino acid sequence that comprises 50 or more amino acids of a palivizumab immunoglobulin sequence. The immunoglobulin region may comprise an amino acid sequence that comprises 100 or more amino acids of a palivizumab immunoglobulin sequence. The immunoglobulin region may comprise an amino acid sequence that comprises 200 or more amino acids of a palivizumab immunoglobulin sequence.

The immunoglobulin region may be based on or derived from an exbivirumab, foravirumab, libivirumab, rafivirumab, regavirumab, sevirumab, tuvirumab, felvizumab, motavizumab, palivizumab, and/or suvizumab immunoglobulin. The immunoglobulin region may comprise at least a portion of an exbivirumab, foravirumab, libivirumab, rafivirumab, regavirumab, sevirumab, tuvirumab, felvizumab, motavizumab, palivizumab, and/or suvizumab immunoglobulin. The immunoglobulin region may comprise an amino acid sequence that is at least about 50% homologous to at least a portion of an exbivirumab, foravirumab, libivirumab, rafivirumab, regavirumab, sevirumab, tuvirumab, felvizumab, motavizumab, palivizumab, and/or suvizumab immunoglobulin. The immunoglobulin region may comprise an amino acid sequence that is at least about 60%, 65%, 70%, 75%, 80%, 85%, 90%, 92%, 95%, or 97% or more homologous to at least a portion of an exbivirumab, foravirumab, libivirumab, rafivirumab, regavirumab, sevirumab, tuvirumab, felvizumab, motavizumab, palivizumab, and/or suvizumab immunoglobulin. The immunoglobulin region may comprise an amino acid sequence that is at least about 70% homologous to at least a portion of an exbivirumab, foravirumab, libivirumab, rafivirumab, regavirumab, sevirumab, tuvirumab, felvizumab, motavizumab, palivizumab, and/or suvizumab immunoglobulin. The immunoglobulin region may comprise an amino acid sequence that is at least about 80% homologous to at least a portion of an exbivirumab, foravirumab, libivirumab, rafivirumab, regavirumab, sevirumab, tuvirumab, felvizumab, motavizumab, palivizumab, and/or suvizumab immunoglobulin.

The immunoglobulin region may comprise an amino acid sequence that comprises 10, 20, 30, 40, 50, 60, 70, 80, 90 or more amino acids of an exbivirumab, foravirumab, libivirumab, rafivirumab, regavirumab, sevirumab, tuvirumab, felvizumab, motavizumab, palivizumab, and/or suvizumab immunoglobulin sequence. The immunoglobulin region may comprise an amino acid sequence that comprises 100, 200, 300, 400, 500, 600, 700, 800, 900 or more amino acids of an exbivirumab, foravirumab, libivirumab, rafivirumab, regavirumab, sevirumab, tuvirumab, felvizumab, motavizumab, palivizumab, and/or suvizumab immunoglobulin sequence. The immunoglobulin region may comprise an amino acid sequence that comprises 50 or more amino acids of an exbivirumab, foravirumab, libivirumab, rafivirumab, regavirumab, sevirumab, tuvirumab, felvizumab, motavizumab, palivizumab, and/or suvizumab immunoglobulin sequence. The immunoglobulin region may comprise an amino acid sequence that comprises 100 or more amino acids of an exbivirumab, foravirumab, libivirumab, rafivirumab, regavirumab, sevirumab, tuvirumab, felvizumab, motavizumab, palivizumab, and/or suvizumab immunoglobulin sequence. The immunoglobulin region may comprise an amino acid sequence that comprises 200 or more amino acids of an exbivirumab, foravirumab, libivirumab, rafivirumab, regavirumab, sevirumab, tuvirumab, felvizumab, motavizumab, palivizumab, and/or suvizumab immunoglobulin sequence.

The immunoglobulin region may be based on or derived from an anti-bacterial immunoglobulin. The anti-bacterial immunoglobulin may be directed against an epitope of a bacterial protein. The anti-bacterial immunoglobulin may target bacteria including, but not limited to, *Acetobacter aurantius, Agrobacterium radiobacter, Anaplasma phagocytophilum, Azorhizobium caulinodans, Bacillus anthracis, Bacillus brevis, Bacillus cereus, Bacillus subtilis, Bacteroides fragilis, Bacteroides gingivalis, Bacteroides melaninogenicus, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacterjejuni, Campylobacter pylori, Chlamydia trachomatis, Chlamydophila pneumoniae, Chlamydophila psittaci, Clostridium botulinum, Clostridium difficile, Corynebacterium diphtheriae, Corynebacterium fusiforme, Coxiella burnetii, Enterobacter cloacae, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus influenzae, Haemophilus parainfluenzae, Haemophilus pertussis, Haemophilus vaginalis, Helicobacter pylori, Klebsiella pneumoniae, Lactobacillus acidophilus, Lactococcus lactis, Legionella pneumophila, Listeria monocytogenes, Methanobacterium extroquens, Microbacterium multiforme, Micrococcus luteus, Moraxella catarrhalis, Mycobacterium phlei, Mycobacterium smegmatis, Mycobacterium tuberculosis, Mycoplasma genitalium, Mycoplasma hominis, Mycoplasma pneumonie, Neisseria gonorrhoeae, Neisseria meningitidis, Pasteurella multocida, Pasteurella tularensis, Peptostreptococcus, Porphyromonas gingivalis, Prevotella melaninogenica, Pseudomonas aeruginosa, Rhizobium radiobacter, Rickettsia rickettsii, Rothia dentocariosa, Salmonella enteritidis, Salmonella typhi, Salmonella typhimurium, Shigella dysenteriae, Staphylococcus aureus, Staphylococcus epidermidis, Stenotrophomonas maltophilia, Streptococcus pneumoniae, Streptococcus pyogenes, Treponema pallidum, Treponema denticola, Vibrio cholerae, Vibrio comma, Vibrio parahaemolyticus, Vibrio vulnificus, Yersinia enterocolitica* and *Yersinia pseudotuberculosis*. The immunoglobulin may be based on or derived from a bacterial vaccine. The anti-viral immunoglobulin may be based on or derived from nebacumab, panobacumab, raxibacumab, edobacomab, pagibaximab, and/or tefibazumab.

The immunoglobulin region may be based on or derived from an anti-bacterial immunoglobulin G. The immunoglobulin region may comprise at least a portion of an anti-bacterial immunoglobulin G. The immunoglobulin region may comprise an amino acid sequence that is at least about 50% homologous to at least a portion of an anti-bacterial immunoglobulin G. The immunoglobulin region may comprise an amino acid sequence that is at least about 60%, 65%, 70%, 75%, 80%, 85%, 90%, 92%, 95%, or 97% or more homologous to at least a portion of an anti-bacterial immunoglobulin G. The immunoglobulin region may comprise an amino acid sequence that is at least about 70% homologous to at least a portion of an anti-bacterial immunoglobulin G. The immunoglobulin region may comprise an amino acid sequence that is at least about 80% homologous to at least a portion of an anti-bacterial immunoglobulin G.

In some embodiments the immunoglobulin region comprises an amino acid sequence based on or derived from an anti-viral immunoglobulin M.

The immunoglobulin region may comprise an amino acid sequence that comprises 10, 20, 30, 40, 50, 60, 70, 80, 90 or more amino acids of an anti-bacterial immunoglobulin G sequence. The immunoglobulin region may comprise an amino acid sequence that comprises 100, 200, 300, 400, 500, 600, 700, 800, 900 or more amino acids of an anti-bacterial immunoglobulin G sequence. The immunoglobulin region may comprise an amino acid sequence that comprises 50 or more amino acids of an anti-bacterial immunoglobulin G sequence. The immunoglobulin region may comprise an amino acid sequence that comprises 100 or more amino acids of an anti-bacterial immunoglobulin G sequence. The immunoglobulin region may comprise an amino acid sequence that comprises 200 or more amino acids of an anti-bacterial immunoglobulin G sequence.

The immunoglobulin region may be based on or derived from a Nebacumab, Panobacumab, Raxibacumab, Edobacomab, Pagibaximab, and/or Tefibazumab immunoglobulin. The immunoglobulin region may comprise at least a portion of a nebacumab, panobacumab, raxibacumab, edobacomab, pagibaximab, and/or tefibazumab immunoglobulin. The immunoglobulin region may comprise an amino acid sequence that is at least about 50% homologous to at least a portion of a nebacumab, panobacumab, raxibacumab, edobacomab, pagibaximab, and/or tefibazumab immunoglobulin. The immunoglobulin region may comprise an amino acid sequence that is at least about 60%, 65%, 70%, 75%, 80%, 85%, 90%, 92%, 95%, or 97% or more homologous to at least a portion of a nebacumab, panobacumab, raxibacumab, edobacomab, pagibaximab, and/or tefibazumab immunoglobulin. The immunoglobulin region may comprise an amino acid sequence that is at least about 70% homologous to at least a portion of a nebacumab, panobacumab, raxibacumab, edobacomab, pagibaximab, and/or tefibazumab immunoglobulin. The immunoglobulin region may comprise an amino acid sequence that is at least about 80% homologous to at least a portion of a nebacumab, panobacumab, raxibacumab, edobacomab, pagibaximab, and/or tefibazumab immunoglobulin.

The immunoglobulin region may comprise an amino acid sequence that comprises 10, 20, 30, 40, 50, 60, 70, 80, 90 or more amino acids of a nebacumab, panobacumab, raxibacumab, edobacomab, pagibaximab, and/or tefibazumab immunoglobulin sequence. The immunoglobulin region may comprise an amino acid sequence that comprises 100, 200, 300, 400, 500, 600, 700, 800, 900 or more amino acids of a nebacumab, panobacumab, raxibacumab, edobacomab, pagibaximab, and/or tefibazumab immunoglobulin sequence. The immunoglobulin region may comprise an amino acid sequence that comprises 50 or more amino acids of a nebacumab, panobacumab, raxibacumab, edobacomab, pagibaximab, and/or tefibazumab immunoglobulin sequence. The immunoglobulin region may comprise an amino acid sequence that comprises 100 or more amino acids of a nebacumab, panobacumab, raxibacumab, edobacomab, pagibaximab, and/or tefibazumab immunoglobulin sequence. The immunoglobulin region may comprise an amino acid sequence that comprises 200 or more amino acids of a nebacumab, panobacumab, raxibacumab, edobacomab, pagibaximab, and/or tefibazumab immunoglobulin sequence.

The immunoglobulin region may be based on or derived from an anti-parasitic immunoglobulin. The anti-parasitic immunoglobulin may be directed against an epitope of a parasite protein. The anti-parasitic immunoglobulin may target parasites or parasite proteins including, but not limited to parasites *Acanthamoeba, Balamuthia mandrillaris, Babesia* (*B. divergens, B. bigemina, B. equi, B. microfti, B. duncani*), *Balantidium coli, Blastocystis, Cryptosporidium, Dientamoeba fragilis, Entamoeba histolytica, Giardia lamblia, Isospora belli, Leishmania, Naegleria fowleri, Plasmodium falciparum, Plasmodium vivax, Plasmodium ovale curtisi, Plasmodium ovale wallikeri, Plasmodium malariae, Plasmodium knowlesi, Rhinosporidium seeberi, Sarcocystis bovihominis, Sarcocystis suihominis, Toxoplasma gondii, Trichomonas vaginalis, Trypanosoma brucei, Trypanosoma cruzi, Cestoda, Taenia multiceps, Diphyllobothrium latum, Echinococcus granulosus, Echinococcus multilocularis, Echinococcus vogeli, Echinococcus oligarthrus, Hymenolepis nana, Hymenolepis diminuta, Taenia saginata, Taenia solium, Bertiella mucronata, Bertiella studeri, Spirometra erinaceieuropaei, Clonorchis sinensis; Clonorchis viverrini, Dicrocoelium dendriticum, Fasciola hepatica, Fasciola gigantica, Fasciolopsis buski, Gnathostoma spinigerum, Gnathostoma hispidum, Metagonimus yokogawai, Opisthorchis viverrini, Opisthorchis felineus, Clonorchis sinensis, Paragonimus westermani; Paragonimus africanus; Paragonimus caliensis; Paragonimus kellicotti; Paragonimus skrjabini; Paragonimus uterobilateralis, Schistosoma* sp., *Schistosoma mansoni, Schistosoma haematobium, Schistosoma japonicum, Schistosoma mekongi, Echinostoma echinatum, Trichobilharzia regenti, Schistosoma tidae, Ancylostoma duodenale, Necator americanus, Angiostrongylus costaricensis, Anisakis, Ascaris* sp. *Ascaris lumbricoides, Baylisascaris procyonis, Brugia malayi, Brugia timori, Dioctophyme renale, Dracunculus medinensis, Enterobius vermicularis, Enterobius gregorii, Halicephalobus gingivalis, Loa filaria, Mansonella streptocerca, Onchocerca volvulus, Strongyloides stercoralis, Thelazia californiensis, Thelazia callipaeda, Toxocara canis, Toxocara cati, Trichinella spiralis, Trichinella britovi, Trichinella nelsoni, Trichinella nativa, Trichuris trichiura, Trichuris vulpis, Wuchereria bancrofti, Archiacantho cephala, Moniliformis moniliformis, Linguatula serrata, Oestroidea, Calliphoridae, Sarcophagidae, Tunga penetrans, Dermatobia hominis, Ixodidae, Argasidae, Cimex lectularius, Pediculus humanus, Pediculus humanus corporis, Pthirus pubis, Demodex folliculorum/brevis/canis, Sarcoptes scabiei, Cochliomyia hominivorax*, and *Pulex irritans*.

The immunoglobulin region may be based on or derived from an anti-parasitic immunoglobulin G. The immunoglobulin region may comprise at least a portion of an anti-parasitic immunoglobulin G. The immunoglobulin region may comprise an amino acid sequence that is at least about 50% homologous to at least a portion of an anti-parasitic immunoglobulin G. The immunoglobulin region may comprise an amino acid sequence that is at least about 60%, 65%, 70%, 75%, 80%, 85%, 90%, 92%, 95%, or 97% or more homologous to at least a portion of an anti-parasitic immunoglobulin G. The immunoglobulin region may comprise an amino acid sequence that is at least about 70% homologous to at least a portion of an anti-parasitic immunoglobulin G. The immunoglobulin region may comprise an amino acid sequence that is at least about 80% homologous to at least a portion of an anti-parasitic immunoglobulin G. In some embodiments the immunoglobulin region comprises an amino acid sequence based on or derived from an anti-parasitic immunoglobulin M.

The immunoglobulin region may comprise an amino acid sequence that comprises 10, 20, 30, 40, 50, 60, 70, 80, 90 or more amino acids of an anti-parasitic immunoglobulin G sequence. The immunoglobulin region may comprise an amino acid sequence that comprises 100, 200, 300, 400, 500, 600, 700, 800, 900 or more amino acids of an anti-parasitic immunoglobulin G sequence. The immunoglobulin region may comprise an amino acid sequence that comprises 50 or more amino acids of an anti-parasitic immunoglobulin G sequence. The immunoglobulin region may comprise an amino acid sequence that comprises 100 or more amino acids of an anti-parasitic immunoglobulin G sequence. The immunoglobulin region may comprise an amino acid sequence that comprises 200 or more amino acids of an anti-parasitic immunoglobulin G sequence.

The immunoglobulin region may be based on or derived from an anti-fungal immunoglobulin. The anti-bacterial immunoglobulin may be directed against an epitope of a fungal protein. The anti-fungal immunoglobulin may target fungi or fungal proteins including, but not limited to *Cryptococcus neoformans, Cryptococcus gattii, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Schizosaccharomyces pombe, Saccharomyces cerevisiae, Brettanomyces bruxellensis, Candida stellata, Schizosaccharomyces pombe, Torulaspora delbrueckii, Zygosaccharomyces bailii, Yarrowia lipolytica, Saccharomyces exiguus* and *Pichia pastoris*. The anti-fungal immunoglobulin may be based on or derived from efungumab.

The immunoglobulin region may be based on or derived from an anti-fungal immunoglobulin G. The immunoglobulin region may comprise at least a portion of an anti-fungal immunoglobulin G. The immunoglobulin region may comprise an amino acid sequence that is at least about 50% homologous to at least a portion of an anti-fungal immunoglobulin G. The immunoglobulin region may comprise an amino acid sequence that is at least about 60%, 65%, 70%, 75%, 80%, 85%, 90%, 92%, 95%, or 97% or more homologous to at least a portion of an anti-fungal immunoglobulin G. The immunoglobulin region may comprise an amino acid sequence that is at least about 70% homologous to at least a portion of an anti-fungal immunoglobulin G. The immunoglobulin region may comprise an amino acid sequence that is at least about 80% homologous to at least a portion of an anti-fungal immunoglobulin G. In some embodiments the immunoglobulin region comprises an amino acid sequence based on or derived from an anti-fungal immunoglobulin M.

The immunoglobulin region may comprise an amino acid sequence that comprises 10, 20, 30, 40, 50, 60, 70, 80, 90 or more amino acids of an anti-fungal immunoglobulin G sequence. The immunoglobulin region may comprise an amino acid sequence that comprises 100, 200, 300, 400, 500, 600, 700, 800, 900 or more amino acids of an anti-fungal immunoglobulin G sequence. The immunoglobulin region may comprise an amino acid sequence that comprises 50 or more amino acids of an anti-fungal immunoglobulin G sequence. The immunoglobulin region may comprise an amino acid sequence that comprises 100 or more amino acids of an anti-fungal immunoglobulin G sequence. The immunoglobulin region may comprise an amino acid sequence that comprises 200 or more amino acids of an anti-fungal immunoglobulin G sequence.

The immunoglobulin region may be based on or derived from an efungumab immunoglobulin. The immunoglobulin region may comprise at least a portion of an efungumab immunoglobulin. The immunoglobulin region may comprise an amino acid sequence that is at least about 50% homologous to at least a portion of an efungumab immunoglobulin. The immunoglobulin region may comprise an amino acid sequence that is at least about 60%, 65%, 70%, 75%, 80%, 85%, 90%, 92%, 95%, or 97% or more homologous to at least a portion of an efungumab immunoglobulin. The immunoglobulin region may comprise an amino acid sequence that is at least about 70% homologous to at least a portion of an efungumab immunoglobulin. The immunoglobulin region may comprise an amino acid sequence that is at least about 80% homologous to at least a portion of an efungumab immunoglobulin.

The immunoglobulin region may comprise an amino acid sequence that comprises 10, 20, 30, 40, 50, 60, 70, 80, 90 or more amino acids of an efungumab immunoglobulin sequence. The immunoglobulin region may comprise an amino acid sequence that comprises 100, 200, 300, 400, 500, 600, 700, 800, 900 or more amino acids of an efungumab immunoglobulin sequence. The immunoglobulin region may comprise an amino acid sequence that comprises 50 or more amino acids of an efungumab immunoglobulin sequence. The immunoglobulin region may comprise an amino acid sequence that comprises 100 or more amino acids of an efungumab immunoglobulin sequence. The immunoglobulin region may comprise an amino acid sequence that comprises 200 or more amino acids of an efungumab immunoglobulin sequence.

The immunoglobulin region may be based on or derived from a trastuzumab immunoglobulin G immunoglobulin. The immunoglobulin region may comprise at least a portion of a trastuzumab immunoglobulin G immunoglobulin. The immunoglobulin region may comprise an amino acid sequence that is at least about 50% homologous to at least a portion of a trastuzumab immunoglobulin G immunoglobulin. The immunoglobulin region may comprise an amino acid sequence that is at least about 60%, 65%, 70%, 75%, 80%, 85%, 90%, 92%, 95%, or 97% or more homologous to at least a portion of a trastuzumab immunoglobulin G immunoglobulin. The immunoglobulin region may comprise an amino acid sequence that is at least about 70% homologous to at least a portion of a trastuzumab immunoglobulin G immunoglobulin. The immunoglobulin region may comprise an amino acid sequence that is at least about 80% homologous to at least a portion of a trastuzumab immunoglobulin G immunoglobulin.

The immunoglobulin region may comprise an amino acid sequence that comprises 10, 20, 30, 40, 50, 60, 70, 80, 90 or more amino acids of a trastuzumab immunoglobulin G immunoglobulin sequence. The immunoglobulin region may comprise an amino acid sequence that comprises 100, 200, 300, 400, 500, 600, 700, 800, 900 or more amino acids of a trastuzumab immunoglobulin G immunoglobulin sequence. The immunoglobulin region may comprise an amino acid sequence that comprises 50 or more amino acids of a trastuzumab immunoglobulin G immunoglobulin sequence. The immunoglobulin region may comprise an amino acid sequence that comprises 100 or more amino acids of a trastuzumab immunoglobulin G immunoglobulin sequence. The immunoglobulin region may comprise an amino acid sequence that comprises 200 or more amino acids of a trastuzumab immunoglobulin G immunoglobulin sequence.

The immunoglobulin region may be based on or derived from an anti-Her2 immunoglobulin. The immunoglobulin region may comprise at least a portion of an anti-Her2 immunoglobulin. The immunoglobulin region may comprise an amino acid sequence that is at least about 50% homologous to at least a portion of an anti-Her2 immunoglobulin. The immunoglobulin region may comprise an amino acid sequence that is at least about 60%, 65%, 70%, 75%, 80%, 85%, 90%, 92%, 95%, or 97% or more homologous to at least a portion of an anti-Her2 immunoglobulin. The immunoglobulin region may comprise an amino acid sequence that is at least about 70% homologous to at least a portion of an anti-Her2 immunoglobulin. The immunoglobulin region may comprise an amino acid sequence that is at least about 80% homologous to at least a portion of an anti-Her2 immunoglobulin.

The immunoglobulin region may comprise an amino acid sequence that comprises 10, 20, 30, 40, 50, 60, 70, 80, 90 or more amino acids of an anti-Her2 immunoglobulin sequence. The immunoglobulin region may comprise an amino acid sequence that comprises 100, 200, 300, 400, 500, 600, 700, 800, 900 or more amino acids of an anti-Her2 immunoglobulin sequence. The immunoglobulin region may comprise an amino acid sequence that comprises 50 or more amino acids of an anti-Her2 immunoglobulin sequence. The immunoglobulin region may comprise an amino acid sequence that comprises 100 or more amino acids of an anti-Her2 immunoglobulin sequence. The immunoglobulin region may comprise an amino acid sequence that comprises 200 or more amino acids of an anti-Her2 immunoglobulin sequence.

The immunoglobulin region may be based on or derived from an anti-CD47 immunoglobulin. The immunoglobulin region may comprise at least a portion of an anti-CD47 immunoglobulin. The immunoglobulin region may comprise an amino acid sequence that is at least about 50% homologous to at least a portion of an anti-CD47 immunoglobulin. The immunoglobulin region may comprise an amino acid sequence that is at least about 60%, 65%, 70%, 75%, 80%, 85%, 90%, 92%, 95%, or 97% or more homologous to at least a portion of an anti-CD47 immunoglobulin. The immunoglobulin region may comprise an amino acid sequence that is at least about 70% homologous to at least a portion of an anti-CD47 immunoglobulin. The immunoglobulin region may comprise an amino acid sequence that is at least about 80% homologous to at least a portion of an anti-CD47 immunoglobulin.

The immunoglobulin region may comprise an amino acid sequence that comprises 10, 20, 30, 40, 50, 60, 70, 80, 90 or more amino acids of an anti-CD47 immunoglobulin sequence. The immunoglobulin region may comprise an amino acid sequence that comprises 100, 200, 300, 400, 500, 600, 700, 800, 900 or more amino acids of an anti-CD47 immunoglobulin sequence. The immunoglobulin region may comprise an amino acid sequence that comprises 50 or more amino acids of an anti-CD47 immunoglobulin sequence. The immunoglobulin region may comprise an amino acid sequence that comprises 100 or more amino acids of an anti-CD47 immunoglobulin sequence. The immunoglobulin region may comprise an amino acid sequence that comprises 200 or more amino acids of an anti-CD47 immunoglobulin sequence.

The immunoglobulin region may be based on or derived from an anti-cancer immunoglobulin. Examples of anti-cancer immunoglobulin include, but are not limited to, abciximab, adalimumab, alemtuzumab, basiliximab, belimumab, bevacizumab, brentuximab, canakinumab, certolizumab, cetuximab, daclizumab, denosumab, eculizumab, efalizumab, gemtuzumab, golimumab, ibritumomab, infliximab, ipilimumab, muromonab-cd3, natalizumab, ofatumumab, omalizumab, palivizumab, panitumumab, ranibizumab, rituximab, tocilizumab, tositumomab, trastuzumab.

The immunoglobulin region may comprise at least a portion of a human immunoglobulin. The immunoglobulin region may comprise at least a portion of a humanized immunoglobulin. The immunoglobulin region may comprise at least a portion of a chimeric immunoglobulin. The immunoglobulin region may be based on or derived from a human immunoglobulin. The immunoglobulin region may be based on or derived from a humanized immunoglobulin. The immunoglobulin region may be based on or derived from a chimeric immunoglobulin. The immunoglobulin region may be based on or derived from a monoclonal immunoglobulin. The immunoglobulin region may be based on or derived from a polyclonal immunoglobulin. The immunoglobulin region may comprise at least a portion of an immunoglobulin from a mammal, avian, reptile, amphibian, or a combination thereof. The mammal may be a human. The mammal may be a non-human primate. The mammal may be a dog, cat, sheep, goat, cow, rabbit, or mouse.

The immunoglobulin region may comprise a sequence based on or derived from one or more immunoglobulin and/or immunoglobulin fragment sequences. The immunoglobulin region may comprise a sequence that is at least about 50%, 55%, 60%, 65%, 70%, 75%, 80%, 85%, 90%, 92%, 95%, 97%, 98%, 99% or more homologous to a sequence based on or derived from one or more immunoglobulin and/or immunoglobulin fragments. The immunoglobulin region may comprise a sequence that is at least about 70% homologous to a sequence based on or derived from one or more immunoglobulin and/or immunoglobulin fragments. The immunoglobulin region may comprise a sequence that is at least about 80% homologous to a sequence based on or derived from one or more immunoglobulin and/or immunoglobulin fragments. The immunoglobulin region may comprise a sequence that is at least about 90% homologous to a sequence based on or derived from one or more immunoglobulin and/or immunoglobulin fragments. The immunoglobulin region may comprise a sequence that is at least about 95% homologous to a sequence based on or derived from one or more immunoglobulin and/or immunoglobulin fragments. The sequence may be a peptide sequence. The sequence may be a nucleic acid sequence.

The immunoglobulin region may comprise a peptide sequence that differs from a peptide sequence based on or derived from one or more immunoglobulin and/or immunoglobulin fragments by less than or equal to about 200, 150, 100, 90, 80, 70, 60, 50, 40, 30, 20, 17, 15, 12, 10, 8, 6, 5, 4 or fewer amino acids. The immunoglobulin region may comprise a peptide sequence that differs from a peptide sequence based on or derived from one or more immunoglobulin and/or immunoglobulin fragments by less than or equal to about 4 or fewer amino acids. The immunoglobulin region may comprise a peptide sequence that differs from a peptide sequence based on or derived from one or more immunoglobulin and/or immunoglobulin fragments by less than or equal to about 3 or fewer amino acids. The immunoglobulin region may comprise a peptide sequence that differs from a peptide sequence based on or derived from one or more immunoglobulin and/or immunoglobulin fragments by less than or equal to about 2 or fewer amino acids. The immunoglobulin region may comprise a peptide sequence that differs from a peptide sequence based on or derived from one or more immunoglobulin and/or immunoglobulin fragments by less than or equal to about 1 or fewer amino acids. The amino acids may be consecutive, nonconsecutive, or a combination thereof. For example, the immunoglobulin region may comprise a peptide sequence that differs from a peptide sequence based on or derived from one or more immunoglobulin and/or immunoglobulin fragments by less than about 3 consecutive amino acids. Alternatively, or additionally, the immunoglobulin region may comprise a peptide sequence that differs from a peptide sequence based on or derived from one or more immunoglobulin and/or immunoglobulin fragments by less than about 2 non-consecutive amino acids. In another example, the immunoglobulin region may comprise a peptide sequence that differs from a peptide sequence based on or derived from one or more immunoglobulin and/or immunoglobulin fragments by less than about 5 amino acids, wherein 2 of the amino acids are consecutive and 2 of the amino acids are non-consecutive.

The immunoglobulin region may comprise a nucleic acid sequence that differs from a nucleic acid sequence based on or derived from one or more antibodies and/or immunoglobulin fragments by less than or equal to about 500, 400, 300, 200, 100, 90, 80, 70, 60, 50, 40, 30, 25, 20, 19, 18, 17, 16, 15, 14, 13, 12, 11, 10, 9, 8, 7, 6, 5, 4 or fewer nucleotides or base pairs. The immunoglobulin region may comprise a nucleic acid sequence that differs from a nucleic acid sequence based on or derived from one or more immunoglobulin and/or immunoglobulin fragments by less than or equal to about 15 or fewer nucleotides or base pairs. The immunoglobulin region may comprise a nucleic acid sequence that differs from a nucleic acid sequence based on or derived from one or more immunoglobulin and/or immunoglobulin fragments by less than or equal to about 12 or fewer nucleotides or base pairs. The immunoglobulin region may comprise a nucleic acid sequence that differs from a nucleic acid sequence based on or derived from one or more immunoglobulin and/or immunoglobulin fragments by less than or equal to about 9 or fewer nucleotides or base pairs. The immunoglobulin region may comprise a nucleic acid sequence that differs from a nucleic acid sequence based on or derived from one or more immunoglobulin and/or immunoglobulin fragments by less than or equal to about 6 or fewer nucleotides or base pairs. The immunoglobulin region may comprise a nucleic acid sequence that differs from a nucleic acid sequence based on or derived from one or more immunoglobulin and/or immunoglobulin fragments by less than or equal to about 4 or fewer nucleotides or base pairs. The immunoglobulin region may comprise a nucleic acid sequence that differs from a nucleic acid sequence based on or derived from one or more immunoglobulin and/or immunoglobulin fragments by less than or equal to about 3 or fewer nucleotides or base pairs. The immunoglobulin region may comprise a nucleic acid sequence that differs from a nucleic acid sequence based on or derived from one or more immunoglobulin and/or immunoglobulin fragments by less than or equal to about 2 or fewer nucleotides or base pairs. The immunoglobulin region may comprise a nucleic acid sequence that differs from a nucleic acid sequence based on or derived from one or more immunoglobulin and/or immunoglobulin fragments by less than or equal to about 1 or fewer nucleotides or base pairs. The nucleotides or base pairs may be consecutive, nonconsecutive, or a combination thereof. For example, the immunoglobulin region may comprise a nucleic acid sequence that differs from a nucleic acid sequence based on or derived from one or more immunoglobulin and/or immunoglobulin fragments by less than about 3 consecutive nucleotides or base pairs. Alternatively, or additionally, the immunoglobulin region may comprise a nucleic acid sequence that differs from a nucleic acid sequence based on or derived from one or more immunoglobulin and/or immunoglobulin fragments by less than about 2 non-consecutive nucleotides or base pairs. In another example, the immunoglobulin region may comprise a nucleic acid sequence that differs from a nucleic acid sequence based on or derived from one or more immunoglobulin and/or immunoglobulin fragments by less than about 5 nucleotides or base pairs, wherein 2 of the nucleotides or base pairs are consecutive and 2 of the nucleotides or base pairs are non-consecutive.

The peptide sequence of the immunoglobulin region may differ from the peptide sequence of the immunoglobulin or immunoglobulin fragment that it is based on and/or derived from by one or more amino acid substitutions. The peptide sequence of the immunoglobulin region may differ from the peptide sequence of the immunoglobulin or immunoglobulin fragment that it is based on and/or derived from by two or more amino acid substitutions. The peptide sequence of the immunoglobulin region may differ from the peptide sequence of the immunoglobulin or immunoglobulin fragment that it is based on and/or derived from by three or more amino acid substitutions. The peptide sequence of the immunoglobulin region may differ from the peptide sequence of the immunoglobulin or immunoglobulin fragment that it is based on and/or derived from by four or more amino acid substitutions. The peptide sequence of the immunoglobulin region may differ from the peptide sequence of the immunoglobulin or immunoglobulin fragment that it is based on and/or derived from by five or more amino acid substitutions. The peptide sequence of the immunoglobulin region may differ from the peptide sequence of the immunoglobulin or immunoglobulin fragment that it is based on and/or derived from by six or more amino acid substitutions. The peptide sequence of the immunoglobulin region may differ from the peptide sequence of the immunoglobulin or immunoglobulin fragment that it is based on and/or derived from by 1, 2, 3, 4, 5, 6, 7, 8, 9, 10, 12, 14, 15, 17, 20, 25 or more amino acid substitutions. The peptide sequence of the immunoglobulin region may differ from the peptide sequence of the immunoglobulin or immunoglobulin fragment that it is based on and/or derived from by about 20-30, 30-40, 40-50, 50-60, 60-70, 80-90, 90-100, 100-150, 150-200, 200-300 or more amino acid substitutions.

The nucleic acid sequence of the immunoglobulin region may differ from the nucleic acid sequence of the immunoglobulin or immunoglobulin fragment that it is based on and/or derived from by one or more nucleotide and/or base pair substitutions. The nucleic acid sequence of the immunoglobulin region may differ from the nucleic acid sequence of the immunoglobulin or immunoglobulin fragment that it is based on and/or derived from by two or more nucleotide and/or base pair substitutions. The nucleic acid sequence of the immunoglobulin region may differ from the nucleic acid sequence of the immunoglobulin or immunoglobulin fragment that it is based on and/or derived from by three or more nucleotide and/or base pair substitutions. The nucleic acid sequence of the immunoglobulin region may differ from the nucleic acid sequence of the immunoglobulin or immunoglobulin fragment that it is based on and/or derived from by four or more nucleotide and/or base pair substitutions. The nucleic acid sequence of the immunoglobulin region may differ from the nucleic acid sequence of the immunoglobulin or immunoglobulin fragment that it is based on and/or derived from by five or more nucleotide and/or base pair substitutions. The nucleic acid sequence of the immunoglobulin region may differ from the nucleic acid sequence of the immunoglobulin or immunoglobulin fragment that it is based on and/or derived from by six or more nucleotide and/or base pair substitutions. The nucleic acid sequence of the immunoglobulin region may differ from the nucleic acid sequence of the immunoglobulin or immunoglobulin fragment that it is based on and/or derived from by nine or more nucleotide and/or base pair substitutions. The nucleic acid sequence of the immunoglobulin region may differ from the nucleic acid sequence of the immunoglobulin or immunoglobulin fragment that it is based on and/or derived from by twelve or more nucleotide and/or base pair substitutions. The nucleic acid sequence of the immunoglobulin region may differ from the nucleic acid sequence of the immunoglobulin or immunoglobulin fragment that it is based on and/or derived from by fifteen or more nucleotide and/or base pair substitutions. The nucleic acid sequence of the immunoglobulin region may differ from the nucleic acid sequence of the immunoglobulin or immunoglobulin fragment that it is based on and/or derived from by eighteen or more nucleotide and/or base pair substitutions. The nucleic acid sequence of the immunoglobulin region may differ from the nucleic acid sequence of the immunoglobulin or immunoglobulin fragment that it is based on and/or derived from by 20, 22, 24, 25, 27, 30 or more nucleotide and/or base pair substitutions. The nucleic acid sequence of the immunoglobulin region may differ from the nucleic acid sequence of the immunoglobulin or immunoglobulin fragment that it is based on and/or derived from by about 30-40, 40-50, 50-60, 60-70, 70-80, 80-90, 90-100, 100-200, 200-300, 300-400 or more nucleotide and/or base pair substitutions.

The immunoglobulin region may comprise at least about 10, 20, 30, 40, 50, 60, 70, 80, 90, 100 or more amino acids. The immunoglobulin region may comprise at least about 125, 150, 175, 200, 225, 250, 275, 300, 325, 350, 375, 400, 425, 450, 475, 500, 525, 550, 575, 600, 625, 650, 675, 700 or more amino acids. The immunoglobulin region may comprise at least about 100 amino acids. The immunoglobulin region may comprise at least about 200 amino acids. The immunoglobulin region may comprise at least about 400 amino acids. The immunoglobulin region may comprise at least about 500 amino acids. The immunoglobulin region may comprise at least about 600 amino acids.

The immunoglobulin region may comprise less than about 2000, 1900, 1800, 1700, 1600, 1500, 1400, 1300, 1200 or 1100 amino acids. The immunoglobulin region may comprise less than about 1000, 950, 900, 850, 800, 750, or 700 amino acids. The immunoglobulin region may comprise less than about 1500 amino acids. The immunoglobulin region may comprise less than about 1000 amino acids. The immunoglobulin region may comprise less than about 800 amino acids. The immunoglobulin region may comprise less than about 700 amino acids.

The immunoglobulin fusion protein may further comprise an immunoglobulin region comprising 30 or fewer consecutive amino acids of a complementarity determining region 3 (CDR3). The immunoglobulin region may comprise 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 or fewer consecutive amino acids of a CDR3. The immunoglobulin region may comprise 15 or fewer consecutive amino acids of a CDR3. The immunoglobulin region may comprise 14 or fewer consecutive amino acids of a CDR3. The immunoglobulin region may comprise 13 or fewer consecutive amino acids of a CDR3. The immunoglobulin region may comprise 12 or fewer consecutive amino acids of a CDR3. The immunoglobulin region may comprise 11 or fewer consecutive amino acids of a CDR3. The immunoglobulin region may comprise 10 or fewer consecutive amino acids of a CDR3. The immunoglobulin region may comprise 9 or fewer consecutive amino acids of a CDR3. The immunoglobulin region may comprise 8 or fewer consecutive amino acids of a CDR3. The immunoglobulin region may comprise 7 or fewer consecutive amino acids of a CDR3. The immunoglobulin region may comprise 6 or fewer consecutive amino acids of a CDR3. The immunoglobulin region may comprise 5 or fewer consecutive amino acids of a CDR3. The immunoglobulin region may comprise 4 or fewer consecutive amino acids of a CDR3. The immunoglobulin region may comprise 3 or fewer consecutive amino acids of a CDR3. The immunoglobulin region may comprise 2 or fewer consecutive amino acids of a CDR3. The immunoglobulin region may comprise 1 or fewer consecutive amino acids of a CDR3. In some instances, the immunoglobulin region does not contain a CDR3.

The immunoglobulin region may comprise an amino acid sequence that is based on or derived from any one of SEQ ID NOS: 29-56, 155, 156, 167. The immunoglobulin region may comprise an amino acid sequence that is at least about 50% homologous to any one of SEQ ID NOS: 29-56, 155, 156, 167. The immunoglobulin region may comprise an amino acid sequence that is at least about 60%, 65%, 70%, 75%, 80%, 85%, 90%, 95%, or 97% homologous to any one of SEQ ID NOs 29-56, 155, 156, 167. The immunoglobulin region may comprise an amino acid sequence that is at least about 70% homologous to any one of SEQ ID NOS: 29-56, 155, 156, 167. The immunoglobulin region may comprise an amino acid sequence that is at least about 80% homologous to any one of SEQ ID NOS: 29-56, 155, 156, 167. The immunoglobulin region may comprise an amino acid sequence that is at least about 50% identical to any one of SEQ ID NOS: 29-56, 155, 156, 167. The immunoglobulin region may comprise an amino acid sequence that is at least about 60%, 65%, 70%, 75%, 80%, 85%, 90%, 95%, or 97% identical to any one of SEQ ID NOs 29-56, 155, 156, 167. The immunoglobulin region may comprise an amino acid sequence that is at least about 70% identical to any one of SEQ ID NOS: 29-56, 155, 156, 167. The immunoglobulin region may comprise an amino acid sequence that is at least about 80% identical to any one of SEQ ID NOS: 29-56, 155, 156, 167. The immunoglobulin region may comprise an amino acid sequence that is 100% identical to any one of SEQ ID NOS: 29-56, 155, 156, 167. In some embodiments, the immunoglobulin region comprises an amino acid sequence that is at least about 50%, 55%, 60%, 65%, 70%, 75%, 80%, 85%, 90%, 95%, or 97% homologous to an amino acid sequence of any one of SEQ ID NOS: 29-56, 155, 156, 167. In some embodiments, the immunoglobulin region comprises an amino acid sequence that is at least about 50%, 55%, 60%, 65%, 70%, 75%, 80%, 85%, 90%, 95%, or 97% identical to an amino acid sequence of any one of SEQ ID NOS: 29-56, 155, 156, 167. The immunoglobulin region includes a Fab region that is based on or derived from a sequence from any one of SEQ ID NOS: 29-56, 155, 156, 167. In some embodiments, the immunoglobulin region comprises an amino acid Fab sequence derived from a sequence that is at least about 70%, 80%, 80%, 90%, 95% or 100% to any one of SEQ ID NOS: 29-56, 155, 156, 167.

The immunoglobulin region may comprise an amino acid sequence comprising 10, 20, 30, 40, 50, 60, 70, 80, 90, 100 or more amino acids based on or derived from any one of SEQ ID NOS: 29-56, 155, 156, 167. The immunoglobulin region may comprise an amino acid sequence comprising 125, 150, 175, 200 or more amino acids based on or derived from any one of SEQ ID NOS: 29-56, 155, 156, 167. The immunoglobulin region may comprise an amino acid sequence comprising 10 or more amino acids based on or derived from any one of SEQ ID NOS: 29-56, 155, 156, 167.

The immunoglobulin region may comprise an amino acid sequence comprising 50 or more amino acids based on or derived from any one of SEQ ID NOS: 29-56, 155, 156, 167. The immunoglobulin region may comprise an amino acid sequence comprising 100 or more amino acids based on or derived from any one of SEQ ID NOS: 29-56, 155, 156, 167. The immunoglobulin region may comprise an amino acid sequence comprising 200 or more amino acids based on or derived from any one of SEQ ID NOS: 29-56, 155, 156, 167. The amino acids may be consecutive. Alternatively, or additionally, the amino acids are nonconsecutive. In some embodiments, the immunoglobulin region comprises amino acids derived from 1, 2, 3, or 4 of SEQ ID NOS: 29-56, 155, 156, 167.

The immunoglobulin region may be encoded by a nucleic acid sequence that is based on or derived from any one of SEQ ID NOS: 1-28, 166. The immunoglobulin region may be encoded by a nucleic acid sequence that is at least about 50% homologous to any one of SEQ ID NOS: 1-28, 166. The immunoglobulin region may be encoded by a nucleic acid sequence that is at least about 60%, 65%, 70%, 75%, 80%, 85%, 90%, 95%, or 97% homologous to any one of SEQ ID NOS: 1-28, 166. The immunoglobulin region may be encoded by a nucleic acid sequence that is at least about 70% homologous to any one of SEQ ID NOS: 1-28, 166. The immunoglobulin region may be encoded by a nucleic acid sequence that is at least about 80% homologous to any one of SEQ ID NOS: 1-28, 166. The immunoglobulin region may be encoded by a nucleic acid sequence that is at least about 50% identical to any one of SEQ ID NOS: 1-28, 166. The immunoglobulin region may be encoded by a nucleic acid sequence that is at least about 60%, 65%, 70%, 75%, 80%, 85%, 90%, 95%, or 97% identical to any one of SEQ ID NOS: 1-28, 166. The immunoglobulin region may be encoded by a nucleic acid sequence that is at least about 70% identical to any one of SEQ ID NOS: 1-28, 166. The immunoglobulin region may be encoded by a nucleic acid sequence that is at least about 80% identical to any one of SEQ ID NOS: 1-28, 166. The immunoglobulin region may be encoded by a nucleic acid sequence that is 100% identical to any one of SEQ ID NOS: 1-28, 166. The immunoglobulin region includes a Fab region that is based on or derived from a sequence from any one of SEQ ID NOS: 1-28, 166. In some embodiments, the immunoglobulin region comprises an amino acid Fab sequence derived from a sequence that is at least about 70%, 80%, 80%, 90%, 95% or 100% to any one of SEQ ID NOS: 1-28, 166.

The immunoglobulin region may be encoded by a nucleic acid sequence comprising 10, 20, 30, 40, 50, 60, 70, 80, 90, 100 or more nucleotides based on or derived from any one of SEQ ID NOS: 1-28, 166. The immunoglobulin region may be encoded by a nucleic acid sequence comprising 125, 150, 175, 200, 225, 250, 275, 300, 325, 350, 375, 400, 425, 450, 475, 450, 500 or more nucleotides based on or derived from any one of SEQ ID NOS: 1-28, 166. The immunoglobulin region may be encoded by a nucleic acid sequence comprising 100 or more nucleotides based on or derived from any one of SEQ ID NOS: 1-28, 166. The immunoglobulin region may be encoded by a nucleic acid sequence comprising 500 or more nucleotides based on or derived from any one of SEQ ID NOS: 1-28, 166. The nucleotides may be consecutive. In some embodiments, the immunoglobulin region is encoded by a nucleic acid sequence derived from 1, 2, 3, or 4 of SEQ ID NOS: 1-28, 166.

Therapeutic Peptide

In one aspect of the disclosure, provided herein are immunoglobulin fusion proteins comprising an insulin therapeutic peptide and an immunoglobulin region. The immunoglobulin fusion proteins may comprise two or more therapeutic peptides. The immunoglobulin fusion proteins disclosed herein may comprise 3, 4, 5, or more therapeutic peptides. The therapeutic peptide may be attached to an immunoglobulin region via a linker. In some embodiments, one or more additional therapeutic peptides are attached to the first or a second immunoglobulin region. The one or more therapeutic peptides may be attached to one or more immunoglobulin regions. The two or more therapeutic peptides may be attached to two or more immunoglobulin regions. The two or more therapeutic peptides may be attached to one or more immunoglobulin chains. The two or more therapeutic peptides may be attached to two or more immunoglobulin chains. The two or more therapeutic peptides may be attached to one or more units within the one or more immunoglobulin regions. The two or therapeutic peptides may be attached to two or more units within the one or more immunoglobulin regions. In some embodiments, the therapeutic peptide is connected to the immunoglobulin region without the aid of a linker.

In one embodiment, the linker comprises from about 0 to about 50 amino acids. In one embodiment, the linker comprises from about 1 to about 50 amino acids. In one embodiment, the linker comprises from about 1 to about 20 amino acids, or about 0, 1, 2, 3, 4, 5, 6, 7, 8, 9, 10, 11, 12, 13, 14, 15, 16, 17, 18, 19 or 20 amino acids. In one embodiment, the amino acids of the linker do not form a regular secondary structure. In one embodiment, the linker comprises an amino acid sequence that is about or at least about 50%, 60%, 70%, 80%, 85%, 86%, 87%, 88%, 89%, 90%, 91%, 92%, 93%, 94%, 95%, 96%, 97%, 98%, 99%, or 100% identical to an amino acid sequence of any one of SEQ ID NOS: 63-69. In one embodiment, the linker comprises 1, 2, 3, 4 or more glycine residues.

The immunoglobulin fusion proteins disclosed herein may comprise one or more therapeutic agents. The therapeutic agent may be a peptide. The therapeutic agent may be a small molecule. The immunoglobulin fusion proteins disclosed herein may comprise two or more therapeutic agents. The immunoglobulin fusion proteins disclosed herein may comprise 3, 4, 5, 6 or more therapeutic agents. The two or more therapeutic agents may be the same. The two or more therapeutic agents may be different.

The therapeutic peptide may comprise any secondary structure, for example alpha helix or beta strand or comprise no regular secondary structure. The therapeutic peptide may comprise amino acids with one or more modifications including, but not limited to, myristoylation, palmitoylation, isoprenylation, glypiation, lipoylation, acylation, acetylation, aklylation, methylation, glycosylation, malonylation, hydroxylation, iodination, nucleotide addition, oxidation, phosphorylation, adenylylation, propionylation, succinylation, sulfation, selenoylation, biotinylation, pegylation, deimination, deamidation, eliminylation, and carbamylation. The therapeutic peptide may comprise one or more amino acids conjugated to one or more small molecules, for example a drug. In some embodiments, the therapeutic peptide comprises one or more non-natural amino acids. In some embodiments, the therapeutic peptide comprises 1, 2, 3, 4, 5, 6, 7, 8, 9, 10, 11, 12, 13, 14, 15, 16, 17, 18, 19, 20, 30, 40, 50 or more non-natural amino acids. In some embodiments, the therapeutic peptide comprises one or more amino acids substitutions. In some embodiments, the therapeutic peptide comprises 1, 2, 3, 4, 5, 6, 7, 8, 9, 10, 11, 12, 13, 14, 15, 16, 17, 18, 19, 20, 30, 40, 50 or more amino acid substitutions.

The therapeutic peptide may be inserted into the immunoglobulin region. Insertion of the therapeutic peptide into the immunoglobulin region may comprise removal or deletion of a portion of the immunoglobulin from which the immunoglobulin region is based on or derived from. The therapeutic peptide may replace at least a portion of a heavy chain. The therapeutic peptide may replace at least a portion of a light chain. The therapeutic peptide may replace at least a portion of a variable domain. The therapeutic peptide may replace at least a portion of a constant domain. The therapeutic peptide may replace at least a portion of a complementarity determining region (CDR). The therapeutic peptide may replace at least a portion of a CDR1. The therapeutic peptide may replace at least a portion of a CDR2. The therapeutic peptide may replace at least a portion of a CDR3. The therapeutic peptide may replace at least about 5%, 10%, 15%, 20%, 25%, 30%, 35%, 40%, 45%, 50%, 55%, 60%, 65%, 70%, 75%, 80%, 85%, 90%, 95%, or more of the immunoglobulin or a portion thereof. For example, the therapeutic peptide may replace at least about 50% of a variable domain. The therapeutic peptide may replace at least about 70% of a variable domain. The therapeutic peptide may replace at least about 80% of a variable domain. The therapeutic peptide may replace at least about 90% of a variable domain. The therapeutic peptide may replace at least about 95% of a variable domain. For example, the therapeutic peptide may replace at least about 50% of an amino terminus of an immunoglobulin region. The therapeutic peptide may replace at least about 70% of an amino terminus of an immunoglobulin region. The therapeutic peptide may replace at least about 80% of an amino terminus of an immunoglobulin region. The therapeutic peptide may replace at least about 90% of an amino terminus of an immunoglobulin region. The therapeutic peptide may replace at least about 95% of an amino terminus of an immunoglobulin region. The therapeutic peptide may replace at least about 50% of a CDR. The therapeutic peptide may replace at least about 70% of a CDR. The therapeutic peptide may replace at least about 80% of a CDR. The therapeutic peptide may replace at least about 90% of a CDR. The therapeutic peptide may replace at least about 95% of a CDR.

In some embodiments, one or more regions of the insulin therapeutic peptide is configured to treat diabetes and/or diabetes related conditions. In some embodiments, 2, 3, 4, 5 or more regions of the therapeutic peptide are configured to treat diabetes and/or diabetes related conditions. Diabetes may include, type I diabetes, type 2 diabetes, gestational diabetes, and prediabetes. In some embodiments, one or more regions of the therapeutic peptide is configured to treat obesity and/or obesity related conditions. In some embodiments, 2, 3, 4, 5 or more regions of the therapeutic peptide are configured to treat obesity and/or obesity related conditions. Conditions may include complications and diseases. Examples of diabetes related conditions include, but are not limited to, diabetic retinopathy, diabetic nephropathy, diabetic heart disease, diabetic foot disorders, diabetic neuropathy, macrovascular disease, diabetic cardiomyopathy, infection and diabetic ketoacidosis. Diabetic neuropathy may include, but is not limited to symmetric polyneuropathy, autonomic neuropathy, radiculopathy, cranial neuropathy, and mononeuropathy. Obesity related conditions include, but are not limited to, heart disease, stroke, high blood pressure, diabetes, osteoarthritis, gout, sleep apnea, asthma, gallbladder disease, gallstones, abnormal blood fats (e.g., abnormal levels of LDL and HDL cholesterol), obesity hypoventilation syndrome, reproductive problems, hepatic steatosis, and mental health conditions.

Insulin immunoglobulin fusion proteins described herein comprise an insulin therapeutic peptide. In some cases, the insulin therapeutic peptide comprises a single amino acid chain having the formula: B-C-A (SEQ ID NO: 182) or A-C-B (SEQ ID NO: 183); wherein B comprises SEQ ID NO: 157 (FVNQHLCGS$X_A$LVEALYLVCGERGFFYT$X_B$$X_C$T); A comprises SEQ ID NO 158: GIVEQCC$X_D$SICSLYQLENYCN; and C comprises a connecting peptide having between 3 and 50 amino acids; and wherein $X_A$, $X_B$, $X_C$ and $X_D$ are independently selected from a naturally or non-naturally occurring amino acid. In some cases, $X_A$ is D or H. In some cases, $X_A$ is D. In some cases, $X_A$ is H. In some cases, $X_B$ is D or P. In some cases, $X_B$ is D. In some cases, $X_B$ is P. In some cases, $X_C$ is P or K. In some cases, $X_C$ is P. In some cases, $X_C$ is K. In some cases, $X_D$ is H or T. In some cases, $X_D$ is H. In some cases, $X_D$ is T. The connecting peptide may comprise an amino acid sequence comprising at least 50% glycine amino acids. The connecting peptide may comprise SEQ ID NO: 159 (GGG$X_1$$X_2$), wherein $X_1$ and $X_2$ are independently selected from a naturally or non-naturally occurring amino acid. In some cases, $X_1$ is P, G or S. In some cases, $X_1$ is P. In some cases, $X_1$ is G. In some cases, $X_1$ is S. In some cases, $X_2$ is R, S, G or K. In some cases, $X_2$ is R. In some cases, $X_2$ is S. In some cases, $X_2$ is G. In some cases, $X_2$ is K. C may comprise a protease cleavage site. As a non-limiting example, RKKR (SEQ ID NO: 184). The insulin therapeutic peptide may comprise an amino acid sequence selected from SEQ ID NOS: 111, 113, 116, 118, 119-140. The insulin therapeutic peptide may comprise an amino acid sequence at least 90% identical to any one of SEQ ID NOS: 111, 113, 116, 118, 119-140.

The insulin therapeutic peptide may comprise a single amino acid chain having the formula B-C-A or A-C-B; wherein B comprises an amino acid sequence having no more than 5, 4, 3, 2 or 1 amino acid differences from SEQ ID NO: 160 (FVNQHLCGSHLVEALYLVCGERGFFYT); A comprises an amino acid sequence having no more than 5, 4, 3, 2 or 1 amino acid differences from SEQ ID NO: 161 (GIVEQCCTSICSLYQLENYC); and C comprises a connecting peptide having between 3 and 50 amino acids. In some cases, B comprises SEQ ID NO: 160. In some cases, A comprises SEQ ID NO: 161. In some cases, the connecting peptide comprises an amino acid sequence having at least 50% glycine amino acids. In some cases, the connecting peptide comprises SEQ ID NO: 159 (GGG$X_1$$X_2$), wherein $X_1$ and $X_2$ are independently selected from a naturally or non-naturally occurring amino acid. In some cases, $X_1$ is P, G or S. In some cases, $X_1$ is P. In some cases, $X_1$ is G. In some cases, $X_1$ is S. In some cases, $X_2$ is R, S, G or K. In some cases, $X_2$ is R. In some cases, $X_2$ is S. In some cases, $X_2$ is G. In some cases, $X_2$ is K. C may comprise a protease cleavage site. As a non-limiting example, RKKR (SEQ ID NO: 184).

The insulin therapeutic peptide may comprise an A peptide comprising SEQ ID NO: 158 (GIVEQCC$X_D$SICSLYQLENYCN), wherein $X_D$ is a naturally or non-naturally occurring amino acid. In some cases, $X_D$ is selected from H and T. In some cases, $X_D$ is H. In some cases, $X_D$ is T. In some cases, one or more cysteine amino acids of the A peptide is present in a disulfide bond with a cysteine amino acid of a B peptide. In some cases, the B peptide comprises SEQ ID NO: 157 (FVNQHLCGS$X_A$LVEALYLVCGERGFFYT$X_B$$X_C$T); and $X_A$, $X_B$, and $X_C$ are independently selected from a naturally or non-naturally occurring amino acid. In some cases, $X_A$ is D or H. In some cases, $X_A$ is D. In some cases, $X_A$ is H. In some cases, $X_B$ is D or P. In some cases, $X_B$ is D. In some cases, $X_B$ is P. In some cases, $X_C$ is P or K. In some cases, $X_C$ is P. In some cases, $X_C$ is K. In some cases, the B peptide comprises an amino acid sequence having no more than 5, 4, 3, 2 or 1 amino acid differences from SEQ ID NO: 160 (FVNQHLCGSHLVEALYLVCGERGFFYT). In some cases, B comprises SEQ ID NO: 160. In some cases, the insulin therapeutic peptide comprises an A peptide comprising an amino acid sequence having no more than 5, 4, 3, 2 or 1 amino acid differences from SEQ ID NO: 161 (GIVEQCCTSICSLYQLENYC). In some cases, the A peptide comprises SEQ ID NO: 161. In some cases, one or more cysteine amino acids of the A peptide is present in a disulfide bond with a cysteine amino acid of a B peptide.

The insulin therapeutic peptide may comprise an A peptide comprising an amino acid sequence having no more than 5, 4, 3, 2 or 1 amino acid differences from SEQ ID NO: 161 (GIVEQCCTSICSLYQLENYC). In some cases, the A peptide comprises SEQ ID NO: 161. In some cases, one or more cysteine amino acids of the A peptide is present in a disulfide bond with a cysteine amino acid of a B peptide. In some cases, the B peptide comprises SEQ ID NO: 157 (FVNQHLCGS$X_A$LVEALYLVCGERGFFYT$X_B X_C$T); and $X_A$, $X_B$, and $X_C$ are independently selected from a naturally or non-naturally occurring amino acid. In some cases, $X_A$ is D or H. In some cases, $X_A$ is D. In some cases, $X_A$ is H. In some cases, $X_B$ is D or P. In some cases, $X_B$ is D. In some cases, $X_B$ is P. In some cases, $X_C$ is P or K. In some cases, $X_C$ is P. In some cases, $X_C$ is K. In some cases, the B peptide comprises an amino acid sequence having no more than 5, 4, 3, 2 or 1 amino acid differences from SEQ ID NO: 160 (FVNQHLCGSHLVEALYLVCGERGFFYT). In some cases the insulin immunoglobulin fusion protein of claim 93, wherein B comprises SEQ ID NO: 160.

In some embodiments, amino acids of the therapeutic peptide, in whole or in part, are based on or derived from any one of SEQ ID NOS: 109-140, 157, 158, 160, 161. The therapeutic peptide may comprise an amino acid sequence that is at least about 50% homologous to any one of SEQ ID NOS: 109-140, 157, 158, 160, 161. The therapeutic peptide may comprise an amino acid sequence that is at least about 60%, 65%, 70%, 75%, 80%, 85%, 90%, 95%, or 97% homologous to any one of SEQ ID NOS: 109-140, 157, 158, 160, 161. The therapeutic peptide may comprise an amino acid sequence that is at least about 70% homologous to any one of SEQ ID NOS: 109-140, 157, 158, 160, 161. The therapeutic peptide may comprise an amino acid sequence that is at least about 80% homologous to any one of SEQ ID NOS: 109-140, 157, 158, 160, 161. The therapeutic peptide may comprise an amino acid sequence that is at least about 50% identical to any one of SEQ ID NOS: 109-140, 157, 158, 160, 161. The therapeutic peptide may comprise an amino acid sequence that is at least about 60%, 65%, 70%, 75%, 80%, 85%, 90%, 95%, or 97% identical to any one of SEQ ID NOS: 109-140, 157, 158, 160, 161. The therapeutic peptide may comprise an amino acid sequence that is at least about 70% identical to any one of SEQ ID NOS: 109-140, 157, 158, 160, 161. The therapeutic peptide may comprise an amino acid sequence that is at least about 80% identical to any one of SEQ ID NOS: 109-140, 157, 158, 160, 161. The therapeutic peptide may comprise an amino acid sequence that is 100% identical to any one of SEQ ID NOS: 109-140, 157, 158, 160, 161. In some embodiments, the therapeutic peptide comprises an amino acid sequence that is at least about 50%, 55%, 60%, 65%, 70%, 75%, 80%, 85%, 90%, 95%, or 97% homologous to an amino acid sequence of any one of SEQ ID NOS: 109-140, 157, 158, 160, 161. In some embodiments, the therapeutic peptide comprises an amino acid sequence that is at least about 50%, 55%, 60%, 65%, 70%, 75%, 80%, 85%, 90%, 95%, or 97% identical to an amino acid sequence of any one of SEQ ID NOS: 109-140, 157, 158, 160, 161. In some embodiments, the therapeutic peptide comprises an amino acid sequence that is 100% identical to an amino acid sequence of any one of SEQ ID NOS: 109-140, 157, 158, 160, 161.

The therapeutic peptide may comprise an amino acid sequence comprising 10, 20, 30, 40, 50, 60 or more amino acids based on or derived from any one of SEQ ID NOS: 109-140, 157, 158, 160, 161. The therapeutic peptide may comprise an amino acid sequence comprising 10 or more amino acids based on or derived from any one of SEQ ID NOS: 109-140, 157, 158, 160, 161. The therapeutic peptide may comprise an amino acid sequence comprising 50 or more amino acids based on or derived from any one of SEQ ID NOS: 109-140, 157, 158, 160, 161. The amino acids may be consecutive. Alternatively, or additionally, the amino acids are nonconsecutive. For example, one or more amino acid sequences are connected by a connecting peptide and/or a disulfide bond. In some embodiments, the therapeutic peptide comprises amino acids derived from 1, 2, 3, or 4 of SEQ ID NOS: 109-140, 157, 158, 160, 161.

The therapeutic peptide may comprise a protease cleavage site. The protease cleavage site may be inserted within the therapeutic peptide. In some embodiments, the therapeutic peptide comprises a first therapeutic peptide region and a second therapeutic peptide region. In some embodiments, the therapeutic peptide comprises a protease cleavage site disposed between the first therapeutic peptide region and the second therapeutic peptide region. In some embodiments, the first therapeutic peptide region and the second therapeutic peptide region are derived from the same protein or set of amino acid sequences. In some embodiments, the first therapeutic peptide region and the second therapeutic peptide regions are derived from different proteins or sets of amino acid sequences. The one or more protease cleavage sites may be attached to the N-terminus, C-terminus or both the N- and C-termini of a region of a therapeutic peptide.

The therapeutic peptide may comprise one or more connecting peptides. The therapeutic peptide may comprise two or more connecting peptides. The therapeutic peptide may comprise 3, 4, 5, 6, 7 or more connecting peptides. The connecting peptides may be different. The connecting peptides may be the same. The one or more connecting peptides may be attached to the N-terminus, C-terminus or both the N- and C-termini of a region of a therapeutic peptide. The connecting peptide may be inserted within the therapeutic peptide. In some embodiments, the therapeutic peptide comprises a first therapeutic peptide region and a second therapeutic peptide region. In some embodiments, the therapeutic peptide comprises a connecting peptide disposed between the first therapeutic peptide region and the second therapeutic peptide region. In some embodiments, the first therapeutic peptide region and the second therapeutic peptide region are derived from the same protein or set of amino acid sequences. In some embodiments, the first therapeutic peptide region and the second therapeutic peptide regions are derived from different proteins or sets of amino acid sequences. In some embodiments, the connecting peptide is derived from and/or comprises an amino acid sequence of any of SEQ ID NOS: 148-154. In some embodiments, the connecting peptide comprises amino acids having repeating sequences. In some embodiments, the connecting peptide has 2, 3, 4, 5, 6, 7, 8, 9, 10 or more repeating sequences. In some embodiments, the connecting peptide is low immunogenic. In some embodiments, the connecting peptide is biodegradable. In some cases, the connecting peptide comprises at least 3, 4, 5 or more glycine residues. In some cases, the at least 3, 4, 5 or more glycine residues are repeated in the connecting peptide sequence. In some embodiments, the connecting peptide comprises GGGS (SEQ ID NO: 185).

In some embodiments, an insulin therapeutic peptide comprises a connecting peptide comprising an amino acid sequence comprising at least 50% glycine amino acids. In some cases, the connecting peptide comprises SEQ ID NO: 159 ($GGGX_1X_2$), wherein $X_1$ and $X_2$ are independently selected from a naturally or non-naturally occurring amino acid. In some cases, $X_1$ is P, G or S. In some cases, $X_1$ is P. In some cases, $X_1$ is G. In some cases, $X_1$ is S. In some cases, $X_2$ is R, S, G or K. In some cases, $X_2$ is R. In some cases, $X_2$ is S. In some cases, $X_2$ is G. In some cases, $X_2$ is K. In some cases, the connecting peptide comprises a protease cleavage site. As a non-limiting example, a RKKR cleavage site (SEQ ID NO: 184).

Proteolytic Cleavage Site

The immunoglobulin fusion proteins disclosed herein may further comprise one or more proteolytic cleavage sites. The immunoglobulin fusion proteins disclosed herein may further comprise 2 or more proteolytic cleavage sites. The immunoglobulin fusion proteins disclosed herein may further comprise 3 or more proteolytic cleavage sites. The immunoglobulin fusion proteins disclosed herein may further comprise 4, 5, 6, 7 or more proteolytic cleavage sites. The therapeutic peptides disclosed herein may further comprise one or more proteolytic cleavage sites.

The one or more proteolytic cleavage sites may be attached to the N-terminus, C-terminus or both N- and C-termini of a therapeutic peptide. The one or more proteolytic cleavage sites may attached to the N-terminus, C-terminus or both N- and C-termini of the extender peptide. The one or more proteolytic cleavage sites may attached to the N-terminus, C-terminus or both N- and C-termini of a linker. The one or more proteolytic cleavage sites may attached to the N-terminus, C-terminus or both N- and C-termini of a connecting peptide. The one or more proteolytic cleavage sites may attached to the N-terminus, C-terminus or both N- and C-termini of a linker. The one or more proteolytic cleavage sites may be attached to a therapeutic peptide, connecting peptide, linker, immunoglobulin region, or a combination thereof.

In some embodiments, the proteolytic cleavage site is located within the amino acid sequence of the therapeutic peptide, connecting peptide, linker, immunoglobulin region, or a combination thereof. The therapeutic peptide may comprise one or more proteolytic cleavage sites within its amino acid sequence.

Two or more proteolytic cleavage sites may surround a therapeutic peptide, connecting peptide, linker, immunoglobulin region, or combination thereof. Digestion of the proteolytic cleavage site may result in release of a peptide fragment located between the two or more proteolytic cleavage sites. For example, the proteolytic cleavage sites may flank a therapeutic peptide-linker peptide. Digestion of the proteolytic cleavage sites may result in release of the therapeutic peptide-linker.

The proteolytic cleavage site may be recognized by one or more proteases. The one or more proteases may be a serine protease, threonine protease, cysteine protease, aspartate protease, glutamic protease, metalloprotease, exopeptidases, endopeptidases, or a combination thereof. The proteases may be selected from the group comprising Factor VII or Factor Xa. Additional examples of proteases include, but are not limited to, aminopeptidases, carboxypeptidases, trypsin, chymotrypsin, pepsin, papain, and elastase. The protease may be a proprotein convertase (PC). In some cases, the protease is PC2. In some embodiments, the protease recognizes the amino acid sequence KR. In some embodiments, the protease recognizes the amino acid sequence RKKR (SEQ ID NO: 184).

In some embodiments, a genetic construct encoding an immunoglobulin fusion protein comprises a nucleic acid sequence encoding a protease cleavage site. In some cases, the protease cleavage site is cleaved after expression in vivo, wherein an endogenous protease and/or a protease co-expressed with the fusion protein cleaves the fusion protein at the cleavage site. In some cases, the protease cleavage site is RKKR (SEQ ID NO: 184) and a protease co-expressed with the fusion protein cleaves at the carboxyl terminus of the site. In some cases, the protease cleavage site is RKKR (SEQ ID NO: 184) and an endogenous protease cleaves at the amino terminus of the site.

Vectors, Host Cells and Recombinant Methods

Immunoglobulin fusion proteins, as disclosed herein, may be expressed and purified by known recombinant and protein purification methods. In some instances, the activity of the immunoglobulin fusion protein is affected by expression and/or purification methods. For example, the activity of an immunoglobulin fusion protein configured for use as a therapeutic, is enhanced or attenuated based on the identity of the expression vector, identity of the recombinant host, identity of the cell line, expression reaction conditions, purification methods, protein processing, or any combination thereof. Expression reaction conditions include, but are not limited to, temperature, % $CO_2$, media, expression time, cofactors, and chaperones. Purification methods include, but are not limited to, purification temperatures, chromatography resins, protease inhibitors, and buffer compositions.

Immunoglobulin fusion proteins, as disclosed herein, may be expressed by recombinant methods. Generally, a nucleic acid encoding an immunoglobulin fusion protein may be isolated and inserted into a replicable vector for further cloning (amplification of the DNA) or for expression. DNA encoding the immunoglobulin fusion protein may be prepared by PCR amplification and sequenced using conventional procedures (e.g., by using oligonucleotide probes that are capable of binding specifically to nucleotides encoding Immunoglobulin fusion proteins). In an exemplary embodiment, nucleic acid encoding an immunoglobulin fusion protein is PCR amplified, restriction enzyme digested and gel purified. The digested nucleic acid may be inserted into a replicable vector. The replicable vector containing the digested immunoglobulin fusion protein insertion may be transformed or transduced into a host cell for further cloning (amplification of the DNA) or for expression. Host cells may be prokaryotic or eukaryotic cells.

Polynucleic acid sequences encoding polypeptide components (e.g., immunoglobulin region, extender peptide, therapeutic peptide) of the immunoglobulin fusion proteins may be obtained by PCR amplification. Polynucleic acid sequences may be isolated and sequenced from cells containing nucleic acids encoding the polypeptide components. Alternatively, or additionally, polynucleotides may be synthesized using nucleotide synthesizer or PCR techniques. Once obtained, sequences encoding the polypeptide components may be inserted into a recombinant vector capable of replicating and expressing heterologous polynucleotides in prokaryotic and/or eukaryotic hosts.

In addition, phage vectors containing replicon and control sequences that are compatible with the host microorganism may be used as transforming vectors in connection with these hosts. For example, bacteriophage such as XGEM™-11 may be utilized in making a recombinant vector which may be used to transform susceptible host cells such as *E. coli* LE392.

Immunoglobulin fusion proteins may be expressed intracellularly (e.g., cytoplasm) or extracellularly (e.g., secretion). For extracellular expression, the vector may comprise a secretion signal which enables translocation of the immunoglobulin fusion proteins to the outside of the cell.

Suitable host cells for cloning or expression of immunoglobulin fusion proteins-encoding vectors include prokaryotic or eukaryotic cells. The host cell may be a eukaryotic. Examples of eukaryotic cells include, but are not limited to, Human Embryonic Kidney (HEK) cell, Chinese Hamster Ovary (CHO) cell, fungi, yeasts, invertebrate cells (e.g., plant cells and insect cells), lymphoid cell (e.g., YO, NSO, Sp20 cell). Other examples of suitable mammalian host cell lines are monkey kidney CV1 line transformed by SV40 (COS-7); baby hamster kidney cells (BHK); mouse sertoli cells; monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells; MRC 5 cells; and FS4 cells. The host cell may be a prokaryotic cell (e.g., *E. coli*).

Host cells may be transformed with vectors containing nucleotides encoding an immunoglobulin fusion proteins. Transformed host cells may be cultured in media. The media may be supplemented with one or more agents for inducing promoters, selecting transformants, or amplifying or expressing the genes encoding the desired sequences. Methods for transforming host cells are known in the art and may include electroporation, calcium chloride, or polyethylene glycol/DMSO.

Alternatively, host cells may be transfected or transduced with vectors containing nucleotides encoding an immunoglobulin fusion proteins. Transfected or transduced host cells may be cultured in media. The media may be supplemented with one or more agents for inducing promoters, selecting transfected or transduced cells, or expressing genes encoding the desired sequences.

The expressed immunoglobulin fusion proteins may be secreted into and recovered from the periplasm of the host cells or transported into the culture media. Protein recovery from the periplasm may involve disrupting the host cell. Disruption of the host cell may comprise osmotic shock, sonication or lysis. Centrifugation or filtration may be used to remove cell debris or whole cells. The immunoglobulin fusion proteins may be further purified, for example, by affinity resin chromatography.

Alternatively, immunoglobulin fusion proteins that are secreted into the culture media may be isolated therein. Cells may be removed from the culture and the culture supernatant being filtered and concentrated for further purification of the proteins produced. The expressed polypeptides may be further isolated and identified using commonly known methods such as polyacrylamide gel electrophoresis (PAGE) and Western blot assay.

Immunoglobulin fusion proteins production may be conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (a preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described herein. Cells may be grown for shorter periods prior to induction. Cells are usually induced for about 12-50 hours, although longer or shorter induction time may be used.

To improve the production yield and quality of the immunoglobulin fusion proteins disclosed herein, various fermentation conditions may be modified. For example, to improve the proper assembly and folding of the secreted immunoglobulin fusion proteins polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) may be used to co-transform the host prokaryotic cells. The chaperone proteins have been demonstrated to facilitate the proper folding and solubility of heterologous proteins produced in bacterial host cells.

To minimize proteolysis of expressed heterologous proteins (especially those that are proteolytically sensitive), certain host strains deficient for proteolytic enzymes may be used for the present disclosure. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available.

Standard protein purification methods known in the art may be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, hydroxylapatite chromatography, gel electrophoresis, dialysis, and affinity chromatography and gel filtration using, for example, Sephadex G-75.

Immunoglobulin fusion proteins may be concentrated using a commercially available protein concentration filter, for example, an Amicon or Millipore Pellicon® ultrafiltration unit.

Protease inhibitors or protease inhibitor cocktails may be included in any of the foregoing steps to inhibit proteolysis of the immunoglobulin fusion proteins.

In some cases, an immunoglobulin fusion protein may not be biologically active upon isolation. Various methods for "refolding" or converting a polypeptide to its tertiary structure and generating disulfide linkages, may be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, and 2-mercaptoethanol(bME)/di-thio-b(ME). In many instances, a cosolvent may be used to increase the efficiency of the refolding, and common reagents used for this purpose include glycerol, polyethylene glycol of various molecular weights, arginine and the like.

Compositions and Combinations

Disclosed herein are compositions comprising an immunoglobulin fusion protein and/or component of an immunoglobulin fusion protein. In some cases, a composition comprises an immunoglobulin fusion protein and an additional therapeutic agent. Compositions may comprise 1, 2, 3, 4, 5 or more immunoglobulin fusion proteins and/or additional therapeutic agents. Immunoglobulin fusion proteins of the composition may comprise different immunoglobulin regions, linkers, therapeutic peptides or a combination thereof. Further disclosed herein are combinations of an immunoglobulin fusion protein and an additional therapeutic agent, wherein the additional therapeutic agent is formulated separately from the insulin immunoglobulin fusion protein. In such cases, the immunoglobulin fusion protein may be administered together or separately from the additional therapeutic agent. In a non-limiting example, the additional therapeutic agent is insulin, for instance, an insulin having at least about 80%, 85%, 90%, 95% or 100% identity to an insulin selected from any one of SEQ ID NOS: 109-140, 157, 158, 160 and 161. The additional insulin may not be part of a molecule that targets the insulin to the liver.

The compositions, immunoglobulin fusion proteins, and additional therapeutic agents may comprise one or more pharmaceutically acceptable salts, excipients or vehicles. Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. Pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer may be about pH 7-8.5. Additional pharmaceutical agents are set forth in Remington's Pharmaceutical Sciences, 18th Edition, A. R. Gennaro, ed., Mack Publishing Company, 1990.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

The compositions, immunoglobulin fusion proteins, and additional therapeutic agents may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; the MONAQUAT™ series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions, immunoglobulin fusion proteins, and additional therapeutic agents described herein may be formulated for controlled or sustained delivery in a manner that provides local concentration of the product (e.g., bolus, depot effect) and/or increased stability or half-life in a particular local environment. The compositions, immunoglobulin fusion proteins, and additional therapeutic agents may be formulated with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then may be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents. See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which may be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This may be determined by routine screening in animal models of the target disorder or, if such models are unavailable, in normal animals.

Compositions, immunoglobulin fusion proteins, and additional therapeutic agents may be microencapsulated.

Compositions, immunoglobulin fusion proteins, and additional therapeutic agents may be suitable for parenteral administration. Exemplary compositions, immunoglobulin fusion proteins, and additional therapeutic agents are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, intralesional, intravascular, intrathecal, intravitreal, infusion, or local), topical, oral, or nasal routes. A parenteral formulation typically will be a sterile, pyrogen-free, isotonic aqueous solution, optionally containing pharmaceutically acceptable preservatives.

Formulations suitable for intramuscular, subcutaneous, peritumoral, or intravenous injection can include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, a fusion protein or additional agent can be optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. The pharmaceutical compositions, immunoglobulin fusion proteins, and additional therapeutic agents described herein can be in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

Alternatively or additionally, compositions, immunoglobulin fusion proteins, and additional therapeutic agents may be administered locally via implantation into the affected area of a membrane, sponge, or other appropriate material on to which an immunoglobulin fusion protein disclosed herein has been absorbed or encapsulated. Where an implantation device is used, the device may be implanted into any suitable tissue or organ, and delivery of an immunoglobulin fusion protein, nucleic acid, or vector disclosed herein may be directly through the device via bolus, or via continuous administration, or via catheter using continuous infusion.

Compositions comprising an immunoglobulin fusion protein and/or additional therapeutic agent disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 μm to 5 μm; however, larger particles may be used, for example, if each particle is fairly porous.

Immunoglobulin fusion proteins or additional therapeutic agents such as insulin may be delivered using an insulin pump, whereby a device periodically dispenses small amounts of therapeutic agent(s) according to a preprogrammed profile set to insulin needs. The pump may dispense a bolus amount of the therapeutic agent(s), for example, during or after a meal. The pump may also dispense the therapeutic agent(s) according to response to measured glucose levels. Exemplary pumps include those marketed by Medtronic (the MiniMed), Animas Corporation, Disetronic, and Dana.

Immunoglobulin fusion proteins or additional therapeutic agents such as insulin may be delivered using a transdermal patch. In some cases, the therapeutic agent(s) are formulated as lipophilic emulsions or buffered aqueous solutions, dissolved and/or dispersed in a polymer or an adhesive. Such patches are constructed for continuous, pulsatile, or on demand delivery of therapeutic agents. In some cases, transdermal delivery is accomplished by means of iontophoretic patches and the like. In some cases, transdermal patches provide controlled delivery. The rate of absorption can be slowed by using rate-controlling membranes or by trapping a therapeutic agent within a polymer matrix or gel. Conversely, absorption enhancers can be used to increase absorption. An absorption enhancer or carrier includes absorbable pharmaceutically acceptable solvents to assist passage through the skin. In some cases, transdermal devices are in the form of a bandage comprising a backing member, a reservoir containing active agents and optional carriers, a rate controlling barrier to deliver the agents to the skin of the subject at a controlled and predetermined rate over a prolonged period of time, and adhesives to secure the device to the skin.

Certain formulations comprising an immunoglobulin fusion protein and/or additional therapeutic agent disclosed herein may be administered orally. Formulations administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also may be employed.

Another preparation may involve an effective quantity of an immunoglobulin fusion protein and/or additional therapeutic agent in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size.

Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

"Pharmaceutically acceptable" may refer to approved or approvable by a regulatory agency of the Federal or a state government or listed in the U.S. Pharmacopeia or other generally recognized pharmacopeia for use in animals, including humans.

"Pharmaceutically acceptable salt" may refer to a salt of a compound that is pharmaceutically acceptable and that possesses the desired pharmacological activity of the parent compound.

"Pharmaceutically acceptable excipient, carrier or adjuvant" may refer to an excipient, carrier or adjuvant that may be administered to a subject, together with at least one immunoglobulin of the present disclosure, and which does not destroy the pharmacological activity thereof and is nontoxic when administered in doses sufficient to deliver a therapeutic amount of the compound.

"Pharmaceutically acceptable vehicle" may refer to a diluent, adjuvant, excipient, or carrier with which at least one immunoglobulin of the present disclosure is administered.

Therapeutic Use

Further disclosed herein are insulin immunoglobulin fusion proteins for and methods of treating, alleviating, inhibiting and/or preventing one or more diseases, disorders and/or conditions. The method may comprise administering to a subject in need thereof a composition comprising one or more insulin immunoglobulin fusion proteins disclosed herein. The insulin immunoglobulin fusion proteins may be used for regulating or ameliorating metabolic defects associated with glucose and insulin metabolism disorders, such as diabetes. In some cases, the subject is in need of reducing at least one of the following indices of metabolism: insulin secretion, insulin resistance, glucose intolerance, hyperinsulinemia, hyperglycemia, and body fat stores. The subject may be human or animal, including but not limited to primates, cows, pigs, sheep, goats, rabbits, horses, chickens, cats, dogs, mice, and the like.

In some embodiments, the subject is administered an immunoglobulin fusion protein comprising an amino acid sequence comprising an antigen binding domain specific for an antigen presented on or expressed by a hepatocyte, thus targeting the immunoglobulin fusion protein to the liver. The insulin immunoglobulin fusion protein may comprise an insulin therapeutic peptide comprising an amino acid sequence having about 50%, 60%, 70%, 80%, 85%, 90%, 95%, 97%, 99% or more amino acid sequence identity to any one of SEQ ID NOS: 109-140, 157, 158, 160, 161. The insulin immunoglobulin fusion protein may comprise an immunoglobulin region comprising an amino acid sequence having about 50%, 60%, 70%, 80%, 85%, 90%, 95%, 97%, 99% or more amino acid sequence identity to any one of SEQ ID NOS: 29, 30, 33-56, 167. The insulin immunoglobulin fusion protein sequence may comprise about 50%, 60%, 70%, 80%, 85%, 90%, 95%, 97%, 99% or more amino acid sequence identity to any one of SEQ ID NOS: 78-98. SEQ ID NOS: The insulin immunoglobulin fusion protein may be encoded by a nucleic acid sequence that is at least about 50%, 60%, 70%, 80%, 85%, 90%, 95%, 97%, 99% or more identical to any one of SEQ ID NOS: 57-77SEQ ID NOS:

In some embodiments, an insulin immunoglobulin fusion protein described herein is administered and/or formulated in combination with an additional therapeutic agent. The two therapeutic agents may be administered at the same time or at different times and/or schedules. For example, a fusion protein may be administered once daily, weekly, monthly, quarterly, etc., and the additional therapeutic agent may be independently administered daily, weekly, monthly, quarterly, etc. The two therapeutic agents may be administered by different means or the same means. As a non-limiting example, each therapeutic agent is independently or jointing administered orally, transdermally, intravenously, nasally, subcutaneously, or any method as described elsewhere herein.

Pharmacological Properties

Further disclosed herein are methods of improving one or more pharmacological properties of a therapeutic peptide. The method may comprise producing an immunoglobulin fusion protein disclosed herein. Examples of pharmacological properties may include, but are not limited to, half-life, stability, solubility, immunogenicity, toxicity, bioavailability, absorption, liberation, distribution, metabolization, and excretion. Liberation may refer to the process of releasing of a therapeutic peptide from the pharmaceutical formulation. Absorption may refer to the process of a substance entering the blood circulation. Distribution may refer to the dispersion or dissemination of substances throughout the fluids and tissues of the body. Metabolization (or biotransformation, or inactivation) may refer to the recognition by an organism that a foreign substance is present and the irreversible transformation of parent compounds into daughter metabolites. Excretion may refer to the removal of the substances from the body.

The half-life of a therapeutic peptide may greater than the half-life of the non-fused therapeutic peptide. The half-life of the therapeutic peptide may be greater than 4 hours, greater than 6 hours, greater than 12 hours, greater than 24 hours, greater than 36 hours, greater than 2 days, greater than 3 days, greater than 4 days, greater than 5 days, greater than 6 days, greater than 7 days, greater than 8 days, greater than 9 days, greater than 10 days, greater than 11 days, greater than 12 days, greater than 13 days, or greater than 14 days when administered to a subject. The half-life of the therapeutic peptide may be greater than 4 hours when administered to a subject. The half-life of the therapeutic peptide may be greater than 6 hours when administered to a subject.

The half-life of the therapeutic peptide may increase by at least about 2, 4, 6, 8, 10, 12, 14, 16, 18, or 20 or more hours. The half-life of the therapeutic peptide may increase by at least about 2 hours. The half-life of the therapeutic peptide may increase by at least about 4 hours. The half-life of the therapeutic peptide may increase by at least about 6 hours. The half-life of the therapeutic peptide may increase by at least about 8 hours.

The half-life of a therapeutic peptide may be at least about 1.5, 2, 2.5, 3, 3.5, 4, 4.5, 5, 5.5, 6, 6.5, 7, 7.5, 8, 8.5, 9, 9.5, or 10-fold greater than the half-life of the non-conjugated therapeutic peptide. The half-life of a therapeutic peptide an immunoglobulin described herein may be at least about 15, 16, 17, 18, 19, 20, 25, 30, 35, 40, 45, or 50-fold greater than the half-life of the non-conjugated therapeutic peptide. The half-life of a therapeutic peptide an immunoglobulin described herein may be at least about 2-fold greater than the half-life of the non-conjugated therapeutic peptide. The half-life of a therapeutic peptide an immunoglobulin described herein may be at least about 5-fold greater than the half-life of the non-conjugated therapeutic peptide. The half-life of a therapeutic peptide an immunoglobulin described herein may be at least about 10-fold greater than the half-life of the non-conjugated therapeutic peptide.

The half-life of a therapeutic peptide an immunoglobulin described herein may be at least about 5%, 10%, 15%, 20%, 25%, 30%, 35%, 40%, 45%, 55%, 60%, 65%, 70%, 75%, 80%, 85%, 90%, 95%, or 97% greater than the half-life of the non-conjugated therapeutic peptide. The half-life of a therapeutic peptide an immunoglobulin described herein may be at least about 10% greater than the half-life of the non-conjugated therapeutic peptide. The half-life of a therapeutic peptide an immunoglobulin described herein may be at least about 20% greater than the half-life of the non-conjugated therapeutic peptide. The half-life of a therapeutic peptide an immunoglobulin described herein may be at least about 30% greater than the half-life of the non-conjugated therapeutic peptide. The half-life of a therapeutic peptide an immunoglobulin described herein may be at least about 40% greater than the half-life of the non-conjugated therapeutic peptide. The half-life of a therapeutic peptide an immunoglobulin described herein may be at least about 50% greater than the half-life of the non-conjugated therapeutic peptide.

Kits

Further disclosed herein are kits which comprise one or more immunoglobulin fusion proteins or components thereof. The immunoglobulin fusion proteins may be packaged in a manner which facilitates their use to practice methods of the present disclosure. For example, a kit comprises an immunoglobulin fusion protein described herein packaged in a container with a label affixed to the container or a package insert that describes use of the immunoglobulin fusion protein in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The kit may comprise a container with an immunoglobulin fusion protein contained therein. The kit may comprise a container with (a) an immunoglobulin fusion protein as described herein and an additional therapeutic agent. The additional therapeutic agent may be an insulin molecule lacking a liver targeting moiety. The kit may further comprise a package insert indicating that the first and second compositions may be used to treat a particular condition. Alternatively, or additionally, the kit may further comprise a second (or third) container comprising a pharmaceutically-acceptable buffer (e.g., bacteriostatic water for injection (BWFI), phosphate-buffered saline, Ringer's solution and dextrose solution). It may further comprise other materials desirable from a commercial and user standpoint, including, but not limited to, other buffers, diluents, filters, needles, and syringes. The immunoglobulin fusion protein may be packaged in a unit dosage form. The kit may further comprise a device suitable for administering the immunoglobulin fusion protein according to a specific route of administration or for practicing a screening assay. The kit may contain a label that describes use of the immunoglobulin fusion protein composition.

The composition comprising the immunoglobulin fusion protein may be formulated in accordance with routine procedures as a pharmaceutical composition adapted for intravenous administration to mammals, such as humans, bovines, felines, canines, and murines. Typically, compositions for intravenous administration comprise solutions in sterile isotonic aqueous buffer. Where necessary, the composition may also include a solubilizing agent and/or a local anaesthetics such as lignocaine to ease pain at the site of the injection. Generally, the ingredients may be supplied either separately or mixed together in unit dosage form. For example, the immunoglobulin fusion protein may be supplied as a dry lyophilized powder or water free concentrate in a hermetically sealed container such as an ampoule or sachette indicating the quantity of the immunoglobulin fusion protein. Where the composition is to be administered by infusion, it may be dispensed with an infusion bottle containing sterile pharmaceutical grade water or saline. Where the composition is administered by injection, an ampoule of sterile water for injection or saline may be provided so that the ingredients may be mixed prior to administration.

The amount of the composition described herein which will be effective in the treatment, inhibition and/or prevention of a disease or disorder associated with aberrant expression and/or activity of a therapeutic peptide may be determined by standard clinical techniques. In addition, in vitro assays may optionally be employed to help identify optimal dosage ranges. The precise dose to be employed in the formulation may also depend on the route of administration, and the seriousness of the disease or disorder, and should be decided according to the judgment of the practitioner and each patient's circumstances. Effective doses may be extrapolated from dose-response curves derived from in vitro, animal model test systems or clinical trials.

EXAMPLES

The activity data provided in the following examples are generally obtained using the immunoglobulin fusion proteins defined in the example and exemplified by the provided SEQ ID. It is to be understood that the activities of any immunoglobulin fusion protein disclosed herein may be enhanced or attenuated depending on conditions not relating to immunoglobulin fusion protein sequence, for example, expression and purification conditions.

Example 1: Construction of Ins-L1-Ab1L and Ins-L1-Ab1H Fusion Proteins for Expression in Mammalian Cells Mouse anti-human ASGPR antibody 5G3 (referred to as anti-ASGPR (5G3) or Ab1) hybridoma was obtained by immunization of mice with human ASGPR extracellular domain. Ab1 heavy chain variable region (Ab1 VH, SEQ ID NO: 11) or Ab1 light chain (Ab1 VL, SEQ ID NO: 13) variable region sequences were obtained by sequencing the Ab1 hybridoma cDNA. A mammalian expression vector encoding Ab1H (SEQ ID NO: 1) was generated by in-frame ligation of amplified Ab1 VH (SEQ ID NO: 11) and human IgG1 CH1 (SEQ ID NO: 12) to pFuse-hIgG1-Fc backbone vector (InvivoGen, CA). Genes encoding antibody Ab1 VL (SEQ ID NO: 13) and human Ig kappa CL (SEQ ID NO: 14) were amplified. The overlap-PCR product of Ab1 VL and human Ig kappa was cloned into the pFuse vector without hIgG1 Fc fragment to generate a mammalian expression vector encoding Ab1L (SEQ ID NO: 2). The gene sequence encoding a single chain insulin with a four-point mutation and a GGGPRR (SEQ ID NO: 148) connecting peptide (Ins1, SEQ ID NO: 99) was synthesized by Integrated DNA Technologies, Inc. (IA, USA), and amplified by polymerase chain reaction (PCR). Nucleic acids encoding linker GGGGS (L1, SEQ ID NO: 141) were cloned between Ins1 and the N-terminus of Ab1H to generate Ins1-L1-Ab1H (SEQ ID NO: 57). Nucleic acids encoding linker GGGGS (L1, SEQ ID NO: 141) were cloned between Ins1 and the N-terminus of Ab1L to generate Ins1-L1-Ab1L (SEQ ID NO: 58). The resulting mammalian expression vectors were confirmed by DNA sequencing.

Figure 2:
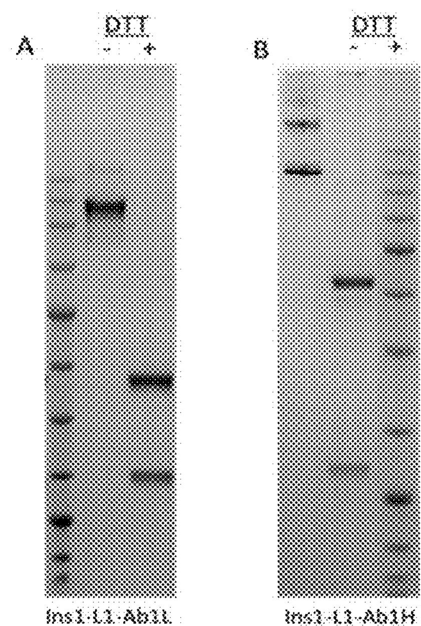
FIG. 2 shows SDS-PAGE gels of purified insulin fusion proteins reduced (+) or not reduced (−) with DTT. Panel A shows a purified insulin fusion protein Ins1-L1-Ab1L IgG comprising Ab1H (SEQ ID NO: 29) and Ins1-L1-Ab1L (SEQ ID NO: 79). Panel B shows a purified insulin fusion protein Ins1-L1-Ab1H IgG comprising Ab1L (SEQ ID NO: 30) and Ins1-L1-Ab1H (SEQ ID NO: 78).

Example 2: Expression and Purification of Ins-L1-Ab1L IgG and Ins-L1-Ab1H Fusion Proteins Ins1-L1-Ab1L (SEQ ID NO: 79) and Ab1H (SEQ ID NO: 29), collectively, Ins1-L1-Ab1L IgG, was expressed through transient transfection of FreeStyle HEK 293 cells with expression vectors of Ab1H (SEQ ID NO: 1) and Ins1-L1-Ab1L (SEQ ID NO: 58), according to the manufacturer's protocol. Briefly, 28 mL FreeStyle HEK 293 cells containing $3\times10^7$ cells were seeded in a 125 mL shaking flask. 15 μg of plasmid encoding Ins1-L1-Ab1L and 15 μg of plasmid encoding Ab1H diluted in 1 mL Opti-MEM medium were added in 1 mL Opti-MEM containing 60 μL 293fectin (Invitrogen, Inc). After the plasmids were incubated with 293fectin for 30 min, lipoplex mixture was added to the cell suspension. Cells were then shaken at 125 rpm in a 5% $CO_2$ environment at 37° C. Culture medium containing secreted proteins (Ins1-L1-Ab1L IgG) were harvested every 48 hours, twice after transfection. Ins1-L1-Ab1L IgG was purified by Protein G chromatography (Thermo Fisher Scientific, IL). Purified proteins were analyzed by SDS-PAGE, as shown in FIG. 2. Ins1-L1-Ab1H (SEQ ID NO: 78) and Ab1L (SEQ ID NO: 30), collectively, Ins1-L1-Ab1H IgG, was expressed and purified as described for Ins1-L1-Ab1L IgG and the purified fusion protein is shown in the SDS-PAGE gel of FIG. 2.

Figure 3:
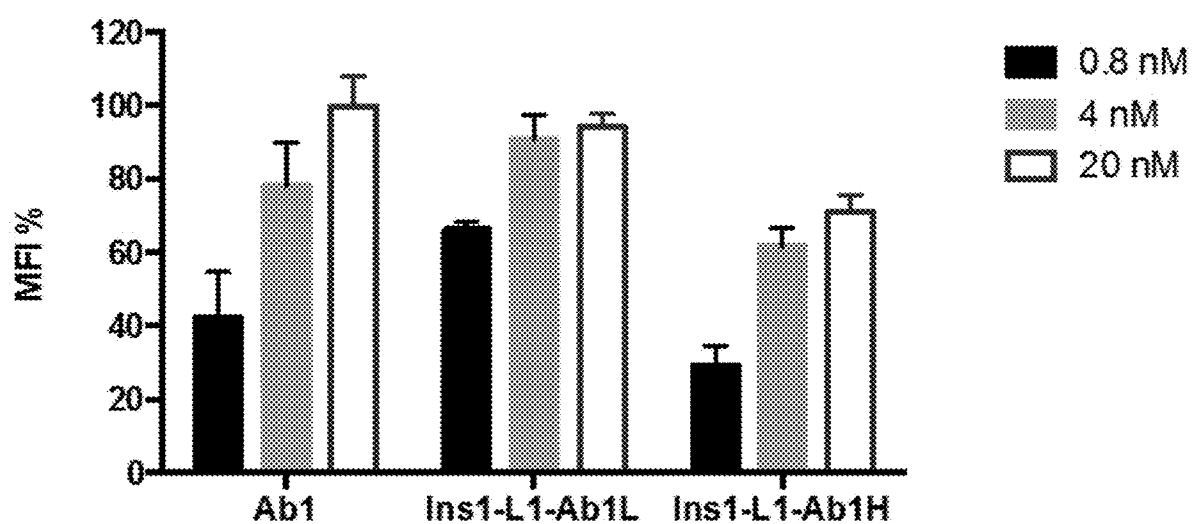
FIG. 3 is a graph showing the binding of insulin immunoglobulin fusion proteins as shown in FIG. 2 (Ins1-L1-Ab1L IgG; Ins1-L1-Ab1H IgG) to human ASGPR in an in vitro assay.
Figure 4:
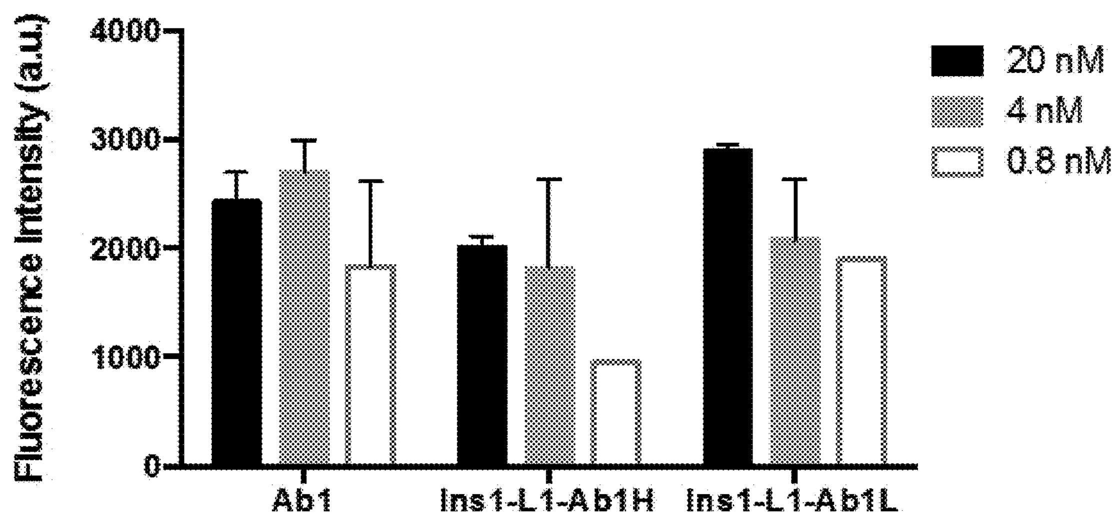
FIG. 4 is a graph showing the binding of insulin immunoglobulin fusion proteins as shown in FIG. 2 (Ins1-L1-Ab1L IgG; Ins1-L1-Ab1H IgG) to rat ASGPR.

Example 3: Ins1-L1-Ab1L IgG and Ins-L1-Ab1H IgG Fusion Proteins Binding Assay for Human ASGPR The activity of anti-ASGPR within the Ins1-L1-Ab1L IgG (SEQ ID NOS: 79, 29) and Ins1-L1-Ab1H IgG (SEQ ID NOS: 78, 30) fusion proteins for human ASGPR was tested by ELISA assay. Briefly, 100 ng/well ASGPR antigen (human, rat and cyno monkey) was coated on 96-well plate in PBS at 4° C. overnight; the wells were blocked with 2% milk/PBST (0.5% Tween-20 in PBS) at room temperature for 1 hr; antibodies were added in concentrations of 10 nM, 1 nM and 0.1 nM in 2% milk/PBST at room temperature for 2 hr; the wells were washed with PBST 4-5 times; anti-light chain kappa (sigma A7164) in 2% milk/PBST was added and the plate incubated at room temperature for 1 hr; the wells were washed with PBST 4-5 times; and the reaction was developed with QuantaBlu fluorogenic peroxidase substrate (Life technologies, 15169), and quantified using a Spectramax fluorescence plate reader with excitation at 325 nm and emission at 420 nm. FIG. 3 shows concentration dependent median fluorescence intensity for binding of Ab1 (anti-ASGPR antibody without a fusion therapeutic peptide (SEQ ID NOS: 29, 30)), Ins1-L1-Ab1L IgG, and Ins1-L1-Ab1H IgG with human ASGPR. FIG. 4 shows concentration dependent fluorescence intensity for binding of Ab1, Ins1-L1-AbL IgG, and Ins1-L1-Ab1H IgG with rat ASGPR. The figures illustrate that anti-ASGPR antibodies fused to insulin therapeutic peptides retain activity for their antigen ASGPR.

Example 4: Insulin Fusion Protein Activity Assay with HepG2 Cells (Phospho-AKT (Ser473) Assay)

Figure 5:
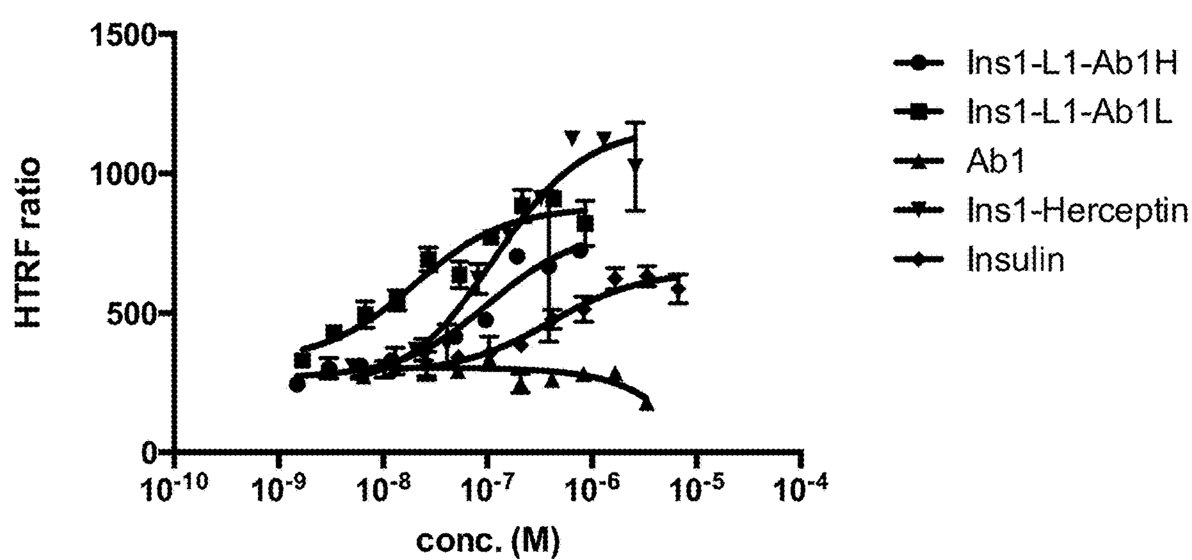
FIG. 5 is a graph showing the activity of insulin immunoglobulin proteins (Ins1-L1-Ab1L IgG; Ins1-L1-Ab1H IgG) on HepG2 cells.
Figure 11:
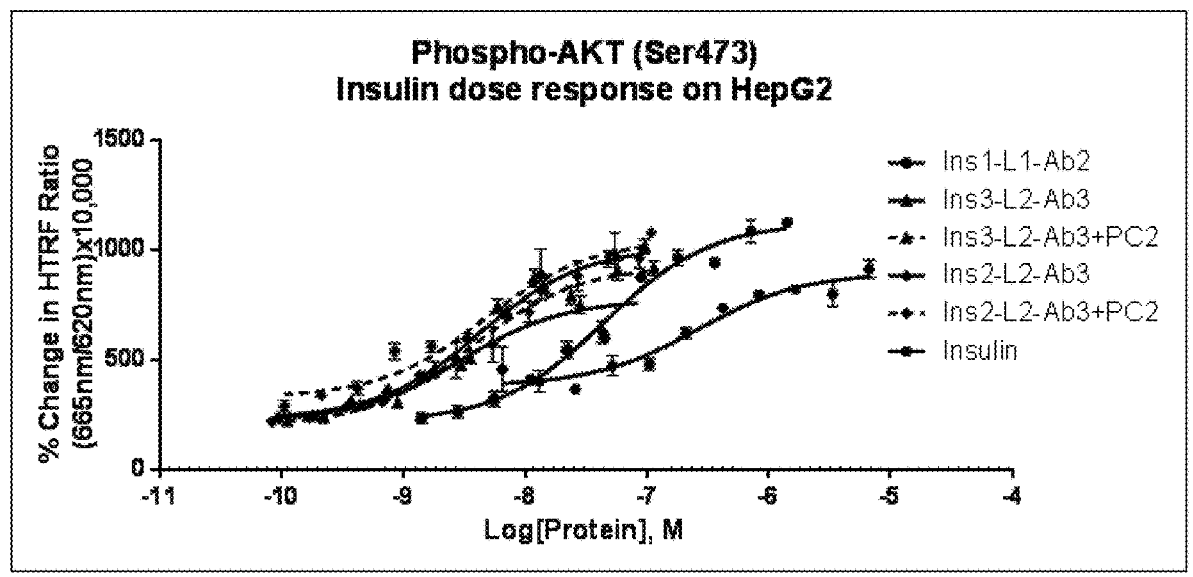
FIG. 11 is a graph showing the activity of insulin immunoglobulin proteins (Ins1-L1-Ab2L IgG; Ins3-L2-Ab1L IgG; Ins3-L2-Ab1L IgG with PC2 cleavage; Ins2-L2-Ab1L IgG; Ins2-L2-Ab1L IgG with PC2 cleavage) on HepG2 cells.
Figure 15:
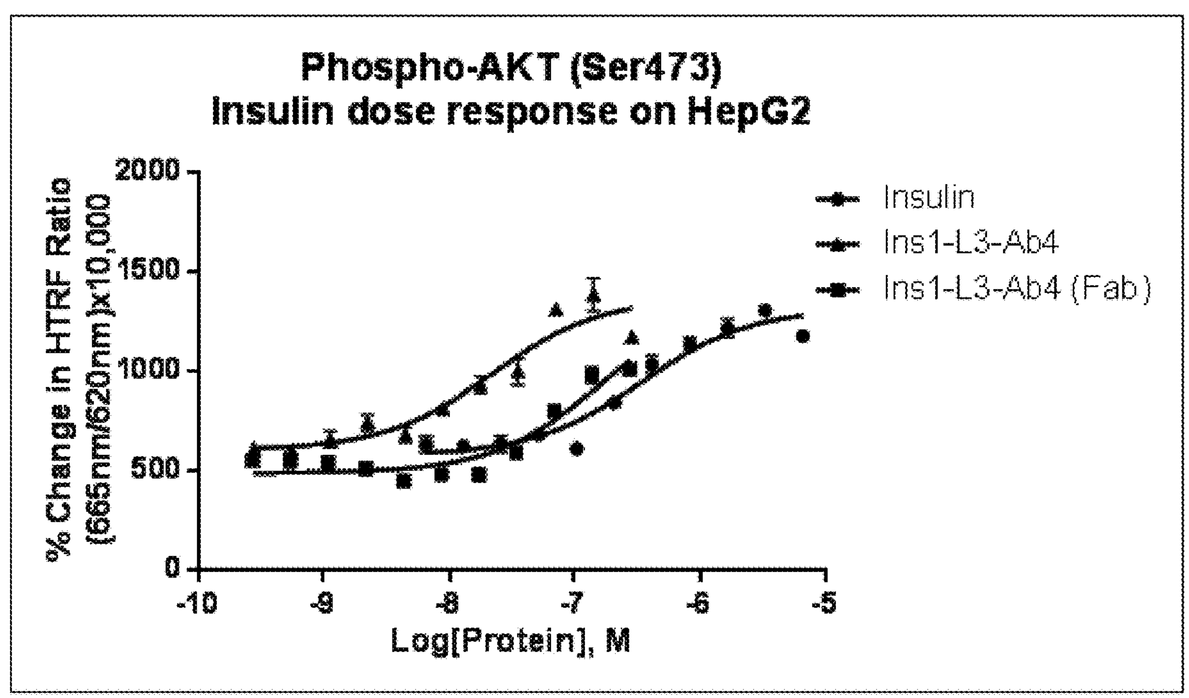
FIG. 15 is a graph showing the activity of insulin immunoglobulin proteins (Ins1-L3-Ab4L IgG; Ins1-L3-Ab4L (Fab)) on HepG2 cells.
Figure 18:
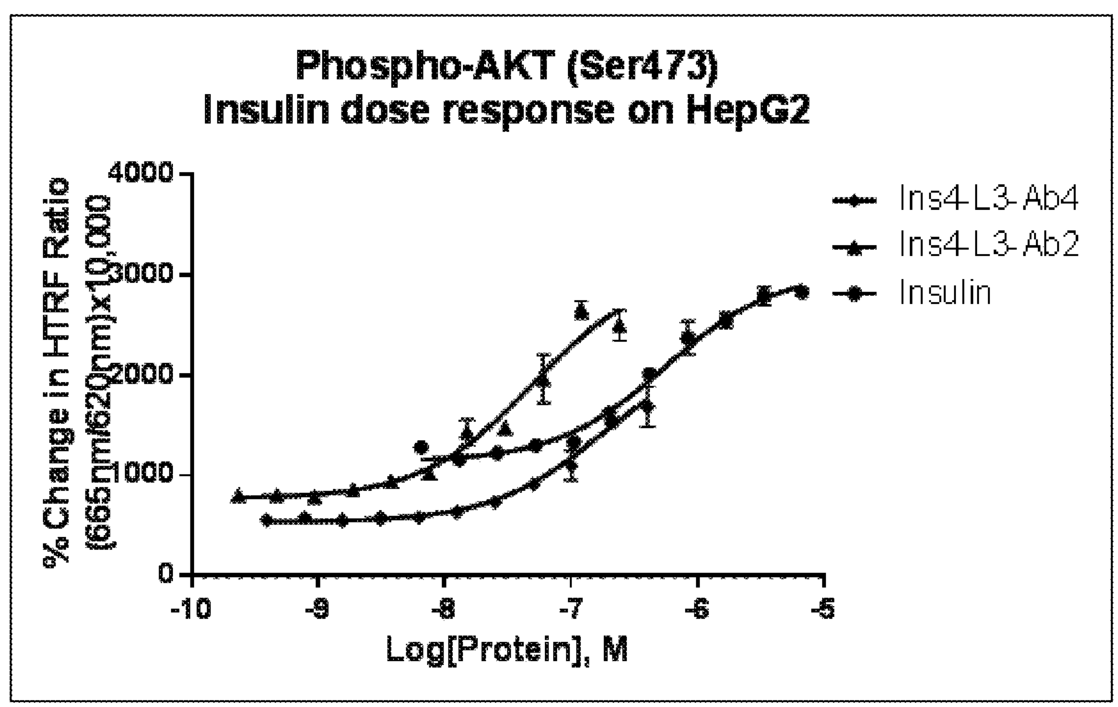
FIG. 18 is a graph showing the activity of insulin immunoglobulin proteins (Ins4-L3-Ab4L and Ab4H; Ins4-L3-Ab2L and Ab42) on HepG2 cells.
Figure 20:
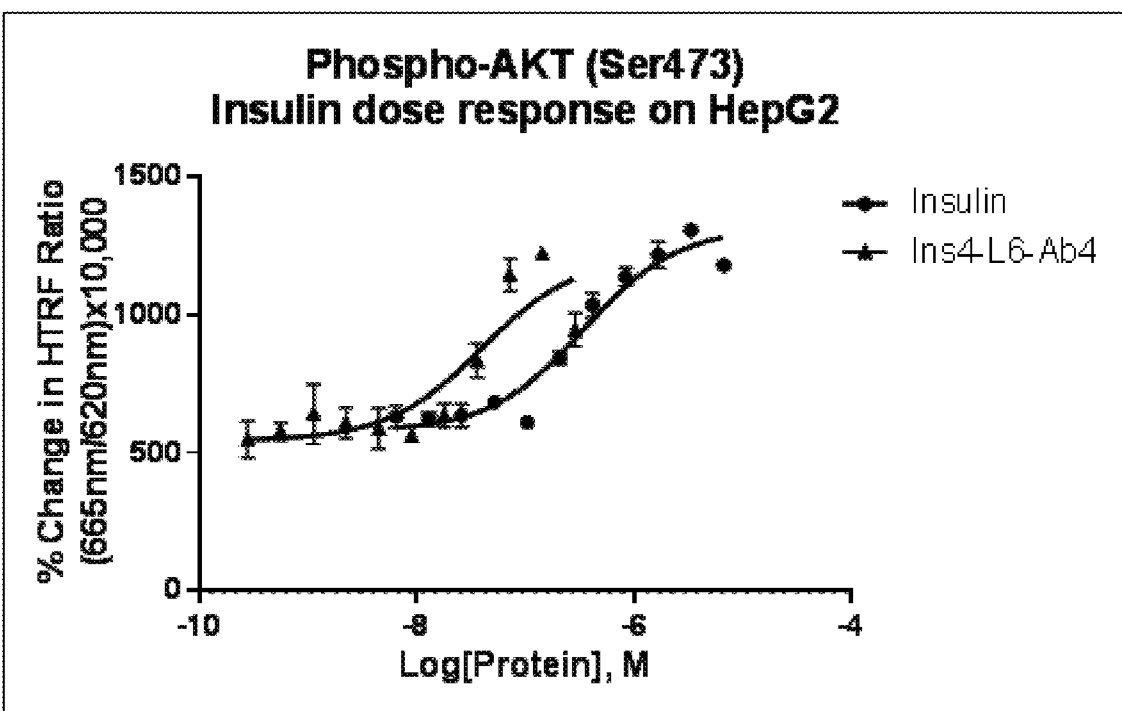
FIG. 20 is a graph showing the activity of insulin immunoglobulin protein Ins4-L6-Ab4L IgG on HepG2 cells.
Figure 21:
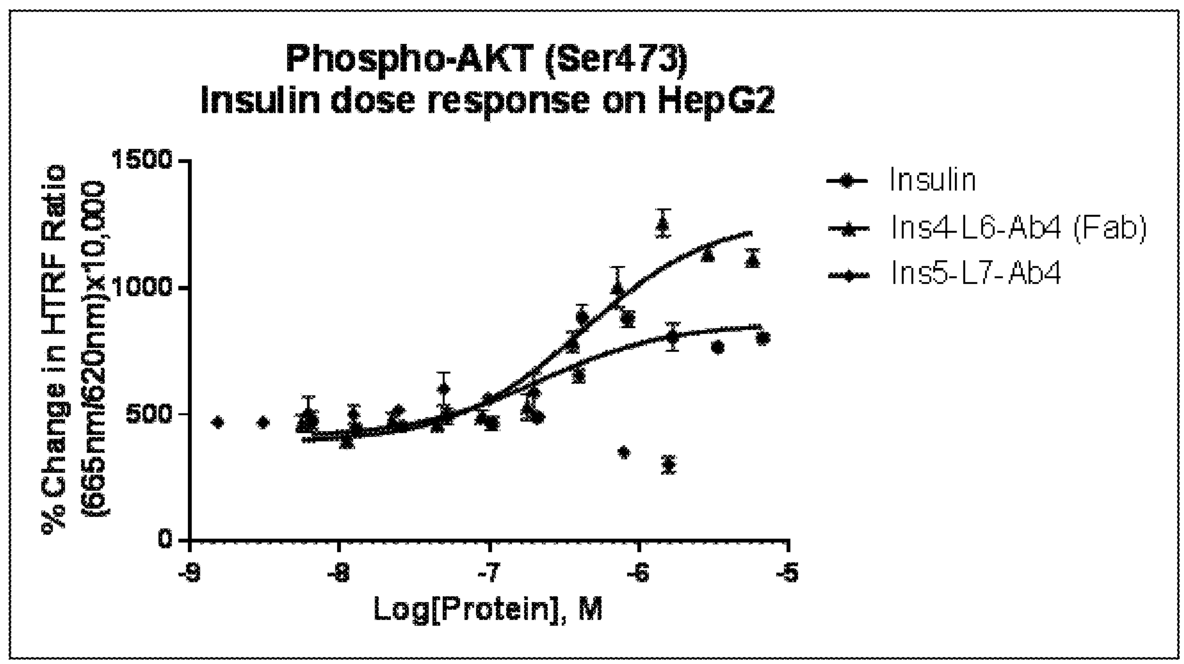
FIG. 21 is a graph showing the activity of insulin immunoglobulin proteins (Ins4-L6-Ab4L(Fab) and Ins5-L7-Ab4L IgG) on HepG2 cells.
Figure 22:
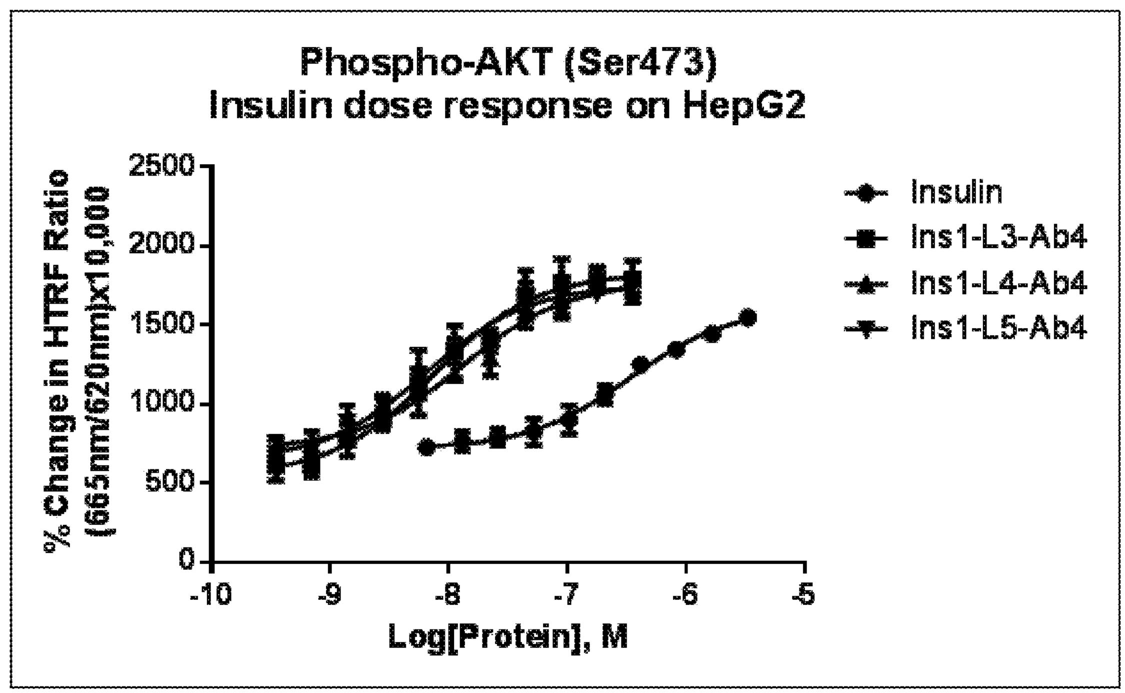
FIG. 22 is a graph showing the activity of insulin immunoglobulin proteins (Ins1-L3-Ab4L IgG; Ins1-L4-Ab4L IgG; Ins1-L5-Ab4L IgG) on HepG2 cells.
Figure 23:
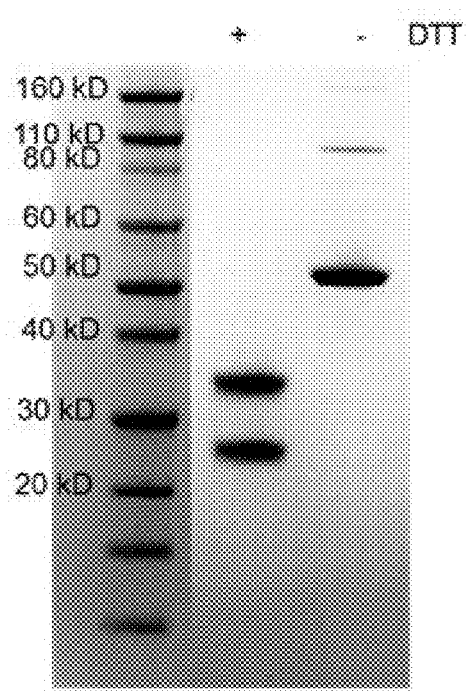
FIG. 23 shows an SDS-PAGE gel of purified Ins1-L3-Ab4 Fab fusion protein.
Figure 24:
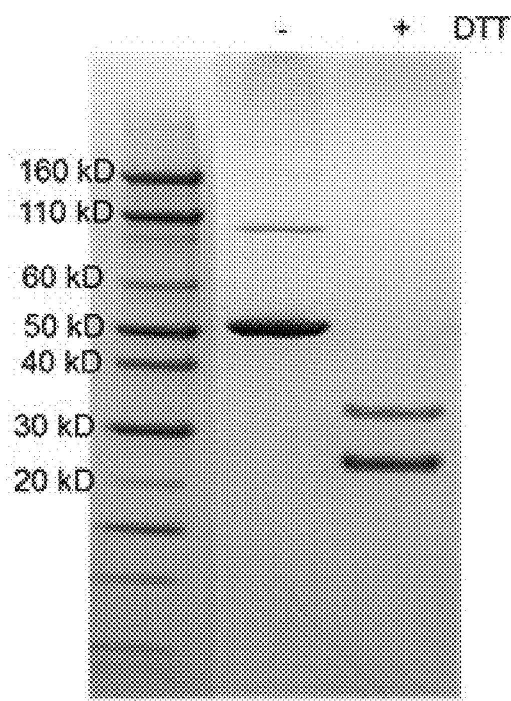
FIG. 24 shows an SDS-PAGE gel of purified Ins1-L3-Ab5 Fab fusion protein.
Figure 25:
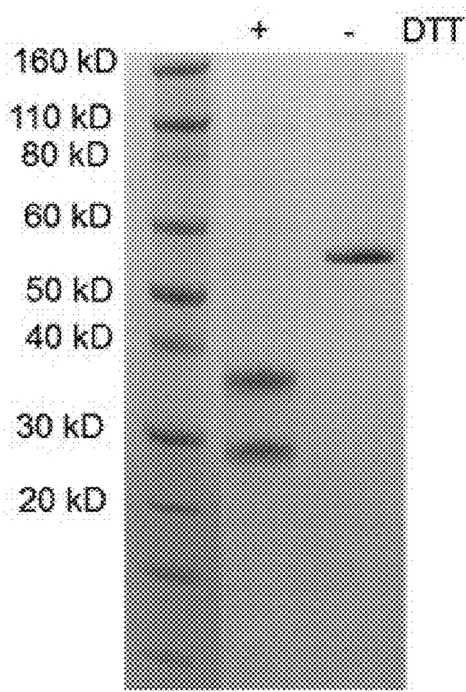
FIG. 25 shows an SDS-PAGE gel of purified Ins7-L3-Ab4 Fab fusion protein.
Figure 26:
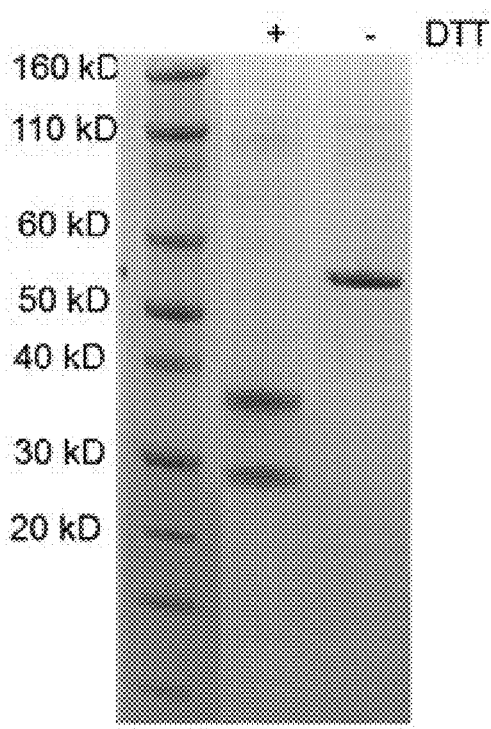
FIG. 26 shows an SDS-PAGE gel of purified Ins7-L3-Ab5 Fab fusion protein.

HepG2, human hepatoma cells, were grown in Minimum Essential Medium (MEM)/F12 (1:1) containing 10% fetal bovine serum (FBS), 100 mM sodium pyruvate and antibiotics (M1). The cells were then seeded in a 384 well plate (15K cell/well) in 8 μL of Dulbecco's modified Eagle's medium (DMEM)/F12 (1:1) containing HEPES and L-glutamine (Life Technologies) FBS and phenol red (M2). The cells were grown overnight (~16 h) at 37° C. in the presence of 5% $CO_2$ gas. The following day, activation of phosphorylated-AKT (Ser473) was evaluated following incubation in each well with various concentrations of insulin or insulin fusion proteins in M2 medium (incubation at 37° C. in the presence of 5% $CO_2$ gas for 10 min). Phosphorylated AKT (Ser473) were detected using the Phospho-AKT (Ser473) Cellular Assay Kits (Cisbio Assay, Cat: 64AKSPEG) according to the manufacturer's protocol. Briefly, the cells were lysed directly in the assay plate by adding 4 μL of lysis buffer. Each well was then supplemented with 4 μL antibody solution containing two monoclonal antibodies that recognize the phosphorylated AKT and emit a time-resolved Fluorescence Resonance Energy Transfer (FRET) signal proportionate to the extent of phosphorylated AKT upon excitation at 320 nm. Emission was measured using an Envision plate reader at 665 nm and 615 nm. FIG. 5 shows the activity of insulin fusion proteins on HepG2 cells with a plot of the HTRF (homogeneous time-resolved fluorescence) ratio as a function of concentration of insulin (SEQ ID NO: 138), Ins1 fused to the amino-terminus of herceptin antibody (Ins1-herceptin comprising SEQ ID NO: 94), anti-ASGPR (SEQ ID NOS: 29, 30), Ins1-L1-Ab1H IgG and Ins-L1-Ab1L IgG. FIG. 5 illustrates that the Ins1 fusion proteins have comparable or enhanced insulin activity on HepG2 cells. The $EC_{50}$ values for test compounds were calculated as 103 nm for Ins1-L1-Ab1H IgG (SEQ ID NOS: 78, 30), 20 nm for Ins1-L1-Ab1L IgG (SEQ ID NOS: 79, 29), 118 nm for Ins1-herceptin IgG (SEQ ID NOS: 94), and 401 nm for wild type insulin (SEQ ID NO: 138). FIGS. 11, 15, 18, 20-22 illustrate that the Ins1, Ins2, Ins3 and Ins4 fusion proteins have comparable or enhanced insulin activity on HepG2 cells. The $EC_{50}$ values for test compounds were calculated as 46 nm for Ins1-L1-Ab2 IgG (SEQ ID NOS: 80, 31), 3.8 nm for Ins3-L2-Ab3 IgG (SEQ ID NOS: 83, 33)+PC2, 4.4 nm for Ins3-L2-Ab3 IgG (SEQ ID NOS: 82, 33), 5.4 nm for Ins2-L2-Ab3 IgG (SEQ ID NOS: 81, 167)+PC2, 21 for Ins2-L2-Ab3 IgG (SEQ ID NOS: 81, 167) and 209 nm for wild type insulin (SEQ ID NO: 138); FIG. 11. The $EC_{50}$ values for test compounds were calculated as 23 nm for Ins1-L3-Ab4 IgG (SEQ ID NOS: 84, 34), 187 nm for Ins1-L3-Ab4(Fab) (SEQ ID NOS: 84, 36) and 345 nm for wild type insulin (SEQ ID NO: 138); FIG. 15. The $EC_{50}$ values for test compounds were calculated as 53 nm for Ins4-L3-Ab4 IgG (SEQ ID NOS: 85, 34), 175 nm for Ins4-L3-Ab2 IgG (SEQ ID NOS: 86, 31) and 569 nm for wild type insulin (SEQ ID NO: 138); FIG. 18. The $EC_{50}$ values for test compounds were calculated as 40 nm for Ins4-L6-Ab4 IgG (SEQ ID NOS: 91, 34) and 345 nm for wild type insulin (SEQ ID NO: 138); FIG. 20. The $EC_{50}$ values for test compounds were calculated as 223 nm for Ins4-L6-Ab4 (Fab) (SEQ ID NOS: 95, 36) IgG, >1580 nm for Ins5-L7-Ab4 IgG (SEQ ID NOS: 90, 34) and 426 nm for wild type insulin (SEQ ID NO: 138); FIG. 21. The $EC_{50}$ values for test compounds were calculated as 8 nm for Ins1-L3-Ab4 IgG (SEQ ID NOS: 84, 34), 13 nm for Ins1-L4-Ab4 IgG (SEQ ID NOS: 87, 34), 6 nm for Ins1-L5-Ab4 IgG (SEQ ID NOS: 88, 34) and 282 nm for wild type insulin (SEQ ID NO: 138); FIG. 22.

Figure 6:
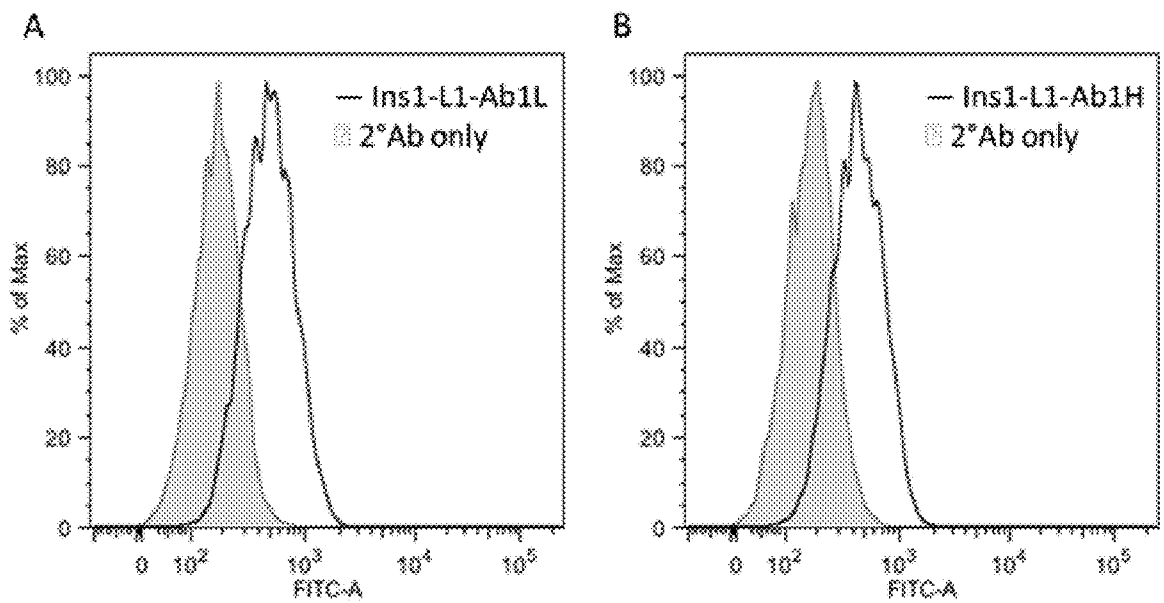
FIG. 6 is flow cytometry histogram showing the binding of insulin immunoglobulin fusion proteins as shown in FIG. 2 (Ins1-L1-Ab1L IgG (panel A); Ins1-L1-Ab1H IgG (panel B)) to HepG2 cells.
Figure 7:
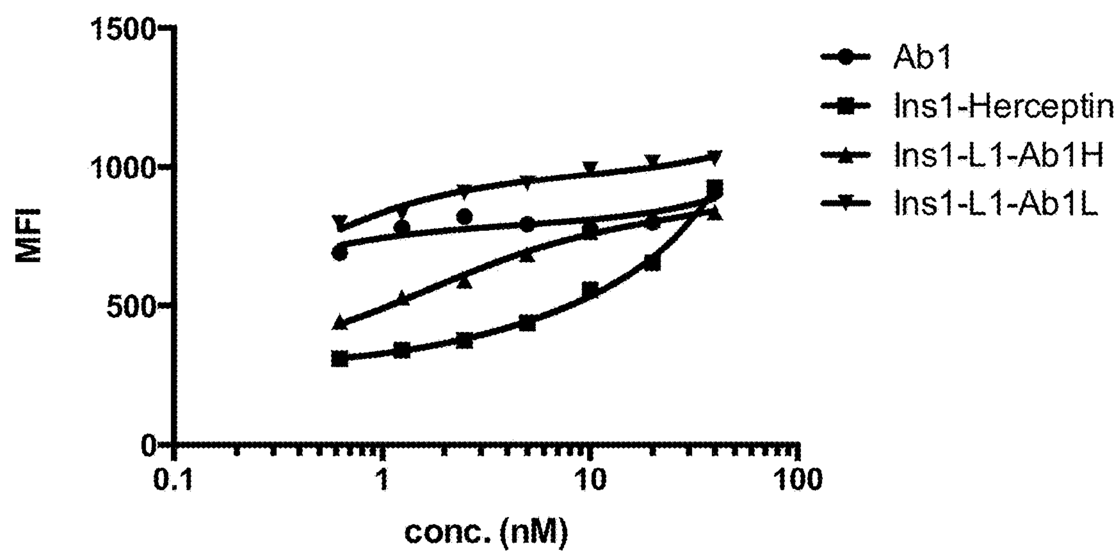
FIG. 7 is graph corresponding to the histograms of FIG. 6.

Example 5: Flow Cytometry Analysis of the Binding Affinity of Insulin Fusion Proteins with HepG2 Cells HepG2 cells were harvested, washed and resuspended in PBS/1% BSA solution at a density of $5\times10^6$ cells/mL. The cell suspension was incubated at 4° C. for 1 hour. Various concentrations (40, 20, 10, 5, 2.5, 1.25, 0.625, 0 nM) of antibodies (Ab1 IgG (SEQ ID NOS: 29, 30), Ins1-L1-Ab1L IgG (SEQ ID NOS: 79, 29), Ins1-L1-Ab1H IgG (SEQ ID NOS: 78, 30), and Ins1-Herceptin (SEQ ID NOS: 94) were added to the cells for a 2-hour incubation at 4° C. with agitation. The cells were then washed 3 times with PBS/1% BSA. FITC-anti-human Kappa antibody (Life Technologies, Inc.) was diluted 500-fold with PBS/1% BSA and then added to the cells for incubation at 4° C. for another 2 hours. Following incubation, the cells were washed twice with PBS/1% BSA and resuspended in PBS/1% BSA solution. Flow cytometry was performed to analyze the amount of bound antibody. FIG. 6 shows binding of Ins1-L1-Ab1L IgG (panel A) and Ins1-L1-Ab1H IgG (panel B) on HepG2 cells. Mean cellular fluorescence (FITC channel) was used to quantify the binding affinity. FIG. 7 shows a plot of the mean fluorescence intensity (MFI) versus concentration for each antibody tested.

Example 6: Construction of Insulin IgG Fusion Proteins for Expression in Mammalian Cells The gene encoding the heavy chain of palivizumab (Ab2H, SEQ ID NO: 3) was cloned into a pFuse vector. Nucleic acids encoding Ins1, SEQ ID NO: 99, (as described in Example 1) were synthesized by Integrated DNA Technologies, Inc. and amplified by PCR. A mammalian expression vector encoding Ins1-L1-Ab2L (SEQ ID NO: 59) was generated by cloning the gene encoding Ins1 (SEQ ID NO: 99) and the light chain of palivizumab (Ab2L, SEQ ID NO: 4) with nucleotides encoding the linker GGGGS (L1, SEQ ID NO: 141) into a pFuse vector. The resulting mammalian expression vector was confirmed by DNA sequencing.

To generate insulin, anti-ASGPR fusion proteins, a gene encoding a nucleic acid sequence of a heavy (SEQ ID NO: 1, 6, 8, 9, 10, 11 or 15) or light chain (SEQ ID NO: 2, 5, 7, 13, or 16) of anti-ASGPR was cloned into a pFuse vector. Nucleic acids encoding insulin selected from SEQ ID NOS: 109-140 were synthesized by Integrated DNA Technologies, Inc. and amplified by PCR. A mammalian expression vector encoding insulin and anti-ASGPR fusion protein was generated by cloning the nucleic acids encoding insulin and a linker into the pFuse vector. The resulting mammalian expression vector was confirmed by DNA sequencing.

Example 7: Expression and Purification of Insulin IgG Fusion Proteins

Figure 8:
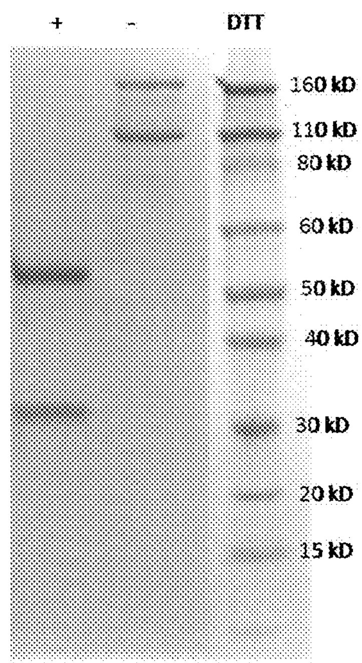
FIG. 8 shows an SDS-PAGE gel of purified Ins1-L1-Ab2L IgG (SEQ ID NOS: 80, 31) fusion protein.

Ins1-L1-Ab2L (SEQ ID NO: 59) and Ab2H (SEQ ID NO: 3), collectively, Ins1-L1-Ab2L IgG, were expressed through transient transfection of FreeStyle HEK 293 cells with expression vectors of Ab2H (SEQ ID NO: 3) and Ins1-L1-Ab2L (SEQ ID NO: 59), according to the manufacturer's protocol. Briefly, 28 mL FreeStyle HEK 293 cells containing $3\times10^7$ cells were seeded in a 125 mL shaking flask. 15 μg of plasmid encoding Ins1-L1-Ab1L and 15 μg of plasmid encoding Ab1H diluted in 1 mL Opti-MEM medium were added in 1 mL Opti-MEM containing 60 μL 293fectin (Invitrogen, Inc). After the plasmids were incubated with 293fectin for 30 min, lipoplex mixture was added to the cell suspension. Cells were then shaken at 125 rpm in a 5% $CO_2$ environment at 37° C. Culture medium containing secreted proteins Ins1-L1-Ab2L IgG (SEQ ID NOS: 80, 31) were harvested every 48 hours, twice after transfection. Ins1-L1-Ab2L IgG was purified by Protein G chromatography (Thermo Fisher Scientific, IL). Purified proteins were analyzed by SDS-PAGE, as shown in FIG. 8.

Figure 9:
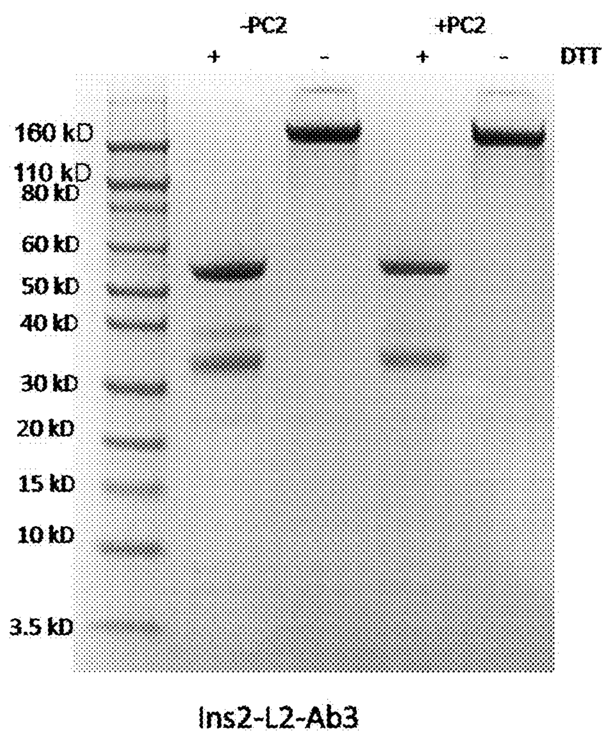
FIG. 9 shows an SDS-PAGE gel of purified Ins2-L2-Ab3L (SEQ ID NO: 81) and Ab3H (SEQ ID NO: 167) fusion protein; with and without proteolytic cleavage by the enzyme PC2.
Figure 10:
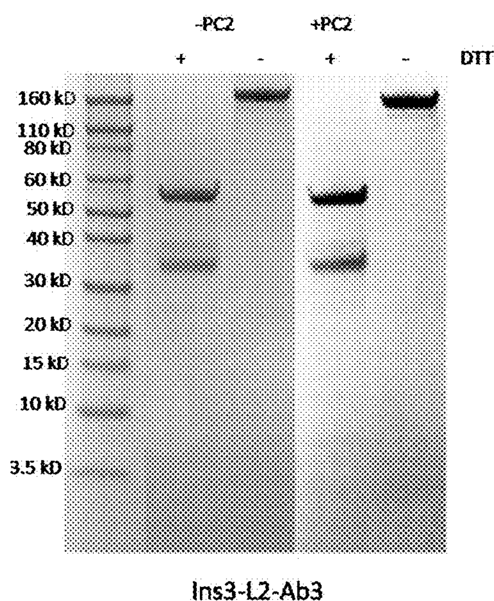
FIG. 10 shows an SDS-PAGE gel of purified Ins3-L2-Ab3L IgG fusion protein.
Figure 12:
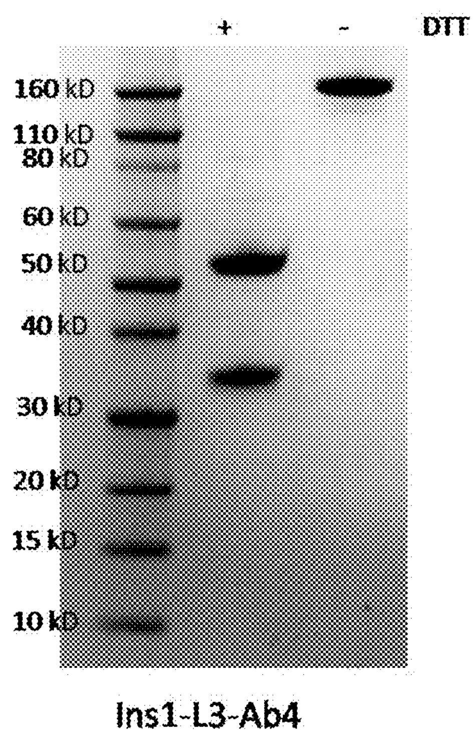
FIG. 12 shows an SDS-PAGE gel of purified Ins1-L3-Ab4L IgG fusion protein.
Figure 13:
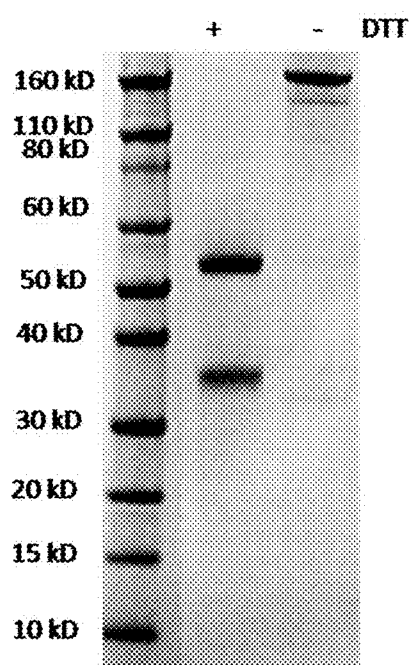
FIG. 13 shows an SDS-PAGE gel of purified Ins1-L3-Ab5L IgG fusion protein.
Figure 14:
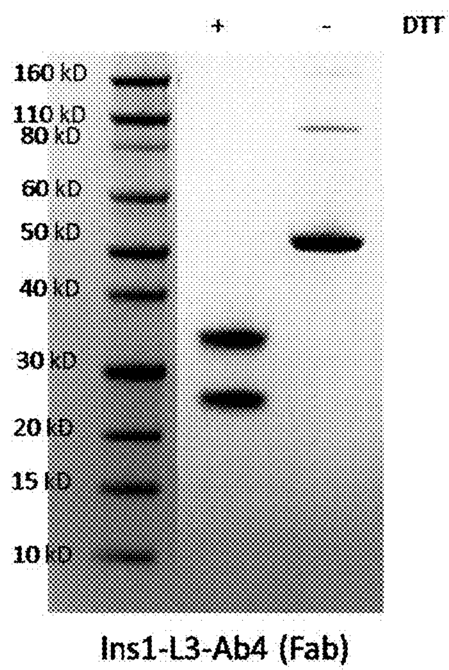
FIG. 14 shows an SDS-PAGE gel of purified Ins1-L3-Ab4L(Fab) fusion protein.
Figure 17:
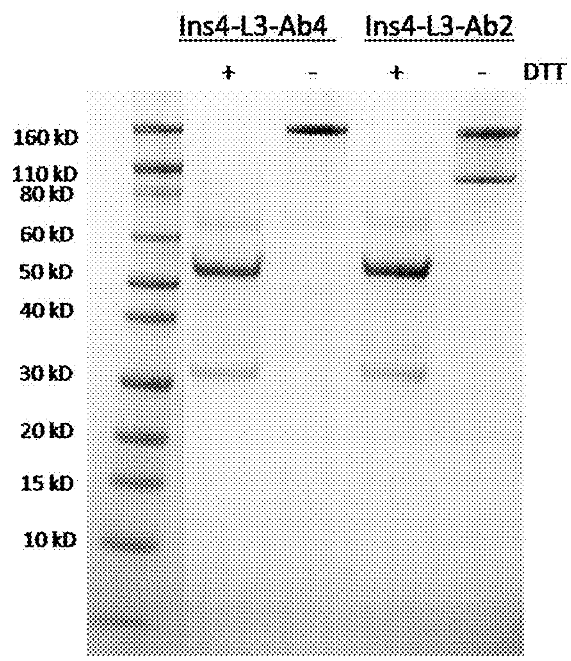
FIG. 17 shows an SDS-PAGE gel of purified Ins4-L3-Ab4L IgG fusion protein and Ins4-L3-Ab2L IgG fusion protein.
Figure 19:
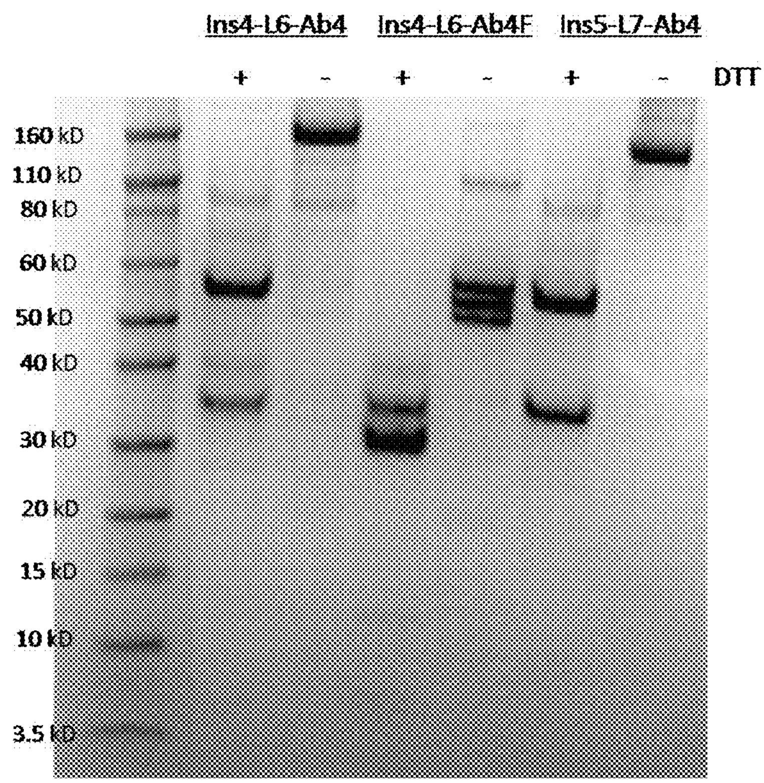
FIG. 19 shows an SDS-PAGE gel of purified Ins4-L6-Ab4L IgG fusion protein; Ins4-L6-Ab4L(Fab) fusion protein; and Ins5-L7-Ab4L IgG fusion protein.

To purify insulin fusion proteins, FreeStyle HEK 293 cells were first transiently transfected with mammalian expression vectors encoding for an insulin fusion protein. Optionally, the cells were co-transfected with a mammalian expression vector encoding a protease such as PC2 to cleave a protease cleavage site within a connecting peptide of the insulin, anti-ASGPR fusion protein. Briefly, 28 mL FreeStyle HEK 293 cells containing $3\times10^7$ cells were seeded in a 125 mL shaking flask. 15 μg of plasmid encoding insulin fusion proteins were diluted in 1 mL Opti-MEM medium were added in 1 mL Opti-MEM containing 60 μL 293fectin (Invitrogen, Inc). After the plasmids were incubated with 293fectin for 30 min, lipoplex mixture was added to the cell suspension. Cells were then shaken at 125 rpm in a 5% $CO_2$ environment at 37° C. Culture medium containing secreted insulin fusion proteins were harvested every 48 hours, twice after transfection. Insulin fusion proteins were purified by Protein G chromatography (Thermo Fisher Scientific, IL). Purified proteins were analyzed by SDS-PAGE, as shown in FIGS. 9, 10, 12-14, 17 and 19. FIG. 9 shows an SDS-PAGE gel of purified Ins2-L2-Ab3L IgG (SEQ ID NO: 81) and Ab3H (SEQ ID NO: 167) fusion protein; with and without proteolytic cleavage by the enzyme PC2. FIG. 10 shows an SDS-PAGE gel of purified Ins3-L2-Ab3L IgG (Ins3-L2-Ab3L, SEQ ID NO: 82; Ab3H, SEQ ID NO: 167) fusion protein. FIG. 12 shows an SDS-PAGE gel of purified Ins1-L3-Ab4L IgG (Ins1-L3-Ab4L, SEQ ID NO: 84; Ab4H, SEQ ID NO: 34) fusion protein. FIG. 13 shows an SDS-PAGE gel of purified Ins1-L3-Ab5L IgG (Ins1-L3-Ab5L, SEQ ID NO: 96; Ab5H, SEQ ID NO: 37) fusion protein. FIG. 14 shows an SDS-PAGE gel of purified Ins1-L3-Ab4L IgG (Ins1-L3-Ab4L, SEQ ID NO: 84; Ab4H(Fab), SEQ ID NO: 36) fusion protein. FIG. 17 shows an SDS-PAGE gel of purified Ins4-L3-Ab4L IgG (Ins4-L3-Ab4L, SEQ ID NO: 85; Ab4H, SEQ ID NO: 34) fusion protein and Ins4-L3-Ab2L IgG (Ins4-L3-Ab2L, SEQ ID NO: 86; Ab2H, SEQ ID NO: 31) fusion protein. FIG. 19 shows an SDS-PAGE gel of purified Ins4-L6-Ab4L IgG (Ins4-L6-Ab4L, SEQ ID NO: 91; Ab4H, SEQ ID NO: 34) fusion protein; Ins4-L6-Ab4L (Fab) (Ins4-L6-Ab4L, SEQ ID NO: 91; Ab4H(Fab), SEQ ID NO: 36) fusion protein; and Ins5-L7-Ab4L IgG (Ins5-L7-Ab4L, SEQ ID NO: 90; Ab4H, SEQ ID NO: 34) fusion protein.

Example 8: Construction, Expression and Purification of Ins1-L3-Ab4 Fab, Ins1-L3-Ab5 Fab, Ins7-L3-Ab4 Fab, and Ins7-L3-Ab5 Fab Fusion Proteins for Expression in Mammalian Cells Mouse anti-human ASGPR antibody 5G3 (referred to as anti-ASGPR (5G3) or Ab1) was humanized to obtain humanized anti-ASGPR or Ab4. To generate Ab5H, Ab4H was mutated to substitute an arginine for a tyrosine at amino acid position 50. The gene sequence encoding Ins1 (SEQ ID NO: 99) or Ins7 (SEQ ID NO: 108) was synthesized by Integrated DNA Technologies, Inc. (IA, USA), and amplified by polymerase chain reaction (PCR). Nucleic acids encoding linker L3 (SEQ ID NO: 143) were cloned between Ins1 or Ins7 and the N-terminus of Ab4L or Ab5L to generate Ins1-L3-Ab4L (SEQ ID NO: 63), Ins1-L3-Ab5L (SEQ ID NO: 75), Ins7-L3-Ab4L (SEQ ID NO: 76) or Ins7-L3-Ab5L (SEQ ID NO: 77). The resulting mammalian expression vectors were confirmed by DNA sequencing.

The fusion proteins were expressed and purified as described generally in Example 2. Purified proteins were analyzed by SDS-PAGE, as shown in FIGS. 23-26. Purified Ins1-L3-Ab4L (SEQ ID NO: 84) and Ab4H (SEQ ID NO: 36), collectively, Ins1-L3-Ab4 Fab, is shown in the SDS-PAGE gel of FIG. 23. Purified Ins1-L3-Ab5L (SEQ ID NO: 96) and Ab5H (SEQ ID NO: 38), collectively, Ins1-L3-Ab5 Fab, is shown in the SDS-PAGE gel of FIG. 24. Purified Ins7-L3-Ab4L (SEQ ID NO: 97) and Ab4H (SEQ ID NO: 36), collectively, Ins7-L3-Ab4 Fab, is shown in the SDS-PAGE gel of FIG. 25. Purified Ins7-L3-Ab5L (SEQ ID NO: 98) and Ab5H (SEQ ID NO: 38), collectively, Ins7-L3-Ab5 Fab, is shown in the SDS-PAGE gel of FIG. 26.

Figure 27:
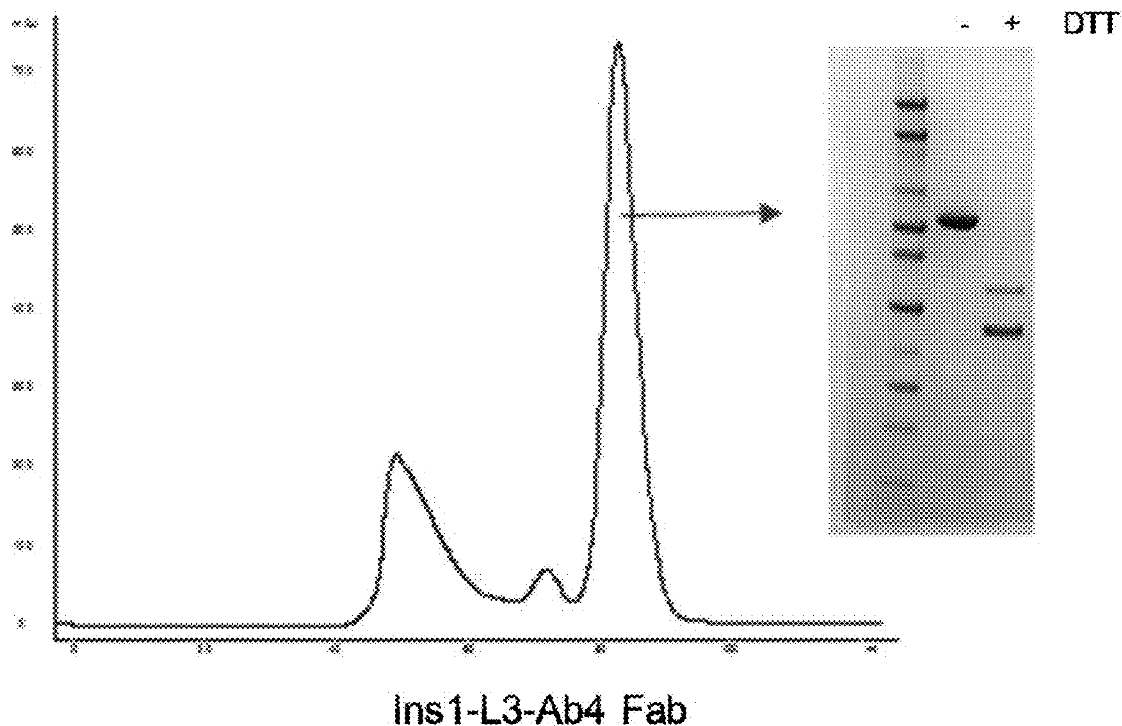
FIG. 27 shows a graph showing size exclusion purification of Ins1-L3-Ab4 Fab fusion protein.
Figure 28:
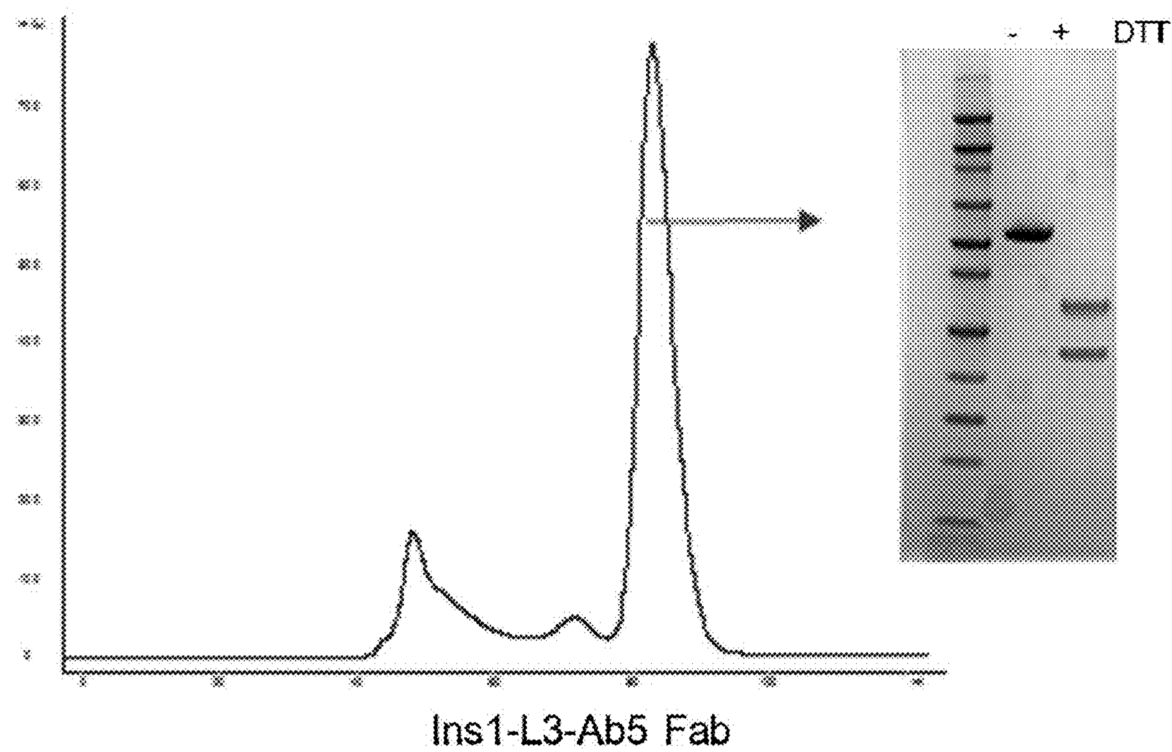
FIG. 28 shows a graph showing size exclusion purification of Ins1-L3-Ab5 Fab fusion protein.
Figure 29:
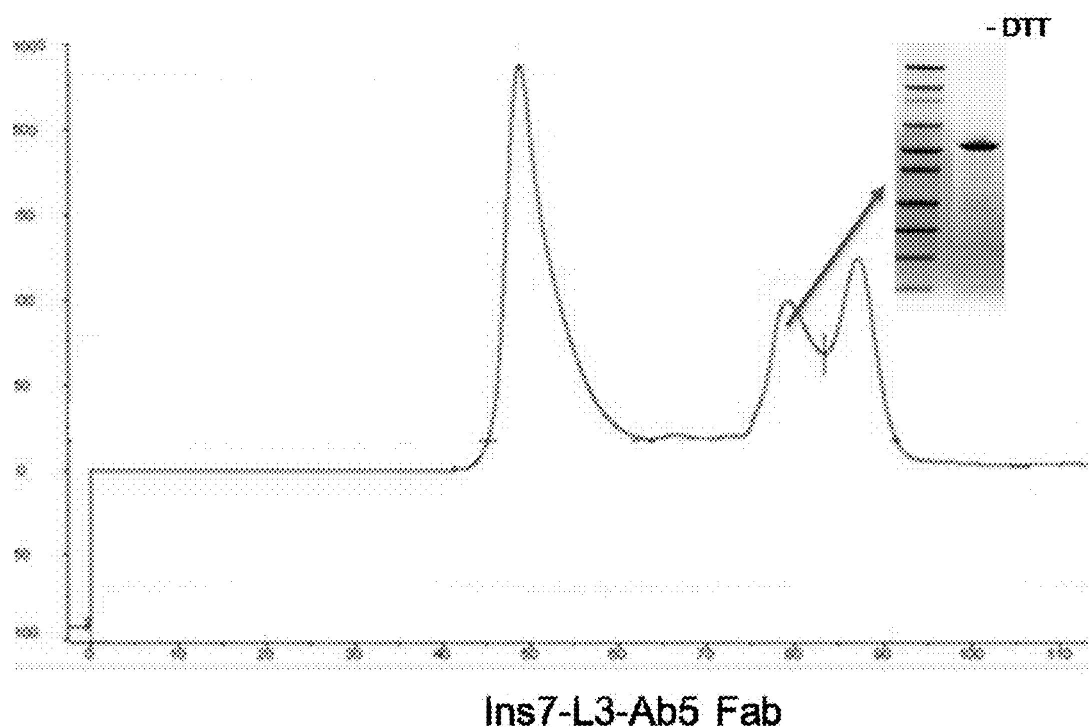
FIG. 29 shows a graph showing size exclusion purification of Ins7-L3-A5 Fab fusion protein.

Following protein purification and analysis by SDS-PAGE, Ins1-L3-Ab4 Fab, Ins1-L3-Ab5 Fab, and Ins7-L3-Ab5 Fab fusion proteins were further purified by Superdex 200 increase size exclusion gel filtration (GE HealthCare LifeSciences) as shown in FIGS. 27-29. As shown in FIG. 27, the major peak for purified Ins1-L3-Ab4L (SEQ ID NO: 84) and Ab4H (SEQ ID NO: 36), collectively, Ins1-L3-Ab4 Fab, was collected at 80-100 min. As shown in FIG. 28, the major peak for purified Ins1-L3-Ab5L (SEQ ID NO: 96) and Ab5H (SEQ ID NO: 38), collectively, Ins1-L3-Ab5 Fab, was collected at 80-100 min. As shown in FIG. 29, the major peak for purified Ins7-L3-Ab5L (SEQ ID NO: 98) and Ab5H (SEQ ID NO: 38), collectively, Ins7-L3-Ab5 Fab, was collected at 75-85 min.

Figure 30:
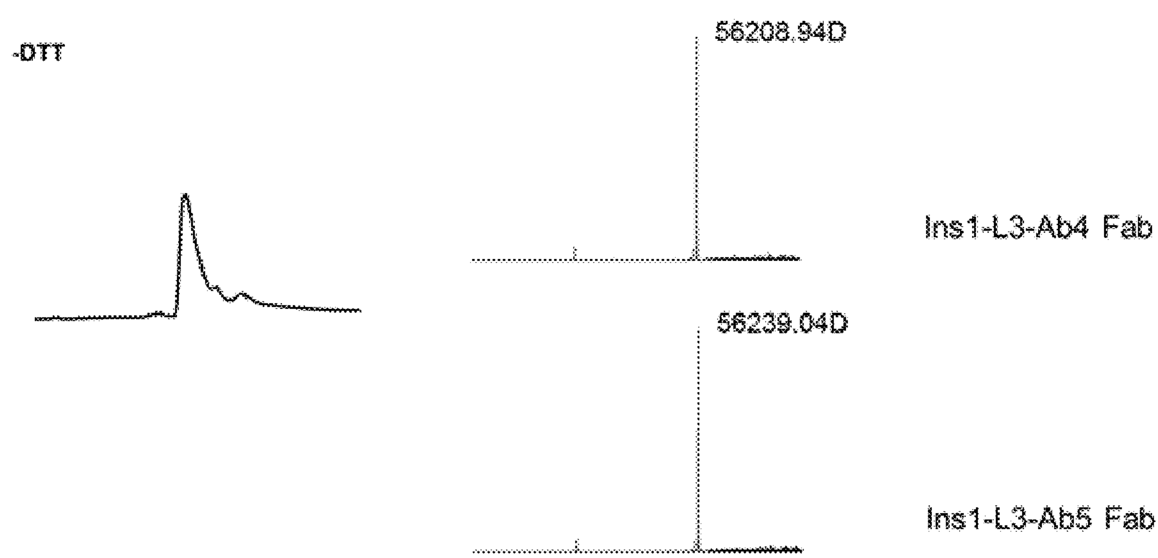
FIG. 30 shows a graph of mass-spectrum characterization of Ins1-L3-Ab4 Fab and Ins1-L3-Ab5 Fab fusion proteins.

ESI-MS was used to characterize Ins1-L3-Ab4 Fab and Ins1-L3-Ab5 Fab that was purified by Protein G chromatography (Thermo Fisher Scientific, IL) and gel filtration as shown in FIG. 30. The observance for Ins1-L3-Ab4 Fab, was 56209, and the observance for Ins1-L3-Ab5 Fab was 56239.

Figure 31A:
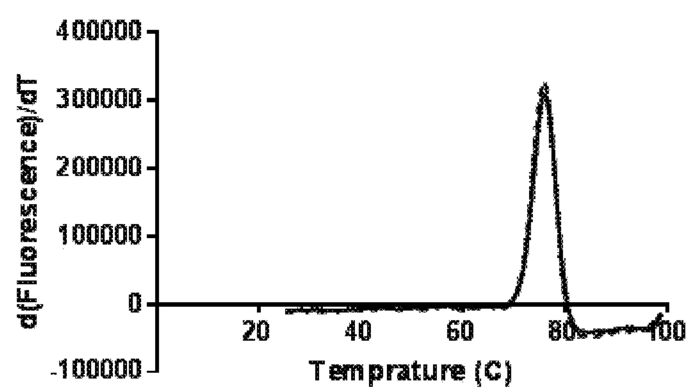
FIG. 31A is a gel filtration graph of A4 Fab showing thermal stability of A4Fab.
Figure 31B:
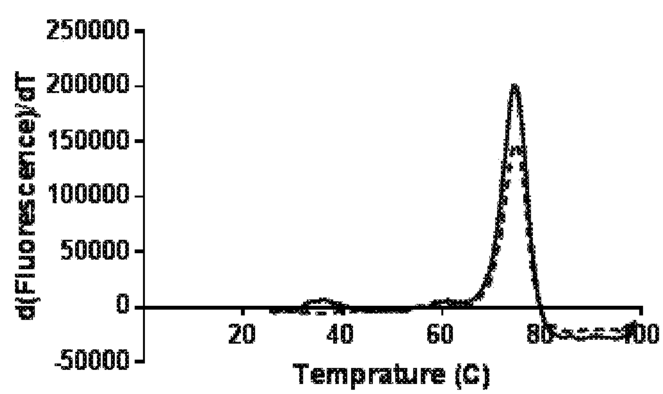
FIG. 31B is a gel filtration graph of Ins1-L3-Ab4 Fab showing thermal stability of Ins1-L3-Ab4 Fab.
Figure 31C:
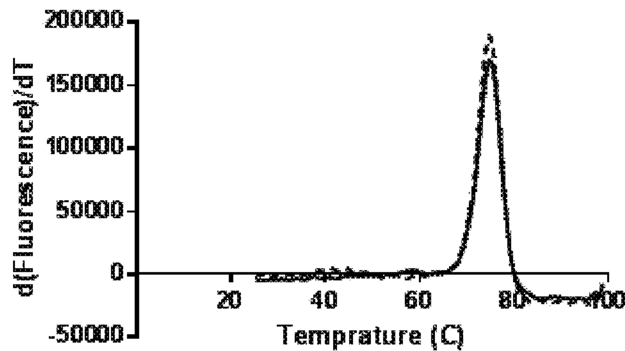
FIG. 31C is a gel filtration graph of Ins1-L3-Ab4 Fab major peak collection showing thermal stability of Ins1-L3-Ab4 Fab.

The thermal stability of A4Fab, Ins1-L3-Ab4 Fab, and Ins1-L3-Ab4 Fab gel filtration major peak collection was determined as shown in FIGS. 31A-31C. 6.25 μg of fusion protein in 12.5 μL of DPBS (pH 7.5) were mixed with 2.5 μL of fresh-diluted thermal shift dye and 5.0 μL of shift buffer (Protein Thermal Shift™ Dye Kit, ThermoFisher Scientific, Cat. 4461146). The detection of fluorescence was coupled with the thermal scanning from 25° C. to 99° C. at a heating rate 0.05° C./s using ViiA™ 7 Real-Time PCR System. The melting temperature (Tm) was calculated by the analysis model "area under curve" in GraphPad Prism7. Assays were repeated 2 times to ensure reproducibility. As seen in FIG. 31A, the Tm for A4 Fab was 76° C. As seen in FIG. 31B, the Tm for Ins1-L3-Ab4 Fab was 74.67° C. The Tm for Ins1-L3-Ab4 Fab gel filtration major peak collection was 74.8° C.

Example 9: Insulin Fusion Protein Activity Assay with HepG2, A673, and SGBS Cells (Phospho-AKT (Ser473) Assay)

Figure 32:
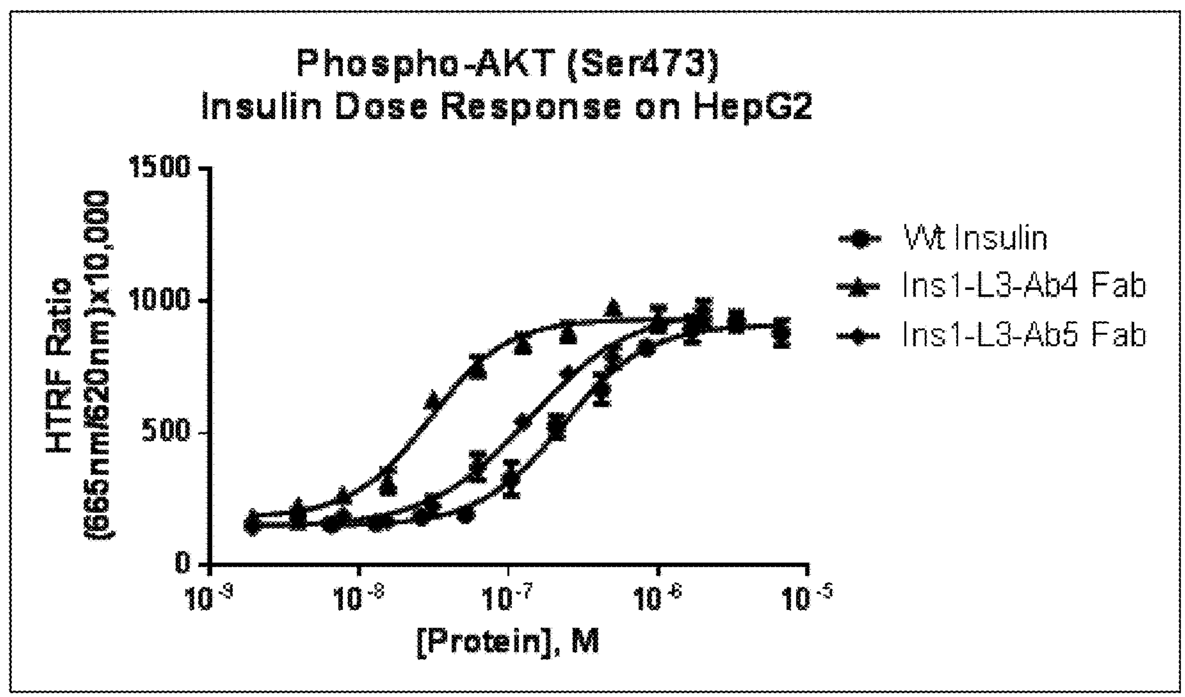
FIG. 32 is a graph showing the activity of insulin binding on HepG2 cells of WT insulin, Ins1-L3-Ab4 Fab, and Ins1-L3-Ab5 Fab.
Figure 33:
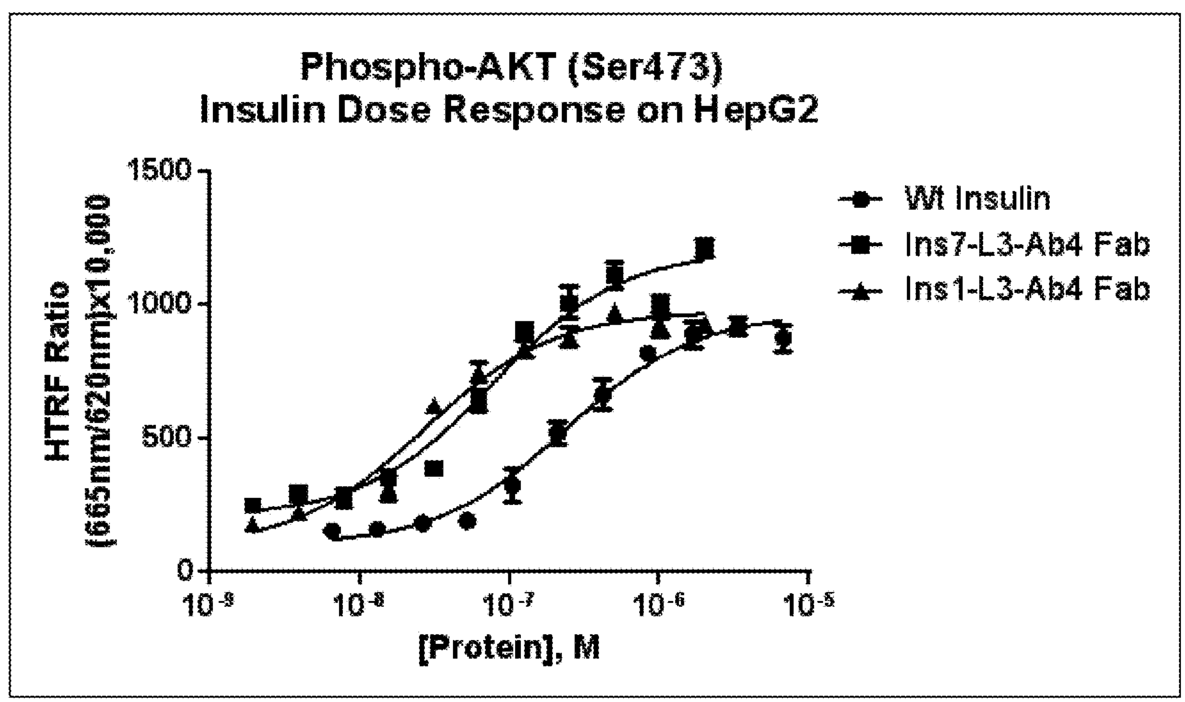
FIG. 33 is a graph showing the activity of insulin binding on HepG2 cells of WT Insulin, Ins1-L3-Ab4 Fab, and Ins7-L3-Ab4 Fab.

The activity of the insulin fusion proteins on AKT was described generally in Example 4. FIG. 32 and FIG. 33 illustrate that the Ins1 fusion proteins have comparable or enhanced insulin activity on HepG2 cells. The $EC_{50}$ values for the fusion proteins were calculated as 30 nM for Ins1-L3-Ab4 Fab, 140 nM for Ins1-L3-Ab5 Fab, 73 nM for Ins7-L3-Ab4 Fab, and 231 nM for WT insulin as seen in FIG. 32 and FIG. 33.

Figure 34:
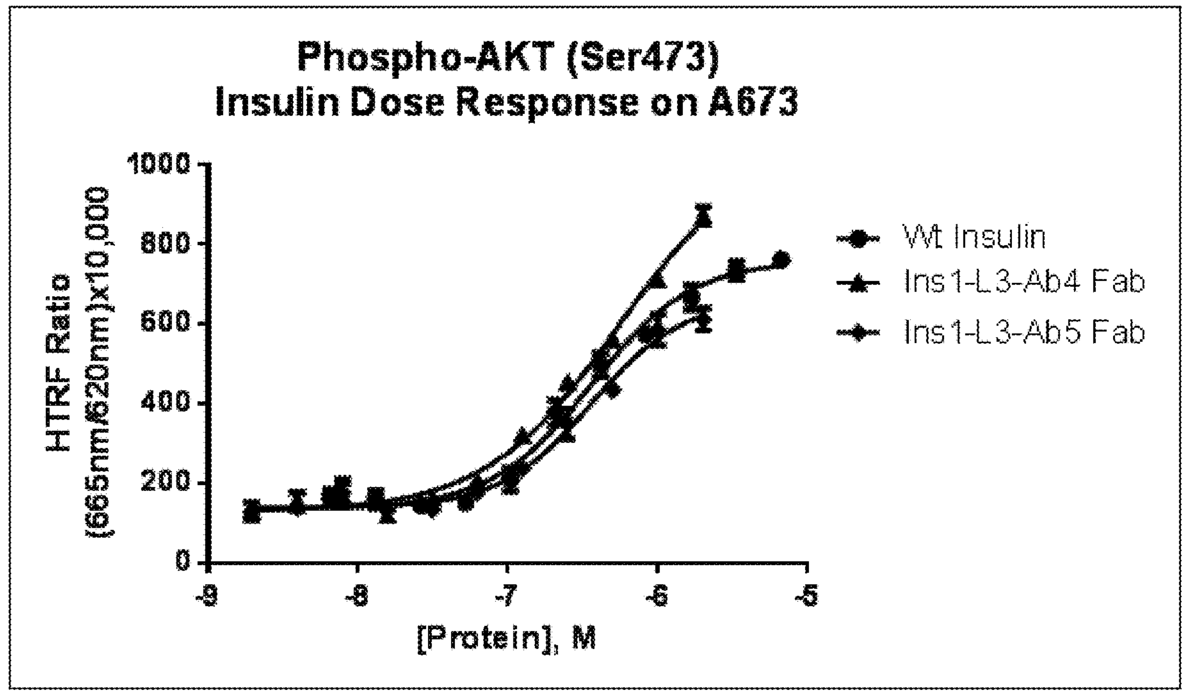
FIG. 34 is a graph showing the activity of insulin binding on A673 cells of WT Insulin, Ins1-L3-Ab4 Fab, and Ins1-L3-Ab5 Fab.

The activity of the insulin fusion proteins on AKT on A673 cells was also measured as seen in FIG. 34. The $EC_{50}$ values for were calculated as 581 nM for Ins1-L3-Ab4 Fab, 351 nM for Ins1-L3-Ab5 Fab, and 362 nM for WT insulin. As seen in FIG. 34, the insulin fusion proteins had comparable or enhanced insulin activity on A673 cells.

Figure 35:
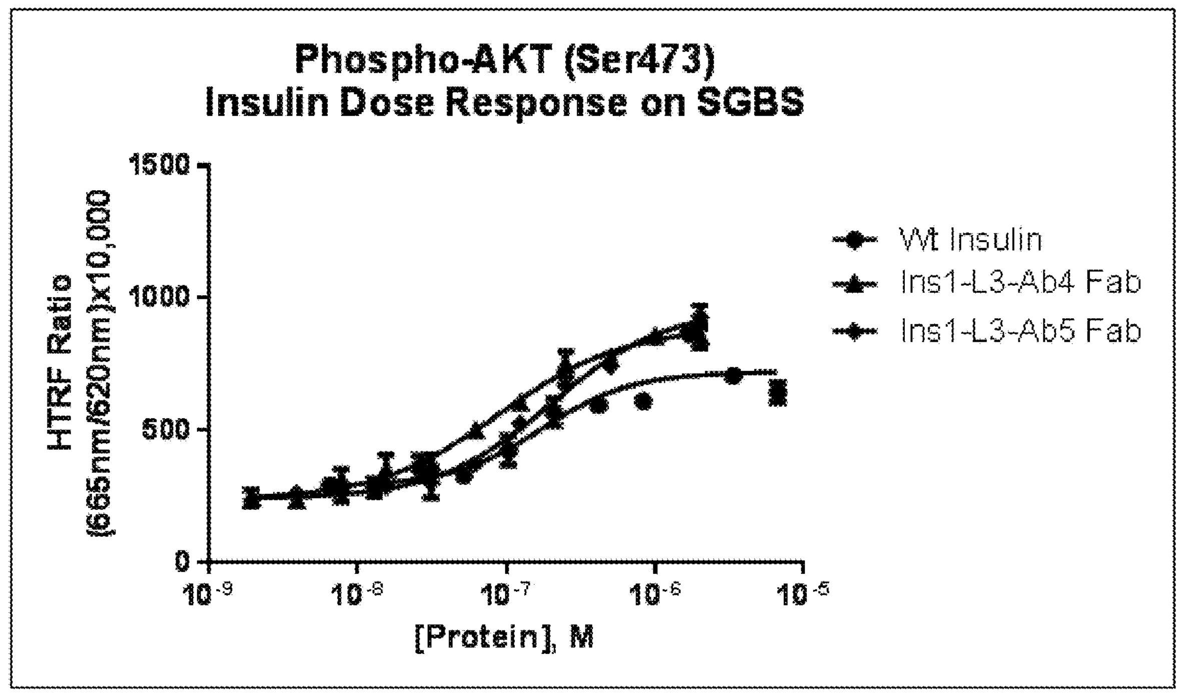
FIG. 35 is a graph showing the activity of insulin binding on SGBS cells of WT Insulin, Ins1-L3-Ab4 Fab, and Ins1-L3-Ab5 Fab.

The activity of insulin fusion proteins on AKT on SGBS cells was also measured as seen in FIG. 35. The $EC_{50}$ values for were calculated as 94 nM for Ins1-L3-Ab4 Fab, 206 nM for Ins1-L3-Ab5 Fab, and 176 nM for WT insulin. The insulin fusion proteins had comparable or enhanced insulin activity on SGBS cells as seen in FIG. 35.

Example 10: Flow Cytometry Analysis of the Binding Affinity of Insulin Fusion Proteins with HepG2, A673, and SGBS Cells Flow cytometry analysis of the binding affinity of insulin fusion proteins with HepG2 was generally described in Example 5. Briefly, $2\times10^5$ HepG2 cells were blocked with 2% FBS, 0.1% $NaN_3$/PBS at 4° C. and mixed with antibodies or fusion proteins at 200 nM 4° C. for 1 hr. After the cells were washed three times with blocking buffer, HepG2 cells were incubated with anti-human FAB-FITC (1:1000, 109-095-006, Immuno JacksonResearch) at 4° C. for 30 min. Following three washes with blocking buffer, FITC signal was obtained by BD Accuri™ 6 Flow Cytometer. Gating was applied to single cell suspension and mean fluorescent intensity (MFI) was plotted versus concentration for comparison. The MFI for Ins1-L3-Ab4 Fab was calculated as 21570 and for Ins1-L3-Ab5 Fab was 8523.

Flow cytometry was also performed to determine the binding affinity of insulin fusion proteins with A673 cells. The MFI for Ins1-L3-Ab4 Fab was calculated as 731 and for Ins1-L3-Ab5 Fab was 630.

Flow cytometry was performed of insulin fusion proteins with SGBS cells. The MFI for Ins1-L3-Ab4 Fab was calculated as 1411 and for Ins1-L3-Ab5 Fab was 1047.

Figure 36:
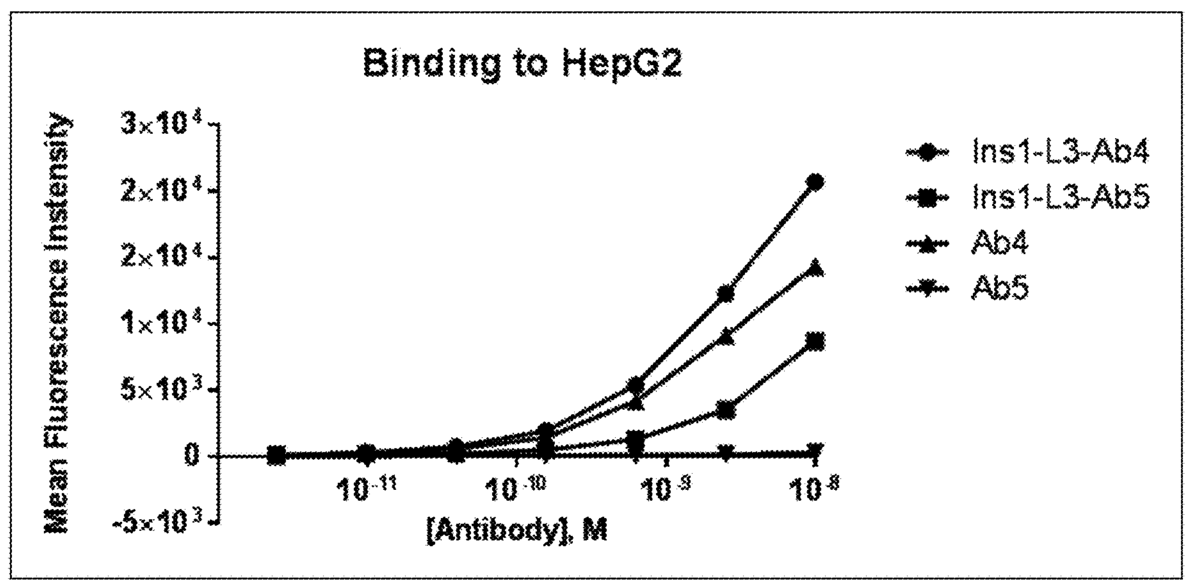
FIG. 36 is a graph of binding Ins1-L3-Ab4 Fab, Ins1-L3-Ab5 Fab, Ab4, and Ab5 on HepG2 cells as measured by flow cytometry.

FIG. 36 illustrates binding to HepG2 of Ins1-L3-Ab4, Ins1-L3-Ab5, Ab4, and Ab5. HepG2 cells, $2\times10^5$, were blocked with 2% FBS, 0.1% $NaN_3$/PBS at 4° C. and mixed with antibodies or fusion proteins from 30 pM to 10 nM at 4° C. for 1 hr. After the cells were washed three times with blocking buffer, HepG2 cells were incubated with anti-human Fc-FITC (1:1000, 02-10-20, KPL) at 4° C. for 30 min. Following three washes with blocking buffer, FITC signal was obtained by BD Accuri™ 6 Flow Cytometer. Gating was applied to single cell suspension and mean fluorescent intensity (MFI) was plotted versus concentration for comparison. FIG. 36 shows a plot of the mean fluorescence intensity (MFI) versus concentration for each antibody or fusion protein tested.

Figure 37:
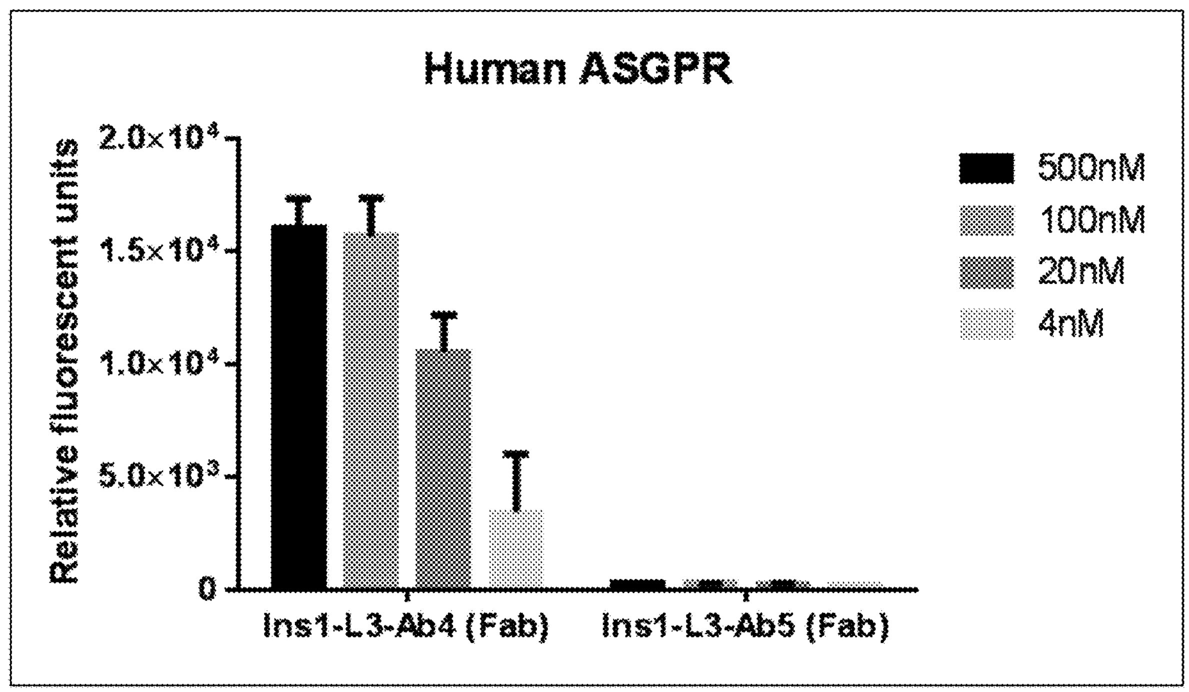
FIG. 37 is a graph of the binding of Ins1-L3-Ab4 Fab and Ins1-L3-Ab5 Fab to extracellular domains of human ASGPR.
Figure 38:
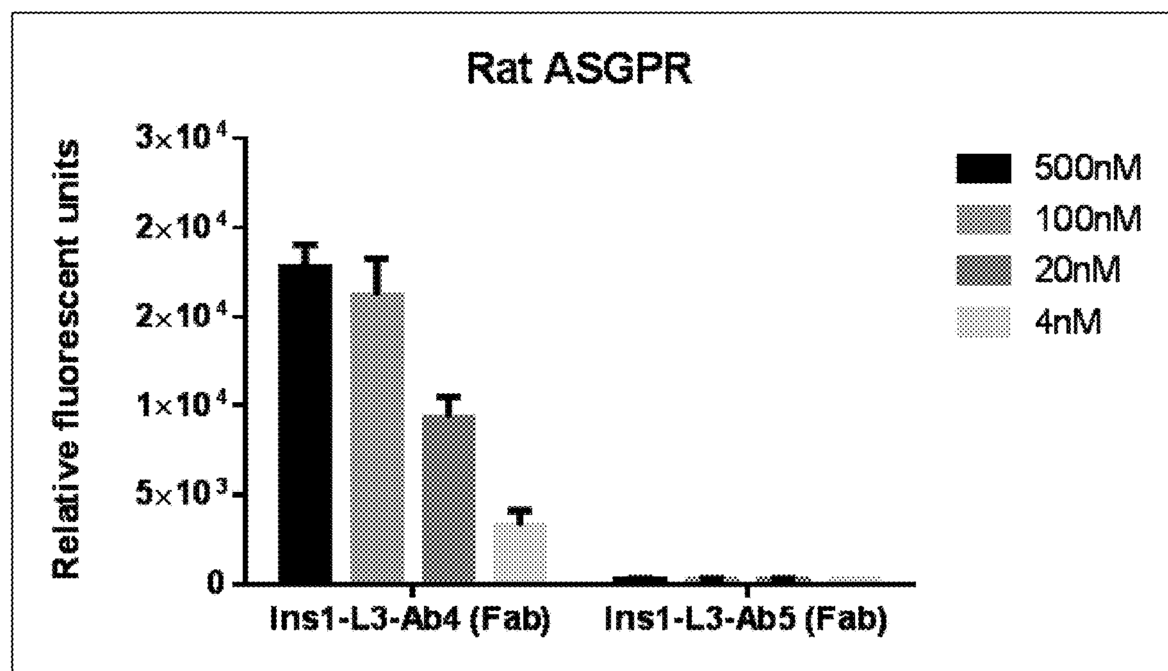
FIG. 38 is a graph of the binding of Ins1-L3-Ab4 Fab and Ins1-L3-Ab5 Fab to extracellular domains of rat ASGPR.
Figure 39:
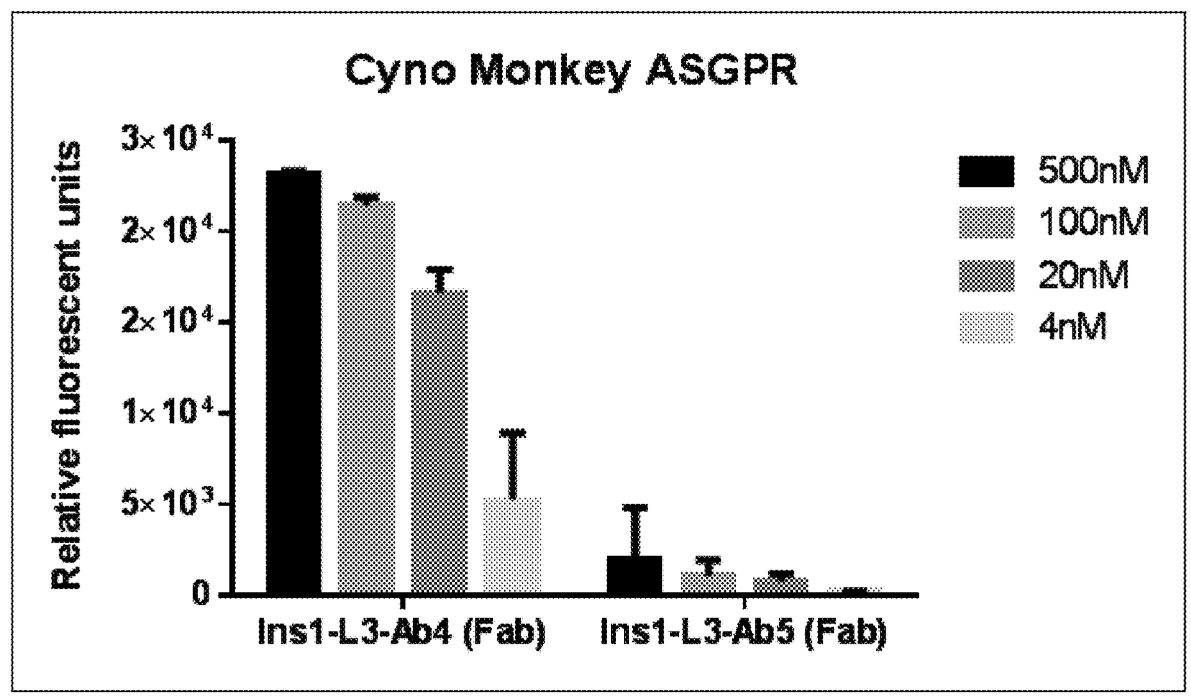
FIG. 39 is a graph of the binding of Ins1-L3-Ab4 Fab and Ins1-L3-Ab5 Fab to extracellular domains of cynomolgus monkey ASGPR.

Example 11: Ins1-L3-Ab4 Fab and Ins1-L3-Ab5 Fab Fusion Proteins Binding Assay for Human, Rat, and Monkey ASGPR The activity of anti-ASGPR within Ins1-L3-Ab4 Fab and Ins1-L3-Ab5 Fab fusion proteins for human, rat, and cyno monkey ASGPR was tested by ELISA assay as shown in FIGS. 37-39 as generally described in Example 3. 100 ng/well ASGPR antigen (human, rat, and cyno monkey) was coated on 96-well plate in PBS 4° C. over night, blocked with 2% milk/PBST (0.5% Tween-20 in PBS) at room temperature for 1 hr, and incubated with the fusion proteins at 4 nM, 20 nM, 100 nM, and 500 nM in 2% milk/PBST at room temperature for 2 hr. Wells were then washed with PBST for 4-5 times, incubated with mouse anti-insulin (MA5-12037, ThermoFisher Scientific) in 2% milk/PBST at room temperature for 2 hr, washed with PBST for 4-5 times, incubated with goat anti-mouse IgG-HRP (115-035-008, Jackson ImmunoResearch) for 30 min, and washed with PBST for 4-5 times The plates were developed with Quant-aBlu fluorogenic peroxidase substrate (Life technologies, 15169), and quantified using Spectramax fluorescence plate reader with excitation at 325 nm and emission at 420 nm.

FIG. 37 shows concentration dependent median fluorescence intensity for binding of Ins1-L3-Ab4 Fab and Ins1-L3-Ab5 Fab with human ASPGR. FIG. 38 shows concentration dependent median fluorescence intensity for binding of Ins1-L3-Ab4 Fab and Ins1-L3-Ab5 Fab with rat ASGPR. FIG. 39 shows concentration dependent median fluorescence intensity for binding of Ins1-L3-Ab4 Fab and Ins1-L3-Ab5 Fab with cyno monkey ASPGR. The figures illustrate that anti-ASGPR antibodies fused to insulin therapeutic peptides retain activity for their antigen ASGPR as determined by ELISA assay.

Figure 16:
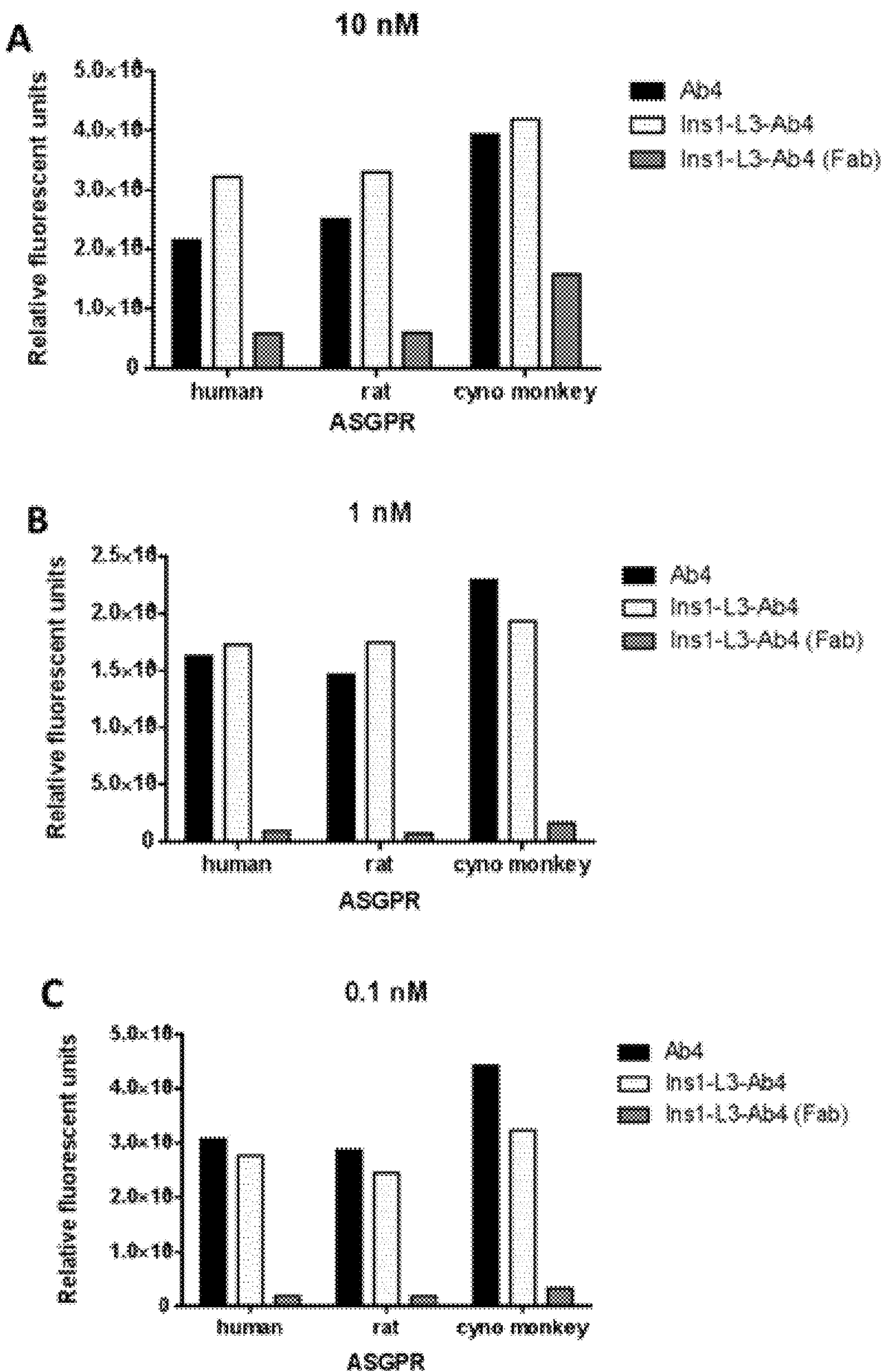
FIG. 16, panels A-C are graphs showing the binding of insulin immunoglobulin fusion proteins (Ins1-L3-Ab4L and Ab4H; Ins1-L3-Ab4L and Ab4H(Fab)) to extracellular domains of human, rat or cynomolgus monkey ASGPR.

FIG. 16, panels A-C are graphs showing the binding of insulin immunoglobulin fusion proteins (Ins1-L3-Ab4L and Ab4H; Ins1-L3-Ab4L and Ab4H(Fab)) to extracellular domains of human, rat or cynomolgus monkey ASGPR as determined by ELISA assay.

Figure 44:
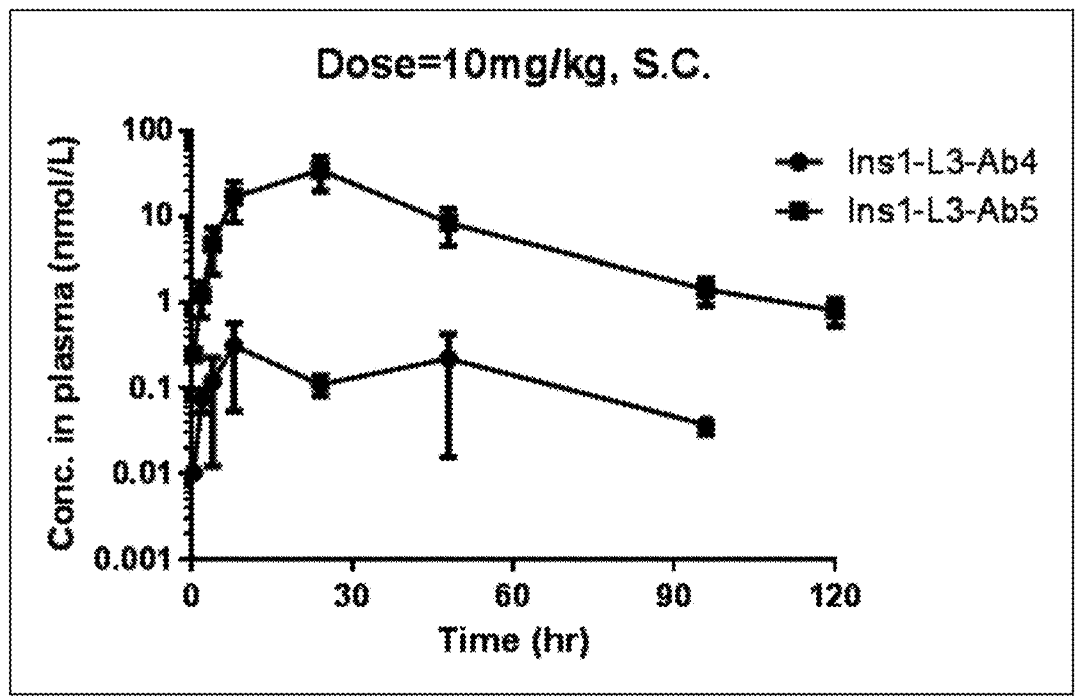
FIG. 44 is a graph of the pharmacology kinetics of Ins1-L3-Ab4 Fab and Ins1-L3-Ab5 Fab at a 10 mg/kg subcutaneous dose.

Example 12: Pharmacology Kinetics and Blood Glucose of Ins1-L3-Ab4 Fab and Ins1-L3-Ab5 Fab in Streptozotocin (STZ) Induced Rats The pharmacology kinetics of Ins1-L3-Ab4 Fab and Ins1-L3-Ab5 Fab was determined in STZ induced rats as seen in FIGS. 40, 42, and 44.

Figure 40:
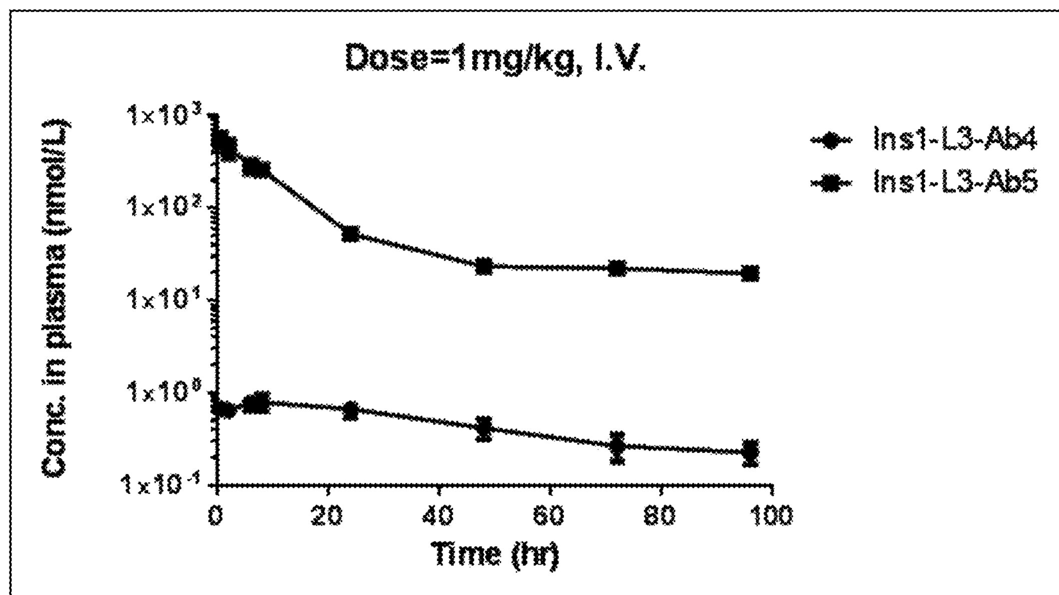
FIG. 40 is a graph of the pharmacology kinetics of Ins1-L3-Ab4 Fab and Ins1-L3-Ab5 Fab at a 1 mg/kg intravenous dose.

FIG. 40 illustrates the pharmacology kinetics in STZ induced rats following intravenous (IV) administration of Ins1-L3-Ab4 Fab and Ins1-L3-Ab5 Fab. 9 week old male Wistar rats were used. STZ was induced with 65 mg/kg IV, and animals were monitored for 2 weeks with fasting blood glucose taken to confirm diabetes. On assay day, animals were fasted for 4 hrs prior to insulin and fusion proteins dose of 1 mg/kg, IV. Pre-dosing, animals were assayed for baseline blood glucose and body weights and sorted (based on body weight and blood glucose) prior to insulin dose. After 8 hrs (12 hrs fasting), food was returned. Standard chow was fed to the rats. Anti-human IgG antibodies (ab98616, Abcam) was coated on 96-well ELISA plate, blocked with 2% milk, incubated with plasma, and then incubated with mouse anti-Insulin (MA5-12037, ThermoFisher Scientific). Signal was detected by goat anti-mouse IgG-HRP antibodies (115-035-008, Jackson ImmunoResearch). Fusion proteins' concentration in plasma were plotted versus time as shown in FIG. 40. As seen in FIG. 40, Ins1-L3-Ab4 Fab and Ins1-L3-Ab5 Fab resulted in a time dependent decrease in concentration of insulin in the plasma.

Figure 41:
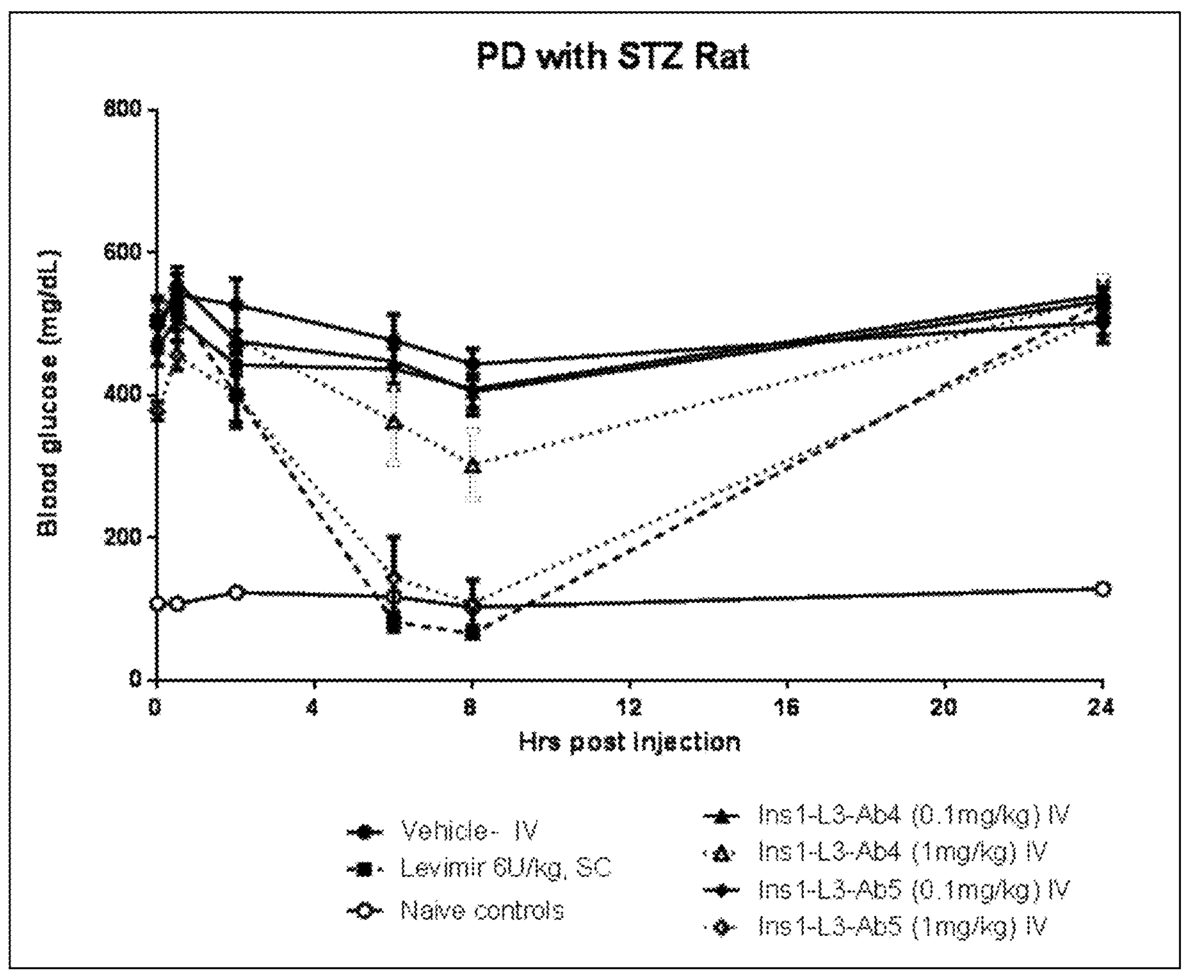
FIG. 41 is a graph of the blood glucose concentration of Ins1-L3-Ab4 Fab and Ins1-L3-Ab5 Fab over time at a 0.1 mg/kg or 1 mg/kg intravenous dose compared to Vehicle, Levimir (6 U/kg, subcutaneous), and Naïve control.

FIG. 41 illustrates the effect on blood glucose concentration in STZ induced rats following IV administration of Ins1-L3-Ab4 Fab and Ins1-L3-Ab5 Fab. Ins1-L3-Ab4 Fab was administered intravenously at either a 0.1 mg/kg or 1 mg/kg dose. Ins1-L3-Ab5 Fab was administered intravenously at either a 0.1 mg/kg or 1 mg/kg dose. Levimir was administered subcutaneously at 6 U/kg. FIG. 41 illustrates the effects of Ins1-L3-Ab4 Fab, Ins1-L3-Ab5 Fab, Levimir, Vehicle, and Naïve control on blood glucose concentration over time.

Figure 42:
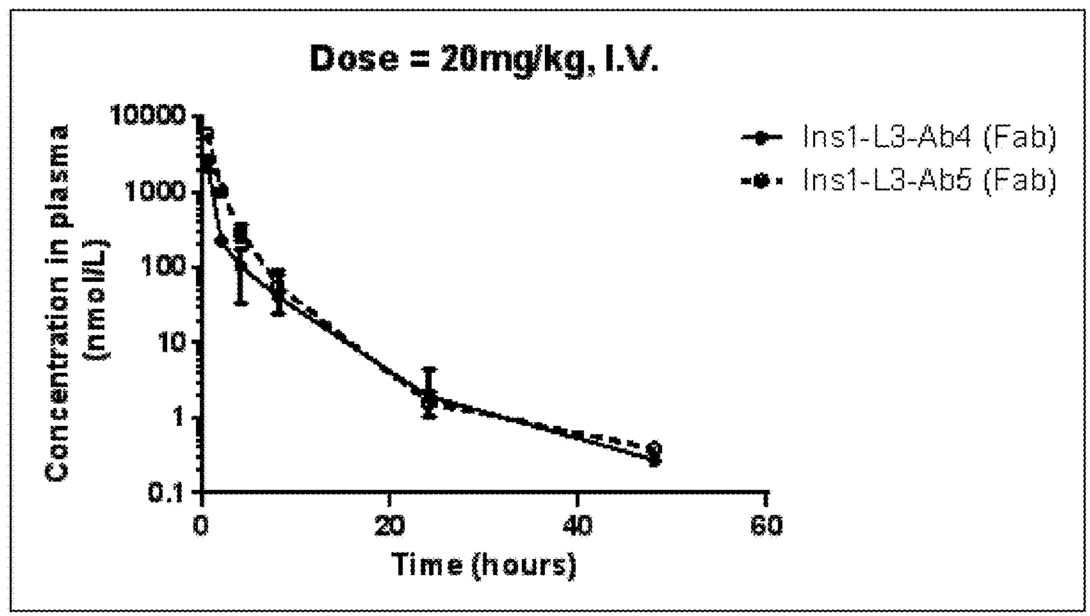
FIG. 42 is a graph of the pharmacology kinetics of Ins1-L3-Ab4 Fab and Ins1-L3-Ab5 Fab at a 20 mg/kg intravenous dose.

FIG. 42 illustrates the pharmacology kinetics in STZ induced rats following IV administration of Ins1-L3-Ab4 Fab and Ins1-L3-Ab5 Fab. 9 week old male Wistar rats were used. STZ was induced with 65 mg/kg IV, and animals were monitored for 2 weeks with fasting blood glucose taken to confirm diabetes. On assay day, animals were fasted for 4 hrs prior to insulin and fusion proteins dose of 20 mg/kg intravenously. Pre-dosing, animals were assayed for baseline blood glucose and body weights and sorted (based on body weight and blood glucose) prior to insulin dose. After 8 hrs (12 hrs fasting), food was returned. Standard chow was fed to the rats. Anti-human Fab antibodies (109-005-097, Jackson ImmunoResearch) was coated on 96-well ELISA plate, blocked with 2% milk, incubated with plasma, and then incubated with mouse anti-Insulin (MA5-12037, ThermoFisher Scientific). Signal was detected by goat anti-mouse IgG-HRP antibodies (115-035-008, Jackson ImmunoResearch). Fusion proteins' concentration in plasma were plotted versus time as shown in FIG. 42 and pharmacokinetic parameters were analyzed by Winnolin. $T_{1/2}$ for Ins1-L3-Ab4 Fab was determined to be 4.8 hr and for Ins1-L3-Ab5 Fab, it was determined to be 4.2 hr. The $C_{max}$ for Ins1-L3-Ab4 Fab was determined to be 2541 nM and for Ins1-L3-Ab5 Fab, it was determined to be 5917 nM. The $T_{max}$, for Ins1-L3-Ab4 Fab and Ins1-L3-Ab5 Fab was 0.5 hr. The area under the curve (AUC) was calculated to be 5145 hr-nM for Ins1-L3-Ab4 Fab and 11886 hr-nM for Ins1-L3-Ab5 Fab.

Figure 43:
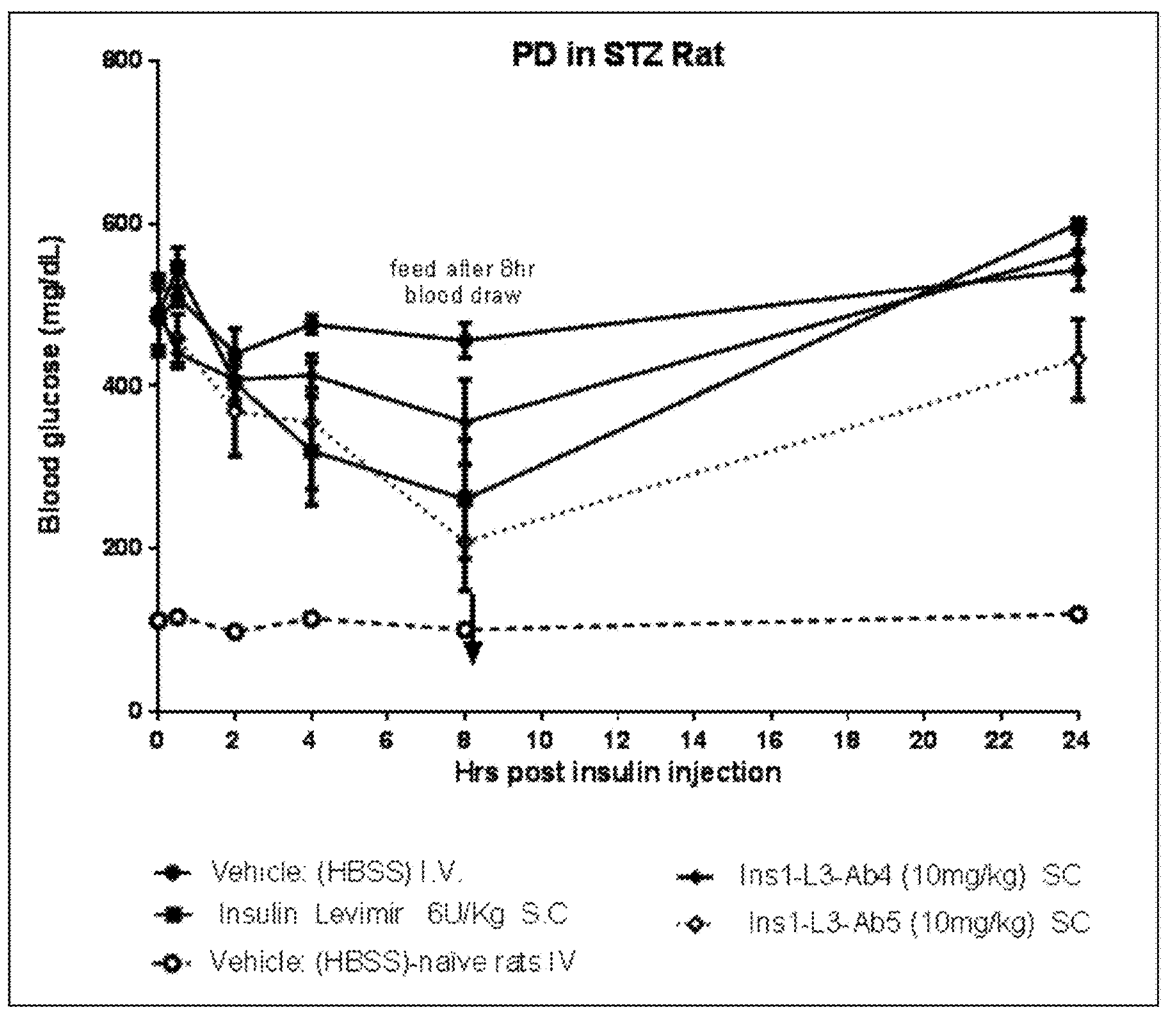
FIG. 43 is a graph of the blood glucose concentration of Ins1-L3-Ab4 Fab and Ins1-L3-Ab5 Fab over time at a 20 mg/kg intravenous dose compared to Vehicle, Levimir (6 U/kg, subcutaneous), and Naïve control.

FIG. 43 illustrates the effect on blood glucose concentration in STZ induced rats following IV administration of Ins1-L3-Ab4 Fab and Ins1-L3-Ab5 Fab. 20 mg/kg dose of Ins1-L3-Ab4 Fab and Ins1-L3-Ab5 Fab were administered intravenously to STD induced rats. Levimir was administered subcutaneously at 6 U/kg. FIG. 43 illustrates the effects of Ins1-L3-Ab4 Fab, Ins1-L3-Ab5 Fab, Levimir, Vehicle (HBSS), and Naïve control on blood glucose concentration over time.

FIG. 44 illustrates the pharmacology kinetics in STZ induced rats following subcutaneous (SC) administration of Ins1-L3-Ab4 Fab and Ins1-L3-Ab5 Fab. Similar to the methods described in this example, rats were administered 10 mg/kg SC of Ins1-L3-Ab4 Fab or Ins1-L3-Ab5 Fab. Fusion proteins' concentration in plasma were plotted versus time as shown in FIG. 44. As seen in FIG. 44, Ins1-L3-Ab4 Fab and Ins1-L3-Ab5 Fab resulted in a time dependent decrease in concentration of insulin in the plasma following 30 hrs.

Figure 45:
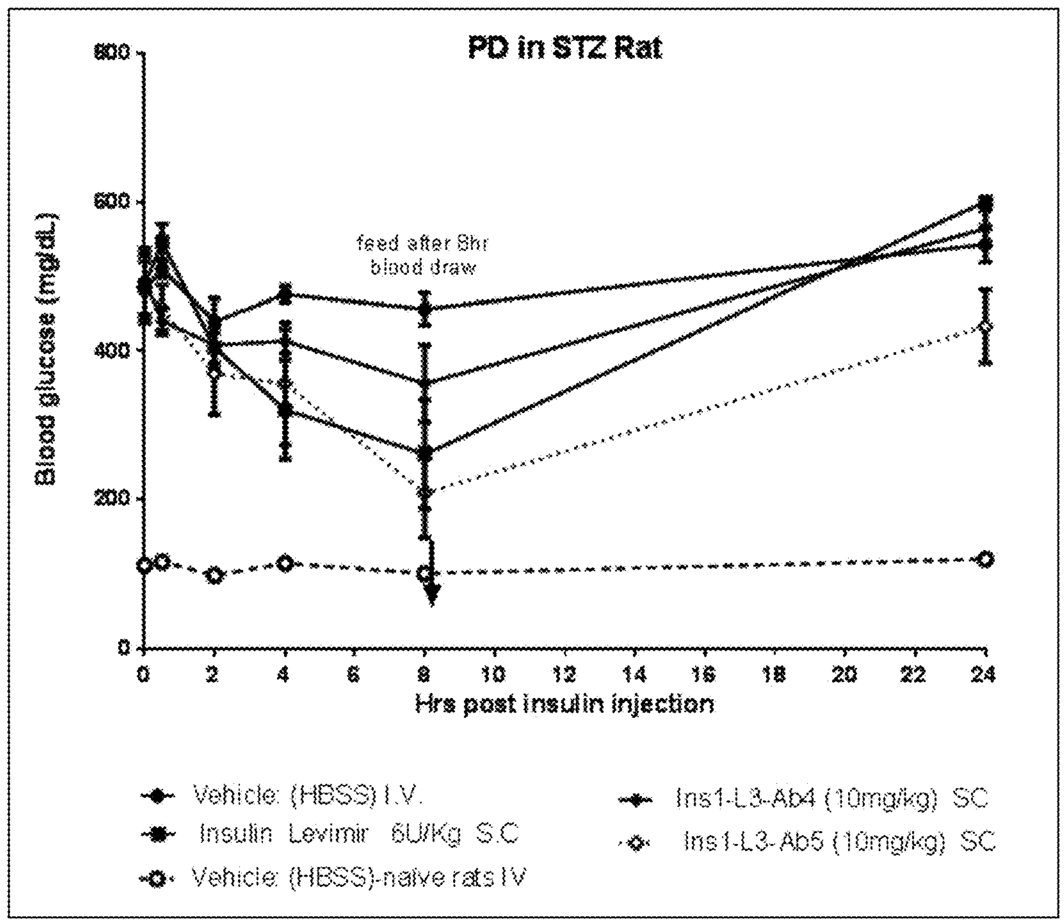
FIG. 45 is a graph of the blood glucose concentration of Ins1-L3-Ab4 Fab and Ins1-L3-Ab5 Fab over time at a 10 mg/kg subcutaneous dose compared to Vehicle, Levimir (6 U/kg, subcutaneous), and Naïve control.

FIG. 45 illustrates the effect on blood glucose concentration in STZ induced rats following SC administration of Ins1-L3-Ab4 Fab and Ins1-L3-Ab5 Fab. 10 mg/kg dose of Ins1-L3-Ab4 Fab and Ins1-L3-Ab5 Fab were administered subcutaneously to STD induced rats. Levimir was administered subcutaneously at 6 U/kg. FIG. 45 illustrates the effects of Ins1-L3-Ab4 Fab, Ins1-L3-Ab5 Fab, Levimir, Vehicle (HBSS), and Naïve control on blood glucose concentration over time.

Figure 46:
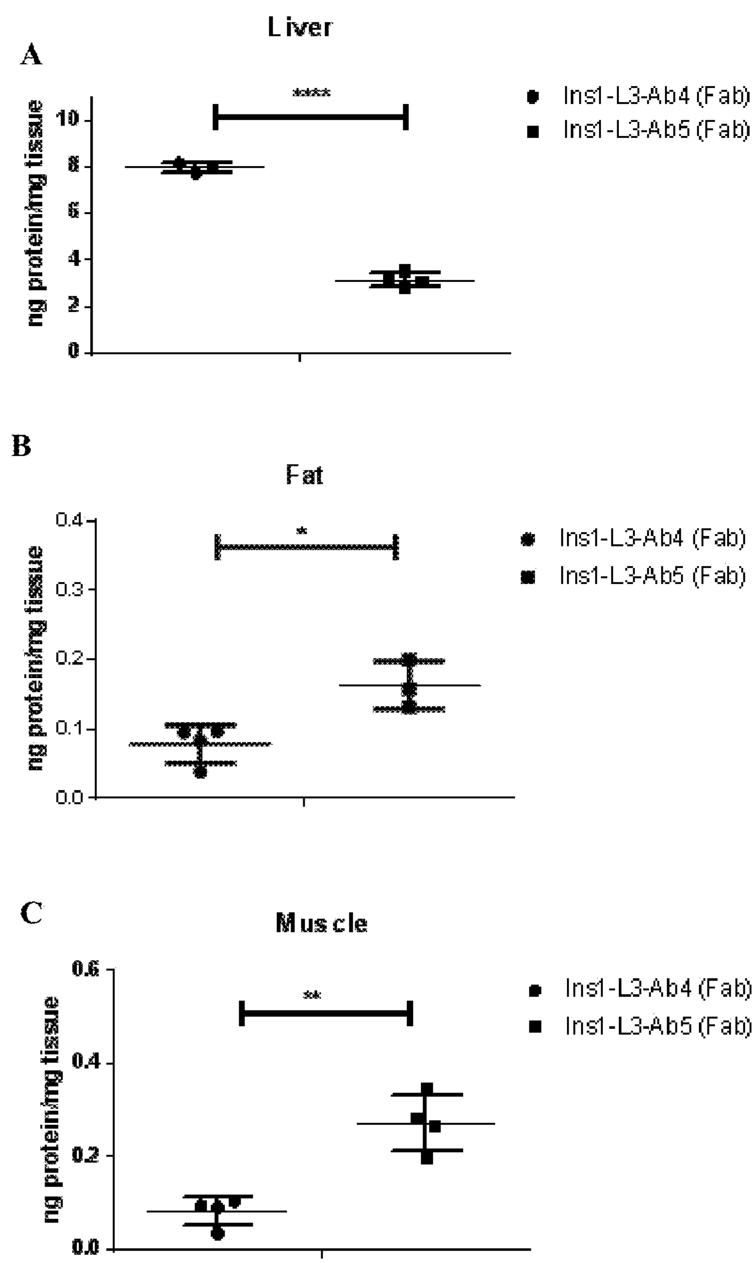
FIG. 46, panels A-C are graphs of the bio-distribution of Ins1-L3-Ab4 Fab and Ins1-L3-Ab5 Fab in normal rats as measured in the liver, muscle, or fat tissue.

Example 13: Bio-Distribution of Ins1-L3-Ab4 Fab and Ins1-L3-Ab5 Fab in Normal Rats FIGS. 46A-46C illustrate the bio-distribution of Ins1-L3-Ab4 Fab and Ins1-L3-Ab5 Fab in normal rats. 9 week old male Wistar rats were fasted for 4 hrs prior to fusion proteins dose (5 mg/kg, IV). Pre-dosing, animals were assayed for baseline blood glucose and body weights and sorted (based on body weight and blood glucose) prior to insulin dose. After 1 hr post dosing, rats were sacrificed, and liver, muscle (quadriceps femoris), and fat (epididymal white adipose) tissue were extracted. Extracted tissue were homogenized as 300 mg/mL in PBS with 1× protease inhibitor, 1 mM EDTA and 0.5% Triton-100. Anti-human Fab antibodies (109-005-097, Jackson ImmunoResearch) was coated on 96-well ELISA plate, blocked with 2% milk, incubated with plasma, and then incubated with mouse anti-Insulin (MA5-12037, ThermoFisher Scientific). Signal was detected by goat anti-mouse IgG-HRP antibodies (115-035-008, Jackson ImmunoResearch).

As seen in FIG. 46A, the amount of Ins1-L3-Ab4 Fab and Ins1-L3-Ab5 Fab in the liver was 7.98 for Ins1-L3-Ab4 Fab and 3.12 for Ins1-L3-Ab5 Fab. As seen in FIG. 46B, the amount of Ins1-L3-Ab4 Fab and Ins1-L3-Ab5 Fab in the fat was 0.08 for Ins1-L3-Ab4 Fab and 0.23 for Ins1-L3-Ab5 Fab. As seen in FIG. 46C, the amount of Ins1-L3-Ab4 Fab and Ins1-L3-Ab5 Fab protein in the muscle was 0.08 for Ins1-L3-Ab4 Fab and 0.27 for Ins1-L3-Ab5 Fab.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All references cited herein are incorporated by reference in their entirety and for all purposes to the same extent as if each individual publication or patent or patent application was specifically and individually indicated to be incorporated by reference in its entirety for all purposes.

TABLE 1

Immunoglobulin Light Chain (LC) and Heavy Chain (HC)-Nucleic acid sequence

| NAME | SEQ ID NO | SEQUENCE |
|---|---|---|
| Ab1H (murine anti-ASGPR HC) | | CAGGTCCAACTGCAGCAGCCTGGGGCTGAGCTTGTGAAGCCTG GGGCTTCAGTGAAACTGTCCTGCAAGGCTTCTGGCTATACCTT CACCAACTACTGGATGCACTGGGTGAAACAGAGGCCTGGACG AGGCCTTGAGTGGATTGGAAGGATTGATCTTAATAGTGGTGGT ACTAATTACAATTACAATGAGAAGTTCAAGACCAAGGCCACA CTGACTGTAGACAAACCCTCCAGCACAGCCTACATGCAGCTCA GCAGCCTGACATCTGAGGACTCTGCGGTCTATTATTGTGCAAA TTACTACGGTAGTAGCTGGTTTGCTTACTGGGGCCAAGGGACC ACTCTCACAGTCTCCTCAGCTAAAACAACAGCCCCATCGGTCT ATCCACTGGCCCCTGTGTGTGGAGATACAACTGGCTCCTCGGT GACTCTAGGATGCCTGGTCAAGGGTTATTTCCCTGAGCCAGTG ACCTTGACCTGGAACTCTGGATCCCTGTCCAGTGGTGTGCACA CCTTCCCAGCTGTCCTGCAGTCTGACCTCTACACCCTCAGCAGC TCAGTGACTGTAACCTCGAGCACCTGGCCCAGCCAGTCCATCA CCTGCAATGTGGCCCACCCGGCAAGCAGCACCAAGGTGGACA AGAAAATTGAGCCCAGAGGGCCCACAATCAAGCCCTGTCCTCC ATGCAAATGCCCAGCACCTAACCTCTTGGGTGGACCATCCGTC TTCATCTTCCCTCCAAAGATCAAGGATGTACTCATGATCTCCCT GAGCCCCATAGTCACATGTGTGGTGGTGGATGTGAGCGAGGAT GACCCAGATGTCCAGATCAGCTGGTTTGTGAACAACGTGGAAG TACACACAGCTCAGACACAAACCCATAGAGAGGATTACAACA GTACTCTCCGGGTGGTCAGTGCCCTCCCCATCCAGCACCAGGA CTGGATGAGTGGCAAGGAGTTCAAATGCAAGGTCAACAACAA AGACCTCCCAGCGCCCATCGAGAGAACCATCTCAAAACCCAA AGGGTCAGTAAGAGCTCCACAGGTATATGTCTTGCCTCCACCA GAAGAAGAGATGACTAAGAAACAGGTCACTCTGACCTGCATG GTCACAGACTTCATGCCTGAAGACATTTACGTGGAGTGGACCA ACAACGGGAAAACAGAGCTAAACTACAAGAACACTGAACCAG TCCTGGACTCTGATGGTTCTTACTTCATGTACAGCAAGCTGAG AGTGGAAAAGAAGAACTGGGTGGAAAGAAATAGCTACTCCTG TTCAGTGGTCCACGAGGGTCTGCACAATCACCACACGACTAAG AGCTTCTCCCGGACTCCGGGTAAA |
| Ab1L (murine anti-ASGPR LC) | | GAAACTGTACTCACCCAGTCTCCAACCACCATGGCTACATCTC CCGGGGAGAAGATCACTATCACCTGCAGTGCCAGCTCAACTAT AAGTTCCAATTACTTGCATTGGTATCAGCAGAAGCCAGGATTC TCCCCTAAACTCTTGATTTATAGGACATCCGATCTGGCTTCTGG AGTCCCAACTCGCTTCAGTGGCAGTGGGTCTGGGACCTCTTAC TCTCTCACAATTGGCACCATGGAGGCTGAAGATGTTGCCACTT ACTACTGCCAGCAGGGTAGTAGTATACCATTCACGTTCGGCTC GGGGACAAAGCTGGAGATTAACCGGGCAGATACAGCACCAAC TGTATCCATCTTCCCACCATCCAGTGAGCAGTTAACATCTGGA GGTGCCTCAGTCGTGTGCTTCTTGAACAACTTCTACCCCAAAG ACATCAATGTCAAGTGGAAGATTGATGGCAGTGAACGACAAA ATGGCGTCCTGAACAGTTGGACTGATCAGGACAGCAAAGACA GCACCTACAGCATGAGCAGCACCCTCACGTTGACCAAGGACG AGTATGAACGACATAACAGCTATACCTGTGAGGCCACTCACAA GACATCAACTTCACCCATTGTCAAGAGCTTCAACAGGAATGAG TGT |
| Ab2H (Palivizumab HC) | | CAGGTGACCCTGCGCGAGTCCGGCCCTGCACTGGTGAAGCCCA CCCAGACCCTGACCCTGACCTGCACCTTCTCCGGCTTCTCCCTG TCCACCTCCGGCATGTCCGTGGGCTGGATCCGGCAGCCTCCCG GCAAGGCCCTGGAGTGGCTGGCTGACATCTGGTGGGACGACA AGAAGGACTACAACCCCTCCCTGAAGTCCCGCCTGACCATCTC CAAGGACACCTCCAAGAACCAGGTGGTGCTGAAGGTGACCAA CATGGACCCCGCCGACACCGCCACCTACTACTGCGCCCGCTCA ATGATTACCAACTGGTACTTCGACGTGTGGGGAGCCGGTACCA CCGTGACCGTGTCTTCCGCCTCCACCAAGGGCCCATCGGTCTT CCCCCTGGCACCCTCCTCCAAGAGCACCTCTGGGGGCACAGCG GCCCTGGGCTGCCTGGTCAAGGACTACTTCCCCGAACCGGTGA CGGTGTCGTGGAACTCAGGCGCCCTGACCAGCGGCGTGCACAC CTTCCCGGCTGTCCTACAGTCCTCAGGACTCTACTCCCTCAGCA GCGTGGTGACTGTGCCCTCTAGCAGCTTGGGCACCCAGACCTA CATCTGCAACGTGAATCACAAGCCCAGCAACACCAAGGTGGA CAAGAAAGTTGAACCCAAATCTTGCGACAAAACTCACACATG CCCACCGTGCCCAGCACCTCCAGTCGCCGGACCGTCAGTCTTC CTCTTCCCTCCAAAACCCAAGGACACCCTCATGATCTCCCGGA CCCCTGAGGTCACATGCGTGGTGGTGGACGTGAGCCACGAAG ACCCTGAGGTCAAGTTCAACTGGTACGTGGACGGCGTGGAGGT GCATAATGCCAAGACAAAGCCGCGGGAGGAGCAGTACAACAG CACGTACCGTGTGGTCAGCGTCCTCACCGTCCTGCACCAGGAC TGGCTGAATGGCAAGGAGTACAAGTGCAAGGTCTCCAACAAA |

TABLE 1-continued

Immunoglobulin Light Chain (LC) and Heavy Chain (HC)-Nucleic acid sequence

| NAME | SEQ ID NO | SEQUENCE |
|---|---|---|
| | | GGCCTCCCAAGCTCCATCGAGAAAACCATCTCCAAAGCCAAA GGGCAGCCCCGAGAACCACAGGTGTACACCCTGCCTCCATCCC GGGATGAGCTGACCAAGAACCAGGTCAGCCTGACCTGCCTGG TCAAAGGCTTCTATCCCAGCGACATCGCCGTGGAGTGGGAGAG CAATGGGCAGCCGGAGAACAACTACAAGACCACGCCTCCCGT GCTGGACTCCGACGGCTCCTTCTTCCTCTACAGCAAGCTCACC GTGGACAAGAGCAGGTGGCAGCAGGGGAACGTCTTCTCATGC TCCGTGATGCATGAGGCTCTGCACAACCACTACACGCAGAAGA GCCTCTCCCTGTCTCCGGGTAAATGATAA |
| Ab2L (Palivizumab LC) | | GACATCCAGATGACCCAGTCCCCCTCCACCCTGTCCGCCTCCG TGGGCGACCGCGTGACCATCACCTGCAAGTGCCAGCTGTCCGT GGGCTACATGCACTGGTACCAGCAGAAGCCCGGCAAGGCCCC CAAGCTGCTGATCTACGACACCTCCAAGCTGGCCTCCGGCGTG CCCTCCCGCTTCTCCGGCTCCGGCTCCGGCACCGAGTTCACCCT GACCATCTCCTCCCTGCAGCCCGACGACTTCGCCACCTACTAC TGCTTCCAGGGCTCCGGCTACCCCTTCACCTTCGGCGGCGGCA CCAAGCTGGAGATCAAACGAACTGTGGCTGCACCATCTGTCTT CATCTTCCCGCCATCTGATGAGCAGTTGAAATCTGGAACTGCC TCTGTCGTGTGCCTGCTGAATAACTTCTATCCCAGAGAGGCCA AAGTACAGTGGAAGGTGGATAACGCCCTCCAATCGGGTAACT CCCAGGAGAGTGTCACAGAGCAGGACAGCAAGGACAGCACCT ACAGCCTCAGCAGCACCCTGACGCTGAGCAAAGCAGACTACG AGAAACACAAAGTCTACGCCTGCGAAGTCACCCATCAGGGCC TGTCCTCGCCCGTCACAAAGAGCTTCAACAGGGGAGAGTGTTG A |
| Ab3L (chimeric anti-ASGPR) | | GAAACTGTACTCACCCAGTCTCCAACCACCATGGCTACATCTC CCGGGGAGAAGATCACTATCACCTGCAGTGCCAGCTCAACTAT AAGTTCCAATTACTTGCATTGGTATCAGCAGAAGCCAGGATTC TCCCCTAAACTCTTGATTTATAGGACATCCGATCTGGCTTCTGG AGTCCCAACTCGCTTCAGTGGCAGTGGGTCTGGGACCTCTTAC TCTCTCACAATTGGCACCATGGAGGCTGAAGATGTTGCCACTT ACTACTGCCAGCAGGGTAGTAGTATACCATTCACGTTCGGCTC GGGGACAAAGTTGGAAATTAAACGAACTGTGGCTGCACCATC TGTCTTCATCTTCCCGCCATCTGATGAGCAGTTGAAATCTGGA ACTGCCTCTGTCGTGTGCCTGCTGAATAACTTCTATCCCAGAG AGGCCAAAGTACAGTGGAAGGTGGATAACGCCCTCCAATCGG GTAACTCCCAGGAGAGTGTCACAGAGCAGGACAGCAAGGACA GCACCTACAGCCTCAGCAGCACCCTGACGCTGAGCAAAGCAG ACTACGAGAAACACAAAGTCTACGCCTGCGAAGTCACCCATC AGGGCCTGTCCTCGCCCGTCACAAAGAGCTTCAACAGGGGAG AGTGTTGA |
| Ab4H (anti-ASGPR HC, humanized) | | CAGGTGCAGCTGGTCCAGTCCGGCGCAGAGGTGAAGAAACCC GGGGCCTCCGTGAAGGTCTCTTGCAAAGCTAGTGGGTACACCT TCACAAACTATTGGATGCACTGGGTGCGACAGGCACCTGGACA GGGCCTGGAATGGATGGGAAGAATCGACCTGAACAGCGGCGG GACTAACTACAATTATGCCCAGAAGTTTCAGGGCAGGGTGACT ATGACCCGCGATACCTCAATTAGCACAGCTTACATGGAGCTGT CACGGCTGAGAAGCGACGATACAGCCGTCTACTATTGTGCTCG GTACTATGGCAGCTCCTGGTTCGCCTATTGGGGGCAGGGAACA CTGGTGACTGTCTCTAGTGCATCAACAAAGGGACCAAGCGTGT TTCCACTGGCCCCCTCAAGCAAGAGCACCTCCGGAGGGACAGC CGCTCTGGGATGTCTGGTGAAAGACTACTTCCCCGAGCCTGTG ACTGTCTCTTGGAATAGTGGCGCTCTGACCTCCGGGGTGCACA CATTTCCAGCAGTCCTGCAGTCCTCTGGACTGTATTCTCTGAGT TCAGTGGTCACCGTGCCCAGCTCCTCTCTGGGCACTCAGACCT ACATCTGCAATGTCAACCATAAGCCTAGTAACACAAAAGTGG ATAAGAAAGTCGAACCAAAGAGCTGTGACAAAACTCACACAT GCCCACCGTGCCCAGCACCTCCAGTCGCCGGACCGTCAGTCTT CCTCTTCCCTCCAAAACCCAAGGACACCCTCATGATCTCCCGG ACCCCTGAGGTCACATGCGTGGTGGTGGACGTGAGCCACGAA GACCCTGAGGTCAAGTTCAACTGGTACGTGGACGGCGTGGAG GTGCATAATGCCAAGACAAAGCCGCGGGAGGAGCAGTACAAC AGCACGTACCGTGTGGTCAGCGTCCTCACCGTCCTGCACCAGG ACTGGCTGAATGGCAAGGAGTACAAGTGCAAGGTCTCCAACA AAGGCCTCCCAAGCTCCATCGAGAAAACCATCTCCAAAGCCA AAGGGCAGCCCCGAGAACCACAGGTGTACACCCTGCCTCCATC CCGGGATGAGCTGACCAAGAACCAGGTCAGCCTGACCTGCCT GGTCAAAGGCTTCTATCCCAGCGACATCGCCGTGGAGTGGGAG AGCAATGGGCAGCCGGAGAACAACTACAAGACCACGCCTCCC GTGCTGGACTCCGACGGCTCCTTCTTCCTCTACAGCAAGCTCA |

TABLE 1-continued

Immunoglobulin Light Chain (LC) and Heavy Chain (HC)-
Nucleic acid sequence

| NAME | SEQ ID NO | SEQUENCE |
|---|---|---|
| | | CCGTGGACAAGAGCAGGTGGCAGCAGGGGAACGTCTTCTCAT<br>GCTCCGTGATGCATGAGGCTCTGCACAACCACTACACGCAGAA<br>GAGCCTCTCCCTGTCTCCGGGTAAA |
| Ab4L (anti-ASGPR LC, humanized) | | GAGATCGTGCTGACTCAGAGCCCAGGAACCCTGTCCCTGTCTC<br>CAGGAGAACGAGCCACCCTGTCCTGCTCCGCCTCATCAACAAT<br>TTCTAGTAACTACCTGCACTGGTATCAGCAGAAGCCAGGACAG<br>GCACCTCGACTGCTGATCTACAGAACTAGTGACCTGGCCTCTG<br>GCATTCCCGATAGGTTCAGCGGCTCCGGGTCTGGAACAGACTT<br>TACCCTGACAATCTCCCGCCTGGAGCCTGAAGATTTCGCTGTC<br>TACTATTGTCAGCAGGGCTCAAGCATCCCATTCACATTTGGCC<br>AGGGGACTAAGCTGGAGATCAAGCGCACAGTGGCAGCCCCCA<br>GCGTCTTCATTTTTCCCCCTTCCGATGAACAGCTGAAGTCCGGC<br>ACTGCTTCTGTGGTCTGTCTGCTGAACAATTTCTATCCCAGAGA<br>GGCCAAGGTGCAGTGGAAAGTGGACAACGCTCTGCAGTCCGG<br>CAACAGCCAGGAGAGTGTGACCGAACAGGATAGTAAGGACAG<br>CACATATTCTCTGTCTAGTACCCTGACACTGAGTAAGGCAGAT<br>TACGAGAAGCACAAAGTGTATGCCTGCGAAGTCACTCATCAG<br>GGACTGTCAAGCCCCGTGACCAAGAGCTTCAACCGGGGCGAG<br>TGT |
| Ab4H Fab (anti-ASGPR HC, humanized, Fab) | | CAGGTGCAGCTGGTCCAGTCCGGCGCAGAGGTGAAGAAACCC<br>GGGGCCTCCGTGAAGGTCTCTTGCAAAGCTAGTGGGTACACCT<br>TCACAAACTATTGGATGCACTGGGTGCGACAGGCACCTGGACA<br>GGGCCTGGAATGGATGGGAAGAATCGACCTGAACAGCGGCGG<br>GACTAACTACAATTATGCCCAGAAGTTTCAGGGCAGGGTGACT<br>ATGACCCGCGATACCTCAATTAGCACAGCTTACATGGAGCTGT<br>CACGGCTGAGAAGCGACGATACAGCCGTCTACTATTGTGCTCG<br>GTACTATGGCAGCTCCTGGTTCGCCTATTGGGGGCAGGGAACA<br>CTGGTGACTGTCTCTAGTGCATCAACAAAGGGACCAAGCGTGT<br>TTCCACTGGCCCCCTCAAGCAAGAGCACCTCCGGAGGGACAGC<br>CGCTCTGGGATGTCTGGTGAAAGACTACTTCCCCGAGCCTGTG<br>ACTGTCTCTTGGAATAGTGGCGCTCTGACCTCCGGGGTGCACA<br>CATTTCCAGCAGTCCTGCAGTCCTCTGGACTGTATTCTCTGAGT<br>TCAGTGGTCACCGTGCCCAGCTCCTCTCTGGGCACTCAGACCT<br>ACATCTGCAATGTCAACCATAAGCCTAGTAACACAAAAGTGG<br>ATAAGAAAGTCGAACCAAAGAGCTGTGGACAAAACTCACACA |
| Ab5H (anti-ASGPR HC, humanized, R50W) | | CAGGTGCAGCTGGTCCAGTCCGGCGCAGAGGTGAAGAAACCC<br>GGGGCCTCCGTGAAGGTCTCTTGCAAAGCTAGTGGGTACACCT<br>TCACAAACTATTGGATGCACTGGGTGCGACAGGCACCTGGACA<br>GGGCCTGGAATGGATGGGATGGATCGACCTGAACAGCGGCGG<br>GACTAACTACAATTATGCCCAGAAGTTTCAGGGCAGGGTGACT<br>ATGACCCGCGATACCTCAATTAGCACAGCTTACATGGAGCTGT<br>CACGGCTGAGAAGCGACGATACAGCCGTCTACTATTGTGCTCG<br>GTACTATGGCAGCTCCTGGTTCGCCTATTGGGGGCAGGGAACA<br>CTGGTGACTGTCTCTAGTGCATCAACAAAGGGACCAAGCGTGT<br>TTCCACTGGCCCCCTCAAGCAAGAGCACCTCCGGAGGGACAGC<br>CGCTCTGGGATGTCTGGTGAAAGACTACTTCCCCGAGCCTGTG<br>ACTGTCTCTTGGAATAGTGGCGCTCTGACCTCCGGGGTGCACA<br>CATTTCCAGCAGTCCTGCAGTCCTCTGGACTGTATTCTCTGAGT<br>TCAGTGGTCACCGTGCCCAGCTCCTCTCTGGGCACTCAGACCT<br>ACATCTGCAATGTCAACCATAAGCCTAGTAACACAAAAGTGG<br>ATAAGAAAGTCGAACCAAAGAGCTGTGACAAAACTCACACAT<br>GCCCACCGTGCCCAGCACCTCCAGTCGCCGGACCGTCAGTCTT<br>CCTCTTCCCTCCAAAACCCAAGGACACCCTCATGATCTCCCGG<br>ACCCCTGAGGTCACATGCGTGGTGGTGGACGTGAGCCACGAA<br>GACCCTGAGGTCAAGTTCAACTGGTACGTGGACGGCGTGGAG<br>GTGCATAATGCCAAGACAAAGCCGCGGGAGGAGCAGTACAAC<br>AGCACGTACCGTGTGGTCAGCGTCCTCACCGTCCTGCACCAGG<br>ACTGGCTGAATGGCAAGGAGTACAAGTGCAAGGTCTCCAACA<br>AAGGCCTCCCAAGCTCCATCGAGAAAACCATCTCCAAAGCCA<br>AAGGGCAGCCCCGAGAACCACAGGTGTACACCCTGCCTCCATC<br>CCGGGATGAGCTGACCAAGAACCAGGTCAGCCTGACCTGCCT<br>GGTCAAAGGCTTCTATCCCAGCGACATCGCCGTGGAGTGGGAG<br>AGCAATGGGCAGCCGGAGAACAACTACAAGACCACGCCTCCC<br>GTGCTGGACTCCGACGGCTCCTTCTTCCTCTACAGCAAGCTCA<br>CCGTGGACAAGAGCAGGTGGCAGCAGGGGAACGTCTTCTCAT<br>GCTCCGTGATGCATGAGGCTCTGCACAACCACTACACGCAGAA<br>GAGCCTCTCCCTGTCTCCGGGTAAA |

TABLE 1-continued

Immunoglobulin Light Chain (LC) and Heavy Chain (HC)-Nucleic acid sequence

| NAME | SEQ ID NO | SEQUENCE |
|---|---|---|
| Ab5H Fab (anti-ASGPR HC, humanized, R50W, Fab) | | CAGGTGCAGCTGGTCCAGTCCGGCGCAGAGGTGAAGAAACCC GGGGCCTCCGTGAAGGTCTCTTGCAAAGCTAGTGGGTACACCT TCACAAACTATTGGATGCACTGGGTGCGACAGGCACCTGGACA GGGCCTGGAATGGATGGGATGGATCGACCTGAACAGCGGCGG GACTAACTACAATTATGCCCAGAAGTTTCAGGGCAGGGTGACT ATGACCCGCGATACCTCAATTAGCACAGCTTACATGGAGCTGT CACGGCTGAGAAGCGACGATACAGCCGTCTACTATTGTGCTCG GTACTATGGCAGCTCCTGGTTCGCCTATTGGGGGCAGGGAACA CTGGTGACTGTCTCTAGTGCATCAACAAAGGGACCAAGCGTGT TTCCACTGGCCCCCTCAAGCAAGAGCACCTCCGGAGGGACAGC CGCTCTGGGATGTCTGGTGAAAGACTACTTCCCCGAGCCTGTG ACTGTCTCTTGGAATAGTGGCGCTCTGACCTCCGGGGTGCACA CATTTCCAGCAGTCCTGCAGTCCTCTGGACTGTATTCTCTGAGT TCAGTGGTCACCGTGCCCAGCTCCTCTCTGGGCACTCAGACCT ACATCTGCAATGTCAACCATAAGCCTAGTAACACAAAAGTGG ATAAGAAAGTCGAACCAAAGAGCTGTGACAAAACTCACACA |
| Ab1 VH | | CAGGTCCAACTGCAGCAGCCTGGGGCTGAGCTTGTGAAGCCTG GGGCTTCAGTGAAACTGTCCTGCAAGGCTTCTGGCTATACCTT CACCAACTACTGGATGCACTGGGTGAAACAGAGGCCTGGACG AGGCCTTGAGTGGATTGGAAGGATTGATCTTAATAGTGGTGGT ACTAATTACAATTACAATGAGAAGTTCAAGACCAAGGCCACA CTGACTGTAGACAAACCCTCCAGCACAGCCTACATGCAGCTCA GCAGCCTGACATCTGAGGACTCTGCGGTCTATTATTGTGCAAA TTACTACGGTAGTAGCTGGTTTGCTTACTGGGGCCAAGGGACC ACTCTCACAGTCTCCTCA |
| human IgG1 CH1 | | GCCTCCACCAAGGGCCCATCGGTCTTCCCCCTGGCACCCTCCT CCAAGAGCACCTCTGGGGGCACAGCGGCCCTGGGCTGCCTGGT CAAGGACTACTTCCCCGAACCGGTGACGGTGTCGTGGAACTCA GGCGCCCTGACCAGCGGCGTGCACACCTTCCCGGCTGTCCTAC AGTCCTCAGGACTCTACTCCCTCAGCAGCGTGGTGACTGTGCC CTCTAGCAGCTTGGGCACCCAGACCTACATCTGCAACGTGAAT CACAAGCCCAGCAACACCAAGGTGGACAAGAAAGTTGAACCC AAATCTTGC |
| Ab1 VL | | GAAACTGTACTCACCCAGTCTCCAACCACCATGGCTACATCTC CCGGGGAGAAGATCACTATCACCTGCAGTGCCAGCTCAACTAT AAGTTCCAATTACTTGCATTGGTATCAGCAGAAGCCAGGATTC TCCCCTAAACTCTTGATTTATAGGACATCCGATCTGGCTTCTGG AGTCCCAACTCGCTTCAGTGGCAGTGGGTCTGGGACCTCTTAC TCTCTCACAATTGGCACCATGGAGGCTGAAGATGTTGCCACTT ACTACTGCCAGCAGGGTAGTAGTATACCATTCACGTTCGGCTC GGGGACAAAGTTGGAAATTAAA |
| human Ig kappa CL | | CGAACTGTGGCTGCACCATCTGTCTTCATCTTCCCGCCATCTGA TGAGCAGTTGAAATCTGGAACTGCCTCTGTCGTGTGCCTGCTG AATAACTTCTATCCCAGAGAGGCCAAAGTACAGTGGAAGGTG GATAACGCCCTCCAATCGGGTAACTCCCAGGAGAGTGTCACAG AGCAGGACAGCAAGGACAGCACCTACAGCCTCAGCAGCACCC TGACGCTGAGCAAAGCAGACTACGAGAAACACAAAGTCTACG CCTGCGAAGTCACCCATCAGGGCCTGTCCTCGCCCGTCACAAA GAGCTTCAACAGGGGAGAGTGT |
| Ab4 VH | | CAGGTGCAGCTGGTCCAGTCCGGCGCAGAGGTGAAGAAACCC GGGGCCTCCGTGAAGGTCTCTTGCAAAGCTAGTGGGTACACCT TCACAAACTATTGGATGCACTGGGTGCGACAGGCACCTGGACA GGGCCTGGAATGGATGGGAAGAATCGACCTGAACAGCGGCGG GACTAACTACAATTATGCCCAGAAGTTTCAGGGCAGGGTGACT ATGACCCGCGATACCTCAATTAGCACAGCTTACATGGAGCTGT CACGGCTGAGAAGCGACGATACAGCCGTCTACTATTGTGCTCG GTACTATGGCAGCTCCTGGTTCGCCTATTGGGGGCAGGGAACA CTGGTGACTGTCTCTAGT |
| Ab4 VL | | GAGATCGTGCTGACTCAGAGCCCAGGAACCCTGTCCCTGTCTC CAGGAGAACGAGCCACCCTGTCCTGCTCCGCCTCATCAACAAT TTCTAGTAACTACCTGCACTGGTATCAGCAGAAGCCAGGACAG GCACCTCGACTGCTGATCTACAGAACTAGTGACCTGGCCTCTG GCATTCCCGATAGGTTCAGCGGCTCCGGGTCTGGAACAGACTT TACCCTGACAATCTCCCGCCTGGAGCCTGAAGATTTCGCTGTC TACTATTGTCAGCAGGGCTCAAGCATCCCATTCACATTTGGCC AGGGGACTAAGCTGGAGATCAAG |

TABLE 1-continued

| Immunoglobulin Light Chain (LC) and Heavy Chain (HC)-Nucleic acid sequence | | |
|---|---|---|
| NAME | SEQ ID NO | SEQUENCE |
| Ab1 VH CDR1 | | GGCTATACCTTCACCAACTACTGGATGCAC |
| Ab1 VH CDR2 | | AGGATTGATCTTAATAGTGGTGGTACTAATTACAATTACAATG AGAAGTTCAAGACC |
| Ab1 VH CDR3 | | TACTACGGTAGTAGCTGGTTTGCTTAC |
| Ab1 VL CDR1 | | AGTGCCAGCTCAACTATAAGTTCCAATTACTTGCAT |
| Ab1 VL CDR2 | | AGGACATCCGATCTGGCTTCT |
| Ab1 VL CDR3 | | CAGCAGGGTAGTAGTATACCATTCACG |
| Ab4L CDR1 | | TCCGCCTCATCAACAATTTCTAGTAACTACCTGCAC |
| Ab4L CDR2 | | AGAACTAGTGACCTGGCCTCT |
| Ab4L CDR3 | | CAGCAGGGCTCAAGCATCCCATTCACA |
| Ab4H CDR1 | | GGGTACACCTTCACAAACTATTGGATGCAC |
| Ab4H CDR2 | | AGAATCGACCTGAACAGCGGCGGGACTAACTACAATTATGCC CAGAAGTTTCAGGGCA |
| Ab4H CDR3 | | TACTATGGCAGCTCCTGGTTCGCCTAT |

TABLE 2

| Immunoglobulin Light Chain (LC) and Heavy Chain (HC)-Amino Acid Sequence | |
|---|---|
| Ab1H (murine anti-ASGPR, HC) | QVQLQQPGAELVKPGASVKLSCKASGYTFTNYWMHWVKQRPG RGLEWIGRIDLNSGGTNYNYNEKFKTKATLTVDKPSSTAYMQLS SLTSEDSAVYYCANYYGSSWFAYWGQGTTLTVSSAKTTAPSVYP LAPVCGDTTGSSVTLGCLVKGYFPEPVTLTWNSGSLSSGVHTFPA VLQSDLYTLSSSVTVTSSTWPSQSITCNVAHPASSTKVDKKIEPRG PTIKPCPPCKCPAPNLLGGPSVFIFPPKIKDVLMISLSPIVTCVVVDV SEDDPDVQISWFVNNVEVHTAQTQTHREDYNSTLRVVSALPIQH QDWMSGKEFKCKVNNKDLPAPIERTISKPKGSVRAPQVYVLPPPE EEMTKKQVTLTCMVTDFMPEDIYVEWTNNGKTELNYKNTEPVL DSDGSYFMYSKLRVEKKNWVERNSYSCSVVHEGLHNHHTTKSFS RTPGK |
| Ab1L (murine anti-ASGPR, LC) | ETVLTQSPTTMATSPGEKITITCSASSTISSNYLHWYQQKPGFSPKL LIYRTSDLASGVPTRFSGSGSGTSYSLTIGTMEAEDVATYYCQQGS SIPFTFGSGTKLEINRADTAPTVSIFPPSSEQLTSGGASVVCFLNNF YPKDINVKWKIDGSERQNGVLNSWTDQDSKDSTYSMSSTLTLTK DEYERHNSYTCEATHKTSTSPIVKSFNRNEC |
| Ab2H (Palivizumab HC) | QVTLRESGPALVKPTQTLTLTCTFSGFSLSTSGMSVGWIRQPPGK ALEWLADIWWDDKKDYNPSLKSRLTISKDTSKNQVVLKVTNMD PADTATYYCARSMITNWYFDVWGAGTTVTVSSASTKGPSVFPLA PSSKSTSGGTAALGCLVKDYFPEPVTVSWNSGALTSGVHTFPAVL QSSGLYSLSSVVTVPSSSLGTQTYICNVNHKPSNTKVDKKVEPKS CDKTHTCPPCPAPPVAGPSVFLFPPKPKDTLMISRTPEVTCVVVDV SHEDPEVKFNWYVDGVEVHNAKTKPREEQYNSTYRVVSVLTVL HQDWLNGKEYKCKVSNKGLPSSIEKTISKAKGQPREPQVYTLPPS RDELTKNQVSLTCLVKGFYPSDIAVEWESNGQPENNYKTTPPVLD SDGSFFLYSKLTVDKSRWQQGNVFSCSVMHEALHNHYTQKSLSL SPGK |
| Ab2L (Palivizumab LC) | DIQMTQSPSTLSASVGDRVTITCKCQLSVGYMHWYQQKPGKAPK LLIYDTSKLASGVPSRFSGSGSGTEFTLTISSLQPDDFATYYCFQGS GYPFTFGGGTKLEIKRTVAAPSVFIFPPSDEQLKSGTASVVCLLNN FYPREAKVQWKVDNALQSGNSQESVTEQDSKDSTYSLSSTLTLS KADYEKHKVYACEVTHQGLSSPVTKSFNRGEC |
| Ab3L (chimeric anti-ASGPR) | ETVLTQSPTTMATSPGEKITITCSASSTISSNYLHWYQQKPGFSPKL LIYRTSDLASGVPTRFSGSGSGTSYSLTIGTMEAEDVATYYCQQGS SIPFTFGSGTKLEIKRTVAAPSVFIFPPSDEQLKSGTASVVCLLNNF |

TABLE 2-continued

| Immunoglobulin Light Chain (LC) and Heavy Chain (HC)-Amino Acid Sequence | |
|---|---|
| | YPREAKVQWKVDNALQSGNSQESVTEQDSKDSTYSLSSTLTLSK ADYEKHKVYACEVTHQGLSSPVTKSFNRGEC |
| Ab4H (anti-ASGPR HC, humanized) | QVQLVQSGAEVKKPGASVKVSCKASGYTFTNYWMHWVRQAPG QGLEWMGRIDLNSGGTNYNYAQKFQGRVTMTRDTSISTAYMEL SRLRSDDTAVYYCARYYGSSWFAYWGQGTLVTVSSASTKGPSVF PLAPSSKSTSGGTAALGCLVKDYFPEPVTVSWNSGALTSGVHTFP AVLQSSGLYSLSSVVTVPSSSLGTQTYICNVNHKPSNTKVDKKVE PKSCDKTHTCPPCPAPPVAGPSVFLFPPKPKDTLMISRTPEVTCVV VDVSHEDPEVKFNWYVDGVEVHNAKTKPREEQYNSTYRVVSVL TVLHQDWLNGKEYKCKVSNKGLPSSIEKTISKAKGQPREPQVYTL PPSRDELTKNQVSLTCLVKGFYPSDIAVEWESNGQPENNYKTTPP VLDSDGSFFLYSKLTVDKSRWQQGNVFSCSVMHEALHNHYTQK SLSLSPGK |
| Ab4L (anti-ASGPR LC, humanized) | EIVLTQSPGTLSLSPGERATLSCSASSTISSNYLHWYQQKPGQAPR LLIYRTSDLASGIPDRFSGSGSGTDFTLTISRLEPEDFAVYYCQQGS SIPFTFGQGTKLEIKRTVAAPSVFIFPPSDEQLKSGTASVVCLLNNF YPREAKVQWKVDNALQSGNSQESVTEQDSKDSTYSLSSTLTLSK ADYEKHKVYACEVTHQGLSSPVTKSFNRGEC |
| Ab4H Fab (anti-ASGPR HC, humanized, Fab) | QVQLVQSGAEVKKPGASVKVSCKASGYTFTNYWMHWVRQAPG QGLEWMGRIDLNSGGTNYNYAQKFQGRVTMTRDTSISTAYMEL SRLRSDDTAVYYCARYYGSSWFAYWGQGTLVTVSSASTKGPSVF PLAPSSKSTSGGTAALGCLVKDYFPEPVTVSWNSGALTSGVHTFP AVLQSSGLYSLSSVVTVPSSSLGTQTYICNVNHKPSNTKVDKKVE PKSCDKTHT |
| Ab5H (anti-ASGPR HC, humanized, R50W) | QVQLVQSGAEVKKPGASVKVSCKASGYTFTNYWMHWVRQAPG QGLEWMGWIDLNSGGTNYNYAQKFQGRVTMTRDTSISTAYMEL SRLRSDDTAVYYCARYYGSSWFAYWGQGTLVTVSSASTKGPSVF PLAPSSKSTSGGTAALGCLVKDYFPEPVTVSWNSGALTSGVHTFP AVLQSSGLYSLSSVVTVPSSSLGTQTYICNVNHKPSNTKVDKKVE PKSCDKTHTCPPCPAPPVAGPSVFLFPPKPKDTLMISRTPEVTCVV VDVSHEDPEVKFNWYVDGVEVHNAKTKPREEQYNSTYRVVSVL TVLHQDWLNGKEYKCKVSNKGLPSSIEKTISKAKGQPREPQVYTL PPSRDELTKNQVSLTCLVKGFYPSDIAVEWESNGQPENNYKTTPP VLDSDGSFFLYSKLTVDKSRWQQGNVFSCSVMHEALHNHYTQK SLSLSPGK |
| Ab5H Fab (anti-ASGPR HC, humanized, R50W, Fab) | QVQLVQSGAEVKKPGASVKVSCKASGYTFTNYWMHWVRQAPG QGLEWMGWIDLNSGGTNYNYAQKFQGRVTMTRDTSISTAYMEL SRLRSDDTAVYYCARYYGSSWFAYWGQGTLVTVSSASTKGPSVF PLAPSSKSTSGGTAALGCLVKDYFPEPVTVSWNSGALTSGVHTFP AVLQSSGLYSLSSVVTVPSSSLGTQTYICNVNHKPSNTKVDKKVE PKSCDKTHT |
| Ab1 VH | QVQLQQPGAELVKPGASVKLSCKASGYTFTNYWMHWVKQRPG RGLEWIGRIDLNSGGTNYNYNEKFKTKATLTVDKPSSTAYMQLS SLTSEDSAVYYCANYYGSSWFAYWGQGTLVTVSA |
| human IgG1 CH1 | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSC |
| Ab1 VL | ETVLTQSPTTMATSPGEKITITCSASSTISSNYLHWYQQKPGFSPKL LIYRTSDLASGVPTRFSGSGSGTSYSLTIGTMEAEDVATYYCQQGS SIPFTFGSGTKLEIK |
| human Ig kappa CL | RTVAAPSVFIFPPSDEQLKSGTASVVCLLNNFYPREAKVQWKVDN ALQSGNSQESVTEQDSKDSTYSLSSTLTLSKADYEKHKVYACEVT HQGLSSPVTKSFNRGEC |
| Ab4 VH | QVQLVQSGAEVKKPGASVKVSCKASGYTFTNYWMHWVRQAPG QGLEWMGRIDLNSGGTNYNYAQKFQGRVTMTRDTSISTAYMEL SRLRSDDTAVYYCARYYGSSWFAYWGQGTLVTVSS |
| Ab4 VL | EIVLTQSPGTLSLSPGERATLSCSASSTISSNYLHWYQQKPGQAPR LLIYRTSDLASGIPDRFSGSGSGTDFTLTISRLEPEDFAVYYCQQGS SIPFTFGQGTKLEIK |
| Ab1 VH CDR1 | GYTFTNYWMH |
| Ab1 VH CDR2 | RIDLNSGGTNYNYNEKFKT |
| Ab1 VH CDR3 | YYGSSWFAY |

TABLE 2-continued

| Immunoglobulin Light Chain (LC) and Heavy Chain (HC)-Amino Acid Sequence | |
|---|---|
| Ab1 VL CDR1 | SASSTISSNYLH |
| Ab1 VL CDR2 | RTSDLAS |
| Ab1 VL CDR3 | QQGSSIPFT |
| Ab4L CDR1 | SASSTISSNYLH |
| Ab4L CDR2 | RTSDLAS |
| Ab4L CDR3 | QQGSSIPFT |
| Ab4H CDR1 | GYTFTNYWMH |
| Ab4H CDR2 | RIDLNSGGTNYNYAQKFQG |
| Ab4H CDR3 | YYGSSWFAY |

TABLE 3

| Immunoglobulin fusion protein - Nucleic acid sequence | | |
|---|---|---|
| NAME | SEQ ID NO | SEQUENCE |
| Ins1-L1-Ab1H Single chain (insulin1 with connecting peptide C1 connecting insulin B chain and insulin A chain; L1 linker; murine anti-ASGPR LC) | | *TTTGTGAACCAACACCTGTGCGGCTCAGACCTGGTGGAAGCTCTCT*<br>*ACCTAGTGTGCGGGGAACGAGGCTTCTTCTACACAGACCCCACC*<br>*GGCGGAGGGCCCCGCCGGGGCATTGTGGAACAATGCTGTCACAGC*<br>*ATCTGCTCCCTCTACCAGCTGGAGAACTACTGCAAC*GGTGGCGGA<br>GGCAGCCAGGTCCAACTGCAGCAGCCTGGGGCTGAGCTTGTG<br>AAGCCTGGGGCTTCAGTGAAACTGTCCTGCAAGGCTTCTGGCT<br>ATACCTTCACCAACTACTGGATGCACTGGGTGAAACAGAGGCC<br>TGGACGAGGCCTTGAGTGGATTGGAAGGATTGATCTTAATAGT<br>GGTGGTACTAATTACAATTACAATGAGAAGTTCAAGACCAAG<br>GCCACACTGACTGTAGACAAACCCTCCAGCACAGCCTACATGC<br>AGCTCAGCAGCCTGACATCTGAGGACTCTGCGGTCTATTATTG<br>TGCAAATTACTACGGTAGTAGCTGGTTTGCTTACTGGGGCCAA<br>GGGACCACTCTCACAGTCTCCTCAGCTAAAACAACAGCCCCAT<br>CGGTCTATCCACTGGCCCCTGTGTGTGGAGATACAACTGGCTC<br>CTCGGTGACTCTAGGATGCCTGGTCAAGGGTTATTTCCCTGAG<br>CCAGTGACCTTGACCTGGAACTCTGGATCCCTGTCCAGTGGTG<br>TGCACACCTTCCCAGCTGTCCTGCAGTCTGACCTCTACACCCTC<br>AGCAGCTCAGTGACTGTAACCTCGAGCACCTGGCCCAGCCAGT<br>CCATCACCTGCAATGTGGCCCACCCGGCAAGCAGCACCAAGGT<br>GGACAAGAAAATTGAGCCCAGAGGGCCCACAATCAAGCCCTG<br>TCCTCCATGCAAATGCCCAGCACCTAACCTCTTGGGTGGACCA<br>TCCGTCTTCATCTTCCCTCCAAAGATCAAGGATGTACTCATGAT<br>CTCCCTGAGCCCCATAGTCACATGTGTGGTGGTGGATGTGAGC<br>GAGGATGACCCAGATGTCCAGATCAGCTGGTTTGTGAACAACG<br>TGGAAGTACACACAGCTCAGACACAAACCCATAGAGAGGATT<br>ACAACAGTACTCTCCGGGTGGTCAGTGCCCTCCCCATCCAGCA<br>CCAGGACTGGATGAGTGGCAAGGAGTTCAAATGCAAGGTCAA<br>CAACAAAGACCTCCCAGCGCCCATCGAGAGAACCATCTCAAA |

TABLE 3-continued

Immunoglobulin fusion protein - Nucleic acid sequence

| NAME | SEQ ID NO | SEQUENCE |
|---|---|---|
| | | ACCCAAAGGGTCAGTAAGAGCTCCACAGGTATATGTCTTGCCT CCACCAGAAGAAGAGATGACTAAGAAACAGGTCACTCTGACC TGCATGGTCACAGACTTCATGCCTGAAGACATTTACGTGGAGT GGACCAACAACGGGAAAACAGAGCTAAACTACAAGAACACTG AACCAGTCCTGGACTCTGATGGTTCTTACTTCATGTACAGCAA GCTGAGAGTGGAAAAGAAGAACTGGGTGGAAAGAAATAGCTA CTCCTGTTCAGTGGTCCACGAGGGTCTGCACAATCACCACACG ACTAAGAGCTTCTCCCGGACTCCGGGTAA |
| Ins-1-L1-Ab1L Single chain (insulin1 with C1 connecting peptide connecting insulin B chain and insulin A chain; L1 linker; murine anti-ASGPR LC) | | *TTTGTGAACCAACACCTGTGCGGCTCAGACCTGGTGGAAGCTCTCT ACCTAGTGTGCGGGGAACGAGGCTTCTTCTACACAGACCCCACC GGCGGAGGGCCCCGCCGGGGCATTGTGGAACAATGCTGTCACAGC ATCTGCTCCCTCTACCAGCTGGAGAACTACTGCAAC*GGTGGCGGA *GGCAGC*GAAACTGTACTCACCCAGTCTCCAACCACCATGGCTA CATCTCCCGGGGAGAAGATCACTATCACCTGCAGTGCCAGCTC AACTATAAGTTCCAATTACTTGCATTGGTATCAGCAGAAGCCA GGATTCTCCCCTAAACTCTTGATTTATAGGACATCCGATCTGGC TTCTGGAGTCCCAACTCGCTTCAGTGGCAGTGGGTCTGGGACC TCTTACTCTCTCACAATTGGCACCATGGAGGCTGAAGATGTTG CCACTTACTACTGCCAGCAGGGTAGTAGTATACCATTCACGTT CGGCTCGGGGACAAAGCTGGAGATTAACCGGGCAGATACAGC ACCAACTGTATCCATCTTCCCACCATCCAGTGAGCAGTTAACA TCTGGAGGTGCCTCAGTCGTGTGCTTCTTGAACAACTTCTACCC CAAAGACATCAATGTCAAGTGGAAGATTGATGGCAGTGAACG ACAAAATGGCGTCCTGAACAGTTGGACTGATCAGGACAGCAA AGACAGCACCTACAGCATGAGCAGCACCCTCACGTTGACCAA GGACGAGTATGAACGACATAACAGCTATACCTGTGAGGCCAC TCACAAGACATCAACTTCACCCATTGTCAAGAGCTTCAACAGG AATGAGTGT |
| Ins-L1-Ab2L Single chain (insulin1 with C1 connecting peptide connecting insulin B chain and insulin A chain; L1 linker; palivizumab LC) | | *TTTGTGAACCAACACCTGTGCGGCTCAGACCTGGTGGAAGCTCTCT ACCTAGTGTGCGGGGAACGAGGCTTCTTCTACACAGACCCCACC GGCGGAGGGCCCCGCCGGGGCATTGTGGAACAATGCTGTCACAGC ATCTGCTCCCTCTACCAGCTGGAGAACTACTGCAAC*GGTGGCGGA GGCAGCGACATCCAGATGACCCAGTCCCCCTCCACCCTGTCCG CCTCCGTGGGCGACCGCGTGACCATCACCTGCAAGTGCCAGCT GTCCGTGGGCTACATGCACTGGTACCAGCAGAAGCCCGGCAA GGCCCCCAAGCTGCTGATCTACGACACCTCCAAGCTGGCCTCC GGCGTGCCCTCCCGCTTCTCCGGCTCCGGCTCCGGCACCGAGT TCACCCTGACCATCTCCTCCCTGCAGCCCGACGACTTCGCCAC CTACTACTGCTTCCAGGGCTCCGGCTACCCCTTCACCTTCGGCG GCGGCACCAAGCTGGAGATCAAACGAACTGTGGCTGCACCAT CTGTCTTCATCTTCCCGCCATCTGATGAGCAGTTGAAATCTGGA ACTGCCTCTGTCGTGTGCCTGCTGAATAACTTCTATCCCAGAG |

TABLE 3-continued

Immunoglobulin fusion protein - Nucleic acid sequence

| NAME | SEQ ID NO | SEQUENCE |
|---|---|---|
| | | AGGCCAAAGTACAGTGGAAGGTGGATAACGCCCTCCAATCGG<br>GTAACTCCCAGGAGAGTGTCACAGAGCAGGACAGCAAGGACA<br>GCACCTACAGCCTCAGCAGCACCCTGACGCTGAGCAAAGCAG<br>ACTACGAGAAACACAAAGTCTACGCCTGCGAAGTCACCCATC<br>AGGGCCTGTCCTCGCCCGTCACAAAGAGCTTCAACAGGGGAG<br>AGTGTTGA |
| Ins2-L2-Ab3L Dual chain (insulin2 B chain with C3 connecting peptide; n = 4; insulin2 A chain; L2 linker; chimeric anti-ASGPR LC) | | *TTTGTGAACCAACACCTGTGCGGCTCAGACCTGGTGGAAGCTCTCT*<br>*ACCTAGTGTGCGGGGAACGAGGCTTCTTCTACACAGACCCCACC*<br>*GGCGGGGGAGGCAGCGGGGGAGGCGGGTCCGGAGGCGGGGGAT*<br>*CTGGCGGGGGAGGCAGTCGGAAAAAGCGTGGCATTGTGGAACAA*<br>*AC*GGAGGCCCTTCCTCCGGAGCTCCACCTCCGTCCGGGGGTGG<br>CGGAGGCGAAACTGTACTCACCCAGTCTCCAACCACCATGGCT<br>ACATCTCCCGGGGAGAAGATCACTATCACCTGCAGTGCCAGCT<br>CAACTATAAGTTCCAATTACTTGCATTGGTATCAGCAGAAGCC<br>AGGATTCTCCCCTAAACTCTTGATTTATAGGACATCCGATCTG<br>GCTTCTGGAGTCCCAACTCGCTTCAGTGGCAGTGGGTCTGGGA<br>CCTCTTACTCTCTCACAATTGGCACCATGGAGGCTGAAGATGT<br>TGCCACTTACTACTGCCAGCAGGGTAGTAGTATACCATTCACG<br>TTCGGCTCGGGGACAAAGTTGGAAATTAAACGAACTGTGGCTG<br>CACCATCTGTCTTCATCTTCCCGCCATCTGATGAGCAGTTGAAA<br>TCTGGAACTGCCTCTGTCGTGTGCCTGCTGAATAACTTCTATCC<br>CAGAGAGGCCAAAGTACAGTGGAAGGTGGATAACGCCCTCCA<br>ATCGGGTAACTCCCAGGAGAGTGTCACAGAGCAGGACAGCAA<br>GGACAGCACCTACAGCCTCAGCAGCACCCTGACGCTGAGCAA<br>AGCAGACTACGAGAAACACAAAGTCTACGCCTGCGAAGTCAC<br>CCATCAGGGCCTGTCCTCGCCCGTCACAAAGAGCTTCAACAGG<br>GGAGAGTGTTGA |
| Ins3-L2-Ab3L Single chain (insulin3 chain with C2 connecting peptide, n = 2, connecting B chain and A chain; L2 linker; chimeric anti-ASGPR LC) | | *TTTGTGAACCAACACCTGTGCGGCTCAGACCTGGTGGAAGCTCTCT*<br>*ACCTAGTGTGCGGGGAACGAGGCTTCTTCTACACAGACCCCACC*<br>GGAGGCGGGGGATCTGGCGGGGGAGGCAGT*GGCATTGTGGAACA*<br>*AAC*GGAGGCCCTTCCTCCGGAGCTCCACCTCCGTCCGGGGGTG<br>GCGGAGGCGAAACTGTACTCACCCAGTCTCCAACCACCATGGC<br>TACATCTCCCGGGGAGAAGATCACTATCACCTGCAGTGCCAGC<br>TCAACTATAAGTTCCAATTACTTGCATTGGTATCAGCAGAAGC<br>CAGGATTCTCCCCTAAACTCTTGATTTATAGGACATCCGATCTG<br>GCTTCTGGAGTCCCAACTCGCTTCAGTGGCAGTGGGTCTGGGA<br>CCTCTTACTCTCTCACAATTGGCACCATGGAGGCTGAAGATGT<br>TGCCACTTACTACTGCCAGCAGGGTAGTAGTATACCATTCACG<br>TTCGGCTCGGGGACAAAGTTGGAAATTAAACGAACTGTGGCTG<br>CACCATCTGTCTTCATCTTCCCGCCATCTGATGAGCAGTTGAAA<br>TCTGGAACTGCCTCTGTCGTGTGCCTGCTGAATAACTTCTATCC |

TABLE 3-continued

| Immunoglobulin fusion protein - Nucleic acid sequence | | |
|---|---|---|
| NAME | SEQ ID NO | SEQUENCE |
| | | CAGAGAGGCCAAAGTACAGTGGAAGGTGGATAACGCCCTCCA ATCGGGTAACTCCCAGGAGAGTGTCACAGAGCAGGACAGCAA GGACAGCACCTACAGCCTCAGCAGCACCCTGACGCTGAGCAA AGCAGACTACGAGAAACACAAAGTCTACGCCTGCGAAGTCAC CCATCAGGGCCTGTCCTCGCCCGTCACAAAGAGCTTCAACAGG GGAGAGTGTTGA |
| Ins3-L2-Ab3L Dual chain (insulin 3 B chain with C3 connecting peptide, n = 4; insulin3 A chain; L2 linker; anti-ASGPR LC) | | *TTTGTGAACCAACACCTGTGCGGCTCAGACCTGGTGGAAGCTCTCT ACCTAGTGTGCGGGGAACGAGGCTTCTTCTACACAGACCCCACC GGAGGCGGGGGATCTGGCGGGGGAGGCAGTCGGAAAAAGCGTGG CATTGTGGAACAATGCTGTCACAGCATCTGCTCCCTCTACCAGCTG GAGAACTACTGCAAC*GGAGGCCCTTCCTCCGGAGCTCCACCTCC GTCCGGGGGTGGCGGAGGCGAAACTGTACTCACCCAGTCTCCA ACCACCATGGCTACATCTCCCGGGGAGAAGATCACTATCACCT GCAGTGCCAGCTCAACTATAAGTTCCAATTACTTGCATTGGTA TCAGCAGAAGCCAGGATTCTCCCCTAAACTCTTGATTTATAGG ACATCCGATCTGGCTTCTGGAGTCCCAACTCGCTTCAGTGGCA GTGGGTCTGGGACCTCTTACTCTCTCACAATTGGCACCATGGA GGCTGAAGATGTTGCCACTTACTACTGCCAGCAGGGTAGTAGT ATACCATTCACGTTCGGCTCGGGGACAAAGTTGGAAATTAAAC GAACTGTGGCTGCACCATCTGTCTTCATCTTCCCGCCATCTGAT GAGCAGTTGAAATCTGGAACTGCCTCTGTCGTGTGCCTGCTGA ATAACTTCTATCCCAGAGAGGCCAAAGTACAGTGGAAGGTGG ATAACGCCCTCCAATCGGGTAACTCCCAGGAGAGTGTCACAGA GCAGGACAGCAAGGACAGCACCTACAGCCTCAGCAGCACCCT GACGCTGAGCAAAGCAGACTACGAGAAACACAAAGTCTACGC CTGCGAAGTCACCCATCAGGGCCTGTCCTCGCCCGTCACAAAG AGCTTCAACAGGGGAGAGTGTTGA |
| Ins1-L3-Ab4L Single chain (insulin1 with C1 connecting peptide connecting insulin B chain and insulin A chain; L3 linker; anti-ASGPR, humanized LC) | | *TTTGTGAACCAACACCTGTGCGGCTCAGACCTGGTGGAAGCTCTCT ACCTAGTGTGCGGGGAACGAGGCTTCTTCTACACAGACCCCACC* GGCGGAGGGCCCCGCCGG*GGCATTGTGGAACAATGCTGTCACAGC ATCTGCTCCCTCTACCAGCTGGAGAACTACTGCAAC*GGGGGTGGC GAAGCAGCTGCTAAGGAGGCAGCCGCAAAGGAAGCAGCTGCA AAGGCAGGAGGCGAGATCGTGCTGACTCAGAGCCCAGGAACC CTGTCCCTGTCTCCAGGAGAACGAGCCACCCTGTCCTGCTCCG CCTCATCAACAATTTCTAGTAACTACCTGCACTGGTATCAGCA GAAGCCAGGACAGGCACCTCGACTGCTGATCTACAGAACTAG TGACCTGGCCTCTGGCATTCCCGATAGGTTCAGCGGCTCCGGG TCTGGAACAGACTTTACCCTGACAATCTCCCGCCTGGAGCCTG AAGATTTCGCTGTCTACTATTGTCAGCAGGGCTCAAGCATCCC ATTCACATTTGGCCAGGGGACTAAGCTGGAGATCAAGCGCAC AGTGGCAGCCCCCAGCGTCTTCATTTTTCCCCCTTCCGATGAAC AGCTGAAGTCCGGCACTGCTTCTGTGGTCTGTCTGCTGAACAA |

TABLE 3-continued

| Immunoglobulin fusion protein - Nucleic acid sequence | | |
|---|---|---|
| NAME | SEQ ID NO | SEQUENCE |
| | | TTTCTATCCCAGAGAGGCCAAGGTGCAGTGGAAAGTGGACAA CGCTCTGCAGTCCGGCAACAGCCAGGAGAGTGTGACCGAACA GGATAGTAAGGACAGCACATATTCTCTGTCTAGTACCCTGACA CTGAGTAAGGCAGATTACGAGAAGCACAAAGTGTATGCCTGC GAAGTCACTCATCAGGGACTGTCAAGCCCCGTGACCAAGAGCT TCAACCGGGGCGAGTGT |
| Ins4-L3-Ab4L Dual chain (insulin4 B chain with C3 connecting peptide, n = 2; insulin4 A chain; L3 linker; anti-ASGPR, humanized LC) | | *TTTGTGAACCAACACCTGTGCGGCTCACACCTGGTGGAAGCTCTCT ACCTAGTGTGCGGGGAACGAGGCTTCTTCTACACACCCAAGACC GGAGGCGGGGGATCTGGCGGGGGAGGCAGTCGGAAAAAGCGTGG CATTGTGGAACAATGCTGTACCAGCATCTGCTCCCTCTACCAGCTG GAGAACTACTGCAAC*GGGGGTGGCGAAGCAGCTGCTAAGGAGG CAGCCGCAAAGGAAGCAGCTGCAAAGGCAGGAGGCGAGATCG TGCTGACTCAGAGCCCAGGAACCCTGTCCCTGTCTCCAGGAGA ACGAGCCACCCTGTCCTGCTCCGCCTCATCAACAATTTCTAGT AACTACCTGCACTGGTATCAGCAGAAGCCAGGACAGGCACCT CGACTGCTGATCTACAGAACTAGTGACCTGGCCTCTGGCATTC CCGATAGGTTCAGCGGCTCCGGGTCTGGAACAGACTTTACCCT GACAATCTCCCGCCTGGAGCCTGAAGATTTCGCTGTCTACTAT TGTCAGCAGGGCTCAAGCATCCCATTCACATTTGGCCAGGGGA CTAAGCTGGAGATCAAGCGCACAGTGGCAGCCCCCAGCGTCTT CATTTTTCCCCCTTCCGATGAACAGCTGAAGTCCGGCACTGCTT CTGTGGTCTGTCTGCTGAACAATTTCTATCCCAGAGAGGCCAA GGTGCAGTGGAAAGTGGACAACGCTCTGCAGTCCGGCAACAG CCAGGAGAGTGTGACCGAACAGGATAGTAAGGACAGCACATA TTCTCTGTCTAGTACCCTGACACTGAGTAAGGCAGATTACGAG AAGCACAAAGTGTATGCCTGCGAAGTCACTCATCAGGGACTGT CAAGCCCCGTGACCAAGAGCTTCAACCGGGGCGAGTGT |
| Ins4-L3-Ab2L Dual chain (insulin4 B chain with C3 connecting peptide, n = 2; insulin4 A chain; L3 linker; palivizumab LC) | | *TTTGTGAACCAACACCTGTGCGGCTCACACCTGGTGGAAGCTCTCT ACCTAGTGTGCGGGGAACGAGGCTTCTTCTACACACCCAAGACC GGAGGCGGGGGATCTGGCGGGGGAGGCAGTCGGAAAAAGCGTGG CATTGTGGAACAATGCTGTACCAGCATCTGCTCCCTCTACCAGCTG GAGAACTACTGCAAC*GGGGGTGGCGAAGCAGCTGCTAAGGAGG CAGCCGCAAAGGAAGCAGCTGCAAAGGCAGGAGGCGACATCC AGATGACCCAGTCCCCCTCCACCCTGTCCGCCTCCGTGGGCGA CCGCGTGACCATCACCTGCAAGTGCCAGCTGTCCGTGGGCTAC ATGCACTGGTACCAGCAGAAGCCCGGCAAGGCCCCCAAGCTG CTGATCTACGACACCTCCAAGCTGGCCTCCGGCGTGCCCTCCC GCTTCTCCGGCTCCGGCTCCGGCACCGAGTTCACCCTGACCAT CTCCTCCCTGCAGCCCGACGACTTCGCCACCTACTACTGCTTCC AGGGCTCCGGCTACCCCTTCACCTTCGGCGGCGGCACCAAGCT GGAGATCAAACGAACTGTGGCTGCACCATCTGTCTTCATCTTC CCGCCATCTGATGAGCAGTTGAAATCTGGAACTGCCTCTGTCG |

TABLE 3-continued

| Immunoglobulin fusion protein - Nucleic acid sequence | | |
|---|---|---|
| NAME | SEQ ID NO | SEQUENCE |
| | | TGTGCCTGCTGAATAACTTCTATCCCAGAGAGGCCAAAGTACA<br>GTGGAAGGTGGATAACGCCCTCCAATCGGGTAACTCCCAGGA<br>GAGTGTCACAGAGCAGGACAGCAAGGACAGCACCTACAGCCT<br>CAGCAGCACCCTGACGCTGAGCAAAGCAGACTACGAGAAACA<br>CAAAGTCTACGCCTGCGAAGTCACCCATCAGGGCCTGTCCTCG<br>CCCGTCACAAAGAGCTTCAACAGGGGAGAGTGT |
| Ins1-L4-Ab4L Single chain (insulin1 with C1 connecting peptide connecting insulin B chain and insulin A chain; L4 linker; anti-ASGPR, humanized LC) | | *TTTGTGAACCAACACCTGTGCGGCTCAGACCTGGTGGAAGCTCTCT*<br>*ACCTAGTGTGCGGGGAACGAGGCTTCTTCTACACAGACCCCACC*<br>GGCGGAGGGCCCCGCCGG*GGCATTGTGGAACAATGCTGTCACAGC*<br>*ATCTGCTCCCTCTACCAGCTGGAGAACTACTGCAAC*GGTGGCGGA<br>GGCAGCGGGGGTGGCGAAGCAGCTGCTAAGGAGGCAGCCGCA<br>AAGGAAGCAGCTGCAAAGGCAGGAGGCGAGATCGTGCTGACT<br>CAGAGCCCAGGAACCCTGTCCCTGTCTCCAGGAGAACGAGCC<br>ACCCTGTCCTGCTCCGCCTCATCAACAATTTCTAGTAACTACCT<br>GCACTGGTATCAGCAGAAGCCAGGACAGGCACCTCGACTGCT<br>GATCTACAGAACTAGTGACCTGGCCTCTGGCATTCCCGATAGG<br>TTCAGCGGCTCCGGGTCTGGAACAGACTTTACCCTGACAATCT<br>CCCGCCTGGAGCCTGAAGATTTCGCTGTCTACTATTGTCAGCA<br>GGGCTCAAGCATCCCATTCACATTTGGCCAGGGGACTAAGCTG<br>GAGATCAAGCGCACAGTGGCAGCCCCCAGCGTCTTCATTTTTC<br>CCCCTTCCGATGAACAGCTGAAGTCCGGCACTGCTTCTGTGGT<br>CTGTCTGCTGAACAATTTCTATCCCAGAGAGGCCAAGGTGCAG<br>TGGAAAGTGGACAACGCTCTGCAGTCCGGCAACAGCCAGGAG<br>AGTGTGACCGAACAGGATAGTAAGGACAGCACATATTCTCTGT<br>CTAGTACCCTGACACTGAGTAAGGCAGATTACGAGAAGCACA<br>AAGTGTATGCCTGCCTGCGAAGTCACTCATCAGGGACTGTCAAGCCC<br>CGTGACCAAGAGCTTCAACCGGGGCGAGTGT |
| Ins1-L5-Ab4L Single chain (insulin1 with C1 connecting peptide connecting insulin B chain and insulin A chain; L5 linker; anti-ASGPR, humanized LC) | | *TTTGTGAACCAACACCTGTGCGGCTCAGACCTGGTGGAAGCTCTCT*<br>*ACCTAGTGTGCGGGGAACGAGGCTTCTTCTACACAGACCCCACC*<br>GGCGGAGGGCCCCGCCGG*GGCATTGTGGAACAATGCTGTCACAGC*<br>*ATCTGCTCCCTCTACCAGCTGGAGAACTACTGCAAC*GGGGGTGGC<br>GAAGCAGCTGCTAAGGAGGCAGCCGCAAAGGAAGCAGCTGCA<br>AAGGCAGGTGGCGGAGGCAGCGGAGGCGAGATCGTGCTGACT<br>CAGAGCCCAGGAACCCTGTCCCTGTCTCCAGGAGAACGAGCC<br>ACCCTGTCCTGCTCCGCCTCATCAACAATTTCTAGTAACTACCT<br>GCACTGGTATCAGCAGAAGCCAGGACAGGCACCTCGACTGCT<br>GATCTACAGAACTAGTGACCTGGCCTCTGGCATTCCCGATAGG<br>TTCAGCGGCTCCGGGTCTGGAACAGACTTTACCCTGACAATCT<br>CCCGCCTGGAGCCTGAAGATTTCGCTGTCTACTATTGTCAGCA<br>GGGCTCAAGCATCCCATTCACATTTGGCCAGGGGACTAAGCTG<br>GAGATCAAGCGCACAGTGGCAGCCCCCAGCGTCTTCATTTTTC |

TABLE 3-continued

| Immunoglobulin fusion protein - Nucleic acid sequence | | |
|---|---|---|
| NAME | SEQ ID NO | SEQUENCE |
| | | CCCCTTCCGATGAACAGCTGAAGTCCGGCACTGCTTCTGTGGT<br>CTGTCTGCTGAACAATTTCTATCCCAGAGAGGCCAAGGTGCAG<br>TGGAAAGTGGACAACGCTCTGCAGTCCGGCAACAGCCAGGAG<br>AGTGTGACCGAACAGGATAGTAAGGACAGCACATATTCTCTGT<br>CTAGTACCCTGACACTGAGTAAGGCAGATTACGAGAAGCACA<br>AAGTGTATGCCTGCGAAGTCACTCATCAGGGACTGTCAAGCCC<br>CGTGACCAAGAGCTTCAACCGGGGCGAGTGT |
| Ins1-L6-Ab4L (insulin1 with C1 connecting peptide connecting insulin B chain and insulin A chain; L6 linker; anti-ASGPR, humanized LC) | | *TTTGTGAACCAACACCTGTGCGGCTCAGACCTGGTGGAAGCTCTCT*<br>*ACCTAGTGTGCGGGGAACGAGGCTTCTTCTACACAGACCCCACC*<br>GGCGGAGGGCCCCGCCGG*GGCATTGTGGAACAATGCTGTCACAGC*<br>*ATCTGCTCCCTCTACCAGCTGGAGAACTACTGCAAC*GGTGGCGGA<br>GGCAGCGGGGGTGGCGAAGCAGCTGCTAAGGAGGCAGCCGCA<br>AAGGAAGCAGCTGCAAAGGCAGGTGGCGGAGGCAGCGGAGG<br>CGAGATCGTGCTGACTCAGAGCCCAGGAACCCTGTCCCTGTCT<br>CCAGGAGAACGAGCCACCCTGTCCTGCTCCGCCTCATCAACAA<br>TTTCTAGTAACTACCTGCACTGGTATCAGCAGAAGCCAGGACA<br>GGCACCTCGACTGCTGATCTACAGAACTAGTGACCTGGCCTCT<br>GGCATTCCCGATAGGTTCAGCGGCTCCGGGTCTGGAACAGACT<br>TTACCCTGACAATCTCCCGCCTGGAGCCTGAAGATTTCGCTGT<br>CTACTATTGTCAGCAGGGCTCAAGCATCCCATTCACATTTGGC<br>CAGGGGACTAAGCTGGAGATCAAGCGCACAGTGGCAGCCCCC<br>AGCGTCTTCATTTTTCCCCCTTCCGATGAACAGCTGAAGTCCGG<br>CACTGCTTCTGTGGTCTGTCTGCTGAACAATTTCTATCCCAGAG<br>AGGCCAAGGTGCAGTGGAAAGTGGACAACGCTCTGCAGTCCG<br>GCAACAGCCAGGAGAGTGTGACCGAACAGGATAGTAAGGACA<br>GCACATATTCTCTGTCTAGTACCCTGACACTGAGTAAGGCAGA<br>TTACGAGAAGCACAAAGTGTATGCCTGCGAAGTCACTCATCAG<br>GGACTGTCAAGCCCCGTGACCAAGAGCTTCAACCGGGGCGAG<br>TGT |
| Ab4-L7-Ins5 Single chain (anti-ASGPR, humanized LC; L7 linker; insulin5 within C4 connecting peptide connecting insulin A chain to insulin B | | GAGATCGTGCTGACTCAGAGCCCAGGAACCCTGTCCCTGTCTC<br>CAGGAGAACGAGCCACCCTGTCCTGCTCCGCCTCATCAACAAT<br>TTCTAGTAACTACCTGCACTGGTATCAGCAGAAGCCAGGACAG<br>GCACCTCGACTGCTGATCTACAGAACTAGTGACCTGGCCTCTG<br>GCATTCCCGATAGGTTCAGCGGCTCCGGGTCTGGAACAGACTT<br>TACCCTGACAATCTCCCGCCTGGAGCCTGAAGATTTCGCTGTC<br>TACTATTGTCAGCAGGGCTCAAGCATCCCATTCACATTTGGCC<br>AGGGGACTAAGCTGGAGATCAAGCGCACAGTGGCAGCCCCCA<br>GCGTCTTCATTTTTCCCCCTTCCGATGAACAGCTGAAGTCCGGC<br>ACTGCTTCTGTGGTCTGTCTGCTGAACAATTTCTATCCCAGAGA<br>GGCCAAGGTGCAGTGGAAAGTGGACAACGCTCTGCAGTCCGG |

TABLE 3-continued

| Immunoglobulin fusion protein - Nucleic acid sequence | | |
|---|---|---|
| NAME | SEQ ID NO | SEQUENCE |
| chain) | | CAACAGCCAGGAGAGTGTGACCGAACAGGATAGTAAGGACAG<br>CACATATTCTCTGTCTAGTACCCTGACACTGAGTAAGGCAGAT<br>TACGAGAAGCACAAAGTGTATGCCTGCGAAGTCACTCATCAG<br>GGACTGTCAAGCCCCGTGACCAAGAGCTTCAACCGGGGCGAG<br>TGTGGCGGAGGTGGTTCTGGGGGAAGCCCCGGAATCGTAGAGC<br>AGTGTTGTACCAGTATTTGCAGCCTCTATCAGCTCGAGAACTATTGT<br>AATGGCGGAGGGTCCGGCGGTGGGAGCGGCTTCGTGAATCAACA<br>CCTGTGCGGGTCCCACCTGGTGGAAGCGTTGTATCTTGTCTGCGG<br>GGAAAGGGGTTTCTTCTACACACCGAAGACC |
| Ins4-L6-Ab4 Dual chain (insulin4 B chain with C3 connecting peptide, n = 2; insulin4 A chain; L6 linker; anti-ASGPR, humanized LC) | | TTTGTGAACCAACACCTGTGCGGCTCACACCTGGTGGAAGCTCTCT<br>ACCTAGTGTGCGGGGAACGAGGCTTCTTCTACACACCCAAGACC<br>GGAGGCGGGGGATCTGGCGGGGGAGGCAGTCGGAAAAAGCGTGG<br>CATTGTGGAACAATGCTGTACCAGCATCTGCTCCCTCTACCAGCTG<br>GAGAACTACTGCAACGGTGGCGGAGGCAGCGGGGGTGGCGAAG<br>CAGCTGCTAAGGAGGCAGCCGCAAAGGAAGCAGCTGCAAAGG<br>CAGGTGGCGGAGGCAGCGGAGGCGAGATCGTGCTGACTCAGA<br>GCCCAGGAACCCTGTCCCTGTCTCCAGGAGAACGAGCCACCCT<br>GTCCTGCTCCGCCTCATCAACAATTTCTAGTAACTACCTGCACT<br>GGTATCAGCAGAAGCCAGGACAGGCACCTCGACTGCTGATCT<br>ACAGAACTAGTGACCTGGCCTCTGGCATTCCCGATAGGTTCAG<br>CGGCTCCGGGTCTGGAACAGACTTTACCCTGACAATCTCCCGC<br>CTGGAGCCTGAAGATTTCGCTGTCTACTATTGTCAGCAGGGCT<br>CAAGCATCCCATTCACATTTGGCCAGGGGACTAAGCTGGAGAT<br>CAAGCGCACAGTGGCAGCCCCCAGCGTCTTCATTTTTCCCCCTT<br>CCGATGAACAGCTGAAGTCCGGCACTGCTTCTGTGGTCTGTCT<br>GCTGAACAATTTCTATCCCAGAGAGGCCAAGGTGCAGTGGAA<br>AGTGGACAACGCTCTGCAGTCCGGCAACAGCCAGGAGAGTGT<br>GACCGAACAGGATAGTAAGGACAGCACATATTCTCTGTCTAGT<br>ACCCTGACACTGAGTAAGGCAGATTACGAGAAGCACAAAGTG<br>TATGCCTGCGAAGTCACTCATCAGGGACTGTCAAGCCCCGTGA<br>CCAAGAGCTTCAACCGGGGCGAGTGT |
| Ins6-L6-Ab4 Dual chain (insulin6 B chain with C7 connecting peptide, n = 2; insulin6 A chain; L6 linker; anti-ASGPR humanized LC) | | TTTGTGAACCAACACCTGTGCGGCTCACACCTGGTGGAAGCTCTCT<br>ACCTAGTGTGCGGGGAACGAGGCTTCTTCTACACACCCAAGACC<br>CGGAAAAAGCGTGGCGGGGGAGGCAGCGGGGGAGGCGGGTCCCG<br>GAAAAAGCGTGGCATTGTGGAACAATGCTGTACCAGCATCTGCTCC<br>CTCTACCAGCTGGAGAACTACTGCAACGGTGGCGGAGGCAGCGG<br>GGGTGGCGAAGCAGCTGCTAAGGAGGCAGCCGCAAAGGAAGC<br>AGCTGCAAAGGCAGGTGGCGGAGGCAGCGGAGGCGAGATCGT<br>GCTGACTCAGAGCCCAGGAACCCTGTCCCTGTCTCCAGGAGAA<br>CGAGCCACCCTGTCCTGCTCCGCCTCATCAACAATTTCTAGTA<br>ACTACCTGCACTGGTATCAGCAGAAGCCAGGACAGGCACCTC<br>GACTGCTGATCTACAGAACTAGTGACCTGGCCTCTGGCATTCC<br>CGATAGGTTCAGCGGCTCCGGGTCTGGAACAGACTTTACCCTG |

TABLE 3-continued

| Immunoglobulin fusion protein - Nucleic acid sequence | | |
|---|---|---|
| NAME | SEQ ID NO | SEQUENCE |
| | | ACAATCTCCCGCCTGGAGCCTGAAGATTTCGCTGTCTACTATT<br>GTCAGCAGGGCTCAAGCATCCCATTCACATTTGGCCAGGGGAC<br>TAAGCTGGAGATCAAGCGCACAGTGGCAGCCCCCAGCGTCTTC<br>ATTTTTCCCCCTTCCGATGAACAGCTGAAGTCCGGCACTGCTTC<br>TGTGGTCTGTCTGCTGAACAATTTCTATCCCAGAGAGGCCAAG<br>GTGCAGTGGAAAGTGGACAACGCTCTGCAGTCCGGCAACAGC<br>CAGGAGAGTGTGACCGAACAGGATAGTAAGGACAGCACATAT<br>TCTCTGTCTAGTACCCTGACACTGAGTAAGGCAGATTACGAGA<br>AGCACAAAGTGTATGCCTGCGAAGTCACTCATCAGGGACTGTC<br>AAGCCCCGTGACCAAGAGCTTCAACCGGGGCGAGTGT |
| Ins1-L1-herceptin HC single chain (insulin1 with connecting peptide C1 connecting insulin B chain and insulin A chain; L1 linker; herceptin HC) | | *TTTGTGAACCAACACCTGTGCGGCTCAGACCTGGTGGAAGCTCTCT*<br>*ACCTAGTGTGCGGGGAACGAGGCTTCTTCTACACAGACCCCACC*<br>*GGCGGAGGGCCCCGCCGGGGCATTGTGGAACAATGCTGTCACAGC*<br>*ATCTGCTCCCTCTACCAGCTGGAGAACTACTGCAAC*GGTGGCGGA<br>GGCAGCGAGGTGCAGCTGGTGGAGTCTGGAGGAGGCTTGGTC<br>CAGCCTGGGGGGTCCCTGAGACTCTCCTGTGCAGCCTCTGGGT<br>TCAATATTAAGGACACTTACATCCACTGGGTCCGCCAGGCTCC<br>AGGGAAGGGGCTGGAGTGGGTCGCACGTATTTATCCTACCAAT<br>GGTTACACACGCTACGCAGACTCCGTGAAGGGCCGATTCACCA<br>TCTCCGCAGACACTTCCAAGAACACGGCGTATCTTCAAATGAA<br>CAGCCTGAGAGCCGAGGACACGGCCGTGTATTACTGTTCGAGA<br>TGGGGCGGTGACGGCTTCTATGCCATGGACTACTGGGGCCAAG<br>GAACCCTGGTCACCGTCTCCTCAGCCTCCACCAAGGGCCCATC<br>GGTCTTCCCCCTGGCACCCTCCTCCAAGAGCACCTCTGGGGGC<br>ACAGCGGCCCTGGGCTGCCTGGTCAAGGACTACTTCCCCGAAC<br>CGGTGACGGTGTCGTGGAACTCAGGCGCCCTGACCAGCGGCGT<br>GCACACCTTCCCGGCTGTCCTACAGTCCTCAGGACTCTACTCCC<br>TCAGCAGCGTGGTGACTGTGCCCTCTAGCAGCTTGGGCACCCA<br>GACCTACATCTGCAACGTGAATCACAAGCCCAGCAACACCAA<br>GGTGGACAAGAAAGTTGAACCCAAATCTTGCGACAAAACTCA<br>CACATGCCCACCGTGCCCAGCACCTCCAGTCGCCGGACCGTCA<br>GTCTTCCTCTTCCCTCCAAAACCCAAGGACACCCTCATGATCTC<br>CCGGACCCCTGAGGTCACATGCGTGGTGGTGGACGTGAGCCAC<br>GAAGACCCTGAGGTCAAGTTCAACTGGTACGTGGACGGCGTG<br>GAGGTGCATAATGCCAAGACAAAGCCGCGGGAGGAGCAGTAC<br>AACAGCACGTACCGTGTGGTCAGCGTCCTCACCGTCCTGCACC<br>AGGACTGGCTGAATGGCAAGGAGTACAAGTGCAAGGTCTCCA<br>ACAAAGGCCTCCCAAGCTCCATCGAGAAAACCATCTCCAAAG<br>CCAAAGGGCAGCCCCGAGAACCACAGGTGTACACCCTGCCTC<br>CATCCCGGGATGAGCTGACCAAGAACCAGGTCAGCCTGACCT<br>GCCTGGTCAAAGGCTTCTATCCCAGCGACATCGCCGTGGAGTG |

TABLE 3-continued

Immunoglobulin fusion protein - Nucleic acid sequence

| NAME | SEQ ID NO | SEQUENCE |
| --- | --- | --- |
| | | GGAGAGCAATGGGCAGCCGGAGAACAACTACAAGACCACGCC<br>TCCCGTGCTGGACTCCGACGGCTCCTTCTTCCTCTACAGCAAGC<br>TCACCGTGGACAAGAGCAGGTGGCAGCAGGGGAACGTCTTCT<br>CATGCTCCGTGATGCATGAGGCTCTGCACAACCACTACACGCA<br>GAAGAGCCTCTCCCTGTCTCCGGGTAAA |
| Ins1-L1-herceptin LC single chain (insulin1 with connecting peptide C1 connecting insulin B chain and insulin A chain; L1 linker; herceptin LC) | | *TTTGTGAACCAACACCTGTGCGGCTFCAGACCTGGTGGAAGCTCTCT*<br>*ACCTAGTGTGCGGGGAACGAGGCTTCTTCTACACAGACCCCACC*<br>*GGCGGAGGGCCCCGCCGGGGCATTGTGGAACAATGCTGTCACAGC*<br>*ATCTGCTCCCTCTACCAGCTGGAGAACTACTGCAAC*GGTGGCGGA<br>GGCAGCGACATCCAGATGACCCAGTCTCCATCCTCCCTGTCTG<br>CATCTGTAGGAGACAGAGTCACCATCACTTGCCGGGCAAGTCA<br>GGATGTGAATACCGCGGTCGCATGGTATCAGCAGAAACCAGG<br>GAAAGCCCCTAAGCTCCTGATCTATTCTGCATCCTTCTTGTATA<br>GTGGGGTCCCATCAAGGTTCAGTGGCAGTAGATCTGGGACAG<br>ATTTCACTCTCACCATCAGCAGTCTGCAACCTGAAGATTTTGC<br>AACTTACTACTGTCAACAGCATTACACTACCCCTCCGACGTTC<br>GGCCAAGGTACCAAGGTTGAGATCAAACGAACTGTGGCTGCA<br>CCATCTGTCTTCATCTTCCCGCCATCTGATGAGCAGTTGAAATC<br>TGGAACTGCCTCTGTCGTGTGCCTGCTGAATAACTTCTATCCCA<br>GAGAGGCCAAAGTACAGTGGAAGGTGGATAACGCCCTCCAAT<br>CGGGTAACTCCCAGGAGAGTGTCACAGAGCAGGACAGCAAGG<br>ACAGCACCTACAGCCTCAGCAGCACCCTGACGCTGAGCAAAG<br>CAGACTACGAGAAACACAAAGTCTACGCCTGCGAAGTCACCC<br>ATCAGGGCCTGTCCTCGCCCGTCACAAAGAGCTTCAACAGGGG<br>AGAGTGT |
| Ins4-L6-Ab4L (Fab) (insulin4 B chain after RKKR (SEQ ID NO: 184) cleavage of C3 connecting peptide, n = 2; insulin4 A chain; L6 linker; anti-ASGPR, humanized LC) | | *TTTGTGAACCAACACCTGTGCGGCTCACACCTGGTGGAAGCTCTCT*<br>*ACCTAGTGTGCGGGGAACGAGGCTTCTTCTACACACCCAAGACC*<br>*GGCGGGGGAGGCAGCGGGGGAGGCGGGTCCCGGAAAAAGCGTGG*<br>*CATTGTGGAACAATGCTGTACCAGCATCTGCTCCCTCTACCAGCTG*<br>*GAGAACTACTGCAAC*GGTGGCGGAGGCAGCGGGGGTGGCGAAG<br>CAGCTGCTAAGGAGGCAGCCGCAAAGGAAGCAGCTGCAAAGG<br>CAGGTGGCGGAGGCAGCGGAGGCGAGATCGTGCTGACTCAGA<br>GCCCAGGAACCCTGTCCCTGTCTCCAGGAGAACGAGCCACCCT<br>GTCCTGCTCCGCCTCATCAACAATTTCTAGTAACTACCTGCACT<br>GGTATCAGCAGAAGCCAGGACAGGCACCTCGACTGCTGATCT<br>ACAGAACTAGTGACCTGGCCTCTGGCATTCCCGATAGGTTCAG<br>CGGCTCCGGGTCTGGAACAGACTTTACCCTGACAATCTCCCGC<br>CTGGAGCCTGAAGATTTCGCTGTCTACTATTGTCAGCAGGGCT<br>CAAGCATCCCATTCACATTTGGCCAGGGGACTAAGCTGGAGAT<br>CAAGCGCACAGTGGCAGCCCCCAGCGTCTTCATTTTTCCCCCTT<br>CCGATGAACAGCTGAAGTCCGGCACTGCTTCTGTGGTCTGTCT<br>GCTGAACAATTTCTATCCCAGAGAGGCCAAGGTGCAGTGGAA |

TABLE 3-continued

| Immunoglobulin fusion protein - Nucleic acid sequence | | |
|---|---|---|
| NAME | SEQ ID NO | SEQUENCE |
| | | AGTGGACAACGCTCTGCAGTCCGGCAACAGCCAGGAGAGTGT<br>GACCGAACAGGATAGTAAGGACAGCACATATTCTCTGTCTAGT<br>ACCCTGACACTGAGTAAGGCAGATTACGAGAAGCACAAAGTG<br>TATGCCTGCGAAGTCACTCATCAGGGACTGTCAAGCCCCGTGA<br>CCAAGAGCTTCAACCGGGGCGAGTGT |
| Ins1-L3-Ab5L single chain (insulin1 with C1 connecting peptide connecting insulin B chain and insulin A chain; L3 linker; anti-ASGPR, humanized LC) | | *TTTGTGAACCAACACCTGTGCGGCTCAGACCTGGTGGAAGCTCTCT*<br>*ACCTAGTGTGCGGGGAACGAGGCTTCTTCTACACAGACCCCACC*<br>GGCGGAGGGCCCCGCCGG*GGCATTGTGGAACAATGCTGTCACAGC*<br>*ATCTGCTCCCTCTACCAGCTGGAGAACTACTGCAAC*GGGGGTGGC<br>GAAGCAGCTGCTAAGGAGGCAGCCGCAAAGGAAGCAGCTGCA<br>AAGGCAGGAGGCGAGATCGTGCTGACTCAGAGCCCAGGAACC<br>CTGTCCCTGTCTCCAGGAGAACGAGCCACCCTGTCCTGCTCCG<br>CCTCATCAACAATTTCTAGTAACTACCTGCACTGGTATCAGCA<br>GAAGCCAGGACAGGCACCTCGACTGCTGATCTACAGAACTAG<br>TGACCTGGCCTCTGGCATTCCCGATAGGTTCAGCGGCTCCGGG<br>TCTGGAACAGACTTTACCCTGACAATCTCCCGCCTGGAGCCTG<br>AAGATTTCGCTGTCTACTATTGTCAGCAGGGCTCAAGCATCCC<br>ATTCACATTTGGCCAGGGGACTAAGCTGGAGATCAAGCGCAC<br>AGTGGCAGCCCCCAGCGTCTTCATTTTTCCCCCTTCCGATGAAC<br>AGCTGAAGTCCGGCACTGCTTCTGTGGTCTGTCTGCTGAACAA<br>TTTCTATCCCAGAGAGGCCAAGGTGCAGTGGAAAGTGGACAA<br>CGCTCTGCAGTCCGGCAACAGCCAGGAGAGTGTGACCGAACA<br>GGATAGTAAGGACAGCACATATTCTCTGTCTAGTACCCTGACA<br>CTGAGTAAGGCAGATTACGAGAAGCACAAAGTGTATGCCTGC<br>GAAGTCACTCATCAGGGACTGTCAAGCCCCGTGACCAAGAGCT<br>TCAACCGGGGCGAGTGT |
| Ins7-L3-Ab4L single chain (insulin7 with C1 connecting peptide connecting insulin B chain and insulin A chain; L3 linker; anti-ASGPR, humanized LC) | | *TTTGTGAACCAACACCTGTGCGGCTCACACCTGGTGGAAGCTCTCT*<br>*ACCTAGTGTGCGGGGAACGAGGCTTCTTCTACACACCCAAGACC*<br>*GGCGGAGGGCCCCGCCGGGGCATTGTGGAACAATGCTGTACCAGC*<br>*ATCTGCTCCCTCTACCAGCTGGAGAACTACTGCAAC***GGGGGTGG**<br>**CGAAGCAGCTGCTAAGGAGGCAGCCGCAAAGGAAGCAGCT**<br>**GCAAAGGCAGGAGGC**GAGATCGTGCTGACTCAGAGCCCAGG<br>AACCCTGTCCCTGTCTCCAGGAGAACGAGCCACCCTGTCCTGC<br>TCCGCCTCATCAACAATTTCTAGTAACTACCTGCACTGGTATCA<br>GCAGAAGCCAGGACAGGCACCTCGACTGCTGATCTACAGAAC<br>TAGTGACCTGGCCTCTGGCATTCCCGATAGGTTCAGCGGCTCC<br>GGGTCTGGAACAGACTTTACCCTGACAATCTCCCGCCTGGAGC<br>CTGAAGATTTCGCTGTCTACTATTGTCAGCAGGGCTCAAGCAT<br>CCCATTCACATTTGGCCAGGGGACTAAGCTGGAGATCAAGCGC<br>ACAGTGGCAGCCCCCAGCGTCTTCATTTTTCCCCCTTCCGATGA<br>ACAGCTGAAGTCCGGCACTGCTTCTGTGGTCTGTCTGCTGAAC |

TABLE 3-continued

| Immunoglobulin fusion protein - Nucleic acid sequence | | |
|---|---|---|
| NAME | SEQ ID NO | SEQUENCE |
| | | AATTTCTATCCCAGAGAGGCCAAGGTGCAGTGGAAAGTGGAC AACGCTCTGCAGTCCGGCAACAGCCAGGAGAGTGTGACCGAA CAGGATAGTAAGGACAGCACATATTCTCTGTCTAGTACCCTGA CACTGAGTAAGGCAGATTACGAGAAGCACAAAGTGTATGCCT GCGAAGTCACTCATCAGGGACTGTCAAGCCCCGTGACCAAGA GCTTCAACCGGGGCGAGTGT |
| Ins7-L3-Ab5L single chain (insulin7 with C1 connecting peptide connecting insulin B chain and insulin A chain; L3 linker; anti-ASGPR, humanized LC) | | *TTTGTGAACCAACACCTGTGCGGCTCACACCTGGTGGAAGCTCTCT ACCTAGTGTGCGGGGAACGAGGCTTCTTCTACACACCCAAGACC GGCGGAGGGCCCCGCCGGGGCATTGTGGAACAATGCTGTACCAGC ATCTGCTCCCTCTACCAGCTGGAGAACTACTGCAAC***GGGGGTGG CGAAGCAGCTGCTAAGGAGGCAGCCGCAAAGGAAGCAGCT GCAAAGGCAGGAGGC**GAGATCGTGCTGACTCAGAGCCCAGG AACCCTGTCCCTGTCTCCAGGAGAACGAGCCACCCTGTCCTGC TCCGCCTCATCAACAATTTCTAGTAACTACCTGCACTGGTATCA GCAGAAGCCAGGACAGGCACCTCGACTGCTGATCTACAGAAC TAGTGACCTGGCCTCTGGCATTCCCGATAGGTTCAGCGGCTCC GGGTCTGGAACAGACTTTACCCTGACAATCTCCCGCCTGGAGC CTGAAGATTTCGCTGTCTACTATTGTCAGCAGGGCTCAAGCAT CCCATTCACATTTGGCCAGGGGACTAAGCTGGAGATCAAGCGC ACAGTGGCAGCCCCCAGCGTCTTCATTTTTCCCCCTTCCGATGA ACAGCTGAAGTCCGGCACTGCTTCTGTGGTCTGTCTGCTGAAC AATTTCTATCCCAGAGAGGCCAAGGTGCAGTGGAAAGTGGAC AACGCTCTGCAGTCCGGCAACAGCCAGGAGAGTGTGACCGAA CAGGATAGTAAGGACAGCACATATTCTCTGTCTAGTACCCTGA CACTGAGTAAGGCAGATTACGAGAAGCACAAAGTGTATGCCT GCGAAGTCACTCATCAGGGACTGTCAAGCCCCGTGACCAAGA GCTTCAACCGGGGCGAGTGT |

For SEQ ID NOS: 57-77

Immunoglobulin region = dashed underline

Therapeutic peptide = *italic*

Therapeutic peptide connecting peptide = *italic*

Linker = bold, thick underline

TABLE 4

| Immunoglobulin fusion protein - Protein Sequence | | |
|---|---|---|
| NAME | SEQ ID NO | SEQUENCE |
| Ins1-L1-Ab1H Single chain (insulin1 with | | *FVNQHLCGSDLVEALYLVCGERGFFYTDPTGGGPRRGIVEQCCHSIC SLYQLENYCN*GGGGSQVQLQQPGAELVKPGASVKLSCKASGYTFT NYWMHWVKQRPGRGLEWIGRIDLNSGGTNYNYNEKFKTKATLT |

TABLE 4-continued

| Immunoglobulin fusion protein - Protein Sequence | | |
|---|---|---|
| NAME | SEQ ID NO | SEQUENCE |
| connecting peptide GGGPRR (SEQ ID NO: 148) connecting insulin B chain and insulin A chain; GGGGS linker (SEQ ID NO: 141); murine anti-ASGPR HC) | | VDKPSSTAYMQLSSLTSEDSAVYYCANYYGSSWFAYWGQGTTL<br>TVSSAKTTAPSVYPLAPVCGDTTGSSVTLGCLVKGYFPEPVTLTW<br>NSGSLSSGVHTFPAVLQSDLYTLSSSVTVTSSTWPSQSITCNVAHP<br>ASSTKVDKKIEPRGPTIKPCPPCKCPAPNLLGGPSVFIFPPKIKDVL<br>MISLSPIVTCVVVDVSEDDPDVQISWFVNNVEVHTAQTQTHREDY<br>NSTLRVVSALPIQHQDWMSGKEFKCKVNNKDLPAPIERTISKPKG<br>SVRAPQVYVLPPPEEEMTKKQVTLTCMVTDFMPEDIYVEWTNNG<br>KTELNYKNTEPVLDSDGSYFMYSKLRVEKKNWVERNSYSCSVV<br>HEGLHNHHTTKSFSRTPGK |
| Ins1-L1-Ab1L Single chain (insulin1 with connecting peptide GGGPRR (SEQ ID NO: 148) connecting insulin B chain and insulin A chain; GGGGS linker (SEQ ID NO: 141); murine anti-ASGPR LC) | | *FVNQHLCGSDLVEALYLVCGERGFFYTDPTGGGPRRGIVEQCCHSIC*<br>*SLYQLENYCN*GGGGSETVLTQSPTTMATSPGEKITITCSASSTISSNY<br>LHWYQQKPGFSPKLLIYRTSDLASGVPTRFSGSGSGTSYSLTIGTM<br>EAEDVATYYCQQGSSIPFTFGSGTKLEINRADTAPTVSIFPPSSEQL<br>TSGGASVVCFLNNFYPKDINVKWKIDGSERQNGVLNSWTDQDSK<br>DSTYSMSSTLTLTKDEYERHNSYTCEATHKTSTSPIVKSFNRNEC |
| Ins1-L1-Ab2L Single chain (insulin1 with connecting peptide GGGPRR (SEQ ID NO: 148) connecting insulin B chain and insulin A chain; GGGGS linker (SEQ ID NO: 141); palivizumab LC) | | *FVNQHLCGSDLVEALYLVCGERGFFYTDPTGGGPRRGIVEQCCHSIC*<br>*SLYQLENYCN*GGGGSDIQMTQSPSTLSASVGDRVTITCKCQLSVGY<br>MHWYQQKPGKAPKLLIYDTSKLASGVPSRFSGSGSGTEFTLTISSL<br>QPDDFATYYCFQGSGYPFTFGGGTKLEIKRTVAAPSVFIFPPSDEQ<br>LKSGTASVVCLLNNFYPREAKVQWKVDNALQSGNSQESVTEQDS<br>KDSTYSLSSTLTLSKADYEKHKVYACEVTHQGLSSPVTKSFNRGEC |
| Ins2-L2-Ab3L Dual chain (insulin2 B chain with C3 connecting peptide, n = 4, after proteolytic cleavage at | and 168 | B CHAIN:<br>*FVNQHLCGSDLVEALYLVCGERGFFYTDPTGGGGSGGGGSGGGGS*<br>GGGGS<br>A CHAIN:<br>*GIVEQCCHSICSLYQLENYCN*GGPSSGAPPPSGGGGGETVLTQSPTT<br>MATSPGEKITITCSASSTISSNYLHWYQQKPGFSPKLLIYRTSDLAS<br>GVPTRFSGSGSGTSYSLTIGTMEAEDVATYYCQQGSSIPFTFGSGT<br>KLEIKRTVAAPSVFIFPPSDEQLKSGTASVVCLLNNFYPREAKVQ |

TABLE 4-continued

| Immunoglobulin fusion protein - Protein Sequence | | |
|---|---|---|
| NAME | SEQ ID NO | SEQUENCE |
| RKKR (SEQ ID NO: 184); insulin2 A chain; CEX5G linker; chimeric anti-ASGPR LC) | | WKVDNALQSGNSQESVTEQDSKDSTYSLSSTLTLSKADYEKHKV YACEVTHQGLSSPVTKSFNRGEC |
| Ins3-L2-Ab3L Single chain (insulin3 chain with C2 connecting peptide, n = 2, connecting B chain and A chain; CEX5G linker; chimeric anti-ASGPR LC) | | *FVNQHLCGSDLVEALYLVCGERGFFYTDPTGGGGSGGGGSGIVEQC CHSICSLYQLENYCN*GGPSSGAPPPSGGGGGETVLTQSPTTMATSP GEKITITCSASSTISSNYLHWYQQKPGFSPKLLIYRTSDLASGVPTR FSGSGSGTSYSLTIGTMEAEDVATYYCQQGSSIPFTFGSGTKLEIK RTVAAPSVFIFPPSDEQLKSGTASVVCLLNNFYPREAKVQWKVDN ALQSGNSQESVTEQDSKDSTYSLSSTLTLSKADYEKHKVYACEVT HQGLSSPVTKSFNRGEC |
| Ins3-L2-Ab3L Dual chain (insulin3 B chain with C3 connecting peptide, n = 2, after proteolytic cleavage at RKKR (SEQ ID NO: 184); insulin3 A chain; CEX5G linker; chimeric anti-ASGPR LC) | and 169 | B CHAIN: *FVNQHLCGSDLVEALYLVCGERGFFYTDPTGGGGSGGGGS* A CHAIN: *GIVEQCCHSICSLYQLENYCN*GGPSSGAPPPSGGGGGETVLTQSPTT MATSPGEKITITCSASSTISSNYLHWYQQKPGFSPKLLIYRTSDLAS GVPTRFSGSGSGTSYSLTIGTMEAEDVATYYCQQGSSIPFTFGSGT KLEIKRTVAAPSVFIFPPSDEQLKSGTASVVCLLNNFYPREAKVQ WKVDNALQSGNSQESVTEQDSKDSTYSLSSTLTLSKADYEKHKV YACEVTHQGLSSPVTKSFNRGEC |
| Ins1-L3-Ab4L Single chain (insulin1 with C1 connecting peptide connecting insulin B chain and insulin A chain; L3 linker; anti-ASGPR, humanized LC) | | *FVNQHLCGSDLVEALYLVCGERGFFYTDPTGGGPRRGIVEQCCHSIC SLYQLENYCN*GGGEAAAKEAAAKEAAAKAGGEIVLTQSPGTLSLS PGERATLSCSASSTISSNYLHWYQQKPGQAPRLLIYRTSDLASGIP DRFSGSGSGTDFTLTISRLEPEDFAVYYCQQGSSIPFTFGQGTKLEI KRTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |
| Ins4-L3-Ab4L Dual chain (insulin4 B chain with C3 connecting | and 170 | B CHAIN: *FVNQHLCGSHLVEALYLVCGERGFFYTPKTGGGGSGGGGS* A CHAIN: *GIVEQCCTSICSLYQLENYCN*GGGEAAAKEAAAKEAAAKAGGEIVL TQSPGTLSLSPGERATLSCSASSTISSNYLHWYQQKPGQAPRLLIY |

TABLE 4-continued

| Immunoglobulin fusion protein - Protein Sequence | | |
|---|---|---|
| NAME | SEQ ID NO | SEQUENCE |
| peptide, n = 2, after proteolytic cleavage at RKKR (SEQ ID NO: 184); L3 linker; anti-ASGPR, humanized LC) | | RTSDLASGIPDRFSGSGSGTDFTLTISRLEPEDFAVYYCQQGSSIPF TFGQGTKLEIKRTVAAPSVFIFPPSDEQLKSGTASVVCLLNNFYPR EAKVQWKVDNALQSGNSQESVTEQDSKDSTYSLSSTLTLSKADY EKHKVYACEVTHQGLSSPVTKSFNRGEC |
| Ins4-L3-Ab2L Dual chain (insulin4 B chain with C3 connecting peptide, n = 2, after proteolytic cleavage at RKKR (SEQ ID NO: 184); insulin4 A chain; L3 linker; palivizumab LC) | and 171 | B CHAIN: *FVNQHLCGSHLVEALYLVCGERGFFYTPKTGGGGSGGGGS* *GIVEQCCTSICLSYQLENYCN*GGGEAAAKEAAAKEAAAKAGGDIQ MTQSPSTLSASVGDRVTITCKCQLSVGYMHWYQQKPGKAPKLLI YDTSKLASGVPSRFSGSGSGTEFTLTISSLQPDDFATYYCFRQGSGY PFTFGGGTKLEIKRTVAAPSVFIFPPSDEQLKSGTASVVCLLNNFY PREAKVQWKVDNALQSGNSQESVTEQDSKDSTYSLSSTLTLSKA DYEKHKVYACEVTHQGLSSPVTKSFNRGEC |
| Ins1-L4-Ab4L Single chain (insulin1 with C1 connecting peptide connecting insulin B chain and insulin A chain; L4 linker; anti-ASGPR, humanized LC) | | *FVNQHLCGSDLVEALYLVCGERGFFYTDPTGGGPRRGIVEQCCHSIC* *SLYQLENYCN*GGGGSGGGEAAAKEAAAKEAAAKAGGEIVLTQSP GTLSLSPGERATLSCSASSTISSNYLHWYQQKPGQAPRLLIYRTSD LASGIPDRFSGSGSGTDFTLTISRLEPEDFAVYYCQQGSSIPFTFGQ GTKLEIKRTVAAPSVFIFPPSDEQLKSGTASVVCLLNNFYPREAKV QWKVDNALQSGNSQESVTEQDSKDSTYSLSSTLTLSKADYEKHK VYACEVTHQGLSSPVTKSFNRGEC |
| Ins1-L5-Ab4L Single chain (insulin1 with C1 connecting peptide connecting insulin B chain and insulin A chain; L5 linker; anti-ASGPR, humanized LC) | | *FVNQHLCGSDLVEALYLVCGERGFFYTDPTGGGPRRGIVEQCCHSIC* *SLYQLENYCN*GGGEAAAKEAAAKEAAAKAGGGGSGGEIVLTQSP GTLSLSPGERATLSCSASSTISSNYLHWYQQKPGQAPRLLIYRTSD LASGIPDRFSGSGSGTDFTLTISRLEPEDFAVYYCQQGSSIPFTFGQ GTKLEIKRTVAAPSVFIFPPSDEQLKSGTASVVCLLNNFYPREAKV QWKVDNALQSGNSQESVTEQDSKDSTYSLSSTLTLSKADYEKHK VYACEVTHQGLSSPVTKSFNRGEC |
| Ins1-L6-Ab4L Single chain (insulin1 with C1 connecting | | *FVNQHLCGSDLVEALYLVCGERGFFYTDPTGGGPRRGIVEQCCHSIC* *SLYQLENYCN*GGGGSGGGEAAAKEAAAKEAAAKAGGGGSGGEIV LTQSPGTLSLSPGERATLSCSASSTISSNYLHWYQQKPGQAPRLLI YRTSDLASGIPDRFSGSGSGTDFTLTISRLEPEDFAVYYCQQGSSIP |

TABLE 4-continued

| Immunoglobulin fusion protein - Protein Sequence | | |
|---|---|---|
| NAME | SEQ ID NO | SEQUENCE |
| peptide connecting insulin B chain and insulin A chain; L6 linker; anti-ASGPR, humanized LC) | | FEFGQGTKLEIKRTVAAPSVFIFPPSDEQLKSGTASVVCLLNNFYP REAKVQWKVDNALQSGNSQESVTEQDSKDSTYSLSSTLTLSKAD YEKHKVYACEVTHQGLSSPVTKSFNRGEC |
| Ab4L-L7-Ins5 Single chain (anti-ASGPR, humanized LC; L7 linker; insulin5 within C4 connecting peptide connecting insulin A chain to insulin B chain) | | EIVLTQSPGTLSLSPGERATLSCSASSTISSNYLHWYQQKPGQAPR LLIYRTSDLASGIPDRFSGSGSGTDFTLTISRLEPEDFAVYYCQQGS SIPFTFGQGTKLEIKRTVAAPSVFIFPPSDEQLKSGTASVVCLLNNF YPREAKVQWKVDNALQSGNSQESVTEQDSKDSTYSLSSTLTLSK ADYEKHKVYACEVTHQGLSSPVTKSFNRGECGGGGSGGSP*GIVE QCCTSICSLYQLENYCN*GGGSGGGSG*FVNQHLCGSHLVEALYLVCGE RGFFYTPKT* |
| Ins4-L6-Ab4 Dual chain (insulin4 B chain with C3 connecting peptide, n = 2, after proteolytic cleavage at RKKR (SEQ ID NO: 184); insulin4 A chain; L6 linker; anti-ASGPR, humanized LC) | and 172 | B CHAIN: *FVNQHLCGSHLVEALYLVCGERGFFYTPKT*GGGGSGGGGS A CHAIN: *GIVEQCCTSICSLYQLENYCN*GGGGSGGGEAAAKEAAAKEAAAKA GGGGSGGEIVLTQSPGTLSLSPGERATLSCSASSTISSNYLHWYQQ KPGQAPRLLIYRTSDLASGIPDRFSGSGSGTDFTLTISRLEPEDFAV YYCQQGSSIPFTFGQGTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| Ins6-L6-Ab4 Dual chain (insulin6 B chain after RKKR (SEQ ID NO: 184) cleavage of C7 connecting peptide; insulin6 A chain; L6 linker; anti-ASGPR, humanized LC) | and 173 | B CHAIN: *FVNQHLCGSHLVEALYLVCGERGFFYTPKT* A CHAIN: *GIVEQCCTSICSLYQLENYCN*GGGGSGGGEAAAKEAAAKEAAAKA GGGGSGGEIVLTQSPGTLSLSPGERATLSCSASSTISSNYLHWYQQ KPGQAPRLLIYRTSDLASGIPDRFSGSGSGTDFTLTISRLEPEDFAV YYCQQGSSIPFTFGQGTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| Ins1-L1-herceptin HC single chain | | *FVNQHLCGSDLVEALYLVCGERGFFYTDPTGGGPRRGIVEQCCHSIC SLYQLENYCN*GGGGSEVQLVESGGGLVQPGGSLRLSCAASGFNIK DTYIHWVRQAPGKGLEWVARIYPTNGYTRYADSVKGRFTISADT |

TABLE 4-continued

| Immunoglobulin fusion protein - Protein Sequence | | |
|---|---|---|
| NAME | SEQ ID NO | SEQUENCE |
| (insulin1 with connecting peptide C1 connecting insulin B chain and insulin A chain; L1 linker; herceptin HC) | | SKNTAYLQMNSLRAEDTAVYYCSRWGGDGFYAMDYWGQGTLV TVSSASTKGPSVFPLAPSSKSTSGGTAALGCLVKDYFPEPVTVSW NSGALTSGVHTFPAVLQSSGLYSLSSVVTVPSSSLGTQTYICNVNH KPSNTKVDKKVEPKSCDKTHTCPPCPAPPVAGPSVFLFPPKPKDT LMISRTPEVTCVVVDVSHEDPEVKFNWYVDGVEVHNAKTKPREE QYNSTYRVVSVLTVLHQDWLNGKEYKCKVSNKGLPSSIEKTISK AKGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPGK |
| Ins1-L1-herceptin LC single chain (insulin1 with connecting peptide C1 connecting insulin B chain and insulin A chain; L1 linker; herceptin LC) | | *FVNQHLCGSDLVEALYLVCGERGFFYTDPTGGGPRRGIVEQCCHSIC SLYQLENYCN*GGGGSDIQMTQSPSSLSASVGDRVTITCRASQDVNT AVAWYQQKPGKAPKLLIYSASFLYSGVPSRFSGSRSGTDFTLTISS LQPEDFATYYCQQHYTTPPTFGQGTKVEIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSFNR GEC |
| Ins4-L6-Ab4L (Fab) (insulin4 B chain after RKKR (SEQ ID NO: 184) cleavage of C3 connecting peptide, n = 2; insulin4 A chain; L6 linker; anti-ASGPR, humanized LC) | ,174 and 175 | HEAVY CHAIN: QVQLVQSGAEVKKPGASVKVSCKASGYTFTNYWMHWVRQAPG QGLEWMGRIDLNSGGTNYNYAQKFQGRVTMTRDTSISTAYMEL SRLRSDDTAVYYCARYYGSSWFAYWGQGTLVTVSSASTKGPSVF PLAPSSKSTSGGTAALGCLVKDYFPEPVTVSWNSGALTSGVHTFP AVLQSSGLYSLSSVVTVPSSSLGTQTYICNVNHKPSNTKVDKKVE PKSCDKTHT<br>LIGHT CHAIN:<br>B CHAIN:<br>*FVNQHLCGSHLVEALYLVCGERGFFYTPKTGGGGSGGGGS*<br>A CHAIN:<br>*GIVEQCCTSICSLYQLENYCNGGGGS*GGGEAAAKEAAAKEAAAKA GGGGSGGEIVLTQSPGTLSLSPGERATLSCSASSTISSNYLHWYQQ KPGQAPRLLIYRTSDLASGIPDRFSGSGSGTDFTLTISRLEPEDFAV YYCQQGSSIPFTFGQGTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| Ins1-L3-Ab5L (Fab) single chain (insulin1 with C1 connecting | | *FVNQHLCGSDLVEALYLVCGERGFFYTDPTGGGPRRGIVEQCCHSIC SLYQLENYCN*GGGEAAAKEAAAKEAAAKAGGEIVLTQSPGTLSLS PGERATLSCSASSTISSNYLHWYQQKPGQAPRLLIYRTSDLASGIP DRFSGSGSGTDFTLTISRLEPEDFAVYYCQQGSSIPFTFGQGTKLEI KRTVAAPSVFIFPPSDEQLKSGTASVVCLLNNFYPREAKVQWKVD |

TABLE 4-continued

| Immunoglobulin fusion protein - Protein Sequence | | |
|---|---|---|
| NAME | SEQ ID NO | SEQUENCE |
| peptide connecting insulin B chain and insulin A chain; L3 linker; anti-ASGPR, humanized LC) | | NALQSGNSQESVTEQDSKDSTYSLSSTLTLSKADYEKHKVYACE VTHQGLSSPVTKSFNRGEC |
| Ins7-L3-Ab4L Single chain (insulin7 with C1 connecting peptide connecting insulin B chain and insulin A chain; L3 linker; anti-ASGPR, humanized LC) | | *FVNQHLCGSHLVEALYLVCGERGFFYTPKTGGGPRRGIVEQCCTSICS LYQLENYCN***GGGEAAAKEAAAKEAAAKAGG**EIVLTQSPGTLSLS PGERATLSCSASSTISSNYLHWYQQKPGQAPRLLIYRTSDLASGIP DRFSGSGSGTDFTLTISRLEPEDFAVYYCQQGSSIPFTFGQGTKLEI KRTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |
| Ins7-L3-Ab5L Single chain (insulin7 with C1 connecting peptide connecting insulin B chain and insulin A chain; L3 linker; anti-ASGPR, humanized LC) | | *FVNQHLCGSHLVEALYLVCGERGFFYTPKTGGGPRRGIVEQCCTSICS LYQLENYCN***GGGEAAAKEAAAKEAAAKAGG**EIVLTQSPGTLSLS PGERATLSCSASSTISSNYLHWYQQKPGQAPRLLIYRTSDLASGIP DRFSGSGSGTDFTLTISRLEPEDFAVYYCQQGSSIPFTFGQGTKLEI KRTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |

For SEQ ID NO: 78-98

Immunoglobulin region = dashed underline

Therapeutic peptide = *italic*

Therapeutic peptide connecting peptide = *italic*

Linker = bold, thick underline

TABLE 5

| Therapeutic Peptides - Nucleic acid sequence | | |
|---|---|---|
| Name | SEQ ID NO | Sequence |
| Ins1 with C1 connecting peptide Single chain | | *TTTGTGAACCAACACCTGTGCGGCTCAGACCTGGTGGAAGCTCTCT ACCTAGTGTGCGGGGAACGAGGCTTCTTCTACACAGACCCCACC GGCGGAGGGCCCCGCCGGGGCATTGTGGAACAATGCTGTCACAGC ATCTGCTCCCTCTACCAGCTGGAGAACTACTGCAAC* |
| Ins2 with C3 connecting peptide Dual chain | | *TTTGTGAACCAACACCTGTGCGGCTCAGACCTGGTGGAAGCTCTCT ACCTAGTGTGCGGGGAACGAGGCTTCTTCTACACAGACCCCACC GGCGGGGGAGGCAGCGGGGGAGGCGGGTCCGGAGGCGGGGGAT CTGGCGGGGGAGGCAGTCGGAAAAAGCGTGGCATTGTGGAACAA TGCTGTCACAGCATCTGCTCCCTCTACCAGCTGGAGAACTACTGCA AC* |

TABLE 5-continued

| Therapeutic Peptides - Nucleic acid sequence | | |
|---|---|---|
| Name | SEQ ID NO | Sequence |
| Ins3 with C2 connecting peptide Single chain | | TTTGTGAACCAACACCTGTGCGGCTCAGACCTGGTGGAAGCTCTCT ACCTAGTGTGCGGGGAACGAGGCTTCTTCTACACAGACCCCACC GGAGGCGGGGGATCTGGCGGGGGAGGCAGTGGCATTGTGGAACA ATGCTGTCACAGCATCTGCTCCCTCTACCAGCTGGAGAACTACTGC AAC |
| Ins3 with C3 connecting peptide Dual chain | | TTTGTGAACCAACACCTGTGCGGCTCAGACCTGGTGGAAGCTCTCT ACCTAGTGTGCGGGGAACGAGGCTTCTTCTACACAGACCCCACC GGAGGCGGGGGATCTGGCGGGGGAGGCAGTCGGAAAAAGCGTGG CATTGTGGAACAATGCTGTCACAGCATCTGCTCCCTCTACCAGCTG GAGAACTACTGCAAC |
| Ins4 with C3 connecting peptide (n = 2) Dual chain | | TTTGTGAACCAACACCTGTGCGGCTCACACCTGGTGGAAGCTCTCT ACCTAGTGTGCGGGGAACGAGGCTTCTTCTACACACCCAAGACC GGAGGCGGGGGATCTGGCGGGGGAGGCAGTCGGAAAAAGCGTGG CATTGTGGAACAATGCTGTACCAGCATCTGCTCCCTCTACCAGCTG GAGAACTACTGCAAC |
| Ins4 with C7 connecting peptide, n = 2 Dual chain | | TTTGTGAACCAACACCTGTGCGGCTCACACCTGGTGGAAGCTCTCT ACCTAGTGTGCGGGGAACGAGGCTTCTTCTACACACCCAAGACC CGGAAAAAGCGTGGCGGGGGAGGCAGCGGGGGAGGCGGGTCCCG GAAAAAGCGTGGCATTGTGGAACAATGCTGTACCAGCATCTGCTCC CTCTACCAGCTGGAGAACTACTGCAAC |
| Ins4 Dual chain | | TTTGTGAACCAACACCTGTGCGGCTCACACCTGGTGGAAGCTCTCT ACCTAGTGTGCGGGGAACGAGGCTTCTTCTACACACCCAAGACC GGCGGGGGAGGCAGCGGGGGAGGCGGGTCCCGGAAAAAGCGTGG CATTGTGGAACAATGCTGTACCAGCATCTGCTCCCTCTACCAGCTG GAGAACTACTGCAAC |
| Ins5 with C4 connecting peptide Single Chain | | GGAATCGTAGAGCAGTGTTGTACCAGTATTTGCAGCCTCTATCAGC TCGAGAACTATTGTAATGGCGGAGGGTCCGGCGGTGGGAGCGGC TTCGTGAATCAACACCTGTGCGGGTCCCACCTGGTGGAAGCGTTG TATCTTGTCTGCGGGGAAAGGGGTTTCTTCTACACACCGAAGACC |
| Ins6 with C7 connecting peptide, n = 2 Dual chain | | TTTGTGAACCAACACCTGTGCGGCTCACACCTGGTGGAAGCTCTCT ACCTAGTGTGCGGGGAACGAGGCTTCTTCTACACACCCAAGACC CGGAAAAAGCGTGGCGGGGGAGGCAGCGGGGGAGGCGGGTCCCG GAAAAAGCGTGGCATTGTGGAACAATGCTGTACCAGCATCTGCTCC CTCTACCAGCTGGAGAACTACTGCAAC |
| Ins7 with C1 connecting peptide Single chain | | TTTGTGAACCAACACCTGTGCGGCTCACACCTGGTGGAAGCTCTCT ACCTAGTGTGCGGGGAACGAGGCTTCTTCTACACACCCAAGACC GGCGGAGGGCCCCGCCGGGGCATTGTGGAACAATGCTGTACCAGC ATCTGCTCCCTCTACCAGCTGGAGAACTACTGCAAC |

Therapeutic peptde = *italic*

Therapeutic peptide connecting peptide = *italic*

TABLE 6

| Therapeutic Peptides - Amino Acid Sequence | | |
|---|---|---|
| Name | SEQ ID NO | Sequence |
| Ins1 with C1 connecting peptide Single chain | | FVNQHLCGSDLVEALYLVCGERGFFYTDPTGGGPRRGIVEQCCHSIC SLYQLENYCN |

TABLE 6-continued

Therapeutic Peptides - Amino Acid Sequence

| Name | SEQ ID NO | Sequence |
|---|---|---|
| Ins2 with cleaved C3 connecting peptide, n = 4 Dual chain | and 176 | B CHAIN: *FVNQHLCGSDLVEALYLVCGERGFFYTDPTGGGGSGGGGGSGGGGSGGGGS* A CHAIN: *GIVEQCCHSICSLYQLENYCN* |
| Ins3 with C2 connecting peptide Single chain | | *FVNQHLCGSDLVEALYLVCGERGFFYTDPTGGGGSGGGGSGIVEQCCHSICSLYQLENYCN* |
| Ins3 with cleaved C3 connecting peptide, n = 2 Dual chain | and 177 | B CHAIN: *FVNQHLCGSDLVEALYLVCGERGFFYTDPTGGGGSGGGGS* A CHAIN: *GIVEQCCHSICSLYQLENYCN* |
| Ins4 with cleaved C3 connecting peptide, n = 2 Dual chain | and 178 | B CHAIN: *FVNQHLCGSHLVEALYLVCGERGFFYTPKTGGGGSGGGGS* A CHAIN: *GIVEQCCTSICSLYQLENYCN* |
| Ins4 with cleaved C3 connecting peptide, n = 2 Dual chain | and 179 | B CHAIN: *FVNQHLCGSHLVEALYLVCGERGFFYTPKTGGGGSGGGGS* A CHAIN: *GIVEQCCTSICSLYQLENYCN* |
| Ins4 Dual chain | and 180 | B CHAIN: *FVNQHLCGSHLVEALYLVCGERGFFYTPKTGGGGSGGGGS* A CHAIN: *GIVEQCCTSICSLYQLENYCN* |
| Ins5 with C4 connecting peptide Single chain | | *GIVEQCCTSICSLYQLENYCNGGGSGGGSGFVNQHLCGSHLVEALYLVCGERGFFYTPKT* |
| Ins6 with cleaved C7 connecting peptide Dual chain | and 181 | B CHAIN: *FVNQHLCGSHLVEALYLVCGERGFFYTPKT* A CHAIN: *GIVEQCCTSICSLYQLENYCN* |
| Ins7 with C1 connecting peptide Single chain | | *FVNQHLCGSHLVEALYLVCGERGFFYTPKTGGGPRRGIVEQCCTSICSLYQLENYCN* |
| InsX Single Chain | | *FVNQHLCGS*$X_A$*LVEALYLVCGERGFFYT*$X_B$$X_C$*T*$X_n$*GIVEQCC*$X_D$*SICSLYQLENYCN* $X_A$ is D or H, $X_B$ is D or P, $X_C$ is P or K, $X_D$ is H or T, $X_n$ is n number of amino acids, wherein each X is independently any natural or non-naturally occurring amino acid |
| InsX1: $X_A$ is D, $X_B$ is D, $X_C$ is P and $X_D$ is H | | *FVNQHLCGSDLVEALYLVCGERGFFYTDPT*$X_n$*GIVEQCCHSICSLYQLENYCN* $X_n$ is n number of amino acids, wherein each X is independently any natural or non-naturally occurring amino acid |
| InsX2: $X_A$ is D, $X_B$ is D, $X_C$ is P and $X_D$ is T | | *FVNQHLCGSDLVEALYLVCGERGFFYTDPT*$X_n$*GIVEQCCTSICSLYQLENYCN* $X_n$ is n number of amino acids, wherein each X is independently any natural or non-naturally occurring amino acid |

TABLE 6-continued

| Therapeutic Peptides - Amino Acid Sequence | | |
|---|---|---|
| Name | SEQ ID NO | Sequence |
| InsX3: $X_A$ is D, $X_B$ is D, $X_C$ is K and $X_D$ is H | | *FVNQHLCGSDLVEALYLVCGERGFFYTDKTX$_n$GIVEQCCHSICSLYQLENYCN* $X_n$ is n number of amino acids, wherein each X is independently any natural or non-naturally occurring amino acid |
| InsX4: $X_A$ is D, $X_B$ is D, $X_C$ is K and $X_D$ is T | | *FVNQHLCGSDLVEALYLVCGERGFFYTDKTX$_n$GIVEQCCTSICSLYQLENYCN* $X_n$ is n number of amino acids, wherein each X is independently any natural or non-naturally occurring amino acid |
| InsX5: $X_A$ is D, $X_B$ is P, $X_C$ is P and $X_D$ is H | | *FVNQHLCGSDLVEALYLVCGERGFFYTPPTX$_n$GIVEQCCHSICSLYQLENYCN* $X_n$ is n number of amino acids, wherein each X is independently any natural or non-naturally occurring amino acid |
| InsX6: $X_A$ is D, $X_B$ is P, $X_C$ is P and $X_D$ is T | | *FVNQHLCGSDLVEALYLVCGERGFFYTPPTX$_n$GIVEQCCTSICSLYQLENYCN* $X_n$ is n number of amino acids, wherein each X is independently any natural or non-naturally occurring amino acid |
| InsX7: $X_A$ is D, $X_B$ is P, $X_C$ is K and $X_D$ is H | | *FVNQHLCGSDLVEALYLVCGERGFFYTPKTX$_n$GIVEQCCHSICSLYQLENYCN* $X_n$ is n number of amino acids, wherein each X is independently any natural or non-naturally occurring amino acid |
| InsX8: $X_A$ is D, $X_B$ is P, $X_C$ is K and $X_D$ is T | | *FVNQHLCGSDLVEALYLVCGERGFFYTPKTX$_n$GIVEQCCTSICSLYQLENYCN* $X_n$ is n number of amino acids, wherein each X is independently any natural or non-naturally occurring amino acid |
| InsX9: $X_A$ is H, $X_B$ is D, $X_C$ is P and $X_D$ is H | | *FVNQHLCGSHLVEALYLVCGERGFFYTDPTX$_n$GIVEQCCHSICSLYQLENYCN* $X_n$ is n number of amino acids, wherein each X is independently any natural or non-naturally occurring amino acid |
| InsX10: $X_A$ is H, $X_B$ is D, $X_C$ is P and $X_D$ is T | | *FVNQHLCGSHLVEALYLVCGERGFFYTDPTX$_n$GIVEQCCTSICSLYQLENYCN* $X_n$ is n number of amino acids, wherein each X is independently any natural or non-naturally occurring amino acid |
| InsX11: $X_A$ is H, $X_B$ is D, $X_C$ is K and $X_D$ is H | | *FVNQHLCGSHLVEALYLVCGERGFFYTDKTX$_n$GIVEQCCHSICSLYQLENYCN* $X_n$ is n number of amino acids, wherein each X is independently any natural or non-naturally occurring amino acid |
| InsX12: $X_A$ is H, $X_B$ is D, $X_C$ is K and $X_D$ is T | | *FVNQHLCGSHLVEALYLVCGERGFFYTDKTX$_n$GIVEQCCTSICSLYQLENYCN* $X_n$ is n number of amino acids, wherein each X is independently any natural or non-naturally occurring amino acid |
| InsX13: $X_A$ is H, $X_B$ is P, $X_C$ is P and $X_D$ is H | | *FVNQHLCGSHLVEALYLVCGERGFFYTPPTX$_n$GIVEQCCHSICSLYQLENYCN* $X_n$ is n number of amino acids, wherein each X is independently any natural or non-naturally occurring amino acid |
| InsX14: $X_A$ is H, $X_B$ is P, $X_C$ is P and $X_D$ is T | | *FVNQHLCGSHLVEALYLVCGERGFFYTPPTX$_n$GIVEQCCTSICSLYQLENYCN* $X_n$ is n number of amino acids, wherein each X is independently any natural or non-naturally occurring amino acid |
| InsX15: $X_A$ is H, $X_B$ is P, $X_C$ is K and $X_D$ is H | | *FVNQHLCGSHLVEALYLVCGERGFFYTPKTX$_n$GIVEQCCHSICSLYQLENYCN* $X_n$ is n number of amino acids, wherein each X is independently any natural or non-naturally occurring amino acid |
| InsX16: $X_A$ is H, $X_B$ is P, $X_C$ is P and $X_D$ is T | | *FVNQHLCGSHLVEALYLVCGERGFFYTPPTX$_n$GIVEQCCTSICSLYQLENYCN* $X_n$ is n number of amino acids, wherein each X is independently any natural or non-naturally occurring amino acid |
| InsX17: Xn is GGGPGG (SEQ ID NO: 152) | | *FVNQHLCGSX$_A$LVEALYLVCGERGFFYTX$_B$X$_C$TGGGPGGGIVEQCCX$_D$SICSLYQLENYCN* $X_n$ is n number of amino acids, wherein each X is independently any natural or non-naturally occurring amino acid |

TABLE 6-continued

| Therapeutic Peptides - Amino Acid Sequence | | |
|---|---|---|
| Name | SEQ ID NO | Sequence |
| InsX18: Xn is GGGPKK (SEQ ID NO: 153) | | *FVNQHLCGSX$_A$LVEALYLVCGERGFFYTX$_B$X$_C$TGGGPKKGIVEQCCX$_D$ SICSLYQLENYCN* X$_n$ is n number of amino acids, wherein each X is independently any natural or non-naturally occurring amino acid |
| Mature human insulin | | FVNQHLCGSHLVEALYLVCGERGFFYTPKT GIVEQCCTSICSLYQLENYCN |
| Mature bovine insulin | | FVNQHLCGSHLVEALYLVCGERGFFYTPKA GIVEQCCASVCSLYQLENYCN |
| Mature porcine insulin | | FVNQHLCGSHLVEALYLVCGERGFFYTPKA GIVEQCCTSICSLYQLENYCN |

Therapeutic peptide = *italic*
Therapeutic peptide connecting peptide = *italic*

TABLE 7

| Linker Sequences | | |
|---|---|---|
| Name | SEQ ID NO | Sequence |
| L1 | | GGGGS |
| L2 (CEX5G) | | GGPSSGAPPPSGGGGG |
| L3 (EAK) | | GGGEAAAKEAAAKEAAAKAGG |
| L4 (GGGGSEAK) | | GGGGSGGGEAAAKEAAAKEAAAKAGG |
| L5 (EAKGGGGS) | | GGGEAAAKEAAAKEAAAKAGGGGSGG |
| L6 (GGGGSEAKGGGGS) | | GGGGSGGGEAAAKEAAAKEAAAKAGGGGSGG |
| L7 (GGGGSGGSP) | | GGGGSGGSP |

TABLE 8

| Connecting Peptide Sequences | | |
|---|---|---|
| Name | SEQ ID NO | Sequence |
| C1 | | GGGPRR |
| C2 | | (GGGGS)$_n$ (n = 1-10) |
| C3 | | (GGGGS)$_n$RKKR (n = 1-10) |
| C4 | | GGGSGGGSG |
| C5 | | GGGPGG |
| C6 | | GGGPKK |
| C7 | | RKKR(GGGGS)nRKKR (n = 1-10) |

TABLE 9

| Additional Sequences | | |
|---|---|---|
| Name | SEQ ID NO | Sequence |
| Amino terminus of anti-ASGPR VH | | QVQLX$_1$QX$_2$GAE, wherein X$_1$ and X$_2$ are independently selected from a naturally or non-naturally occurring amino acid |
| Amino terminus of anti-ASGPR VL | | EX$_1$VLTQSPX$_2$T, wherein X$_1$ and X$_2$ are independently selected from a naturally or non-naturally occurring amino acid |
| insulin B peptide | | FVNQHLCGSX$_A$LVEALYLVCGERGFFYTX$_B$X$_C$T, wherein X$_A$, X$_B$, X$_C$ and X$_D$ are independently selected from a naturally or non-naturally occurring amino acid |
| insulin A peptide | | GIVEQCCX$_D$SICSLYQLENYCN, wherein X$_D$ is a naturally or non-naturally occurring amino acid |
| connecting peptide | | GGGX$_1$X$_2$, wherein X$_1$ and X$_2$ are independently selected from a naturally or non-naturally occurring amino acid |

TABLE 9-continued

| Additional Sequences | | |
|---|---|---|
| Name | SEQ ID NO | Sequence |
| insulin B chain | | FVNQHLCGSHLVEALYLVCGERGFFYT |
| insulin A chain | | GIVEQCCTSICSLYQLENYC |
| human ASGPR | | QNSQLQEELRGLRETFSNFTASTEAQVKGLSTQGGNVGRK MKSLESQLEK QQKDLSEDHSSLLLHVKQFVSDLRSLSCQMAALQGNGSER TCCPVNWVEH ERSCYWFSRSGKAWADADNYCRLEDAHLVVVTSWEEQKF VQHHIGPVNTW MGLHDQNGPWKWVDGTDYETGFKNWRPEQPDDWYGHGL GGGEDCAHFTDD GRWNDDVCQRPYRWVCETELDKASQEPPLL |
| Cyno Monkey ASGPR | | QNAQLQRELRGLRETLSNFTASTEAQVKGLSTQGGNVGRK MKSLESQLEK QQKDLSEDHSSLLLHVKQFVSDLRSLSCQMAALQGNGSER ACCPVNWVEH ERSCYWFSRSGKAWADADNYCRLEDAHLVVVTSWEEQKF VQHHIGPVNTW MGLHDQNGPWKWVDGTDYETGFKNWRPEQPDDWYGHGL GGGEDCAHFTDD GRWNDDVCQRPYRWVCETELHKASQEPPLL |
| rat ASGPR | | QNSQLREDLRVLRQNFSNFTVSTEDQVKALTTQGERVGRK MKLVESQLEK HQEDLREDHSRLLLHVKQLVSDVRSLSCQMAALRGNGSERI CCPINWVEY EGSCYWFSSSVKPWTEADKYCQLENAHLVVVTSWEEQRFV QQHMGPLNTW IGLTDQNGPWKWVDGTDYETGFKNWRPGQPDDWYGHGL GGGEDCAHFTTD GHWNDDVCRRPYRWVCETELGKAN |
| mouse ASGPR | | QNSQLREDLLALRQNFSNLTVSTEDQVKALSTQGSSVGRK MKLVESKLEK QQKDLTEDHSSLLLHVKQLVSDVRSLSCQMAAFRGNGSER TCCPINWVEY EGSCYWFSSSVRPWTEADKYCQLENAHLVVVTSRDEQNFL QRHMGPLNTW IGLTDQNGPWKWVDGTDYETGFQNWRPEQPDNWYGHGL GGGEDCAHFTTD GRWNDDVCRRPYRWVCETKLDKAN |
| Ab3H (anti-ASGPR, chimeric HC) | | CAGGTCCAACTGCAGCAGCCTGGGGCTGAGCTTGTGAAG CCTGGGGCTTCAGTGAAACTGTCCTGCAAGGCTTCTGGCT ATACCTTCACCAACTACTGGATGCACTGGGTGAAACAGA GGCCTGGACGAGGCCTTGAGTGGATTGGAAGGATTGATC TTAATAGTGGTGGTACTAATTACAATTACAATGAGAAGT TCAAGACCAAGGCCACACTGACTGTAGACAAACCCTCCA GCACAGCCTACATGCAGCTCAGCAGCCTGACATCTGAGG ACTCTGCGGTCTATTATTGTGCAAATTACTACGGTAGTAG CTGGTTTGCTTACTGGGGCCAAGGGACTCTGGTCACTGTC TCTGCAGCCTCCACCAAGGGCCCATCGGTCTTCCCCCTGG CACCCTCCTCCAAGAGCACCTCTGGGGGCACAGCGGCCC TGGGCTGCCTGGTCAAGGACTACTTCCCCGAACCGGTGA CGGTGTCGTGGAACTCAGGCGCCCTGACCAGCGGCGTGC ACACCTTCCCGGCTGTCCTACAGTCCTCAGGACTCTACTC CCTCAGCAGCGTGGTGACTGTGCCCTCTAGCAGCTTGGG CACCCAGACCTACATCTGCAACGTGAATCACAAGCCCAG CAACACCAAGGTGGACAAGAAAGTTGAACCCAAATCTTG CGACAAAACTCACACATGCCCACCGTGCCCAGCACCTCC AGTCGCCGGACCGTCAGTCTTCCTCTTCCCTCCAAAACCC AAGGACACCCTCATGATCTCCCGGACCCCTGAGGTCACA TGCGTGGTGGTGGACGTGAGCCACGAAGACCCTGAGGTC AAGTTCAACTGGTACGTGGACGGCGTGGAGGTGCATAAT GCCAAGACAAAGCCGCGGGAGGAGCAGTACAACAGCAC GTACCGTGTGGTCAGCGTCCTCACCGTCCTGCACCAGGA CTGGCTGAATGGCAAGGAGTACAAGTGCAAGGTCTCCAA CAAAGGCCTCCCAAGCTCCATCGAGAAAACCATCTCCAA AGCCAAAGGGCAGCCCCGAGAACCACAGGTGTACACCCT GCCTCCATCCCGGGATGAGCTGACCAAGAACCAGGTCAG CCTGACCTGCCTGGTCAAAGGCTTCTATCCCAGCGACATC GCCGTGGAGTGGGAGAGCAATGGGCAGCCGGAGAACAA |

TABLE 9-continued

| Additional Sequences | | |
|---|---|---|
| Name | SEQ ID NO | Sequence |
| | | CTACAAGACCACGCCTCCCGTGCTGGACTCCGACGGCTC CTTCTTCCTCTACAGCAAGCTCACCGTGGACAAGAGCAG GTGGCAGCAGGGGAACGTCTTCTCATGCTCCGTGATGCA TGAGGCTCTGCACAACCACTACACGCAGAAGAGCCTCTC CCTGTCTCCGGGTAAA |
| Ab3H (anti-ASGPR, chimeric HC) | | QVQLQQPGAELVKPGASVKLSCKASGYTFTNYWMHWVKQ RPGRGLEWIGRIDLNSGGTNYNYNEKFKTKATLTVDKPSST AYMQLSSLTSEDSAVYYCANYYGSSWFAYWGQGTLVTVS AASTKGPSVFPLAPSSKSTSGGTAALGCLVKDYFPEPVTVS WNSGALTSGVHTFPAVLQSSGLYSLSSVVTVPSSSLGTQTYI CNVNHKPSNTKVDKKVEPKSCDKTHTCPPCPAPPVAGPSVF LFPPKPKDTLMISRTPEVTCVVVDVSHEDPEVKFNWYVDGV EVHNAKTKPREEQYNSTYRVVSVLTVLHQDWLNGKEYKC KVSNKGLPSSIEKTISKAKGQPREPQVYTLPPSRDELTKNQV SLTCLVKGFYPSDIAVEWESNGQPENNYKTTPPVLDSDGSFF LYSKLTVDKSRWQQGNVFSCSVMHEALHNHYTQKSLSLSP GK |

What is claimed is:

1. A composition comprising a molecule of Formula XVII:

I-L-G (Formula XVII)

wherein:

I has the formula B-C-A or A-C-B; wherein B comprises an insulin B chain; A comprises an insulin A chain; C comprises a connecting peptide connecting B and A;

L comprises a linker; and

G comprises an immunoglobulin or immunoglobulin fragment that specifically binds to an asialoglycoprotein receptor (ASGPR).

2. The composition of claim 1, wherein A and B are linked by a disulfide bond.

3. The composition of claim 1, wherein the insulin B chain comprises an amino acid sequence having no more than 1, 2, 3 or 4 amino acid differences from SEQ ID NO: 160 (FVNQHLCGSHLVEALYLVCGERGFFYT).

4. The composition of claim 1, wherein the insulin A chain comprises an amino acid sequence having no more than 1, 2, 3 or 4 amino acid differences from SEQ ID NO: 161 (GIVEQCCTSICSLYQLENYC).

5. The composition of claim 1, wherein the linker comprises a linker peptide.

6. The composition of claim 5, wherein the linker peptide comprises an amino acid sequence selected from: (a) an amino acid sequence having at least 50% glycine, serine, or glycine and serine amino acids; and (b) an amino acid sequence having at least 50% glycine, alanine, or glycine and alanine amino acids.

7. A method of treating a disease or condition associated with glucose metabolism in a subject in need thereof, the method comprising administering an effective amount of the composition of claim 1.

8. The composition of claim 1, wherein the insulin therapeutic peptide comprises SEQ ID NOS: 160 and 161.

9. The composition of claim 1, wherein the connecting peptide comprises SEQ ID NO: 159 (GGG$X_1X_2$), wherein $X_1$ and $X_2$ are independently a naturally or a non-naturally occurring amino acid.

10. The composition of claim 9, wherein $X_1$ is P, G, or S.

11. The composition of claim 9, wherein $X_2$ is R, S, G, or K.

12. The composition of claim 1, wherein C comprises a protease cleavage site.

13. The composition of claim 1, wherein the insulin B chain comprises SEQ ID NO: 157 (FVNQHLCGS$X_A$LVEALYLVCGERGFFYT$X_BX_C$T); and $X_A$, $X_B$, and $X_C$ are independently a naturally or a non-naturally occurring amino acid.

14. The composition of claim 13, wherein the $X_A$ is D or H; the $X_B$ is D or P; or the $X_C$ is P or K.

15. The composition of claim 1, wherein the insulin A chain comprises SEQ ID NO: 158 (GIVEQCC$X_D$SICSLYQLENYCN), and $X_D$ is a naturally or a non-naturally occurring amino acid.

16. The composition of claim 15, wherein $X_D$ is selected from H and T.

* * * * *

SEQUENCE LISTING

<160> NUMBER OF SEQ ID NOS: 185

<210> SEQ ID NO 1
<211> LENGTH: 1350
<212> TYPE: DNA
<213> ORGANISM: Mus sp.

<400> SEQUENCE: 1

```
caggtccaac tgcagcagcc tggggctgag cttgtgaagc ctggggcttc agtgaaactg     60
tcctgcaagg cttctggcta taccttcacc aactactgga tgcactgggt gaaacagagg    120
cctggacgag gccttgagtg gattggaagg attgatctta atagtggtgg tactaattac    180
aattacaatg agaagttcaa gaccaaggcc acactgactg tagacaaacc ctccagcaca    240
gcctacatgc agctcagcag cctgacatct gaggactctg cggtctatta ttgtgcaaat    300
tactacggta gtagctggtt tgcttactgg ggccaaggga ccactctcac agtctcctca    360
gctaaaacaa cagccccatc ggtctatcca ctggcccctg tgtgtggaga tacaactggc    420
tcctcggtga ctctaggatg cctggtcaag ggttatttcc ctgagccagt gaccttgacc    480
tggaactctg gatccctgtc cagtggtgtg cacaccttcc cagctgtcct gcagtctgac    540
ctctacaccc tcagcagctc agtgactgta acctcgagca cctggcccag ccagtccatc    600
acctgcaatg tggcccaccc ggcaagcagc accaaggtgg acaagaaaat tgagcccaga    660
gggcccacaa tcaagccctg tcctccatgc aaatgcccag cacctaacct cttgggtgga    720
ccatccgtct tcatcttccc tccaaagatc aaggatgtac tcatgatctc cctgagcccc    780
atagtcacat gtgtggtggt ggatgtgagc gaggatgacc cagatgtcca gatcagctgg    840
tttgtgaaca acgtggaagt acacacagct cagacacaaa cccatagaga ggattacaac    900
agtactctcc gggtggtcag tgccctcccc atccagcacc aggactggat gagtggcaag    960
gagttcaaat gcaaggtcaa caacaaagac ctcccagcgc ccatcgagag aaccatctca   1020
aaacccaaag ggtcagtaag agctccacag gtatatgtct tgcctccacc agaagaagag   1080
atgactaaga aacaggtcac tctgacctgc atggtcacag acttcatgcc tgaagacatt   1140
tacgtggagt ggaccaacaa cgggaaaaca gagctaaact acaagaacac tgaaccagtc   1200
```

```
ctggactctg atggttctta cttcatgtac agcaagctga gagtggaaaa gaagaactgg   1260

gtggaaagaa atagctactc ctgttcagtg gtccacgagg gtctgcacaa tcaccacacg   1320

actaagagct tctcccggac tccgggtaaa                                    1350


<210> SEQ ID NO 2
<211> LENGTH: 645
<212> TYPE: DNA
<213> ORGANISM: Mus sp.

<400> SEQUENCE: 2

gaaactgtac tcacccagtc tccaaccacc atggctacat ctcccgggga gaagatcact     60

atcacctgca gtgccagctc aactataagt tccaattact tgcattggta tcagcagaag    120

ccaggattct cccctaaact cttgatttat aggacatccg atctggcttc tggagtccca    180

actcgcttca gtggcagtgg gtctgggacc tcttactctc tcacaattgg caccatggag    240

gctgaagatg ttgccactta ctactgccag cagggtagta gtataccatt cacgttcggc    300

tcggggacaa agctggagat taaccgggca gatacagcac caactgtatc catcttccca    360

ccatccagtg agcagttaac atctggaggt gcctcagtcg tgtgcttctt gaacaacttc    420

taccccaaag acatcaatgt caagtggaag attgatggca gtgaacgaca aaatggcgtc    480

ctgaacagtt ggactgatca ggacagcaaa gacagcacct acagcatgag cagcaccctc    540

acgttgacca aggacgagta tgaacgacat aacagctata cctgtgaggc cactcacaag    600

acatcaactt cacccattgt caagagcttc aacaggaatg agtgt                    645


<210> SEQ ID NO 3
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

caggtgaccc tgcgcgagtc cggccctgca ctggtgaagc ccacccagac cctgaccctg     60

acctgcacct tctccggctt ctccctgtcc acctccggca tgtccgtggg ctggatccgg    120

cagcctcccg gcaaggccct ggagtggctg gctgacatct ggtgggacga caagaaggac    180

tacaacccct ccctgaagtc ccgcctgacc atctccaagg acacctccaa gaaccaggtg    240

gtgctgaagg tgaccaacat ggaccccgcc gacaccgcca cctactactg cgcccgctca    300

atgattacca actggtactt cgacgtgtgg ggagccggta ccaccgtgac cgtgtcttcc    360

gcctccacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgact gtgccctcta gcagcttggg cacccagacc    600

tacatctgca acgtgaatca caagcccagc aacaccaagg tggacaagaa agttgaaccc    660

aaatcttgcg acaaaactca cacatgccca ccgtgcccag cacctccagt cgccggaccg    720

tcagtcttcc tcttccctcc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960
```

```
tacaagtgca aggtctccaa caaaggcctc ccaagctcca tcgagaaaac catctccaaa   1020

gccaaagggc agccccgaga accacaggtg tacaccctgc ctccatcccg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctacagc aagctcaccg tggacaagag caggtggcag   1260

caggggaacg tcttctcatg ctccgtgatg catgaggctc tgcacaacca ctacacgcag   1320

aagagcctct ccctgtctcc gggtaaatga taa                                1353
```

<210> SEQ ID NO 4
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
gacatccaga tgacccagtc cccctccacc ctgtccgcct ccgtgggcga ccgcgtgacc     60

atcacctgca agtgccagct gtccgtgggc tacatgcact ggtaccagca gaagcccggc    120

aaggccccca agctgctgat ctacgacacc tccaagctgg cctccggcgt gccctcccgc    180

ttctccggct ccggctccgg caccgagttc accctgacca tctcctccct gcagcccgac    240

gacttcgcca cctactactg cttccagggc tccggctacc ccttcacctt cggcggcggc    300

accaagctgg agatcaaacg aactgtggct gcaccatctg tcttcatctt cccgccatct    360

gatgagcagt tgaaatctgg aactgcctct gtcgtgtgcc tgctgaataa cttctatccc    420

agagaggcca aagtacagtg gaaggtggat aacgccctcc aatcgggtaa ctcccaggag    480

agtgtcacag agcaggacag caaggacagc acctacagcc tcagcagcac cctgacgctg    540

agcaaagcag actacgagaa acacaaagtc tacgcctgcg aagtcaccca tcagggcctg    600

tcctcgcccg tcacaaagag cttcaacagg ggagagtgtt ga                       642
```

<210> SEQ ID NO 5
<211> LENGTH: 648
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
gaaactgtac tcacccagtc tccaaccacc atggctacat ctcccgggga gaagatcact     60

atcacctgca gtgccagctc aactataagt tccaattact tgcattggta tcagcagaag    120

ccaggattct cccctaaact cttgatttat aggacatccg atctggcttc tggagtccca    180

actcgcttca gtggcagtgg gtctgggacc tcttactctc tcacaattgg caccatggag    240

gctgaagatg ttgccactta ctactgccag cagggtagta gtataccatt cacgttcggc    300

tcggggacaa agttggaaat taaacgaact gtggctgcac catctgtctt catcttcccg    360

ccatctgatg agcagttgaa atctggaact gcctctgtcg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600
```

ggcctgtcct cgcccgtcac aaagagcttc aacaggggag agtgttga 648

<210> SEQ ID NO 6
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
caggtgcagc tggtccagtc cggcgcagag gtgaagaaac ccggggcctc cgtgaaggtc 60
tcttgcaaag ctagtgggta caccttcaca aactattgga tgcactgggt gcgacaggca 120
cctggacagg gcctggaatg gatgggaaga atcgacctga acagcggcgg gactaactac 180
aattatgccc agaagtttca gggcagggtg actatgaccc gcgatacctc aattagcaca 240
gcttacatgg agctgtcacg gctgagaagc gacgatacag ccgtctacta ttgtgctcgg 300
tactatggca gctcctggtt cgcctattgg gggcagggaa cactggtgac tgtctctagt 360
gcatcaacaa agggaccaag cgtgtttcca ctggccccct caagcaagag cacctccgga 420
gggacagccg ctctgggatg tctggtgaaa gactacttcc ccgagcctgt gactgtctct 480
tggaatagtg gcgctctgac ctccggggtg cacacatttc cagcagtcct gcagtcctct 540
ggactgtatt ctctgagttc agtggtcacc gtgcccagct cctctctggg cactcagacc 600
tacatctgca atgtcaacca taagcctagt aacacaaaag tggataagaa agtcgaacca 660
aagagctgtg acaaaactca cacatgccca ccgtgcccag cacctccagt cgccggaccg 720
tcagtcttcc tcttccctcc aaaacccaag gacaccctca tgatctcccg gacccctgag 780
gtcacatgcg tggtggtgga cgtgagccac gaagaccctg aggtcaagtt caactggtac 840
gtggacggcg tggaggtgca taatgccaag acaaagccgc gggaggagca gtacaacagc 900
acgtaccgtg tggtcagcgt cctcaccgtc ctgcaccagg actggctgaa tggcaaggag 960
tacaagtgca aggtctccaa caaaggcctc ccaagctcca tcgagaaaac catctccaaa 1020
gccaaagggc agccccgaga accacaggtg tacaccctgc ctccatcccg ggatgagctg 1080
accaagaacc aggtcagcct gacctgcctg gtcaaaggct tctatcccag cgacatcgcc 1140
gtggagtggg agagcaatgg gcagccggag aacaactaca agaccacgcc tcccgtgctg 1200
gactccgacg gctccttctt cctctacagc aagctcaccg tggacaagag caggtggcag 1260
caggggaacg tcttctcatg ctccgtgatg catgaggctc tgcacaacca ctacacgcag 1320
aagagcctct ccctgtctcc gggtaaa 1347

<210> SEQ ID NO 7
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
gagatcgtgc tgactcagag cccaggaacc ctgtccctgt ctccaggaga acgagccacc 60
ctgtcctgct ccgcctcatc aacaatttct agtaactacc tgcactggta tcagcagaag 120
ccaggacagg cacctcgact gctgatctac agaactagtg acctggcctc tggcattccc 180
gataggttca gcggctccgg gtctggaaca gactttaccc tgacaatctc ccgcctggag 240
cctgaagatt tcgctgtcta ctattgtcag cagggctcaa gcatcccatt cacatttggc 300

```
caggggacta agctggagat caagcgcaca gtggcagccc ccagcgtctt cattttttccc    360

ccttccgatg aacagctgaa gtccggcact gcttctgtgg tctgtctgct gaacaatttc    420

tatcccagag aggccaaggt gcagtggaaa gtggacaacg ctctgcagtc cggcaacagc    480

caggagagtg tgaccgaaca ggatagtaag gacagcacat attctctgtc tagtaccctg    540

acactgagta aggcagatta cgagaagcac aaagtgtatg cctgcgaagt cactcatcag    600

ggactgtcaa gccccgtgac caagagcttc aaccggggcg agtgt                    645
```

<210> SEQ ID NO 8
<211> LENGTH: 685
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
caggtgcagc tggtccagtc cggcgcagag gtgaagaaac ccggggcctc cgtgaaggtc     60

tcttgcaaag ctagtgggta caccttcaca aactattgga tgcactgggt gcgacaggca    120

cctggacagg gcctggaatg gatgggaaga atcgacctga acagcggcgg gactaactac    180

aattatgccc agaagtttca gggcagggtg actatgaccc gcgatacctc aattagcaca    240

gcttacatgg agctgtcacg gctgagaagc gacgatacag ccgtctacta ttgtgctcgg    300

tactatggca gctcctggtt cgcctattgg gggcagggaa cactggtgac tgtctctagt    360

gcatcaacaa agggaccaag cgtgtttcca ctggccccct caagcaagag cacctccgga    420

gggacagccg ctctgggatg tctggtgaaa gactacttcc ccgagcctgt gactgtctct    480

tggaatagtg gcgctctgac ctccggggtg cacacatttc cagcagtcct gcagtcctct    540

ggactgtatt ctctgagttc agtggtcacc gtgcccagct cctctctggg cactcagacc    600

tacatctgca atgtcaacca taagcctagt aacacaaaag tggataagaa agtcgaacca    660

aagagctgtg gacaaaactc acaca                                          685
```

<210> SEQ ID NO 9
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
caggtgcagc tggtccagtc cggcgcagag gtgaagaaac ccggggcctc cgtgaaggtc     60

tcttgcaaag ctagtgggta caccttcaca aactattgga tgcactgggt gcgacaggca    120

cctggacagg gcctggaatg gatgggatgg atcgacctga acagcggcgg gactaactac    180

aattatgccc agaagtttca gggcagggtg actatgaccc gcgatacctc aattagcaca    240

gcttacatgg agctgtcacg gctgagaagc gacgatacag ccgtctacta ttgtgctcgg    300

tactatggca gctcctggtt cgcctattgg gggcagggaa cactggtgac tgtctctagt    360

gcatcaacaa agggaccaag cgtgtttcca ctggccccct caagcaagag cacctccgga    420

gggacagccg ctctgggatg tctggtgaaa gactacttcc ccgagcctgt gactgtctct    480

tggaatagtg gcgctctgac ctccggggtg cacacatttc cagcagtcct gcagtcctct    540

ggactgtatt ctctgagttc agtggtcacc gtgcccagct cctctctggg cactcagacc    600
```

```
tacatctgca atgtcaacca taagcctagt aacacaaaag tggataagaa agtcgaacca    660

aagagctgtg acaaaactca cacatgccca ccgtgcccag cacctccagt cgccggaccg    720

tcagtcttcc tcttccctcc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaaggcctc ccaagctcca tcgagaaaac catctccaaa   1020

gccaaagggc agccccgaga accacaggtg tacaccctgc ctccatcccg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctacagc aagctcaccg tggacaagag caggtggcag   1260

caggggaacg tcttctcatg ctccgtgatg catgaggctc tgcacaacca ctacacgcag   1320

aagagcctct ccctgtctcc gggtaaa                                       1347


<210> SEQ ID NO 10
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

caggtgcagc tggtccagtc cggcgcagag gtgaagaaac ccggggcctc cgtgaaggtc     60

tcttgcaaag ctagtgggta caccttcaca aactattgga tgcactgggt gcgacaggca    120

cctggacagg gcctggaatg gatgggatgg atcgacctga acagcggcgg gactaactac    180

aattatgccc agaagtttca gggcagggtg actatgaccc gcgatacctc aattagcaca    240

gcttacatgg agctgtcacg gctgagaagc gacgatacag ccgtctacta ttgtgctcgg    300

tactatggca gctcctggtt cgcctattgg gggcagggaa cactggtgac tgtctctagt    360

gcatcaacaa agggaccaag cgtgtttcca ctggcccccct caagcaagag cacctccgga    420

gggacagccg ctctgggatg tctggtgaaa gactacttcc ccgagcctgt gactgtctct    480

tggaatagtg gcgctctgac ctccggggtg cacacatttc cagcagtcct gcagtcctct    540

ggactgtatt ctctgagttc agtggtcacc gtgcccagct cctctctggg cactcagacc    600

tacatctgca atgtcaacca taagcctagt aacacaaaag tggataagaa agtcgaacca    660

aagagctgtg acaaaactca caca                                           684


<210> SEQ ID NO 11
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

caggtccaac tgcagcagcc tggggctgag cttgtgaagc ctggggcttc agtgaaactg     60

tcctgcaagg cttctggcta caccttcacc aactactgga tgcactgggt gaaacagagg    120

cctggacgag gccttgagtg gattggaagg attgatctta atagtggtgg tactaattac    180

aattacaatg agaagttcaa gaccaaggcc acactgactg tagacaaacc ctccagcaca    240
```

```
gcctacatgc agctcagcag cctgacatct gaggactctg cggtctatta ttgtgcaaat    300

tactacggta gtagctggtt tgcttactgg ggccaaggga ccactctcac agtctcctca    360


<210> SEQ ID NO 12
<211> LENGTH: 309
<212> TYPE: DNA
<213> ORGANISM: Homo sapiens

<400> SEQUENCE: 12

gcctccacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgact gtgccctcta gcagcttggg cacccagacc    240

tacatctgca acgtgaatca caagcccagc aacaccaagg tggacaagaa agttgaaccc    300

aaatcttgc                                                            309


<210> SEQ ID NO 13
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

gaaactgtac tcacccagtc tccaaccacc atggctacat ctcccgggga gaagatcact     60

atcacctgca gtgccagctc aactataagt tccaattact tgcattggta tcagcagaag    120

ccaggattct cccctaaact cttgatttat aggacatccg atctggcttc tggagtccca    180

actcgcttca gtggcagtgg gtctgggacc tcttactctc tcacaattgg caccatggag    240

gctgaagatg ttgccactta ctactgccag cagggtagta gtataccatt cacgttcggc    300

tcggggacaa agttggaaat taaa                                           324


<210> SEQ ID NO 14
<211> LENGTH: 321
<212> TYPE: DNA
<213> ORGANISM: Homo sapiens

<400> SEQUENCE: 14

cgaactgtgg ctgcaccatc tgtcttcatc ttcccgccat ctgatgagca gttgaaatct     60

ggaactgcct ctgtcgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgtcctcgcc cgtcacaaag    300

agcttcaaca ggggagagtg t                                              321


<210> SEQ ID NO 15
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
```

```
caggtgcagc tggtccagtc cggcgcagag gtgaagaaac ccggggcctc cgtgaaggtc     60

tcttgcaaag ctagtgggta caccttcaca aactattgga tgcactgggt gcgacaggca    120

cctggacagg gcctggaatg gatgggaaga atcgacctga acagcggcgg gactaactac    180

aattatgccc agaagtttca gggcagggtg actatgaccc gcgatacctc aattagcaca    240

gcttacatgg agctgtcacg gctgagaagc gacgatacag ccgtctacta ttgtgctcgg    300

tactatggca gctcctggtt cgcctattgg gggcagggaa cactggtgac tgtctctagt    360
```

<210> SEQ ID NO 16
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
gagatcgtgc tgactcagag cccaggaacc ctgtccctgt ctccaggaga acgagccacc     60

ctgtcctgct ccgcctcatc aacaatttct agtaactacc tgcactggta tcagcagaag    120

ccaggacagg cacctcgact gctgatctac agaactagtg acctggcctc tggcattccc    180

gataggttca gcggctccgg gtctggaaca gactttaccc tgacaatctc ccgcctggag    240

cctgaagatt tcgctgtcta ctattgtcag cagggctcaa gcatcccatt cacatttggc    300

caggggacta agctggagat caag                                           324
```

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17

```
ggctatacct tcaccaacta ctggatgcac                                      30
```

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18

```
aggattgatc ttaatagtgg tggtactaat tacaattaca atgagaagtt caagacc        57
```

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19

```
tactacggta gtagctggtt tgcttac                                         27
```

<210> SEQ ID NO 20
<211> LENGTH: 36
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 20

agtgccagct caactataag ttccaattac ttgcat                             36


<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

aggacatccg atctggcttc t                                             21


<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

cagcagggta gtagtatacc attcacg                                       27


<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

tccgcctcat caacaatttc tagtaactac ctgcac                             36


<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

agaactagtg acctggcctc t                                             21


<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

cagcagggct caagcatccc attcaca                                       27


<210> SEQ ID NO 26
<211> LENGTH: 30
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 26
gggtacacct tcacaaacta ttggatgcac                                        30

<210> SEQ ID NO 27
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agaatcgacc tgaacagcgg cgggactaac tacaattatg cccagaagtt tcagggca        58

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tactatggca gctcctggtt cgcctat                                           27

<210> SEQ ID NO 29
<211> LENGTH: 450
<212> TYPE: PRT
<213> ORGANISM: Mus sp.

<400> SEQUENCE: 29

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Arg Gly Leu Glu Trp Ile
        35                  40                  45

Gly Arg Ile Asp Leu Asn Ser Gly Gly Thr Asn Tyr Asn Tyr Asn Glu
    50                  55                  60

Lys Phe Lys Thr Lys Ala Thr Leu Thr Val Asp Lys Pro Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Asn Tyr Tyr Gly Ser Ser Trp Phe Ala Tyr Trp Gly Gln
            100                 105                 110

Gly Thr Thr Leu Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

```
Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450


<210> SEQ ID NO 30
<211> LENGTH: 215
<212> TYPE: PRT
<213> ORGANISM: Mus sp.

<400> SEQUENCE: 30

Glu Thr Val Leu Thr Gln Ser Pro Thr Thr Met Ala Thr Ser Pro Gly
1               5                   10                  15

Glu Lys Ile Thr Ile Thr Cys Ser Ala Ser Ser Thr Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asp Leu Ala Ser Gly Val Pro Thr Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Phe Thr Phe Gly Ser Gly Thr Lys Leu Glu Ile Asn Arg Ala Asp Thr
            100                 105                 110

Ala Pro Thr Val Ser Ile Phe Pro Pro Ser Ser Glu Gln Leu Thr Ser
```

```
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215


<210> SEQ ID NO 31
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 32
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 33
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Thr Val Leu Thr Gln Ser Pro Thr Thr Met Ala Thr Ser Pro Gly
1               5                   10                  15

Glu Lys Ile Thr Ile Thr Cys Ser Ala Ser Ser Thr Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asp Leu Ala Ser Gly Val Pro Thr Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Phe Thr Phe Gly Ser Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 34
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Arg Ile Asp Leu Asn Ser Gly Gly Thr Asn Tyr Asn Tyr Ala Gln
    50                  55                  60

Lys Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Arg Tyr Tyr Gly Ser Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
```

```
        435                 440                 445

Lys


<210> SEQ ID NO 35
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Thr Ile Ser Ser Asn
            20                  25                  30

Tyr Leu His Trp Tyr Gln Gln Lys Pro Gly Gln Ala Pro Arg Leu Leu
        35                  40                  45

Ile Tyr Arg Thr Ser Asp Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Ser Ile Pro
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 36
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Arg Ile Asp Leu Asn Ser Gly Gly Thr Asn Tyr Asn Tyr Ala Gln
    50                  55                  60
```

```
Lys Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Arg Tyr Tyr Gly Ser Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225


<210> SEQ ID NO 37
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Trp Ile Asp Leu Asn Ser Gly Gly Thr Asn Tyr Asn Tyr Ala Gln
    50                  55                  60

Lys Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Arg Tyr Tyr Gly Ser Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 38
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Trp Ile Asp Leu Asn Ser Gly Gly Thr Asn Tyr Asn Tyr Ala Gln
    50                  55                  60

Lys Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
```

```
                85                  90                  95

Tyr Cys Ala Arg Tyr Tyr Gly Ser Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225


<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Arg Gly Leu Glu Trp Ile
        35                  40                  45

Gly Arg Ile Asp Leu Asn Ser Gly Gly Thr Asn Tyr Asn Tyr Asn Glu
    50                  55                  60

Lys Phe Lys Thr Lys Ala Thr Leu Thr Val Asp Lys Pro Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Asn Tyr Tyr Gly Ser Ser Trp Phe Ala Tyr Trp Gly Gln
            100                 105                 110

Gly Thr Leu Val Thr Val Ser Ala
        115                 120


<210> SEQ ID NO 40
<211> LENGTH: 103
<212> TYPE: PRT
<213> ORGANISM: Homo sapiens

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100


<210> SEQ ID NO 41
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Thr Val Leu Thr Gln Ser Pro Thr Thr Met Ala Thr Ser Pro Gly
1               5                   10                  15

Glu Lys Ile Thr Ile Thr Cys Ser Ala Ser Ser Thr Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asp Leu Ala Ser Gly Val Pro Thr Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Phe Thr Phe Gly Ser Gly Thr Lys Leu Glu Ile Lys
            100                 105


<210> SEQ ID NO 42
<211> LENGTH: 107
<212> TYPE: PRT
<213> ORGANISM: Homo sapiens

<400> SEQUENCE: 42

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 43
<211> LENGTH: 120
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Arg Ile Asp Leu Asn Ser Gly Gly Thr Asn Tyr Asn Tyr Ala Gln
    50                  55                  60

Lys Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Arg Tyr Tyr Gly Ser Ser Trp Phe Ala Tyr Trp Gly Gln
            100                 105                 110

Gly Thr Leu Val Thr Val Ser Ser
        115                 120


<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Thr Ile Ser Ser Asn
            20                  25                  30

Tyr Leu His Trp Tyr Gln Gln Lys Pro Gly Gln Ala Pro Arg Leu Leu
        35                  40                  45

Ile Tyr Arg Thr Ser Asp Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Ser Ile Pro
                85                  90                  95

Phe Thr Phe Gly Gln Gly Thr Lys Leu Glu Ile Lys
            100                 105


<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Tyr Thr Phe Thr Asn Tyr Trp Met His
1               5                   10


<210> SEQ ID NO 46
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ile Asp Leu Asn Ser Gly Gly Thr Asn Tyr Asn Tyr Asn Glu Lys
1               5                   10                  15

Phe Lys Thr


<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Tyr Gly Ser Ser Trp Phe Ala Tyr
1               5


<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Ala Ser Ser Thr Ile Ser Ser Asn Tyr Leu His
1               5                   10


<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Thr Ser Asp Leu Ala Ser
1               5


<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Gln Gly Ser Ser Ile Pro Phe Thr
1               5


<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 51

Ser Ala Ser Ser Thr Ile Ser Ser Asn Tyr Leu His
1 5 10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Arg Thr Ser Asp Leu Ala Ser
1 5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Gln Gln Gly Ser Ser Ile Pro Phe Thr
1 5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Gly Tyr Thr Phe Thr Asn Tyr Trp Met His
1 5 10

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Arg Ile Asp Leu Asn Ser Gly Gly Thr Asn Tyr Asn Tyr Ala Gln Lys
1 5 10 15

Phe Gln Gly

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Tyr Tyr Gly Ser Ser Trp Phe Ala Tyr
1 5

<210> SEQ ID NO 57

<211> LENGTH: 1535
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 57
tttgtgaacc aacacctgtg cggctcagac ctggtggaag ctctctacct agtgtgcggg 60
gaacgaggct tcttctacac agaccccacc ggcggagggc cccgccgggg cattgtggaa 120
caatgctgtc acagcatctg ctccctctac cagctggaga actactgcaa cggtggcgga 180
ggcagccagg tccaactgca gcagcctggg gctgagcttg tgaagcctgg ggcttcagtg 240
aaactgtcct gcaaggcttc tggctatacc ttcaccaact actggatgca ctgggtgaaa 300
cagaggcctg gacgaggcct tgagtggatt ggaaggattg atcttaatag tggtggtact 360
aattacaatt acaatgagaa gttcaagacc aaggccacac tgactgtaga caaaccctcc 420
agcacagcct acatgcagct cagcagcctg acatctgagg actctgcggt ctattattgt 480
gcaaattact acggtagtag ctggtttgct tactggggcc aagggaccac tctcacagtc 540
tcctcagcta aaacaacagc cccatcggtc tatccactgg cccctgtgtg tggagataca 600
actggctcct cggtgactct aggatgcctg gtcaagggtt atttccctga gccagtgacc 660
ttgacctgga actctggatc cctgtccagt ggtgtgcaca ccttcccagc tgtcctgcag 720
tctgacctct acaccctcag cagctcagtg actgtaacct cgagcacctg gcccagccag 780
tccatcacct gcaatgtggc ccacccggca agcagcacca aggtggacaa gaaaattgag 840
cccagagggc ccacaatcaa gccctgtcct ccatgcaaat gcccagcacc taacctcttg 900
ggtggaccat ccgtcttcat cttccctcca aagatcaagg atgtactcat gatctccctg 960
agccccatag tcacatgtgt ggtggtggat gtgagcgagg atgacccaga tgtccagatc 1020
agctggtttg tgaacaacgt ggaagtacac acagctcaga cacaaaccca tagagaggat 1080
tacaacagta ctctccgggt ggtcagtgcc ctccccatcc agcaccagga ctggatgagt 1140
ggcaaggagt tcaaatgcaa ggtcaacaac aaagacctcc cagcgcccat cgagagaacc 1200
atctcaaaac ccaaagggtc agtaagagct ccacaggtat atgtcttgcc tccaccagaa 1260
gaagagatga ctaagaaaca ggtcactctg acctgcatgg tcacagactt catgcctgaa 1320
gacatttacg tggagtggac caacaacggg aaaacagagc taaactacaa gaacactgaa 1380
ccagtcctgg actctgatgg ttcttacttc atgtacagca agctgagagt ggaaaagaag 1440
aactgggtgg aaagaaatag ctactcctgt tcagtggtcc acgagggtct gcacaatcac 1500
cacacgacta agagcttctc ccggactccg ggtaa 1535

<210> SEQ ID NO 58
<211> LENGTH: 831
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 58
tttgtgaacc aacacctgtg cggctcagac ctggtggaag ctctctacct agtgtgcggg 60
gaacgaggct tcttctacac agaccccacc ggcggagggc cccgccgggg cattgtggaa 120
caatgctgtc acagcatctg ctccctctac cagctggaga actactgcaa cggtggcgga 180
ggcagcgaaa ctgtactcac ccagtctcca accaccatgg ctacatctcc cggggagaag 240
atcactatca cctgcagtgc cagctcaact ataagttcca attacttgca ttggtatcag 300
cagaagccag gattctcccc taaactcttg atttatagga catccgatct ggcttctgga 360
gtcccaactc gcttcagtgg cagtgggtct gggacctctt actctctcac aattggcacc 420
atggaggctg aagatgttgc cacttactac tgccagcagg gtagtagtat accattcacg 480
ttcggctcgg ggacaaagct ggagattaac cgggcagata cagcaccaac tgtatccatc 540
ttcccaccat ccagtgagca gttaacatct ggaggtgcct cagtcgtgtg cttcttgaac 600
aacttctacc ccaaagacat caatgtcaag tggaagattg atggcagtga acgacaaaat 660
ggcgtcctga acagttggac tgatcaggac agcaaagaca gcacctacag catgagcagc 720
accctcacgt tgaccaagga cgagtatgaa cgacataaca gctatacctg tgaggccact 780
cacaagacat caacttcacc cattgtcaag agcttcaaca ggaatgagtg t 831

<210> SEQ ID NO 59
<211> LENGTH: 828
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59
tttgtgaacc aacacctgtg cggctcagac ctggtggaag ctctctacct agtgtgcggg 60
gaacgaggct tcttctacac agaccccacc ggcggagggc cccgccgggg cattgtggaa 120
caatgctgtc acagcatctg ctccctctac cagctggaga actactgcaa cggtggcgga 180
ggcagcgaca tccagatgac ccagtccccc tccaccctgt ccgcctccgt gggcgaccgc 240
gtgaccatca cctgcaagtg ccagctgtcc gtgggctaca tgcactggta ccagcagaag 300
cccggcaagg cccccaagct gctgatctac gacacctcca agctggcctc cggcgtgccc 360
tcccgcttct ccggctccgg ctccggcacc gagttcaccc tgaccatctc ctccctgcag 420
cccgacgact tcgccaccta ctactgcttc cagggctccg gctacccctt caccttcggc 480
ggcggcacca agctggagat caaacgaact gtggctgcac catctgtctt catcttcccg 540
ccatctgatg agcagttgaa atctggaact gcctctgtcg tgtgcctgct gaataacttc 600
tatcccagag aggccaaagt acagtggaag gtggataacg ccctccaatc gggtaactcc 660
caggagagtg tcacagagca ggacagcaag gacagcacct acagcctcag cagcaccctg 720
acgctgagca aagcagacta cgagaaacac aaagtctacg cctgcgaagt cacccatcag 780
ggcctgtcct cgcccgtcac aaagagcttc aacaggggag agtgttga 828

<210> SEQ ID NO 60
<211> LENGTH: 921
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 60
tttgtgaacc aacacctgtg cggctcagac ctggtggaag ctctctacct agtgtgcggg 60
gaacgaggct tcttctacac agaccccacc ggcgggggag gcagcggggg aggcgggtcc 120
ggaggcgggg gatctggcgg gggaggcagt cggaaaaagc gtggcattgt ggaacaatgc 180
tgtcacagca tctgctccct ctaccagctg gagaactact gcaacggagg cccttcctcc 240

```
ggagctccac ctccgtccgg gggtggcgga ggcgaaactg tactcaccca gtctccaacc    300

accatggcta catctcccgg ggagaagatc actatcacct gcagtgccag ctcaactata    360

agttccaatt acttgcattg gtatcagcag aagccaggat tctcccctaa actcttgatt    420

tataggacat ccgatctggc ttctggagtc ccaactcgct tcagtggcag tgggtctggg    480

acctcttact ctctcacaat tggcaccatg gaggctgaag atgttgccac ttactactgc    540

cagcagggta gtagtatacc attcacgttc ggctcgggga caaagttgga aattaaacga    600

actgtggctg caccatctgt cttcatcttc ccgccatctg atgagcagtt gaaatctgga    660

actgcctctg tcgtgtgcct gctgaataac ttctatccca gagaggccaa agtacagtgg    720

aaggtggata acgccctcca atcgggtaac tcccaggaga gtgtcacaga gcaggacagc    780

aaggacagca cctacagcct cagcagcacc ctgacgctga gcaaagcaga ctacgagaaa    840

cacaaagtct acgcctgcga agtcacccat cagggcctgt cctcgcccgt cacaaagagc    900

ttcaacaggg gagagtgttg a                                               921
```

<210> SEQ ID NO 61
<211> LENGTH: 879
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
tttgtgaacc aacacctgtg cggctcagac ctggtggaag ctctctacct agtgtgcggg     60

gaacgaggct tcttctacac agaccccacc ggaggcgggg gatctggcgg gggaggcagt    120

ggcattgtgg aacaatgctg tcacagcatc tgctccctct accagctgga gaactactgc    180

aacggaggcc cttcctccgg agctccacct ccgtccgggg gtggcggagg cgaaactgta    240

ctcacccagt ctccaaccac catggctaca tctcccgggg agaagatcac tatcacctgc    300

agtgccagct caactataag ttccaattac ttgcattggt atcagcagaa gccaggattc    360

tcccctaaac tcttgattta taggacatcc gatctggctt ctggagtccc aactcgcttc    420

agtggcagtg ggtctgggac ctcttactct ctcacaattg gcaccatgga ggctgaagat    480

gttgccactt actactgcca gcagggtagt agtataccat tcacgttcgg ctcggggaca    540

aagttggaaa ttaaacgaac tgtggctgca ccatctgtct tcatcttccc gccatctgat    600

gagcagttga aatctggaac tgcctctgtc gtgtgcctgc tgaataactt ctatcccaga    660

gaggccaaag tacagtggaa ggtggataac gccctccaat cgggtaactc ccaggagagt    720

gtcacagagc aggacagcaa ggacagcacc tacagcctca gcagcaccct gacgctgagc    780

aaagcagact acgagaaaca caaagtctac gcctgcgaag tcacccatca gggcctgtcc    840

tcgcccgtca caaagagctt caacagggga gagtgttga                           879
```

<210> SEQ ID NO 62
<211> LENGTH: 891
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

```
tttgtgaacc aacacctgtg cggctcagac ctggtggaag ctctctacct agtgtgcggg     60

gaacgaggct tcttctacac agaccccacc ggaggcgggg gatctggcgg gggaggcagt    120
```

```
cggaaaaagc gtggcattgt ggaacaatgc tgtcacagca tctgctccct ctaccagctg    180

gagaactact gcaacggagg cccttcctcc ggagctccac ctccgtccgg gggtggcgga    240

ggcgaaactg tactcaccca gtctccaacc accatggcta catctcccgg ggagaagatc    300

actatcacct gcagtgccag ctcaactata agttccaatt acttgcattg gtatcagcag    360

aagccaggat tctcccctaa actcttgatt tataggacat ccgatctggc ttctggagtc    420

ccaactcgct tcagtggcag tgggtctggg acctcttact ctctcacaat tggcaccatg    480

gaggctgaag atgttgccac ttactactgc cagcagggta gtagtatacc attcacgttc    540

ggctcgggga caaagttgga aattaaacga actgtggctg caccatctgt cttcatcttc    600

ccgccatctg atgagcagtt gaaatctgga actgcctctg tcgtgtgcct gctgaataac    660

ttctatccca gagaggccaa agtacagtgg aaggtggata acgccctcca atcgggtaac    720

tcccaggaga gtgtcacaga gcaggacagc aaggacagca cctacagcct cagcagcacc    780

ctgacgctga gcaaagcaga ctacgagaaa cacaaagtct acgcctgcga agtcacccat    840

cagggcctgt cctcgcccgt cacaaagagc ttcaacaggg gagagtgttg a             891
```

<210> SEQ ID NO 63
<211> LENGTH: 879
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
tttgtgaacc aacacctgtg cggctcagac ctggtggaag ctctctacct agtgtgcggg     60

gaacgaggct tcttctacac agaccccacc ggcggagggc cccgccgggg cattgtggaa    120

caatgctgtc acagcatctg ctccctctac cagctggaga actactgcaa cgggggtggc    180

gaagcagctg ctaaggaggc agccgcaaag gaagcagctg caaaggcagg aggcgagatc    240

gtgctgactc agagcccagg aaccctgtcc ctgtctccag gagaacgagc caccctgtcc    300

tgctccgcct catcaacaat ttctagtaac tacctgcact ggtatcagca gaagccagga    360

caggcacctc gactgctgat ctacagaact agtgacctgg cctctggcat tcccgatagg    420

ttcagcggct ccgggtctgg aacagacttt accctgacaa tctcccgcct ggagcctgaa    480

gatttcgctg tctactattg tcagcagggc tcaagcatcc cattcacatt tggccagggg    540

actaagctgg agatcaagcg cacagtggca gcccccagcg tcttcatttt tccccccttcc    600

gatgaacagc tgaagtccgg cactgcttct gtggtctgtc tgctgaacaa tttctatccc    660

agagaggcca aggtgcagtg gaaagtggac aacgctctgc agtccggcaa cagccaggag    720

agtgtgaccg aacaggatag taaggacagc acatattctc tgtctagtac cctgacactg    780

agtaaggcag attacgagaa gcacaaagtg tatgcctgcg aagtcactca tcagggactg    840

tcaagccccg tgaccaagag cttcaaccgg ggcgagtgt                           879
```

<210> SEQ ID NO 64
<211> LENGTH: 903
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
tttgtgaacc aacacctgtg cggctcacac ctggtggaag ctctctacct agtgtgcggg     60
gaacgaggct tcttctacac acccaagacc ggaggcgggg gatctggcgg gggaggcagt    120
cggaaaaagc gtggcattgt ggaacaatgc tgtaccagca tctgctccct ctaccagctg    180
gagaactact gcaacggggg tggcgaagca gctgctaagg aggcagccgc aaaggaagca    240
gctgcaaagg caggaggcga gatcgtgctg actcagagcc caggaaccct gtccctgtct    300
ccaggagaac gagccaccct gtcctgctcc gcctcatcaa caatttctag taactacctg    360
cactggtatc agcagaagcc aggacaggca cctcgactgc tgatctacag aactagtgac    420
ctggcctctg gcattcccga taggttcagc ggctccgggt ctggaacaga ctttaccctg    480
acaatctccc gcctggagcc tgaagatttc gctgtctact attgtcagca gggctcaagc    540
atcccattca catttggcca ggggactaag ctggagatca agcgcacagt ggcagccccc    600
agcgtcttca tttttccccc ttccgatgaa cagctgaagt ccggcactgc ttctgtggtc    660
tgtctgctga acaatttcta tcccagagag gccaaggtgc agtggaaagt ggacaacgct    720
ctgcagtccg gcaacagcca ggagagtgtg accgaacagg atagtaagga cagcacatat    780
tctctgtcta gtaccctgac actgagtaag gcagattacg agaagcacaa agtgtatgcc    840
tgcgaagtca ctcatcaggg actgtcaagc cccgtgacca agagcttcaa ccggggcgag    900
tgt                                                                  903
```

<210> SEQ ID NO 65
<211> LENGTH: 897
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
tttgtgaacc aacacctgtg cggctcacac ctggtggaag ctctctacct agtgtgcggg     60
gaacgaggct tcttctacac acccaagacc ggaggcgggg gatctggcgg gggaggcagt    120
cggaaaaagc gtggcattgt ggaacaatgc tgtaccagca tctgctccct ctaccagctg    180
gagaactact gcaacggggg tggcgaagca gctgctaagg aggcagccgc aaaggaagca    240
gctgcaaagg caggaggcga catccagatg acccagtccc cctccaccct gtccgcctcc    300
gtgggcgacc gcgtgaccat cacctgcaag tgccagctgt ccgtgggcta catgcactgg    360
taccagcaga agcccggcaa ggcccccaag ctgctgatct acgacacctc caagctggcc    420
tccggcgtgc cctcccgctt ctccggctcc ggctccggca ccgagttcac cctgaccatc    480
tcctccctgc agcccgacga cttcgccacc tactactgct tccagggctc cggctacccc    540
ttcaccttcg gcggcggcac caagctggag atcaaacgaa ctgtggctgc accatctgtc    600
ttcatcttcc cgccatctga tgagcagttg aaatctggaa ctgcctctgt cgtgtgcctg    660
ctgaataact tctatcccag agaggccaaa gtacagtgga aggtggataa cgccctccaa    720
tcgggtaact cccaggagag tgtcacagag caggacagca aggacagcac ctacagcctc    780
agcagcaccc tgacgctgag caaagcagac tacgagaaac acaaagtcta cgcctgcgaa    840
gtcacccatc agggcctgtc ctcgcccgtc acaaagagct tcaacagggg agagtgt       897
```

<210> SEQ ID NO 66
<211> LENGTH: 894
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 66

```
tttgtgaacc aacacctgtg cggctcagac ctggtggaag ctctctacct agtgtgcggg     60

gaacgaggct tcttctacac agaccccacc ggcggagggc cccgccgggg cattgtggaa    120

caatgctgtc acagcatctg ctccctctac cagctggaga actactgcaa cggtggcgga    180

ggcagcgggg gtggcgaagc agctgctaag gaggcagccg caaaggaagc agctgcaaag    240

gcaggaggcg agatcgtgct gactcagagc ccaggaaccc tgtccctgtc tccaggagaa    300

cgagccaccc tgtcctgctc cgcctcatca acaatttcta gtaactacct gcactggtat    360

cagcagaagc caggacaggc acctcgactg ctgatctaca gaactagtga cctggcctct    420

ggcattcccg ataggttcag cggctccggg tctggaacag actttaccct gacaatctcc    480

cgcctggagc ctgaagattt cgctgtctac tattgtcagc agggctcaag catcccattc    540

acatttggcc aggggactaa gctggagatc aagcgcacag tggcagcccc cagcgtcttc    600

atttttcccc cttccgatga acagctgaag tccggcactg cttctgtggt ctgtctgctg    660

aacaatttct atcccagaga ggccaaggtg cagtggaaag tggacaacgc tctgcagtcc    720

ggcaacagcc aggagagtgt gaccgaacag gatagtaagg acagcacata ttctctgtct    780

agtaccctga cactgagtaa ggcagattac gagaagcaca aagtgtatgc ctgcgaagtc    840

actcatcagg gactgtcaag ccccgtgacc aagagcttca accggggcga gtgt          894
```

<210> SEQ ID NO 67
<211> LENGTH: 894
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
tttgtgaacc aacacctgtg cggctcagac ctggtggaag ctctctacct agtgtgcggg     60

gaacgaggct tcttctacac agaccccacc ggcggagggc cccgccgggg cattgtggaa    120

caatgctgtc acagcatctg ctccctctac cagctggaga actactgcaa cgggggtggc    180

gaagcagctg ctaaggaggc agccgcaaag gaagcagctg caaaggcagg tggcggaggc    240

agcggaggcg agatcgtgct gactcagagc ccaggaaccc tgtccctgtc tccaggagaa    300

cgagccaccc tgtcctgctc cgcctcatca acaatttcta gtaactacct gcactggtat    360

cagcagaagc caggacaggc acctcgactg ctgatctaca gaactagtga cctggcctct    420

ggcattcccg ataggttcag cggctccggg tctggaacag actttaccct gacaatctcc    480

cgcctggagc ctgaagattt cgctgtctac tattgtcagc agggctcaag catcccattc    540

acatttggcc aggggactaa gctggagatc aagcgcacag tggcagcccc cagcgtcttc    600

atttttcccc cttccgatga acagctgaag tccggcactg cttctgtggt ctgtctgctg    660

aacaatttct atcccagaga ggccaaggtg cagtggaaag tggacaacgc tctgcagtcc    720

ggcaacagcc aggagagtgt gaccgaacag gatagtaagg acagcacata ttctctgtct    780

agtaccctga cactgagtaa ggcagattac gagaagcaca aagtgtatgc ctgcgaagtc    840

actcatcagg gactgtcaag ccccgtgacc aagagcttca accggggcga gtgt          894
```

<210> SEQ ID NO 68
<211> LENGTH: 909

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
tttgtgaacc aacacctgtg cggctcagac ctggtggaag ctctctacct agtgtgcggg     60

gaacgaggct tcttctacac agaccccacc ggcggagggc cccgccgggg cattgtggaa    120

caatgctgtc acagcatctg ctccctctac cagctggaga actactgcaa cggtggcgga    180

ggcagcgggg gtggcgaagc agctgctaag gaggcagccg caaaggaagc agctgcaaag    240

gcaggtggcg gaggcagcgg aggcgagatc gtgctgactc agagcccagg aaccctgtcc    300

ctgtctccag gagaacgagc caccctgtcc tgctccgcct catcaacaat ttctagtaac    360

tacctgcact ggtatcagca gaagccagga caggcacctc gactgctgat ctacagaact    420

agtgacctgg cctctggcat tcccgatagg ttcagcggct ccgggtctgg aacagacttt    480

accctgacaa tctcccgcct ggagcctgaa gatttcgctg tctactattg tcagcagggc    540

tcaagcatcc cattcacatt tggccagggg actaagctgg agatcaagcg cacagtggca    600

gcccccagcg tcttcatttt tccccttcc gatgaacagc tgaagtccgg cactgcttct    660

gtggtctgtc tgctgaacaa tttctatccc agagaggcca aggtgcagtg gaaagtggac    720

aacgctctgc agtccggcaa cagccaggag agtgtgaccg aacaggatag taaggacagc    780

acatattctc tgtctagtac cctgacactg agtaaggcag attacgagaa gcacaaagtg    840

tatgcctgcg aagtcactca tcagggactg tcaagccccg tgaccaagag cttcaaccgg    900

ggcgagtgt                                                            909
```

<210> SEQ ID NO 69
<211> LENGTH: 852
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
gagatcgtgc tgactcagag cccaggaacc ctgtccctgt ctccaggaga acgagccacc     60

ctgtcctgct ccgcctcatc aacaatttct agtaactacc tgcactggta tcagcagaag    120

ccaggacagg cacctcgact gctgatctac agaactagtg acctggcctc tggcattccc    180

gataggttca gcggctccgg gtctggaaca gactttaccc tgacaatctc ccgcctggag    240

cctgaagatt tcgctgtcta ctattgtcag cagggctcaa gcatcccatt cacatttggc    300

caggggacta agctggagat caagcgcaca gtggcagccc ccagcgtctt catttttccc    360

ccttccgatg aacagctgaa gtccggcact gcttctgtgg tctgtctgct gaacaatttc    420

tatcccagag aggccaaggt gcagtggaaa gtggacaacg ctctgcagtc cggcaacagc    480

caggagagtg tgaccgaaca ggatagtaag gacagcacat attctctgtc tagtaccctg    540

acactgagta aggcagatta cgagaagcac aaagtgtatg cctgcgaagt cactcatcag    600

ggactgtcaa gccccgtgac caagagcttc aaccggggcg agtgtggcgg aggtggttct    660

gggggaagcc ccggaatcgt agagcagtgt tgtaccagta tttgcagcct ctatcagctc    720

gagaactatt gtaatggcgg agggtccggc ggtgggagcg gcttcgtgaa tcaacacctg    780

tgcgggtccc acctggtgga agcgttgtat cttgtctgcg ggaaaggggg tttcttctac    840
```

acacgaaga cc 852

<210> SEQ ID NO 70
<211> LENGTH: 933
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70
tttgtgaacc aacacctgtg cggctcacac ctggtggaag ctctctacct agtgtgcggg 60
gaacgaggct tcttctacac acccaagacc ggaggcgggg gatctggcgg gggaggcagt 120
cggaaaaagc gtggcattgt ggaacaatgc tgtaccagca tctgctccct ctaccagctg 180
gagaactact gcaacggtgg cggaggcagc gggggtggcg aagcagctgc taaggaggca 240
gccgcaaagg aagcagctgc aaaggcaggt ggcggaggca gcggaggcga gatcgtgctg 300
actcagagcc caggaaccct gtccctgtct ccaggagaac gagccaccct gtcctgctcc 360
gcctcatcaa caatttctag taactacctg cactggtatc agcagaagcc aggacaggca 420
cctcgactgc tgatctacag aactagtgac ctggcctctg gcattcccga taggttcagc 480
ggctccgggt ctggaacaga ctttaccctg acaatctccc gcctggagcc tgaagatttc 540
gctgtctact attgtcagca gggctcaagc atcccattca catttggcca ggggactaag 600
ctggagatca agcgcacagt ggcagccccc agcgtcttca tttttccccc ttccgatgaa 660
cagctgaagt ccggcactgc ttctgtggtc tgtctgctga acaatttcta tcccagagag 720
gccaaggtgc agtggaaagt ggacaacgct ctgcagtccg gcaacagcca ggagagtgtg 780
accgaacagg atagtaagga cagcacatat tctctgtcta gtaccctgac actgagtaag 840
gcagattacg agaagcacaa agtgtatgcc tgcgaagtca ctcatcaggg actgtcaagc 900
cccgtgacca agagcttcaa ccggggcgag tgt 933

<210> SEQ ID NO 71
<211> LENGTH: 945
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
tttgtgaacc aacacctgtg cggctcacac ctggtggaag ctctctacct agtgtgcggg 60
gaacgaggct tcttctacac acccaagacc cggaaaaagc gtggcggggg aggcagcggg 120
ggaggcgggt cccggaaaaa gcgtggcatt gtggaacaat gctgtaccag catctgctcc 180
ctctaccagc tggagaacta ctgcaacggt ggcggaggca gcgggggtgg cgaagcagct 240
gctaaggagg cagccgcaaa ggaagcagct gcaaaggcag gtggcggagg cagcggaggc 300
gagatcgtgc tgactcagag cccaggaacc ctgtccctgt ctccaggaga acgagccacc 360
ctgtcctgct ccgcctcatc aacaatttct agtaactacc tgcactggta tcagcagaag 420
ccaggacagg cacctcgact gctgatctac agaactagtg acctggcctc tggcattccc 480
gataggttca gcggctccgg gtctggaaca gactttaccc tgacaatctc ccgcctggag 540
cctgaagatt tcgctgtcta ctattgtcag cagggctcaa gcatcccatt cacatttggc 600
caggggacta agctggagat caagcgcaca gtggcagccc ccagcgtctt catttttccc 660
ccttccgatg aacagctgaa gtccggcact gcttctgtgg tctgtctgct gaacaatttc 720

```
tatcccagag aggccaaggt gcagtggaaa gtggacaacg ctctgcagtc cggcaacagc    780

caggagagtg tgaccgaaca ggatagtaag gacagcacat attctctgtc tagtaccctg    840

acactgagta aggcagatta cgagaagcac aaagtgtatg cctgcgaagt cactcatcag    900

ggactgtcaa gccccgtgac caagagcttc aaccggggcg agtgt                    945
```

<210> SEQ ID NO 72
<211> LENGTH: 1533
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
tttgtgaacc aacacctgtg cggctcagac ctggtggaag ctctctacct agtgtgcggg     60

gaacgaggct tcttctacac agaccccacc ggcggagggc cccgccgggg cattgtggaa    120

caatgctgtc acagcatctg ctccctctac cagctggaga actactgcaa cggtggcgga    180

ggcagcgagg tgcagctggt ggagtctgga ggaggcttgg tccagcctgg ggggtccctg    240

agactctcct gtgcagcctc tggtttcaat attaaggaca cttacatcca ctgggtccgc    300

caggctccag ggaaggggct ggagtgggtc gcacgtattt atcctaccaa tggttacaca    360

cgctacgcag actccgtgaa gggccgattc accatctccg cagacacttc caagaacacg    420

gcgtatcttc aaatgaacag cctgagagcc gaggacacgg ccgtgtatta ctgttcgaga    480

tggggcggtg acggcttcta tgccatggac tactggggcc aaggaaccct ggtcaccgtc    540

tcctcagcct ccaccaaggg cccatcggtc ttccccctgg caccctcctc caagagcacc    600

tctgggggca cagcggccct gggctgcctg gtcaaggact acttccccga accggtgacg    660

gtgtcgtgga actcaggcgc cctgaccagc ggcgtgcaca ccttcccggc tgtcctacag    720

tcctcaggac tctactccct cagcagcgtg gtgactgtgc cctctagcag cttgggcacc    780

cagacctaca tctgcaacgt gaatcacaag cccagcaaca ccaaggtgga caagaaagtt    840

gaacccaaat cttgcgacaa aactcacaca tgcccaccgt gcccagcacc tccagtcgcc    900

ggaccgtcag tcttcctctt ccctccaaaa cccaaggaca ccctcatgat ctcccggacc    960

cctgaggtca catgcgtggt ggtggacgtg agccacgaag accctgaggt caagttcaac   1020

tggtacgtgg acggcgtgga ggtgcataat gccaagacaa agccgcggga ggagcagtac   1080

aacagcacgt accgtgtggt cagcgtcctc accgtcctgc accaggactg gctgaatggc   1140

aaggagtaca agtgcaaggt ctccaacaaa ggcctcccaa gctccatcga gaaaaccatc   1200

tccaaagcca aagggcagcc ccgagaacca caggtgtaca ccctgcctcc atcccgggat   1260

gagctgacca agaaccaggt cagcctgacc tgcctggtca aaggcttcta tcccagcgac   1320

atcgccgtgg agtgggagag caatgggcag ccggagaaca actacaagac cacgcctccc   1380

gtgctggact ccgacggctc cttcttcctc tacagcaagc tcaccgtgga caagagcagg   1440

tggcagcagg ggaacgtctt ctcatgctcc gtgatgcatg aggctctgca caaccactac   1500

acgcagaaga gcctctccct gtctccgggt aaa                                1533
```

<210> SEQ ID NO 73
<211> LENGTH: 828
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
tttgtgaacc aacacctgtg cggctcagac ctggtggaag ctctctacct agtgtgcggg     60
gaacgaggct tcttctacac agaccccacc ggcggagggc cccgccgggg cattgtggaa    120
caatgctgtc acagcatctg ctccctctac cagctggaga actactgcaa cggtggcgga    180
ggcagcgaca tccagatgac ccagtctcca tcctccctgt ctgcatctgt aggagacaga    240
gtcaccatca cttgccgggc aagtcaggat gtgaataccg cggtcgcatg gtatcagcag    300
aaaccaggga aagcccctaa gctcctgatc tattctgcat ccttcttgta tagtggggtc    360
ccatcaaggt tcagtggcag tagatctggg acagatttca ctctcaccat cagcagtctg    420
caacctgaag attttgcaac ttactactgt caacagcatt acactacccc tccgacgttc    480
ggccaaggta ccaaggttga gatcaaacga actgtggctg caccatctgt cttcatcttc    540
ccgccatctg atgagcagtt gaaatctgga actgcctctg tcgtgtgcct gctgaataac    600
ttctatccca gagaggccaa agtacagtgg aaggtggata acgccctcca atcgggtaac    660
tcccaggaga gtgtcacaga gcaggacagc aaggacagca cctacagcct cagcagcacc    720
ctgacgctga gcaaagcaga ctacgagaaa cacaaagtct acgcctgcga agtcacccat    780
cagggcctgt cctcgcccgt cacaaagagc ttcaacaggg gagagtgt                 828
```

<210> SEQ ID NO 74
<211> LENGTH: 933
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74

```
tttgtgaacc aacacctgtg cggctcacac ctggtggaag ctctctacct agtgtgcggg     60
gaacgaggct tcttctacac acccaagacc ggcgggggag gcagcggggg aggcgggtcc    120
cggaaaaagc gtggcattgt ggaacaatgc tgtaccagca tctgctccct ctaccagctg    180
gagaactact gcaacggtgg cggaggcagc gggggtggcg aagcagctgc taaggaggca    240
gccgcaaagg aagcagctgc aaaggcaggt ggcggaggca gcggaggcga gatcgtgctg    300
actcagagcc caggaaccct gtccctgtct ccaggagaac gagccaccct gtcctgctcc    360
gcctcatcaa caatttctag taactacctg cactggtatc agcagaagcc aggacaggca    420
cctcgactgc tgatctacag aactagtgac ctggcctctg gcattcccga taggttcagc    480
ggctccgggt ctggaacaga ctttaccctg acaatctccc gcctggagcc tgaagatttc    540
gctgtctact attgtcagca gggctcaagc atcccattca catttggcca ggggactaag    600
ctggagatca agcgcacagt ggcagccccc agcgtcttca tttttccccc ttccgatgaa    660
cagctgaagt ccggcactgc ttctgtggtc tgtctgctga acaatttcta tcccagagag    720
gccaaggtgc agtggaaagt ggacaacgct ctgcagtccg gcaacagcca ggagagtgtg    780
accgaacagg atagtaagga cagcacatat tctctgtcta gtaccctgac actgagtaag    840
gcagattacg agaagcacaa agtgtatgcc tgcgaagtca ctcatcaggg actgtcaagc    900
cccgtgacca agagcttcaa ccggggcgag tgt                                 933
```

<210> SEQ ID NO 75
<211> LENGTH: 879
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 75

```
tttgtgaacc aacacctgtg cggctcagac ctggtggaag ctctctacct agtgtgcggg     60

gaacgaggct tcttctacac agaccccacc ggcggagggc cccgccgggg cattgtggaa    120

caatgctgtc acagcatctg ctccctctac cagctggaga actactgcaa cgggggtggc    180

gaagcagctg ctaaggaggc agccgcaaag gaagcagctg caaaggcagg aggcgagatc    240

gtgctgactc agagcccagg aaccctgtcc ctgtctccag gagaacgagc caccctgtcc    300

tgctccgcct catcaacaat ttctagtaac tacctgcact ggtatcagca gaagccagga    360

caggcacctc gactgctgat ctacagaact agtgacctgg cctctggcat tcccgatagg    420

ttcagcggct ccgggtctgg aacagacttt accctgacaa tctcccgcct ggagcctgaa    480

gatttcgctg tctactattg tcagcagggc tcaagcatcc cattcacatt tggccagggg    540

actaagctgg agatcaagcg cacagtggca gcccccagcg tcttcatttt tccccccttcc    600

gatgaacagc tgaagtccgg cactgcttct gtggtctgtc tgctgaacaa tttctatccc    660

agagaggcca aggtgcagtg gaaagtggac aacgctctgc agtccggcaa cagccaggag    720

agtgtgaccg aacaggatag taaggacagc acatattctc tgtctagtac cctgacactg    780

agtaaggcag attacgagaa gcacaaagtg tatgcctgcg aagtcactca tcagggactg    840

tcaagccccg tgaccaagag cttcaaccgg ggcgagtgt                          879
```

<210> SEQ ID NO 76
<211> LENGTH: 879
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

```
tttgtgaacc aacacctgtg cggctcacac ctggtggaag ctctctacct agtgtgcggg     60

gaacgaggct tcttctacac acccaagacc ggcggagggc cccgccgggg cattgtggaa    120

caatgctgta ccagcatctg ctccctctac cagctggaga actactgcaa cgggggtggc    180

gaagcagctg ctaaggaggc agccgcaaag gaagcagctg caaaggcagg aggcgagatc    240

gtgctgactc agagcccagg aaccctgtcc ctgtctccag gagaacgagc caccctgtcc    300

tgctccgcct catcaacaat ttctagtaac tacctgcact ggtatcagca gaagccagga    360

caggcacctc gactgctgat ctacagaact agtgacctgg cctctggcat tcccgatagg    420

ttcagcggct ccgggtctgg aacagacttt accctgacaa tctcccgcct ggagcctgaa    480

gatttcgctg tctactattg tcagcagggc tcaagcatcc cattcacatt tggccagggg    540

actaagctgg agatcaagcg cacagtggca gcccccagcg tcttcatttt tccccccttcc    600

gatgaacagc tgaagtccgg cactgcttct gtggtctgtc tgctgaacaa tttctatccc    660

agagaggcca aggtgcagtg gaaagtggac aacgctctgc agtccggcaa cagccaggag    720

agtgtgaccg aacaggatag taaggacagc acatattctc tgtctagtac cctgacactg    780

agtaaggcag attacgagaa gcacaaagtg tatgcctgcg aagtcactca tcagggactg    840

tcaagccccg tgaccaagag cttcaaccgg ggcgagtgt                          879
```

<210> SEQ ID NO 77
<211> LENGTH: 879
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 77

```
tttgtgaacc aacacctgtg cggctcacac ctggtggaag ctctctacct agtgtgcggg     60

gaacgaggct tcttctacac acccaagacc ggcggagggc cccgccgggg cattgtggaa    120

caatgctgta ccagcatctg ctccctctac cagctggaga actactgcaa cgggggtggc    180

gaagcagctg ctaaggaggc agccgcaaag gaagcagctg caaaggcagg aggcgagatc    240

gtgctgactc agagcccagg aaccctgtcc ctgtctccag gagaacgagc caccctgtcc    300

tgctccgcct catcaacaat ttctagtaac tacctgcact ggtatcagca gaagccagga    360

caggcacctc gactgctgat ctacagaact agtgacctgg cctctggcat tcccgatagg    420

ttcagcggct ccgggtctgg aacagacttt accctgacaa tctcccgcct ggagcctgaa    480

gatttcgctg tctactattg tcagcagggc tcaagcatcc cattcacatt tggccagggg    540

actaagctgg agatcaagcg cacagtggca gcccccagcg tcttcatttt tccccccttcc   600

gatgaacagc tgaagtccgg cactgcttct gtggtctgtc tgctgaacaa tttctatccc    660

agagaggcca aggtgcagtg gaaagtggac aacgctctgc agtccggcaa cagccaggag    720

agtgtgaccg aacaggatag taaggacagc acatattctc tgtctagtac cctgacactg    780

agtaaggcag attacgagaa gcacaaagtg tatgcctgcg aagtcactca tcagggactg    840

tcaagccccg tgaccaagag cttcaaccgg ggcgagtgt                           879
```

<210> SEQ ID NO 78
<211> LENGTH: 512
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 78

```
Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ser Gln Val
    50                  55                  60

Gln Leu Gln Gln Pro Gly Ala Glu Leu Val Lys Pro Gly Ala Ser Val
65                  70                  75                  80

Lys Leu Ser Cys Lys Ala Ser Gly Tyr Thr Phe Thr Asn Tyr Trp Met
                85                  90                  95

His Trp Val Lys Gln Arg Pro Gly Arg Gly Leu Glu Trp Ile Gly Arg
            100                 105                 110

Ile Asp Leu Asn Ser Gly Gly Thr Asn Tyr Asn Tyr Asn Glu Lys Phe
        115                 120                 125

Lys Thr Lys Ala Thr Leu Thr Val Asp Lys Pro Ser Ser Thr Ala Tyr
    130                 135                 140

Met Gln Leu Ser Ser Leu Thr Ser Glu Asp Ser Ala Val Tyr Tyr Cys
```

```
145                 150                 155                 160

Ala Asn Tyr Tyr Gly Ser Ser Trp Phe Ala Tyr Trp Gly Gln Gly Thr
                165                 170                 175

Thr Leu Thr Val Ser Ser Ala Lys Thr Thr Ala Pro Ser Val Tyr Pro
            180                 185                 190

Leu Ala Pro Val Cys Gly Asp Thr Thr Gly Ser Ser Val Thr Leu Gly
        195                 200                 205

Cys Leu Val Lys Gly Tyr Phe Pro Glu Pro Val Thr Leu Thr Trp Asn
    210                 215                 220

Ser Gly Ser Leu Ser Ser Gly Val His Thr Phe Pro Ala Val Leu Gln
225                 230                 235                 240

Ser Asp Leu Tyr Thr Leu Ser Ser Ser Val Thr Val Thr Ser Ser Thr
                245                 250                 255

Trp Pro Ser Gln Ser Ile Thr Cys Asn Val Ala His Pro Ala Ser Ser
            260                 265                 270

Thr Lys Val Asp Lys Lys Ile Glu Pro Arg Gly Pro Thr Ile Lys Pro
        275                 280                 285

Cys Pro Pro Cys Lys Cys Pro Ala Pro Asn Leu Leu Gly Gly Pro Ser
    290                 295                 300

Val Phe Ile Phe Pro Pro Lys Ile Lys Asp Val Leu Met Ile Ser Leu
305                 310                 315                 320

Ser Pro Ile Val Thr Cys Val Val Val Asp Val Ser Glu Asp Asp Pro
                325                 330                 335

Asp Val Gln Ile Ser Trp Phe Val Asn Asn Val Glu Val His Thr Ala
            340                 345                 350

Gln Thr Gln Thr His Arg Glu Asp Tyr Asn Ser Thr Leu Arg Val Val
        355                 360                 365

Ser Ala Leu Pro Ile Gln His Gln Asp Trp Met Ser Gly Lys Glu Phe
    370                 375                 380

Lys Cys Lys Val Asn Asn Lys Asp Leu Pro Ala Pro Ile Glu Arg Thr
385                 390                 395                 400

Ile Ser Lys Pro Lys Gly Ser Val Arg Ala Pro Gln Val Tyr Val Leu
                405                 410                 415

Pro Pro Pro Glu Glu Glu Met Thr Lys Lys Gln Val Thr Leu Thr Cys
            420                 425                 430

Met Val Thr Asp Phe Met Pro Glu Asp Ile Tyr Val Glu Trp Thr Asn
        435                 440                 445

Asn Gly Lys Thr Glu Leu Asn Tyr Lys Asn Thr Glu Pro Val Leu Asp
    450                 455                 460

Ser Asp Gly Ser Tyr Phe Met Tyr Ser Lys Leu Arg Val Glu Lys Lys
465                 470                 475                 480

Asn Trp Val Glu Arg Asn Ser Tyr Ser Cys Ser Val Val His Glu Gly
                485                 490                 495

Leu His Asn His His Thr Thr Lys Ser Phe Ser Arg Thr Pro Gly Lys
            500                 505                 510
```

<210> SEQ ID NO 79
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

```
Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ser Glu Thr
    50                  55                  60

Val Leu Thr Gln Ser Pro Thr Thr Met Ala Thr Ser Pro Gly Glu Lys
65                  70                  75                  80

Ile Thr Ile Thr Cys Ser Ala Ser Ser Thr Ile Ser Ser Asn Tyr Leu
                85                  90                  95

His Trp Tyr Gln Gln Lys Pro Gly Phe Ser Pro Lys Leu Leu Ile Tyr
            100                 105                 110

Arg Thr Ser Asp Leu Ala Ser Gly Val Pro Thr Arg Phe Ser Gly Ser
        115                 120                 125

Gly Ser Gly Thr Ser Tyr Ser Leu Thr Ile Gly Thr Met Glu Ala Glu
    130                 135                 140

Asp Val Ala Thr Tyr Tyr Cys Gln Gln Gly Ser Ser Ile Pro Phe Thr
145                 150                 155                 160

Phe Gly Ser Gly Thr Lys Leu Glu Ile Asn Arg Ala Asp Thr Ala Pro
                165                 170                 175

Thr Val Ser Ile Phe Pro Pro Ser Ser Glu Gln Leu Thr Ser Gly Gly
            180                 185                 190

Ala Ser Val Val Cys Phe Leu Asn Asn Phe Tyr Pro Lys Asp Ile Asn
        195                 200                 205

Val Lys Trp Lys Ile Asp Gly Ser Glu Arg Gln Asn Gly Val Leu Asn
    210                 215                 220

Ser Trp Thr Asp Gln Asp Ser Lys Asp Ser Thr Tyr Ser Met Ser Ser
225                 230                 235                 240

Thr Leu Thr Leu Thr Lys Asp Glu Tyr Glu Arg His Asn Ser Tyr Thr
                245                 250                 255

Cys Glu Ala Thr His Lys Thr Ser Thr Ser Pro Ile Val Lys Ser Phe
            260                 265                 270

Asn Arg Asn Glu Cys
        275
```

<210> SEQ ID NO 80
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ser Asp Ile
    50                  55                  60

Gln Met Thr Gln Ser Pro Ser Thr Leu Ser Ala Ser Val Gly Asp Arg
65                  70                  75                  80
```

```
Val Thr Ile Thr Cys Lys Cys Gln Leu Ser Val Gly Tyr Met His Trp
                85                  90                  95

Tyr Gln Gln Lys Pro Gly Lys Ala Pro Lys Leu Leu Ile Tyr Asp Thr
            100                 105                 110

Ser Lys Leu Ala Ser Gly Val Pro Ser Arg Phe Ser Gly Ser Gly Ser
        115                 120                 125

Gly Thr Glu Phe Thr Leu Thr Ile Ser Ser Leu Gln Pro Asp Asp Phe
    130                 135                 140

Ala Thr Tyr Tyr Cys Phe Gln Gly Ser Gly Tyr Pro Phe Thr Phe Gly
145                 150                 155                 160

Gly Gly Thr Lys Leu Glu Ile Lys Arg Thr Val Ala Ala Pro Ser Val
                165                 170                 175

Phe Ile Phe Pro Pro Ser Asp Glu Gln Leu Lys Ser Gly Thr Ala Ser
            180                 185                 190

Val Val Cys Leu Leu Asn Asn Phe Tyr Pro Arg Glu Ala Lys Val Gln
        195                 200                 205

Trp Lys Val Asp Asn Ala Leu Gln Ser Gly Asn Ser Gln Glu Ser Val
    210                 215                 220

Thr Glu Gln Asp Ser Lys Asp Ser Thr Tyr Ser Leu Ser Ser Thr Leu
225                 230                 235                 240

Thr Leu Ser Lys Ala Asp Tyr Glu Lys His Lys Val Tyr Ala Cys Glu
                245                 250                 255

Val Thr His Gln Gly Leu Ser Ser Pro Val Thr Lys Ser Phe Asn Arg
            260                 265                 270

Gly Glu Cys
        275


<210> SEQ ID NO 81
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Gly Ser Gly Gly Gly Gly Ser Gly Gly Gly Gly Ser Gly Gly Gly
        35                  40                  45

Gly Ser
    50


<210> SEQ ID NO 82
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30
```

```
Gly Gly Ser Gly Gly Gly Gly Ser Gly Ile Val Glu Gln Cys Cys His
        35                  40                  45

Ser Ile Cys Ser Leu Tyr Gln Leu Glu Asn Tyr Cys Asn Gly Gly Pro
    50                  55                  60

Ser Ser Gly Ala Pro Pro Pro Ser Gly Gly Gly Gly Gly Glu Thr Val
65                  70                  75                  80

Leu Thr Gln Ser Pro Thr Thr Met Ala Thr Ser Pro Gly Glu Lys Ile
                85                  90                  95

Thr Ile Thr Cys Ser Ala Ser Ser Thr Ile Ser Ser Asn Tyr Leu His
            100                 105                 110

Trp Tyr Gln Gln Lys Pro Gly Phe Ser Pro Lys Leu Leu Ile Tyr Arg
        115                 120                 125

Thr Ser Asp Leu Ala Ser Gly Val Pro Thr Arg Phe Ser Gly Ser Gly
    130                 135                 140

Ser Gly Thr Ser Tyr Ser Leu Thr Ile Gly Thr Met Glu Ala Glu Asp
145                 150                 155                 160

Val Ala Thr Tyr Tyr Cys Gln Gln Gly Ser Ser Ile Pro Phe Thr Phe
                165                 170                 175

Gly Ser Gly Thr Lys Leu Glu Ile Lys Arg Thr Val Ala Ala Pro Ser
            180                 185                 190

Val Phe Ile Phe Pro Pro Ser Asp Glu Gln Leu Lys Ser Gly Thr Ala
        195                 200                 205

Ser Val Val Cys Leu Leu Asn Asn Phe Tyr Pro Arg Glu Ala Lys Val
    210                 215                 220

Gln Trp Lys Val Asp Asn Ala Leu Gln Ser Gly Asn Ser Gln Glu Ser
225                 230                 235                 240

Val Thr Glu Gln Asp Ser Lys Asp Ser Thr Tyr Ser Leu Ser Ser Thr
                245                 250                 255

Leu Thr Leu Ser Lys Ala Asp Tyr Glu Lys His Lys Val Tyr Ala Cys
            260                 265                 270

Glu Val Thr His Gln Gly Leu Ser Ser Pro Val Thr Lys Ser Phe Asn
        275                 280                 285

Arg Gly Glu Cys
    290


<210> SEQ ID NO 83
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Gly Ser Gly Gly Gly Gly Ser
        35                  40


<210> SEQ ID NO 84
<211> LENGTH: 293
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 84

```
Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Glu Ala Ala Ala
    50                  55                  60

Lys Glu Ala Ala Ala Lys Glu Ala Ala Ala Lys Ala Gly Gly Glu Ile
65                  70                  75                  80

Val Leu Thr Gln Ser Pro Gly Thr Leu Ser Leu Ser Pro Gly Glu Arg
                85                  90                  95

Ala Thr Leu Ser Cys Ser Ala Ser Ser Thr Ile Ser Ser Asn Tyr Leu
            100                 105                 110

His Trp Tyr Gln Gln Lys Pro Gly Gln Ala Pro Arg Leu Leu Ile Tyr
        115                 120                 125

Arg Thr Ser Asp Leu Ala Ser Gly Ile Pro Asp Arg Phe Ser Gly Ser
    130                 135                 140

Gly Ser Gly Thr Asp Phe Thr Leu Thr Ile Ser Arg Leu Glu Pro Glu
145                 150                 155                 160

Asp Phe Ala Val Tyr Tyr Cys Gln Gln Gly Ser Ser Ile Pro Phe Thr
                165                 170                 175

Phe Gly Gln Gly Thr Lys Leu Glu Ile Lys Arg Thr Val Ala Ala Pro
            180                 185                 190

Ser Val Phe Ile Phe Pro Pro Ser Asp Glu Gln Leu Lys Ser Gly Thr
        195                 200                 205

Ala Ser Val Val Cys Leu Leu Asn Asn Phe Tyr Pro Arg Glu Ala Lys
    210                 215                 220

Val Gln Trp Lys Val Asp Asn Ala Leu Gln Ser Gly Asn Ser Gln Glu
225                 230                 235                 240

Ser Val Thr Glu Gln Asp Ser Lys Asp Ser Thr Tyr Ser Leu Ser Ser
                245                 250                 255

Thr Leu Thr Leu Ser Lys Ala Asp Tyr Glu Lys His Lys Val Tyr Ala
            260                 265                 270

Cys Glu Val Thr His Gln Gly Leu Ser Ser Pro Val Thr Lys Ser Phe
        275                 280                 285

Asn Arg Gly Glu Cys
    290
```

<210> SEQ ID NO 85
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Gly
            20                  25                  30

Gly Gly Ser Gly Gly Gly Gly Ser
```

```
        35                  40


<210> SEQ ID NO 86
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Gly
            20                  25                  30

Gly Gly Ser Gly Gly Gly Gly Ser
        35                  40


<210> SEQ ID NO 87
<211> LENGTH: 298
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ser Gly Gly
    50                  55                  60

Gly Glu Ala Ala Ala Lys Glu Ala Ala Ala Lys Glu Ala Ala Ala Lys
65                  70                  75                  80

Ala Gly Gly Glu Ile Val Leu Thr Gln Ser Pro Gly Thr Leu Ser Leu
                85                  90                  95

Ser Pro Gly Glu Arg Ala Thr Leu Ser Cys Ser Ala Ser Ser Thr Ile
            100                 105                 110

Ser Ser Asn Tyr Leu His Trp Tyr Gln Gln Lys Pro Gly Gln Ala Pro
        115                 120                 125

Arg Leu Leu Ile Tyr Arg Thr Ser Asp Leu Ala Ser Gly Ile Pro Asp
    130                 135                 140

Arg Phe Ser Gly Ser Gly Ser Gly Thr Asp Phe Thr Leu Thr Ile Ser
145                 150                 155                 160

Arg Leu Glu Pro Glu Asp Phe Ala Val Tyr Tyr Cys Gln Gln Gly Ser
                165                 170                 175

Ser Ile Pro Phe Thr Phe Gly Gln Gly Thr Lys Leu Glu Ile Lys Arg
            180                 185                 190

Thr Val Ala Ala Pro Ser Val Phe Ile Phe Pro Pro Ser Asp Glu Gln
        195                 200                 205

Leu Lys Ser Gly Thr Ala Ser Val Val Cys Leu Leu Asn Asn Phe Tyr
    210                 215                 220

Pro Arg Glu Ala Lys Val Gln Trp Lys Val Asp Asn Ala Leu Gln Ser
225                 230                 235                 240

Gly Asn Ser Gln Glu Ser Val Thr Glu Gln Asp Ser Lys Asp Ser Thr
```

```
                245                 250                 255

Tyr Ser Leu Ser Ser Thr Leu Thr Leu Ser Lys Ala Asp Tyr Glu Lys
            260                 265                 270

His Lys Val Tyr Ala Cys Glu Val Thr His Gln Gly Leu Ser Ser Pro
        275                 280                 285

Val Thr Lys Ser Phe Asn Arg Gly Glu Cys
    290                 295


<210> SEQ ID NO 88
<211> LENGTH: 298
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Glu Ala Ala Ala
    50                  55                  60

Lys Glu Ala Ala Ala Lys Glu Ala Ala Ala Lys Ala Gly Gly Gly Gly
65                  70                  75                  80

Ser Gly Gly Glu Ile Val Leu Thr Gln Ser Pro Gly Thr Leu Ser Leu
                85                  90                  95

Ser Pro Gly Glu Arg Ala Thr Leu Ser Cys Ser Ala Ser Ser Thr Ile
            100                 105                 110

Ser Ser Asn Tyr Leu His Trp Tyr Gln Gln Lys Pro Gly Gln Ala Pro
        115                 120                 125

Arg Leu Leu Ile Tyr Arg Thr Ser Asp Leu Ala Ser Gly Ile Pro Asp
    130                 135                 140

Arg Phe Ser Gly Ser Gly Ser Gly Thr Asp Phe Thr Leu Thr Ile Ser
145                 150                 155                 160

Arg Leu Glu Pro Glu Asp Phe Ala Val Tyr Tyr Cys Gln Gln Gly Ser
                165                 170                 175

Ser Ile Pro Phe Thr Phe Gly Gln Gly Thr Lys Leu Glu Ile Lys Arg
            180                 185                 190

Thr Val Ala Ala Pro Ser Val Phe Ile Phe Pro Pro Ser Asp Glu Gln
        195                 200                 205

Leu Lys Ser Gly Thr Ala Ser Val Val Cys Leu Leu Asn Asn Phe Tyr
    210                 215                 220

Pro Arg Glu Ala Lys Val Gln Trp Lys Val Asp Asn Ala Leu Gln Ser
225                 230                 235                 240

Gly Asn Ser Gln Glu Ser Val Thr Glu Gln Asp Ser Lys Asp Ser Thr
                245                 250                 255

Tyr Ser Leu Ser Ser Thr Leu Thr Leu Ser Lys Ala Asp Tyr Glu Lys
            260                 265                 270

His Lys Val Tyr Ala Cys Glu Val Thr His Gln Gly Leu Ser Ser Pro
        275                 280                 285

Val Thr Lys Ser Phe Asn Arg Gly Glu Cys
    290                 295
```

<210> SEQ ID NO 89
<211> LENGTH: 303
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

```
Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ser Gly Gly
    50                  55                  60

Gly Glu Ala Ala Ala Lys Glu Ala Ala Ala Lys Glu Ala Ala Ala Lys
65                  70                  75                  80

Ala Gly Gly Gly Gly Ser Gly Gly Glu Ile Val Leu Thr Gln Ser Pro
                85                  90                  95

Gly Thr Leu Ser Leu Ser Pro Gly Glu Arg Ala Thr Leu Ser Cys Ser
            100                 105                 110

Ala Ser Ser Thr Ile Ser Ser Asn Tyr Leu His Trp Tyr Gln Gln Lys
        115                 120                 125

Pro Gly Gln Ala Pro Arg Leu Leu Ile Tyr Arg Thr Ser Asp Leu Ala
    130                 135                 140

Ser Gly Ile Pro Asp Arg Phe Ser Gly Ser Gly Ser Gly Thr Asp Phe
145                 150                 155                 160

Thr Leu Thr Ile Ser Arg Leu Glu Pro Glu Asp Phe Ala Val Tyr Tyr
                165                 170                 175

Cys Gln Gln Gly Ser Ser Ile Pro Phe Thr Phe Gly Gln Gly Thr Lys
            180                 185                 190

Leu Glu Ile Lys Arg Thr Val Ala Ala Pro Ser Val Phe Ile Phe Pro
        195                 200                 205

Pro Ser Asp Glu Gln Leu Lys Ser Gly Thr Ala Ser Val Val Cys Leu
    210                 215                 220

Leu Asn Asn Phe Tyr Pro Arg Glu Ala Lys Val Gln Trp Lys Val Asp
225                 230                 235                 240

Asn Ala Leu Gln Ser Gly Asn Ser Gln Glu Ser Val Thr Glu Gln Asp
                245                 250                 255

Ser Lys Asp Ser Thr Tyr Ser Leu Ser Ser Thr Leu Thr Leu Ser Lys
            260                 265                 270

Ala Asp Tyr Glu Lys His Lys Val Tyr Ala Cys Glu Val Thr His Gln
        275                 280                 285

Gly Leu Ser Ser Pro Val Thr Lys Ser Phe Asn Arg Gly Glu Cys
    290                 295                 300
```

<210> SEQ ID NO 90
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Thr Ile Ser Ser Asn
            20                  25                  30

Tyr Leu His Trp Tyr Gln Gln Lys Pro Gly Gln Ala Pro Arg Leu Leu
        35                  40                  45

Ile Tyr Arg Thr Ser Asp Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Ser Ile Pro
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Gly Ser Gly Gly Ser Pro
    210                 215                 220

Gly Ile Val Glu Gln Cys Cys Thr Ser Ile Cys Ser Leu Tyr Gln Leu
225                 230                 235                 240

Glu Asn Tyr Cys Asn Gly Gly Gly Ser Gly Gly Gly Ser Gly Phe Val
                245                 250                 255

Asn Gln His Leu Cys Gly Ser His Leu Val Glu Ala Leu Tyr Leu Val
            260                 265                 270

Cys Gly Glu Arg Gly Phe Phe Tyr Thr Pro Lys Thr
        275                 280
```

<210> SEQ ID NO 91
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Gly
            20                  25                  30

Gly Gly Ser Gly Gly Gly Gly Ser
        35                  40
```

<210> SEQ ID NO 92
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 93
<211> LENGTH: 511
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

```
Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ser Glu Val
    50                  55                  60

Gln Leu Val Glu Ser Gly Gly Gly Leu Val Gln Pro Gly Gly Ser Leu
65                  70                  75                  80

Arg Leu Ser Cys Ala Ala Ser Gly Phe Asn Ile Lys Asp Thr Tyr Ile
                85                  90                  95

His Trp Val Arg Gln Ala Pro Gly Lys Gly Leu Glu Trp Val Ala Arg
            100                 105                 110

Ile Tyr Pro Thr Asn Gly Tyr Thr Arg Tyr Ala Asp Ser Val Lys Gly
        115                 120                 125

Arg Phe Thr Ile Ser Ala Asp Thr Ser Lys Asn Thr Ala Tyr Leu Gln
    130                 135                 140

Met Asn Ser Leu Arg Ala Glu Asp Thr Ala Val Tyr Tyr Cys Ser Arg
145                 150                 155                 160

Trp Gly Gly Asp Gly Phe Tyr Ala Met Asp Tyr Trp Gly Gln Gly Thr
                165                 170                 175

Leu Val Thr Val Ser Ser Ala Ser Thr Lys Gly Pro Ser Val Phe Pro
            180                 185                 190

Leu Ala Pro Ser Ser Lys Ser Thr Ser Gly Gly Thr Ala Ala Leu Gly
        195                 200                 205

Cys Leu Val Lys Asp Tyr Phe Pro Glu Pro Val Thr Val Ser Trp Asn
    210                 215                 220

Ser Gly Ala Leu Thr Ser Gly Val His Thr Phe Pro Ala Val Leu Gln
225                 230                 235                 240

Ser Ser Gly Leu Tyr Ser Leu Ser Ser Val Val Thr Val Pro Ser Ser
                245                 250                 255

Ser Leu Gly Thr Gln Thr Tyr Ile Cys Asn Val Asn His Lys Pro Ser
            260                 265                 270

Asn Thr Lys Val Asp Lys Lys Val Glu Pro Lys Ser Cys Asp Lys Thr
        275                 280                 285

His Thr Cys Pro Pro Cys Pro Ala Pro Pro Val Ala Gly Pro Ser Val
    290                 295                 300
```

```
Phe Leu Phe Pro Pro Lys Pro Lys Asp Thr Leu Met Ile Ser Arg Thr
305                 310                 315                 320

Pro Glu Val Thr Cys Val Val Val Asp Val Ser His Glu Asp Pro Glu
                325                 330                 335

Val Lys Phe Asn Trp Tyr Val Asp Gly Val Glu Val His Asn Ala Lys
            340                 345                 350

Thr Lys Pro Arg Glu Glu Gln Tyr Asn Ser Thr Tyr Arg Val Val Ser
        355                 360                 365

Val Leu Thr Val Leu His Gln Asp Trp Leu Asn Gly Lys Glu Tyr Lys
    370                 375                 380

Cys Lys Val Ser Asn Lys Gly Leu Pro Ser Ser Ile Glu Lys Thr Ile
385                 390                 395                 400

Ser Lys Ala Lys Gly Gln Pro Arg Glu Pro Gln Val Tyr Thr Leu Pro
                405                 410                 415

Pro Ser Arg Asp Glu Leu Thr Lys Asn Gln Val Ser Leu Thr Cys Leu
            420                 425                 430

Val Lys Gly Phe Tyr Pro Ser Asp Ile Ala Val Glu Trp Glu Ser Asn
        435                 440                 445

Gly Gln Pro Glu Asn Asn Tyr Lys Thr Thr Pro Pro Val Leu Asp Ser
    450                 455                 460

Asp Gly Ser Phe Phe Leu Tyr Ser Lys Leu Thr Val Asp Lys Ser Arg
465                 470                 475                 480

Trp Gln Gln Gly Asn Val Phe Ser Cys Ser Val Met His Glu Ala Leu
                485                 490                 495

His Asn His Tyr Thr Gln Lys Ser Leu Ser Leu Ser Pro Gly Lys
            500                 505                 510
```

<210> SEQ ID NO 94
<211> LENGTH: 276
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Gly Ser Asp Ile
    50                  55                  60

Gln Met Thr Gln Ser Pro Ser Ser Leu Ser Ala Ser Val Gly Asp Arg
65                  70                  75                  80

Val Thr Ile Thr Cys Arg Ala Ser Gln Asp Val Asn Thr Ala Val Ala
                85                  90                  95

Trp Tyr Gln Gln Lys Pro Gly Lys Ala Pro Lys Leu Leu Ile Tyr Ser
            100                 105                 110

Ala Ser Phe Leu Tyr Ser Gly Val Pro Ser Arg Phe Ser Gly Ser Arg
        115                 120                 125

Ser Gly Thr Asp Phe Thr Leu Thr Ile Ser Ser Leu Gln Pro Glu Asp
    130                 135                 140

Phe Ala Thr Tyr Tyr Cys Gln Gln His Tyr Thr Thr Pro Pro Thr Phe
```

```
145                 150                 155                 160

Gly Gln Gly Thr Lys Val Glu Ile Lys Arg Thr Val Ala Ala Pro Ser
                165                 170                 175

Val Phe Ile Phe Pro Pro Ser Asp Glu Gln Leu Lys Ser Gly Thr Ala
            180                 185                 190

Ser Val Val Cys Leu Leu Asn Asn Phe Tyr Pro Arg Glu Ala Lys Val
        195                 200                 205

Gln Trp Lys Val Asp Asn Ala Leu Gln Ser Gly Asn Ser Gln Glu Ser
    210                 215                 220

Val Thr Glu Gln Asp Ser Lys Asp Ser Thr Tyr Ser Leu Ser Ser Thr
225                 230                 235                 240

Leu Thr Leu Ser Lys Ala Asp Tyr Glu Lys His Lys Val Tyr Ala Cys
                245                 250                 255

Glu Val Thr His Gln Gly Leu Ser Ser Pro Val Thr Lys Ser Phe Asn
            260                 265                 270

Arg Gly Glu Cys
        275


<210> SEQ ID NO 95
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Arg Ile Asp Leu Asn Ser Gly Gly Thr Asn Tyr Asn Tyr Ala Gln
    50                  55                  60

Lys Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Arg Tyr Tyr Gly Ser Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

```
Lys Thr His Thr
225


<210> SEQ ID NO 96
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn Gly Gly Gly Glu Ala Ala Ala
    50                  55                  60

Lys Glu Ala Ala Ala Lys Glu Ala Ala Ala Lys Ala Gly Gly Glu Ile
65                  70                  75                  80

Val Leu Thr Gln Ser Pro Gly Thr Leu Ser Leu Ser Pro Gly Glu Arg
                85                  90                  95

Ala Thr Leu Ser Cys Ser Ala Ser Ser Thr Ile Ser Ser Asn Tyr Leu
            100                 105                 110

His Trp Tyr Gln Gln Lys Pro Gly Gln Ala Pro Arg Leu Leu Ile Tyr
        115                 120                 125

Arg Thr Ser Asp Leu Ala Ser Gly Ile Pro Asp Arg Phe Ser Gly Ser
    130                 135                 140

Gly Ser Gly Thr Asp Phe Thr Leu Thr Ile Ser Arg Leu Glu Pro Glu
145                 150                 155                 160

Asp Phe Ala Val Tyr Tyr Cys Gln Gln Gly Ser Ser Ile Pro Phe Thr
                165                 170                 175

Phe Gly Gln Gly Thr Lys Leu Glu Ile Lys Arg Thr Val Ala Ala Pro
            180                 185                 190

Ser Val Phe Ile Phe Pro Pro Ser Asp Glu Gln Leu Lys Ser Gly Thr
        195                 200                 205

Ala Ser Val Val Cys Leu Leu Asn Asn Phe Tyr Pro Arg Glu Ala Lys
    210                 215                 220

Val Gln Trp Lys Val Asp Asn Ala Leu Gln Ser Gly Asn Ser Gln Glu
225                 230                 235                 240

Ser Val Thr Glu Gln Asp Ser Lys Asp Ser Thr Tyr Ser Leu Ser Ser
                245                 250                 255

Thr Leu Thr Leu Ser Lys Ala Asp Tyr Glu Lys His Lys Val Tyr Ala
            260                 265                 270

Cys Glu Val Thr His Gln Gly Leu Ser Ser Pro Val Thr Lys Ser Phe
        275                 280                 285

Asn Arg Gly Glu Cys
    290


<210> SEQ ID NO 97
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 97

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Asn Gly Gly Gly Glu Ala Ala Ala
    50                  55                  60

Lys Glu Ala Ala Ala Lys Glu Ala Ala Ala Lys Ala Gly Gly Glu Ile
65                  70                  75                  80

Val Leu Thr Gln Ser Pro Gly Thr Leu Ser Leu Ser Pro Gly Glu Arg
                85                  90                  95

Ala Thr Leu Ser Cys Ser Ala Ser Ser Thr Ile Ser Ser Asn Tyr Leu
            100                 105                 110

His Trp Tyr Gln Gln Lys Pro Gly Gln Ala Pro Arg Leu Leu Ile Tyr
        115                 120                 125

Arg Thr Ser Asp Leu Ala Ser Gly Ile Pro Asp Arg Phe Ser Gly Ser
    130                 135                 140

Gly Ser Gly Thr Asp Phe Thr Leu Thr Ile Ser Arg Leu Glu Pro Glu
145                 150                 155                 160

Asp Phe Ala Val Tyr Tyr Cys Gln Gln Gly Ser Ser Ile Pro Phe Thr
                165                 170                 175

Phe Gly Gln Gly Thr Lys Leu Glu Ile Lys Arg Thr Val Ala Ala Pro
            180                 185                 190

Ser Val Phe Ile Phe Pro Pro Ser Asp Glu Gln Leu Lys Ser Gly Thr
        195                 200                 205

Ala Ser Val Val Cys Leu Leu Asn Asn Phe Tyr Pro Arg Glu Ala Lys
    210                 215                 220

Val Gln Trp Lys Val Asp Asn Ala Leu Gln Ser Gly Asn Ser Gln Glu
225                 230                 235                 240

Ser Val Thr Glu Gln Asp Ser Lys Asp Ser Thr Tyr Ser Leu Ser Ser
                245                 250                 255

Thr Leu Thr Leu Ser Lys Ala Asp Tyr Glu Lys His Lys Val Tyr Ala
            260                 265                 270

Cys Glu Val Thr His Gln Gly Leu Ser Ser Pro Val Thr Lys Ser Phe
        275                 280                 285

Asn Arg Gly Glu Cys
    290
```

<210> SEQ ID NO 98
<211> LENGTH: 293
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Gly
            20                  25                  30

Gly Pro Arg Arg Gly Ile Val Glu Gln Cys Cys Thr Ser Ile Cys Ser
        35                  40                  45
```

```
Leu Tyr Gln Leu Glu Asn Tyr Cys Asn Gly Gly Gly Glu Ala Ala Ala
    50                  55                  60

Lys Glu Ala Ala Ala Lys Glu Ala Ala Ala Lys Ala Gly Gly Glu Ile
65                  70                  75                  80

Val Leu Thr Gln Ser Pro Gly Thr Leu Ser Leu Ser Pro Gly Glu Arg
                85                  90                  95

Ala Thr Leu Ser Cys Ser Ala Ser Ser Thr Ile Ser Ser Asn Tyr Leu
            100                 105                 110

His Trp Tyr Gln Gln Lys Pro Gly Gln Ala Pro Arg Leu Leu Ile Tyr
        115                 120                 125

Arg Thr Ser Asp Leu Ala Ser Gly Ile Pro Asp Arg Phe Ser Gly Ser
    130                 135                 140

Gly Ser Gly Thr Asp Phe Thr Leu Thr Ile Ser Arg Leu Glu Pro Glu
145                 150                 155                 160

Asp Phe Ala Val Tyr Tyr Cys Gln Gln Gly Ser Ser Ile Pro Phe Thr
                165                 170                 175

Phe Gly Gln Gly Thr Lys Leu Glu Ile Lys Arg Thr Val Ala Ala Pro
            180                 185                 190

Ser Val Phe Ile Phe Pro Pro Ser Asp Glu Gln Leu Lys Ser Gly Thr
        195                 200                 205

Ala Ser Val Val Cys Leu Leu Asn Asn Phe Tyr Pro Arg Glu Ala Lys
    210                 215                 220

Val Gln Trp Lys Val Asp Asn Ala Leu Gln Ser Gly Asn Ser Gln Glu
225                 230                 235                 240

Ser Val Thr Glu Gln Asp Ser Lys Asp Ser Thr Tyr Ser Leu Ser Ser
                245                 250                 255

Thr Leu Thr Leu Ser Lys Ala Asp Tyr Glu Lys His Lys Val Tyr Ala
            260                 265                 270

Cys Glu Val Thr His Gln Gly Leu Ser Ser Pro Val Thr Lys Ser Phe
        275                 280                 285

Asn Arg Gly Glu Cys
    290
```

<210> SEQ ID NO 99
<211> LENGTH: 171
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99

```
tttgtgaacc aacacctgtg cggctcagac ctggtggaag ctctctacct agtgtgcggg     60

gaacgaggct tcttctacac agaccccacc ggcggagggc cccgccgggg cattgtggaa    120

caatgctgtc acagcatctg ctccctctac cagctggaga actactgcaa c             171
```

<210> SEQ ID NO 100
<211> LENGTH: 225
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100

```
tttgtgaacc aacacctgtg cggctcagac ctggtggaag ctctctacct agtgtgcggg     60
```

```
gaacgaggct tcttctacac agaccccacc ggcgggggag gcagcggggg aggcgggtcc    120

ggaggcgggg gatctggcgg gggaggcagt cggaaaaagc gtggcattgt ggaacaatgc    180

tgtcacagca tctgctccct ctaccagctg gagaactact gcaac                    225
```

<210> SEQ ID NO 101
<211> LENGTH: 183
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

```
tttgtgaacc aacacctgtg cggctcagac ctggtggaag ctctctacct agtgtgcggg     60

gaacgaggct tcttctacac agaccccacc ggaggcgggg gatctggcgg gggaggcagt    120

ggcattgtgg aacaatgctg tcacagcatc tgctccctct accagctgga gaactactgc    180

aac                                                                  183
```

<210> SEQ ID NO 102
<211> LENGTH: 195
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102

```
tttgtgaacc aacacctgtg cggctcagac ctggtggaag ctctctacct agtgtgcggg     60

gaacgaggct tcttctacac agaccccacc ggaggcgggg gatctggcgg gggaggcagt    120

cggaaaaagc gtggcattgt ggaacaatgc tgtcacagca tctgctccct ctaccagctg    180

gagaactact gcaac                                                     195
```

<210> SEQ ID NO 103
<211> LENGTH: 195
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103

```
tttgtgaacc aacacctgtg cggctcacac ctggtggaag ctctctacct agtgtgcggg     60

gaacgaggct tcttctacac acccaagacc ggaggcgggg gatctggcgg gggaggcagt    120

cggaaaaagc gtggcattgt ggaacaatgc tgtaccagca tctgctccct ctaccagctg    180

gagaactact gcaac                                                     195
```

<210> SEQ ID NO 104
<211> LENGTH: 207
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 104

```
tttgtgaacc aacacctgtg cggctcacac ctggtggaag ctctctacct agtgtgcggg     60

gaacgaggct tcttctacac acccaagacc cggaaaaagc gtggcggggg aggcagcggg    120

ggaggcgggt cccggaaaaa gcgtggcatt gtggaacaat gctgtaccag catctgctcc    180
```

ctctaccagc tggagaacta ctgcaac 207

<210> SEQ ID NO 105
<211> LENGTH: 195
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105
tttgtgaacc aacacctgtg cggctcacac ctggtggaag ctctctacct agtgtgcggg 60
gaacgaggct tcttctacac acccaagacc ggcgggggag gcagcggggg aggcgggtcc 120
cggaaaaagc gtggcattgt ggaacaatgc tgtaccagca tctgctccct ctaccagctg 180
gagaactact gcaac 195

<210> SEQ ID NO 106
<211> LENGTH: 180
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106
ggaatcgtag agcagtgttg taccagtatt tgcagcctct atcagctcga gaactattgt 60
aatggcggag ggtccggcgg tgggagcggc ttcgtgaatc aacacctgtg cgggtcccac 120
ctggtggaag cgttgtatct tgtctgcggg gaaaggggtt tcttctacac accgaagacc 180

<210> SEQ ID NO 107
<211> LENGTH: 207
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107
tttgtgaacc aacacctgtg cggctcacac ctggtggaag ctctctacct agtgtgcggg 60
gaacgaggct tcttctacac acccaagacc cggaaaaagc gtggcggggg aggcagcggg 120
ggaggcgggt cccggaaaaa gcgtggcatt gtggaacaat gctgtaccag catctgctcc 180
ctctaccagc tggagaacta ctgcaac 207

<210> SEQ ID NO 108
<211> LENGTH: 171
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108
tttgtgaacc aacacctgtg cggctcacac ctggtggaag ctctctacct agtgtgcggg 60
gaacgaggct tcttctacac acccaagacc ggcggagggc cccgccgggg cattgtggaa 120
caatgctgta ccagcatctg ctccctctac cagctggaga actactgcaa c 171

<210> SEQ ID NO 109
<211> LENGTH: 57
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 109

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Pro Arg Arg Gly Ile Val Glu Gln Cys Cys His Ser Ile Cys Ser
        35                  40                  45

Leu Tyr Gln Leu Glu Asn Tyr Cys Asn
    50                  55


<210> SEQ ID NO 110
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Gly Ser Gly Gly Gly Gly Ser Gly Gly Gly Gly Ser Gly Gly Gly
        35                  40                  45

Gly Ser
    50


<210> SEQ ID NO 111
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Gly Gly
            20                  25                  30

Gly Gly Ser Gly Gly Gly Gly Ser Gly Ile Val Glu Gln Cys Cys His
        35                  40                  45

Ser Ile Cys Ser Leu Tyr Gln Leu Glu Asn Tyr Cys Asn
    50                  55                  60


<210> SEQ ID NO 112
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Phe Val Asn Gln His Leu Cys Gly Ser Asp Leu Val Glu Ala Leu Tyr
1               5                   10                  15
```

```
Leu Val Cys Gly Glu Arg Gly Phe Phe Tyr Thr Asp Pro Thr Gly Gly
            20                  25                  30

Gly Gly Ser Gly Gly Gly Gly Ser
        35                  40


<210> SEQ ID NO 113
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Gly
            20                  25                  30

Gly Gly Ser Gly Gly Gly Gly Ser
        35                  40


<210> SEQ ID NO 114
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Gly
            20                  25                  30

Gly Gly Ser Gly Gly Gly Gly Ser
        35                  40


<210> SEQ ID NO 115
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Gly
            20                  25                  30

Gly Gly Ser Gly Gly Gly Gly Ser
        35                  40


<210> SEQ ID NO 116
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gly Ile Val Glu Gln Cys Cys Thr Ser Ile Cys Ser Leu Tyr Gln Leu
1               5                   10                  15
```

```
Glu Asn Tyr Cys Asn Gly Gly Gly Ser Gly Gly Gly Ser Gly Phe Val
            20                  25                  30

Asn Gln His Leu Cys Gly Ser His Leu Val Glu Ala Leu Tyr Leu Val
        35                  40                  45

Cys Gly Glu Arg Gly Phe Phe Tyr Thr Pro Lys Thr
    50                  55                  60


<210> SEQ ID NO 117
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30


<210> SEQ ID NO 118
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Gly
            20                  25                  30

Gly Pro Arg Arg Gly Ile Val Glu Gln Cys Cys Thr Ser Ile Cys Ser
        35                  40                  45

Leu Tyr Gln Leu Glu Asn Tyr Cys Asn
    50                  55


<210> SEQ ID NO 119
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Asp or His
<220> FEATURE:
<221> NAME/KEY: MOD_RES
<222> LOCATION: (28)..(28)
<223> OTHER INFORMATION: Asp or Pro
<220> FEATURE:
<221> NAME/KEY: MOD_RES
<222> LOCATION: (29)..(29)
<223> OTHER INFORMATION: Pro or Lys
<220> FEATURE:
<221> NAME/KEY: MOD_RES
<222> LOCATION: (31)..(31)
<223> OTHER INFORMATION: Any naturally or non-naturally occurring amino
      acid
<220> FEATURE:
<221> NAME/KEY: MOD_RES
<222> LOCATION: (39)..(39)
<223> OTHER INFORMATION: His or Thr
```

```
<400> SEQUENCE: 119

Phe Val Asn Gln His Leu Cys Gly Ser Xaa Leu Val Glu Ala Leu Tyr
1               5                   10                  15

Leu Val Cys Gly Glu Arg Gly Phe Phe Tyr Thr Xaa Xaa Thr Xaa Gly
            20                  25                  30

Ile Val Glu Gln Cys Cys Xaa Ser Ile Cys Ser Leu Tyr Gln Leu Glu
        35                  40                  45

Asn Tyr Cys Asn
    50


<210> SEQ ID NO 120
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 120

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Xaa Gly
            20                  25                  30

Ile Val Glu Gln Cys Cys His Ser Ile Cys Ser Leu Tyr Gln Leu Glu
        35                  40                  45

Asn Tyr Cys Asn
    50


<210> SEQ ID NO 121
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 121

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Pro Thr Xaa Gly
            20                  25                  30

Ile Val Glu Gln Cys Cys Thr Ser Ile Cys Ser Leu Tyr Gln Leu Glu
        35                  40                  45

Asn Tyr Cys Asn
    50


<210> SEQ ID NO 122
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 122

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Lys Thr Xaa Gly
            20                  25                  30

Ile Val Glu Gln Cys Cys His Ser Ile Cys Ser Leu Tyr Gln Leu Glu
        35                  40                  45

Asn Tyr Cys Asn
    50


<210> SEQ ID NO 123
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 123

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Asp Lys Thr Xaa Gly
            20                  25                  30

Ile Val Glu Gln Cys Cys Thr Ser Ile Cys Ser Leu Tyr Gln Leu Glu
        35                  40                  45

Asn Tyr Cys Asn
    50


<210> SEQ ID NO 124
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 124

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Pro Pro Thr Xaa Gly
            20                  25                  30

Ile Val Glu Gln Cys Cys His Ser Ile Cys Ser Leu Tyr Gln Leu Glu
        35                  40                  45

Asn Tyr Cys Asn
    50


<210> SEQ ID NO 125
<211> LENGTH: 52
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 125

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Pro Pro Thr Xaa Gly
            20                  25                  30

Ile Val Glu Gln Cys Cys Thr Ser Ile Cys Ser Leu Tyr Gln Leu Glu
        35                  40                  45

Asn Tyr Cys Asn
    50


<210> SEQ ID NO 126
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 126

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Pro Lys Thr Xaa Gly
            20                  25                  30

Ile Val Glu Gln Cys Cys His Ser Ile Cys Ser Leu Tyr Gln Leu Glu
        35                  40                  45

Asn Tyr Cys Asn
    50


<210> SEQ ID NO 127
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 127

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Pro Lys Thr Xaa Gly
            20                  25                  30

Ile Val Glu Gln Cys Cys Thr Ser Ile Cys Ser Leu Tyr Gln Leu Glu
        35                  40                  45

Asn Tyr Cys Asn
```

50

<210> SEQ ID NO 128
<211> LENGTH: 52
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (31)..(31)
<223> OTHER INFORMATION: Any naturally or non-naturally occurring amino acid

<400> SEQUENCE: 128

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Xaa Gly
            20                  25                  30

Ile Val Glu Gln Cys Cys His Ser Ile Cys Ser Leu Tyr Gln Leu Glu
        35                  40                  45

Asn Tyr Cys Asn
    50
```

<210> SEQ ID NO 129
<211> LENGTH: 52
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (31)..(31)
<223> OTHER INFORMATION: Any naturally or non-naturally occurring amino acid

<400> SEQUENCE: 129

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Xaa Gly
            20                  25                  30

Ile Val Glu Gln Cys Cys Thr Ser Ile Cys Ser Leu Tyr Gln Leu Glu
        35                  40                  45

Asn Tyr Cys Asn
    50
```

<210> SEQ ID NO 130
<211> LENGTH: 52
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (31)..(31)
<223> OTHER INFORMATION: Any naturally or non-naturally occurring amino acid

<400> SEQUENCE: 130

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr Xaa Gly
            20                  25                  30
```

```
Ile Val Glu Gln Cys Cys His Ser Ile Cys Ser Leu Tyr Gln Leu Glu
        35                  40                  45

Asn Tyr Cys Asn
    50


<210> SEQ ID NO 131
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 131

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr Xaa Gly
            20                  25                  30

Ile Val Glu Gln Cys Cys Thr Ser Ile Cys Ser Leu Tyr Gln Leu Glu
        35                  40                  45

Asn Tyr Cys Asn
    50


<210> SEQ ID NO 132
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 132

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Pro Thr Xaa Gly
            20                  25                  30

Ile Val Glu Gln Cys Cys His Ser Ile Cys Ser Leu Tyr Gln Leu Glu
        35                  40                  45

Asn Tyr Cys Asn
    50


<210> SEQ ID NO 133
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 133
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Pro Thr Xaa Gly
            20                  25                  30

Ile Val Glu Gln Cys Cys Thr Ser Ile Cys Ser Leu Tyr Gln Leu Glu
        35                  40                  45

Asn Tyr Cys Asn
    50


<210> SEQ ID NO 134
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 134

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Xaa Gly
            20                  25                  30

Ile Val Glu Gln Cys Cys His Ser Ile Cys Ser Leu Tyr Gln Leu Glu
        35                  40                  45

Asn Tyr Cys Asn
    50


<210> SEQ ID NO 135
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Any naturally or non-naturally occurring amino
      acid

<400> SEQUENCE: 135

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Pro Thr Xaa Gly
            20                  25                  30

Ile Val Glu Gln Cys Cys Thr Ser Ile Cys Ser Leu Tyr Gln Leu Glu
        35                  40                  45

Asn Tyr Cys Asn
    50


<210> SEQ ID NO 136
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
```

<223> OTHER INFORMATION: Any naturally or non-naturally occurring amino acid
<220> FEATURE:
<221> NAME/KEY: MOD_RES
<222> LOCATION: (28)..(29)
<223> OTHER INFORMATION: Any naturally or non-naturally occurring amino acid
<220> FEATURE:
<221> NAME/KEY: MOD_RES
<222> LOCATION: (44)..(44)
<223> OTHER INFORMATION: Any naturally or non-naturally occurring amino acid

<400> SEQUENCE: 136

```
Phe Val Asn Gln His Leu Cys Gly Ser Xaa Leu Val Glu Ala Leu Tyr
1               5                   10                  15

Leu Val Cys Gly Glu Arg Gly Phe Phe Tyr Thr Xaa Xaa Thr Gly Gly
            20                  25                  30

Gly Pro Gly Gly Gly Ile Val Glu Gln Cys Cys Xaa Ser Ile Cys Ser
        35                  40                  45

Leu Tyr Gln Leu Glu Asn Tyr Cys Asn
    50                  55
```

<210> SEQ ID NO 137
<211> LENGTH: 57
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (10)..(10)
<223> OTHER INFORMATION: Any naturally or non-naturally occurring amino acid
<220> FEATURE:
<221> NAME/KEY: MOD_RES
<222> LOCATION: (28)..(29)
<223> OTHER INFORMATION: Any naturally or non-naturally occurring amino acid
<220> FEATURE:
<221> NAME/KEY: MOD_RES
<222> LOCATION: (44)..(44)
<223> OTHER INFORMATION: Any naturally or non-naturally occurring amino acid

<400> SEQUENCE: 137

```
Phe Val Asn Gln His Leu Cys Gly Ser Xaa Leu Val Glu Ala Leu Tyr
1               5                   10                  15

Leu Val Cys Gly Glu Arg Gly Phe Phe Tyr Thr Xaa Xaa Thr Gly Gly
            20                  25                  30

Gly Pro Lys Lys Gly Ile Val Glu Gln Cys Cys Xaa Ser Ile Cys Ser
        35                  40                  45

Leu Tyr Gln Leu Glu Asn Tyr Cys Asn
    50                  55
```

<210> SEQ ID NO 138
<211> LENGTH: 51
<212> TYPE: PRT
<213> ORGANISM: Homo sapiens

<400> SEQUENCE: 138

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Ile
            20                  25                  30
```

```
Val Glu Gln Cys Cys Thr Ser Ile Cys Ser Leu Tyr Gln Leu Glu Asn
        35                  40                  45

Tyr Cys Asn
    50


<210> SEQ ID NO 139
<211> LENGTH: 51
<212> TYPE: PRT
<213> ORGANISM: Bos sp.

<400> SEQUENCE: 139

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Gly Ile
            20                  25                  30

Val Glu Gln Cys Cys Ala Ser Val Cys Ser Leu Tyr Gln Leu Glu Asn
        35                  40                  45

Tyr Cys Asn
    50


<210> SEQ ID NO 140
<211> LENGTH: 51
<212> TYPE: PRT
<213> ORGANISM: Unknown
<220> FEATURE:
<223> OTHER INFORMATION: Description of Unknown:
      Porcine sequence

<400> SEQUENCE: 140

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Gly Ile
            20                  25                  30

Val Glu Gln Cys Cys Thr Ser Ile Cys Ser Leu Tyr Gln Leu Glu Asn
        35                  40                  45

Tyr Cys Asn
    50


<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Gly Gly Gly Ser
1               5


<210> SEQ ID NO 142
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Gly Pro Ser Ser Gly Ala Pro Pro Pro Ser Gly Gly Gly Gly Gly
1               5                   10                  15


<210> SEQ ID NO 143
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gly Gly Glu Ala Ala Ala Lys Glu Ala Ala Ala Lys Glu Ala Ala
1               5                   10                  15

Ala Lys Ala Gly Gly
            20


<210> SEQ ID NO 144
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Gly Gly Gly Ser Gly Gly Gly Glu Ala Ala Ala Lys Glu Ala Ala
1               5                   10                  15

Ala Lys Glu Ala Ala Ala Lys Ala Gly Gly
            20                  25


<210> SEQ ID NO 145
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Gly Glu Ala Ala Ala Lys Glu Ala Ala Ala Lys Glu Ala Ala
1               5                   10                  15

Ala Lys Ala Gly Gly Gly Gly Ser Gly Gly
            20                  25


<210> SEQ ID NO 146
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gly Gly Gly Gly Ser Gly Gly Gly Glu Ala Ala Ala Lys Glu Ala Ala
1               5                   10                  15

Ala Lys Glu Ala Ala Ala Lys Ala Gly Gly Gly Gly Ser Gly Gly
            20                  25                  30


<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Gly Gly Gly Ser Gly Gly Ser Pro
1               5
```

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Gly Gly Pro Arg Arg
1               5

<210> SEQ ID NO 149
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 150
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Arg Lys Lys Arg
    50

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Gly Gly Ser Gly Gly Gly Ser Gly
1               5

<210> SEQ ID NO 152
<211> LENGTH: 6
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 152

Gly Gly Gly Pro Gly Gly
1               5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Gly Gly Pro Lys Lys
1               5

<210> SEQ ID NO 154
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (5)..(54)
<223> OTHER INFORMATION: This region may encompass 1-10 “Gly Gly Gly Gly
      Ser” repeating units, wherein some positions may be absent

<400> SEQUENCE: 154

Arg Lys Lys Arg Gly Gly Gly Gly Ser Gly Gly Gly Gly Ser Gly Gly
1               5                   10                  15

Gly Gly Ser Gly Gly Gly Gly Ser Gly Gly Gly Gly Ser Gly Gly Gly
            20                  25                  30

Gly Ser Gly Gly Gly Gly Ser Gly Gly Gly Gly Ser Gly Gly Gly Gly
        35                  40                  45

Ser Gly Gly Gly Gly Ser Arg Lys Lys Arg
    50                  55

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any naturally or non-naturally occurring amino
      acid
<220> FEATURE:
<221> NAME/KEY: MOD_RES
<222> LOCATION: (7)..(7)
<223> OTHER INFORMATION: Any naturally or non-naturally occurring amino
      acid

<400> SEQUENCE: 155

Gln Val Gln Leu Xaa Gln Xaa Gly Ala Glu
1               5                   10

<210> SEQ ID NO 156
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any naturally or non-naturally occurring amino
      acid
<220> FEATURE:
<221> NAME/KEY: MOD_RES
<222> LOCATION: (9)..(9)
<223> OTHER INFORMATION: Any naturally or non-naturally occurring amino
      acid

<400> SEQUENCE: 156

Glu Xaa Val Leu Thr Gln Ser Pro Xaa Thr
1               5                   10


<210> SEQ ID NO 157
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any naturally or non-naturally occurring amino
      acid
<220> FEATURE:
<221> NAME/KEY: MOD_RES
<222> LOCATION: (28)..(29)
<223> OTHER INFORMATION: Any naturally or non-naturally occurring amino
      acid

<400> SEQUENCE: 157

Phe Val Asn Gln His Leu Cys Gly Ser Xaa Leu Val Glu Ala Leu Tyr
1               5                   10                  15

Leu Val Cys Gly Glu Arg Gly Phe Phe Tyr Thr Xaa Xaa Thr
            20                  25                  30


<210> SEQ ID NO 158
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any naturally or non-naturally occurring amino
      acid

<400> SEQUENCE: 158

Gly Ile Val Glu Gln Cys Cys Xaa Ser Ile Cys Ser Leu Tyr Gln Leu
1               5                   10                  15

Glu Asn Tyr Cys Asn
            20


<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (4)..(5)
<223> OTHER INFORMATION: Any naturally or non-naturally occurring amino
      acid

<400> SEQUENCE: 159

Gly Gly Gly Xaa Xaa
1               5


<210> SEQ ID NO 160
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Phe Val Asn Gln His Leu Cys Gly Ser His Leu Val Glu Ala Leu Tyr
1               5                   10                  15

Leu Val Cys Gly Glu Arg Gly Phe Phe Tyr Thr
            20                  25


<210> SEQ ID NO 161
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Ile Val Glu Gln Cys Cys Thr Ser Ile Cys Ser Leu Tyr Gln Leu
1               5                   10                  15

Glu Asn Tyr Cys
            20


<210> SEQ ID NO 162
<211> LENGTH: 230
<212> TYPE: PRT
<213> ORGANISM: Homo sapiens

<400> SEQUENCE: 162

Gln Asn Ser Gln Leu Gln Glu Glu Leu Arg Gly Leu Arg Glu Thr Phe
1               5                   10                  15

Ser Asn Phe Thr Ala Ser Thr Glu Ala Gln Val Lys Gly Leu Ser Thr
            20                  25                  30

Gln Gly Gly Asn Val Gly Arg Lys Met Lys Ser Leu Glu Ser Gln Leu
        35                  40                  45

Glu Lys Gln Gln Lys Asp Leu Ser Glu Asp His Ser Ser Leu Leu Leu
    50                  55                  60

His Val Lys Gln Phe Val Ser Asp Leu Arg Ser Leu Ser Cys Gln Met
65                  70                  75                  80

Ala Ala Leu Gln Gly Asn Gly Ser Glu Arg Thr Cys Cys Pro Val Asn
                85                  90                  95

Trp Val Glu His Glu Arg Ser Cys Tyr Trp Phe Ser Arg Ser Gly Lys
            100                 105                 110

Ala Trp Ala Asp Ala Asp Asn Tyr Cys Arg Leu Glu Asp Ala His Leu
        115                 120                 125

Val Val Val Thr Ser Trp Glu Glu Gln Lys Phe Val Gln His His Ile
    130                 135                 140
```

```
Gly Pro Val Asn Thr Trp Met Gly Leu His Asp Gln Asn Gly Pro Trp
145                 150                 155                 160

Lys Trp Val Asp Gly Thr Asp Tyr Glu Thr Gly Phe Lys Asn Trp Arg
                165                 170                 175

Pro Glu Gln Pro Asp Asp Trp Tyr Gly His Gly Leu Gly Gly Gly Glu
            180                 185                 190

Asp Cys Ala His Phe Thr Asp Asp Gly Arg Trp Asn Asp Asp Val Cys
        195                 200                 205

Gln Arg Pro Tyr Arg Trp Val Cys Glu Thr Glu Leu Asp Lys Ala Ser
    210                 215                 220

Gln Glu Pro Pro Leu Leu
225                 230


<210> SEQ ID NO 163
<211> LENGTH: 230
<212> TYPE: PRT
<213> ORGANISM: Macaca fascicularis

<400> SEQUENCE: 163

Gln Asn Ala Gln Leu Gln Arg Glu Leu Arg Gly Leu Arg Glu Thr Leu
1               5                   10                  15

Ser Asn Phe Thr Ala Ser Thr Glu Ala Gln Val Lys Gly Leu Ser Thr
            20                  25                  30

Gln Gly Gly Asn Val Gly Arg Lys Met Lys Ser Leu Glu Ser Gln Leu
        35                  40                  45

Glu Lys Gln Gln Lys Asp Leu Ser Glu Asp His Ser Ser Leu Leu Leu
    50                  55                  60

His Val Lys Gln Phe Val Ser Asp Leu Arg Ser Leu Ser Cys Gln Met
65                  70                  75                  80

Ala Ala Leu Gln Gly Asn Gly Ser Glu Arg Ala Cys Cys Pro Val Asn
                85                  90                  95

Trp Val Glu His Glu Arg Ser Cys Tyr Trp Phe Ser Arg Ser Gly Lys
            100                 105                 110

Ala Trp Ala Asp Ala Asp Asn Tyr Cys Arg Leu Glu Asp Ala His Leu
        115                 120                 125

Val Val Val Thr Ser Trp Glu Glu Gln Lys Phe Val Gln His His Ile
    130                 135                 140

Gly Pro Val Asn Thr Trp Met Gly Leu His Asp Gln Asn Gly Pro Trp
145                 150                 155                 160

Lys Trp Val Asp Gly Thr Asp Tyr Glu Thr Gly Phe Lys Asn Trp Arg
                165                 170                 175

Pro Glu Gln Pro Asp Asp Trp Tyr Gly His Gly Leu Gly Gly Gly Glu
            180                 185                 190

Asp Cys Ala His Phe Thr Asp Asp Gly Arg Trp Asn Asp Asp Val Cys
        195                 200                 205

Gln Arg Pro Tyr Arg Trp Val Cys Glu Thr Glu Leu His Lys Ala Ser
    210                 215                 220

Gln Glu Pro Pro Leu Leu
225                 230


<210> SEQ ID NO 164
<211> LENGTH: 224
<212> TYPE: PRT
<213> ORGANISM: Rattus sp.

<400> SEQUENCE: 164
```

```
Gln Asn Ser Gln Leu Arg Glu Asp Leu Arg Val Leu Arg Gln Asn Phe
1               5                   10                  15

Ser Asn Phe Thr Val Ser Thr Glu Asp Gln Val Lys Ala Leu Thr Thr
            20                  25                  30

Gln Gly Glu Arg Val Gly Arg Lys Met Lys Leu Val Glu Ser Gln Leu
        35                  40                  45

Glu Lys His Gln Glu Asp Leu Arg Glu Asp His Ser Arg Leu Leu Leu
    50                  55                  60

His Val Lys Gln Leu Val Ser Asp Val Arg Ser Leu Ser Cys Gln Met
65                  70                  75                  80

Ala Ala Leu Arg Gly Asn Gly Ser Glu Arg Ile Cys Cys Pro Ile Asn
                85                  90                  95

Trp Val Glu Tyr Glu Gly Ser Cys Tyr Trp Phe Ser Ser Ser Val Lys
            100                 105                 110

Pro Trp Thr Glu Ala Asp Lys Tyr Cys Gln Leu Glu Asn Ala His Leu
        115                 120                 125

Val Val Val Thr Ser Trp Glu Glu Gln Arg Phe Val Gln Gln His Met
    130                 135                 140

Gly Pro Leu Asn Thr Trp Ile Gly Leu Thr Asp Gln Asn Gly Pro Trp
145                 150                 155                 160

Lys Trp Val Asp Gly Thr Asp Tyr Glu Thr Gly Phe Lys Asn Trp Arg
                165                 170                 175

Pro Gly Gln Pro Asp Asp Trp Tyr Gly His Gly Leu Gly Gly Gly Glu
            180                 185                 190

Asp Cys Ala His Phe Thr Thr Asp Gly His Trp Asn Asp Asp Val Cys
        195                 200                 205

Arg Arg Pro Tyr Arg Trp Val Cys Glu Thr Glu Leu Gly Lys Ala Asn
    210                 215                 220


<210> SEQ ID NO 165
<211> LENGTH: 224
<212> TYPE: PRT
<213> ORGANISM: Mus sp.

<400> SEQUENCE: 165

Gln Asn Ser Gln Leu Arg Glu Asp Leu Leu Ala Leu Arg Gln Asn Phe
1               5                   10                  15

Ser Asn Leu Thr Val Ser Thr Glu Asp Gln Val Lys Ala Leu Ser Thr
            20                  25                  30

Gln Gly Ser Ser Val Gly Arg Lys Met Lys Leu Val Glu Ser Lys Leu
        35                  40                  45

Glu Lys Gln Gln Lys Asp Leu Thr Glu Asp His Ser Ser Leu Leu Leu
    50                  55                  60

His Val Lys Gln Leu Val Ser Asp Val Arg Ser Leu Ser Cys Gln Met
65                  70                  75                  80

Ala Ala Phe Arg Gly Asn Gly Ser Glu Arg Thr Cys Cys Pro Ile Asn
                85                  90                  95

Trp Val Glu Tyr Glu Gly Ser Cys Tyr Trp Phe Ser Ser Ser Val Arg
            100                 105                 110

Pro Trp Thr Glu Ala Asp Lys Tyr Cys Gln Leu Glu Asn Ala His Leu
        115                 120                 125

Val Val Val Thr Ser Arg Asp Glu Gln Asn Phe Leu Gln Arg His Met
    130                 135                 140

Gly Pro Leu Asn Thr Trp Ile Gly Leu Thr Asp Gln Asn Gly Pro Trp
145                 150                 155                 160
```

```
Lys Trp Val Asp Gly Thr Asp Tyr Glu Thr Gly Phe Gln Asn Trp Arg
                165                 170                 175

Pro Glu Gln Pro Asp Asn Trp Tyr Gly His Gly Leu Gly Gly Gly Glu
            180                 185                 190

Asp Cys Ala His Phe Thr Thr Asp Gly Arg Trp Asn Asp Asp Val Cys
        195                 200                 205

Arg Arg Pro Tyr Arg Trp Val Cys Glu Thr Lys Leu Asp Lys Ala Asn
    210                 215                 220
```

<210> SEQ ID NO 166
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 166

```
caggtccaac tgcagcagcc tggggctgag cttgtgaagc ctggggcttc agtgaaactg     60

tcctgcaagg cttctggcta caccttcacc aactactgga tgcactgggt gaaacagagg    120

cctggacgag gccttgagtg gattggaagg attgatctta atagtggtgg tactaattac    180

aattacaatg agaagttcaa gaccaaggcc acactgactg tagacaaacc ctccagcaca    240

gcctacatgc agctcagcag cctgacatct gaggactctg cggtctatta ttgtgcaaat    300

tactacggta gtagctggtt tgcttactgg ggccaaggga ctctggtcac tgtctctgca    360

gcctccacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgact gtgccctcta gcagcttggg cacccagacc    600

tacatctgca acgtgaatca caagcccagc aacaccaagg tggacaagaa agttgaaccc    660

aaatcttgcg acaaaactca cacatgccca ccgtgcccag cacctccagt cgccggaccg    720

tcagtcttcc tcttccctcc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaaggcctc ccaagctcca tcgagaaaac catctccaaa   1020

gccaaagggc agccccgaga accacaggtg tacaccctgc ctccatcccg ggatgagctg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctacagc aagctcaccg tggacaagag caggtggcag   1260

caggggaacg tcttctcatg ctccgtgatg catgaggctc tgcacaacca ctacacgcag   1320

aagagcctct ccctgtctcc gggtaaa                                       1347
```

<210> SEQ ID NO 167
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Arg Gly Leu Glu Trp Ile
        35                  40                  45

Gly Arg Ile Asp Leu Asn Ser Gly Gly Thr Asn Tyr Asn Tyr Asn Glu
    50                  55                  60

Lys Phe Lys Thr Lys Ala Thr Leu Thr Val Asp Lys Pro Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Asn Tyr Tyr Gly Ser Ser Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 168
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gly Ile Val Glu Gln Cys Cys His Ser Ile Cys Ser Leu Tyr Gln Leu
1               5                   10                  15

Glu Asn Tyr Cys Asn Gly Gly Pro Ser Ser Gly Ala Pro Pro Pro Ser
            20                  25                  30

Gly Gly Gly Gly Gly Glu Thr Val Leu Thr Gln Ser Pro Thr Thr Met
        35                  40                  45

Ala Thr Ser Pro Gly Glu Lys Ile Thr Ile Thr Cys Ser Ala Ser Ser
    50                  55                  60

Thr Ile Ser Ser Asn Tyr Leu His Trp Tyr Gln Gln Lys Pro Gly Phe
65                  70                  75                  80

Ser Pro Lys Leu Leu Ile Tyr Arg Thr Ser Asp Leu Ala Ser Gly Val
                85                  90                  95

Pro Thr Arg Phe Ser Gly Ser Gly Ser Gly Thr Ser Tyr Ser Leu Thr
            100                 105                 110

Ile Gly Thr Met Glu Ala Glu Asp Val Ala Thr Tyr Tyr Cys Gln Gln
        115                 120                 125

Gly Ser Ser Ile Pro Phe Thr Phe Gly Ser Gly Thr Lys Leu Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 169
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169
```

```
Gly Ile Val Glu Gln Cys Cys His Ser Ile Cys Ser Leu Tyr Gln Leu
1               5                   10                  15

Glu Asn Tyr Cys Asn Gly Gly Pro Ser Ser Gly Ala Pro Pro Pro Ser
            20                  25                  30

Gly Gly Gly Gly Gly Glu Thr Val Leu Thr Gln Ser Pro Thr Thr Met
        35                  40                  45

Ala Thr Ser Pro Gly Glu Lys Ile Thr Ile Thr Cys Ser Ala Ser Ser
    50                  55                  60

Thr Ile Ser Ser Asn Tyr Leu His Trp Tyr Gln Gln Lys Pro Gly Phe
65                  70                  75                  80

Ser Pro Lys Leu Leu Ile Tyr Arg Thr Ser Asp Leu Ala Ser Gly Val
                85                  90                  95

Pro Thr Arg Phe Ser Gly Ser Gly Ser Gly Thr Ser Tyr Ser Leu Thr
            100                 105                 110

Ile Gly Thr Met Glu Ala Glu Asp Val Ala Thr Tyr Tyr Cys Gln Gln
        115                 120                 125

Gly Ser Ser Ile Pro Phe Thr Phe Gly Ser Gly Thr Lys Leu Glu Ile
    130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250


<210> SEQ ID NO 170
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gly Ile Val Glu Gln Cys Cys Thr Ser Ile Cys Ser Leu Tyr Gln Leu
1               5                   10                  15

Glu Asn Tyr Cys Asn Gly Gly Gly Glu Ala Ala Ala Lys Glu Ala Ala
            20                  25                  30

Ala Lys Glu Ala Ala Ala Lys Ala Gly Gly Glu Ile Val Leu Thr Gln
        35                  40                  45

Ser Pro Gly Thr Leu Ser Leu Ser Pro Gly Glu Arg Ala Thr Leu Ser
    50                  55                  60

Cys Ser Ala Ser Ser Thr Ile Ser Ser Asn Tyr Leu His Trp Tyr Gln
65                  70                  75                  80

Gln Lys Pro Gly Gln Ala Pro Arg Leu Leu Ile Tyr Arg Thr Ser Asp
                85                  90                  95

Leu Ala Ser Gly Ile Pro Asp Arg Phe Ser Gly Ser Gly Ser Gly Thr
            100                 105                 110
```

```
Asp Phe Thr Leu Thr Ile Ser Arg Leu Glu Pro Glu Asp Phe Ala Val
        115                 120                 125

Tyr Tyr Cys Gln Gln Gly Ser Ser Ile Pro Phe Thr Phe Gly Gln Gly
    130                 135                 140

Thr Lys Leu Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys


<210> SEQ ID NO 171
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gly Ile Val Glu Gln Cys Cys Thr Ser Ile Cys Ser Leu Tyr Gln Leu
1               5                   10                  15

Glu Asn Tyr Cys Asn Gly Gly Gly Glu Ala Ala Ala Lys Glu Ala Ala
            20                  25                  30

Ala Lys Glu Ala Ala Ala Lys Ala Gly Gly Asp Ile Gln Met Thr Gln
        35                  40                  45

Ser Pro Ser Thr Leu Ser Ala Ser Val Gly Asp Arg Val Thr Ile Thr
    50                  55                  60

Cys Lys Cys Gln Leu Ser Val Gly Tyr Met His Trp Tyr Gln Gln Lys
65                  70                  75                  80

Pro Gly Lys Ala Pro Lys Leu Leu Ile Tyr Asp Thr Ser Lys Leu Ala
                85                  90                  95

Ser Gly Val Pro Ser Arg Phe Ser Gly Ser Gly Ser Gly Thr Glu Phe
            100                 105                 110

Thr Leu Thr Ile Ser Ser Leu Gln Pro Asp Asp Phe Ala Thr Tyr Tyr
        115                 120                 125

Cys Phe Gln Gly Ser Gly Tyr Pro Phe Thr Phe Gly Gly Gly Thr Lys
    130                 135                 140

Leu Glu Ile Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205
```

```
Ser Lys Asp Ser Thr Tyr Ser Leu Ser Ser Thr Leu Thr Leu Ser Lys
    210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255


<210> SEQ ID NO 172
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gly Ile Val Glu Gln Cys Cys Thr Ser Ile Cys Ser Leu Tyr Gln Leu
1               5                   10                  15

Glu Asn Tyr Cys Asn Gly Gly Gly Gly Ser Gly Gly Gly Glu Ala Ala
            20                  25                  30

Ala Lys Glu Ala Ala Ala Lys Glu Ala Ala Ala Lys Ala Gly Gly Gly
        35                  40                  45

Gly Ser Gly Gly Glu Ile Val Leu Thr Gln Ser Pro Gly Thr Leu Ser
    50                  55                  60

Leu Ser Pro Gly Glu Arg Ala Thr Leu Ser Cys Ser Ala Ser Ser Thr
65                  70                  75                  80

Ile Ser Ser Asn Tyr Leu His Trp Tyr Gln Gln Lys Pro Gly Gln Ala
                85                  90                  95

Pro Arg Leu Leu Ile Tyr Arg Thr Ser Asp Leu Ala Ser Gly Ile Pro
            100                 105                 110

Asp Arg Phe Ser Gly Ser Gly Ser Gly Thr Asp Phe Thr Leu Thr Ile
        115                 120                 125

Ser Arg Leu Glu Pro Glu Asp Phe Ala Val Tyr Tyr Cys Gln Gln Gly
    130                 135                 140

Ser Ser Ile Pro Phe Thr Phe Gly Gln Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265


<210> SEQ ID NO 173
<211> LENGTH: 267
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 173

```
Gly Ile Val Glu Gln Cys Cys Thr Ser Ile Cys Ser Leu Tyr Gln Leu
1               5                   10                  15

Glu Asn Tyr Cys Asn Gly Gly Gly Gly Ser Gly Gly Gly Glu Ala Ala
            20                  25                  30

Ala Lys Glu Ala Ala Ala Lys Glu Ala Ala Ala Lys Ala Gly Gly Gly
        35                  40                  45

Gly Ser Gly Gly Glu Ile Val Leu Thr Gln Ser Pro Gly Thr Leu Ser
    50                  55                  60

Leu Ser Pro Gly Glu Arg Ala Thr Leu Ser Cys Ser Ala Ser Ser Thr
65                  70                  75                  80

Ile Ser Ser Asn Tyr Leu His Trp Tyr Gln Gln Lys Pro Gly Gln Ala
                85                  90                  95

Pro Arg Leu Leu Ile Tyr Arg Thr Ser Asp Leu Ala Ser Gly Ile Pro
            100                 105                 110

Asp Arg Phe Ser Gly Ser Gly Ser Gly Thr Asp Phe Thr Leu Thr Ile
        115                 120                 125

Ser Arg Leu Glu Pro Glu Asp Phe Ala Val Tyr Tyr Cys Gln Gln Gly
    130                 135                 140

Ser Ser Ile Pro Phe Thr Phe Gly Gln Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265
```

<210> SEQ ID NO 174
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 174

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Gly
            20                  25                  30

Gly Gly Ser Gly Gly Gly Gly Ser
        35                  40
```

<210> SEQ ID NO 175
<211> LENGTH: 267
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 175

Gly Ile Val Glu Gln Cys Cys Thr Ser Ile Cys Ser Leu Tyr Gln Leu
1               5                   10                  15

Glu Asn Tyr Cys Asn Gly Gly Gly Gly Ser Gly Gly Gly Glu Ala Ala
            20                  25                  30

Ala Lys Glu Ala Ala Ala Lys Glu Ala Ala Ala Lys Ala Gly Gly Gly
        35                  40                  45

Gly Ser Gly Gly Glu Ile Val Leu Thr Gln Ser Pro Gly Thr Leu Ser
    50                  55                  60

Leu Ser Pro Gly Glu Arg Ala Thr Leu Ser Cys Ser Ala Ser Ser Thr
65                  70                  75                  80

Ile Ser Ser Asn Tyr Leu His Trp Tyr Gln Gln Lys Pro Gly Gln Ala
                85                  90                  95

Pro Arg Leu Leu Ile Tyr Arg Thr Ser Asp Leu Ala Ser Gly Ile Pro
            100                 105                 110

Asp Arg Phe Ser Gly Ser Gly Ser Gly Thr Asp Phe Thr Leu Thr Ile
        115                 120                 125

Ser Arg Leu Glu Pro Glu Asp Phe Ala Val Tyr Tyr Cys Gln Gln Gly
    130                 135                 140

Ser Ser Ile Pro Phe Thr Phe Gly Gln Gly Thr Lys Leu Glu Ile Lys
145                 150                 155                 160

Arg Thr Val Ala Ala Pro Ser Val Phe Ile Phe Pro Pro Ser Asp Glu
                165                 170                 175

Gln Leu Lys Ser Gly Thr Ala Ser Val Val Cys Leu Leu Asn Asn Phe
            180                 185                 190

Tyr Pro Arg Glu Ala Lys Val Gln Trp Lys Val Asp Asn Ala Leu Gln
        195                 200                 205

Ser Gly Asn Ser Gln Glu Ser Val Thr Glu Gln Asp Ser Lys Asp Ser
    210                 215                 220

Thr Tyr Ser Leu Ser Ser Thr Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys
            260                 265


<210> SEQ ID NO 176
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Ile Val Glu Gln Cys Cys His Ser Ile Cys Ser Leu Tyr Gln Leu
1               5                   10                  15

Glu Asn Tyr Cys Asn
            20


<210> SEQ ID NO 177
<211> LENGTH: 21
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 177

Gly Ile Val Glu Gln Cys Cys His Ser Ile Cys Ser Leu Tyr Gln Leu
1 5 10 15

Glu Asn Tyr Cys Asn
20

<210> SEQ ID NO 178
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Gly Ile Val Glu Gln Cys Cys Thr Ser Ile Cys Ser Leu Tyr Gln Leu
1 5 10 15

Glu Asn Tyr Cys Asn
20

<210> SEQ ID NO 179
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

Gly Ile Val Glu Gln Cys Cys Thr Ser Ile Cys Ser Leu Tyr Gln Leu
1 5 10 15

Glu Asn Tyr Cys Asn
20

<210> SEQ ID NO 180
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

Gly Ile Val Glu Gln Cys Cys Thr Ser Ile Cys Ser Leu Tyr Gln Leu
1 5 10 15

Glu Asn Tyr Cys Asn
20

<210> SEQ ID NO 181
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 181

Gly Ile Val Glu Gln Cys Cys Thr Ser Ile Cys Ser Leu Tyr Gln Leu
1 5 10 15

Glu Asn Tyr Cys Asn

20

<210> SEQ ID NO 182
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (10)..(10)
<223> OTHER INFORMATION: Any naturally or non-naturally occurring amino acid
<220> FEATURE:
<221> NAME/KEY: MOD_RES
<222> LOCATION: (28)..(29)
<223> OTHER INFORMATION: Any naturally or non-naturally occurring amino acid
<220> FEATURE:
<221> NAME/KEY: MOD_RES
<222> LOCATION: (31)..(80)
<223> OTHER INFORMATION: Any amino acid
<220> FEATURE:
<221> NAME/KEY: MISC_FEATURE
<222> LOCATION: (31)..(80)
<223> OTHER INFORMATION: This region may encompass 3-50 residues
<220> FEATURE:
<221> NAME/KEY: MOD_RES
<222> LOCATION: (88)..(88)
<223> OTHER INFORMATION: Any naturally or non-naturally occurring amino acid

<400> SEQUENCE: 182

```
Phe Val Asn Gln His Leu Cys Gly Ser Xaa Leu Val Glu Ala Leu Tyr
1               5                   10                  15

Leu Val Cys Gly Glu Arg Gly Phe Phe Tyr Thr Xaa Xaa Thr Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Gly Ile Val Glu Gln Cys Cys Xaa Ser Ile Cys Ser Leu Tyr Gln Leu
                85                  90                  95

Glu Asn Tyr Cys Asn
            100
```

<210> SEQ ID NO 183
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (8)..(8)
<223> OTHER INFORMATION: Any naturally or non-naturally occurring amino acid
<220> FEATURE:
<221> NAME/KEY: MOD_RES
<222> LOCATION: (22)..(71)
<223> OTHER INFORMATION: Any amino acid
<220> FEATURE:
<221> NAME/KEY: MOD_RES
<222> LOCATION: (22)..(71)
<223> OTHER INFORMATION: This region may encompass 3-50 residues
<220> FEATURE:

-continued

```
<221> NAME/KEY: MOD_RES
<222> LOCATION: (81)..(81)
<223> OTHER INFORMATION: Any naturally or non-naturally occurring amino
      acid
<220> FEATURE:
<221> NAME/KEY: MOD_RES
<222> LOCATION: (99)..(100)
<223> OTHER INFORMATION: Any naturally or non-naturally occurring amino
      acid

<400> SEQUENCE: 183

Gly Ile Val Glu Gln Cys Cys Xaa Ser Ile Cys Ser Leu Tyr Gln Leu
1               5                   10                  15

Glu Asn Tyr Cys Asn Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Phe Val Asn Gln His Leu Cys Gly Ser
65                  70                  75                  80

Xaa Leu Val Glu Ala Leu Tyr Leu Val Cys Gly Glu Arg Gly Phe Phe
                85                  90                  95

Tyr Thr Xaa Xaa Thr
            100


<210> SEQ ID NO 184
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Lys Lys Arg
1


<210> SEQ ID NO 185
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Gly Gly Ser
1
```